(12) United States Patent
Konermann et al.

(10) Patent No.: US 11,236,327 B2
(45) Date of Patent: Feb. 1, 2022

(54) CELL SORTING

(71) Applicants: The Broad Institute, Inc., Cambridge, MA (US); Massachusetts Institute of Technology, Cambridge, MA (US)

(72) Inventors: Silvana Konermann, Cambridge, MA (US); David Feldman, Cambridge, MA (US); Feng Zhang, Cambridge, MA (US); Paul Blainey, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/842,315

(22) Filed: Dec. 14, 2017

(65) Prior Publication Data

US 2018/0127745 A1    May 10, 2018

Related U.S. Application Data

(63) Continuation of application No. PCT/US2016/038234, filed on Jun. 17, 2016.

(60) Provisional application No. 62/181,704, filed on Jun. 18, 2015.

(51) Int. Cl.
| | |
|---|---|
| *C12N 15/10* | (2006.01) |
| *C12N 7/00* | (2006.01) |
| *C12N 9/22* | (2006.01) |
| *C12N 9/96* | (2006.01) |
| *C12N 15/11* | (2006.01) |
| *C12N 15/90* | (2006.01) |

(52) U.S. Cl.
CPC .......... *C12N 15/1065* (2013.01); *C12N 7/00* (2013.01); *C12N 9/22* (2013.01); *C12N 9/96* (2013.01); *C12N 15/1082* (2013.01); *C12N 15/11* (2013.01); *C12N 15/907* (2013.01); *C12N 2310/20* (2017.05); *C12N 2310/531* (2013.01); *C12N 2740/15043* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 4,873,316 A | 10/1989 | Meade et al. | |
| 5,543,158 A | 8/1996 | Gref et al. | |
| 5,580,859 A | 12/1996 | Felgner et al. | |
| 5,589,466 A | 12/1996 | Felgner et al. | |
| 5,593,972 A | 1/1997 | Weiner et al. | |
| 5,846,946 A | 12/1998 | Huebner et al. | |
| 5,855,913 A | 1/1999 | Hanes et al. | |
| 5,985,309 A | 11/1999 | Edwards et al. | |
| 6,007,845 A | 12/1999 | Domb et al. | |
| 6,603,061 B1 | 8/2003 | Armstrong et al. | |
| 6,750,059 B1 | 6/2004 | Blakesley et al. | |
| 7,259,015 B2 | 8/2007 | Kingsman et al. | |
| 7,303,910 B2 | 12/2007 | Bebbington et al. | |
| 7,351,585 B2 | 4/2008 | Mitrophanous et al. | |
| 7,745,651 B2 | 6/2010 | Heyes et al. | |
| 7,776,321 B2 | 8/2010 | Cascalho et al. | |
| 7,799,565 B2 | 9/2010 | MacLachlan et al. | |
| 7,803,397 B2 | 9/2010 | Heyes et al. | |
| 7,838,658 B2 | 11/2010 | MacLachlan et al. | |
| 7,868,149 B2 | 1/2011 | Boukharov et al. | |
| 7,901,708 B2 | 3/2011 | MacLachlan et al. | |
| 7,915,399 B2 | 3/2011 | MacLachlan et al. | |
| 7,982,027 B2 | 7/2011 | Maclachlan et al. | |
| 8,058,069 B2 | 11/2011 | Yaworski et al. | |
| 8,101,741 B2 | 1/2012 | Maclachlan et al. | |
| 8,188,263 B2 | 5/2012 | Maclachlan et al. | |
| 8,236,943 B2 | 8/2012 | Lee et al. | |
| 8,283,333 B2 | 10/2012 | Yaworski et al. | |
| 8,404,658 B2 | 3/2013 | Hajjar et al. | |
| 8,454,972 B2 | 6/2013 | Nabel et al. | |
| 8,697,359 B1 | 4/2014 | Zhang | |
| 8,709,843 B2 | 4/2014 | Shakuda | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,895,308 B1 | 11/2014 | Zhang et al. | |
| 8,906,616 B2 | 12/2014 | Zhang et al. | |

(Continued)

FOREIGN PATENT DOCUMENTS

| | | |
|---|---|---|
| EP | 0264166 A1 | 4/1988 |
| EP | 1519714 A1 | 4/2005 |

(Continued)

OTHER PUBLICATIONS

Abudayyeh et al., "C2c2 is a single-component programmable RNA-guided RNA-targeting CRISPR effector" 363(6299) Science 557 aaf5573-1-9 (Jun. 2, 2016).*

Sorek et al., "CRISPR-Mediated Adaptive Immune Systems in Bacteria and Archaea" 82 Annual Review of Biochemistry 2370266 (2013).*

(Continued)

*Primary Examiner* — Nancy J Leith

(74) *Attorney, Agent, or Firm* — Johnson, Marcou, Isaacs & Nix, LLC; F. Brent Nix, Esq.; Michael B. Scher, Esq.

(57) ABSTRACT

The invention provides for use of CRISPR-Cas systems to sort barcoded cells or molecules. Cells or nucleic acid molecules may be sorted from a heterogenous population by targeting a barcode of interest specific for a cell or cell progeny or nucleic acid molecule of interest.

8 Claims, 21 Drawing Sheets

Specification includes a Sequence Listing.

(56) References Cited

U.S. PATENT DOCUMENTS

| | | |
|---|---|---|
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 2004/0013648 A1 | 1/2004 | Kingsman et al. |
| 2004/0171156 A1 | 9/2004 | Hartley et al. |
| 2004/0242517 A1 | 12/2004 | Cascalho et al. |
| 2005/0019923 A1 | 1/2005 | Uchegbu et al. |
| 2006/0281180 A1 | 12/2006 | Radcliffe et al. |
| 2007/0025970 A1 | 2/2007 | Kingsman et al. |
| 2007/0054961 A1 | 3/2007 | Maden et al. |
| 2008/0267903 A1 | 10/2008 | Uchegbu et al. |
| 2009/0007284 A1 | 1/2009 | Radcliffe et al. |
| 2009/0017543 A1 | 1/2009 | Wilkes et al. |
| 2009/0100536 A1 | 4/2009 | Adams et al. |
| 2009/0111106 A1 | 4/2009 | Mitrophanous et al. |
| 2010/0317109 A1 | 12/2010 | Maden et al. |
| 2011/0027239 A1 | 2/2011 | Paek |
| 2011/0059502 A1 | 3/2011 | Chalasani |
| 2011/0117189 A1 | 5/2011 | Mazzone et al. |
| 2011/0293571 A1 | 12/2011 | Widdowson et al. |
| 2011/0293703 A1 | 12/2011 | Mahon et al. |
| 2012/0251560 A1 | 10/2012 | Dahlman et al. |
| 2012/0251618 A1 | 10/2012 | Schrum et al. |
| 2012/0295960 A1 | 11/2012 | Palfi et al. |
| 2013/0244279 A1 | 9/2013 | De Fougerolles et al. |
| 2013/0245107 A1 | 9/2013 | De Fougerolles et al. |
| 2013/0252281 A1 | 9/2013 | De Fougerolles et al. |
| 2013/0302401 A1 | 11/2013 | Ma et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2018/0057810 A1 | 3/2018 | Zhang et al. |

FOREIGN PATENT DOCUMENTS

| | | |
|---|---|---|
| EP | 1664316 A1 | 6/2006 |
| EP | 1766035 A1 | 3/2007 |
| EP | 1781593 A2 | 5/2007 |
| EP | 2771468 A1 | 9/2014 |
| EP | 2784162 A1 | 10/2014 |
| EP | 2784162 B1 | 4/2015 |
| EP | 2764103 B1 | 8/2015 |
| WO | 9639154 A1 | 12/1996 |
| WO | 9703211 A1 | 1/1997 |
| WO | 2011028929 A3 | 3/2011 |
| WO | 2012135025 A2 | 10/2012 |
| WO | 2014018423 A2 | 1/2014 |
| WO | 2014047561 A1 | 3/2014 |
| WO | 2014093595 A1 | 6/2014 |
| WO | 2014093622 A2 | 6/2014 |
| WO | 2014093635 A1 | 6/2014 |
| WO | 2014093655 A2 | 6/2014 |
| WO | 2014093661 A2 | 6/2014 |
| WO | 2014093694 A1 | 6/2014 |
| WO | 2014093701 A1 | 6/2014 |
| WO | 2014093709 A1 | 6/2014 |
| WO | 2014093712 A1 | 6/2014 |
| WO | 2014093718 A1 | 6/2014 |
| WO | 2014204723 A1 | 12/2014 |
| WO | 2014204724 A1 | 12/2014 |
| WO | 2014204725 A1 | 12/2014 |
| WO | 2014204726 A1 | 12/2014 |
| WO | 2014204727 A1 | 12/2014 |
| WO | 2014204728 A1 | 12/2014 |
| WO | 2014204729 A1 | 12/2014 |
| WO | 2015006294 | 1/2015 |
| WO | 2015065964 A1 | 5/2015 |
| WO | 2016040476 A1 | 3/2016 |
| WO | 2016205745 A2 | 12/2016 |

OTHER PUBLICATIONS

Brooks, et al., "Efficient Gene Editing in Tomato in the First Generation Using the Clustered Regularly Interspaced Short Palindromic Repeats/CRISPR-Associated9 System", Plant Physiology, vol. 166, No. 3, Sep. 15, 2014, 1292-1297.

Caliando, et al., "Targeted DNA Degradation using a CRISPR Device Stably Carried in the Host Genome", Nature Communications, vol. 6, May 19, 2015, 10 pages.

Chen, et al., "Genome-Wide CRISPR Screen in a Mouse Model of Tumor Growth and Metastasis", Cell, vol. 160, No. 6, Mar. 12, 2015, 1246-1260.

Chen, et al., "Predicting Peptide-Mediated Interactions on a Genome-Wide Scale", PLOS Computational Biology, vol. 11, No. 5, May 2015, 13 pages.

Doench, et al., "Rational Design of Highly Active Sgrnas for CRISPR-Cas9-Mediated Gene Inactivation", Nature Biotechnology, vol. 32, No. 12, Sep. 3, 2014, 1262-1267.

Feng, et al., "Efficient Genome Editing in Plants using a CRISPR/Cas System", Cell Research, vol. 23, Aug. 20, 2013, 1229-1232.

Fu, et al., "High Frequency Off-Target Mutagenesis Induced by CRISPR-Cas Nucleases in Human Cells", Nature Biotechnology, vol. 31, No. 9, Sep. 2013, 822-826.

Fu, et al., "Improving CRISPR-Cas Nuclease Specificity Using Truncated Guide RNAS", Nature Biotechnology, vol. 32, No. 3, Mar. 2014, 279-284.

Hsu, et al., "Development and Applications of CRISPR-Cas9 for Genome Engineering", Cell, vol. 157, No. 6,, Jun. 5, 2014, 1262-1278.

Hsu, et al., "DNA Targeting Specificity of RNA-Guided Cas9 Nucleases", Nat. Biotechnol. vol. 31, No. 9, Sep. 2013, 827-832.

Jiang, et al., "RNA-guided editing of bacterial genomes using CRISPR-Cas systems", Nature Biotechnology, vol. 31, Issue 3, Mar. 2013, 233-239.

Nekrasov, et al., "Plant Genome Editing Made Easy: Targeted Mutagenesis In Model and Crop Plants Using the CRISPR/Cas System", Plant Methods, vol. 9, No. 39, 2013, 10 pages.

Nishimasu, et al., "Crystal Structure of Cas9 in Complex with Guide RNA and Target DNA", Cell, vol. 156, No. 5, Feb. 27, 2014, 935-949.

Nishimasu, et al., "Crystal Structure of *Staphylococcus aureus* Cas9", Cell, vol. 162, No. 5, Aug. 27, 2015, 1113-1126.

Parnas, et al., "A Genome-Wide CRISPR Screen in Primary Immune Cells to Dissect Regulatory Networks", Cell, vol. 162, No. 3, Jul. 30, 2015, 675-686.

Platt, et al., "CRISPR-Cas9 Knockin Mice for Genome Editing and Cancer Modelling", Cell, vol. 159, No. 2, Oct. 9, 2014, 440-455.

Ramanan, et al., "CRISPR/Cas9 Cleavage of Viral DNA Efficiently Suppresses Hepatitis B Virus", Scientific Reports, vol. 5, Article No. 10833, 2015, 9 pages.

Ran, et al., "Double Nicking by RNA-Guided CRISPR Cas9 for Enhanced Genome Editing Specificity", Cell, vol. 154, No. 6, Sep. 12, 2013, 1380-1389.

Ran, et al., "Genome Engineering using the CRISPR-Cas9 System", Nature Protocols, vol. 8, No. 11, Nov. 2013, 2281-2308.

Ran, et al., "In Vivo Genome Editing using *Staphylococcus aureau* Cas9", Nature, vol. 520, No. 7546, Apr. 9, 2015, 186-191.

Shalem, et al., "Genome-Scale CRISPR-Cas9 Knockout Screening in Human Cells", Science, vol. 343, No. 6166, 2014, 84-87.

(56) References Cited

OTHER PUBLICATIONS

Shalem, et al., "High-Throughput Functional Genomics Using CRISPR-Cas9", Nature Reviews Genetics, vol. 16, No. 5, May 2015, 299-311.
Shan, et al., "Targeted Genome Modification of Crop Plants using a CRISPR-Cas System", Nature biotechnology, vol. 31, Issue 8, Aug. 2013, 686-688.
Shengdar, et al., "Dimeric CRISPR RNA-guided Fokl nucleases for highly specific genome editing", Nature Biotechnology, vol. 32, No. 6, 2014, 569-576.
Shmakov, et al., "Discovery and Functional Characterization of Diverse Class 2 CRISPR-Cas Systems", Molecular Cell, vol. 60, No. 3, Nov. 5, 2013, 385-397.
Swiech, et al., "In Vivo Interrogation of Gene Function in the Mammalian Brain using CRISPR-Cas9", Nature Biotechnology, vol. 33, No. 1, Oct. 19, 2014, 102-106.
Wang, et al., "Genetic Screens in Human Cells Using the CRISPR/Cas9 System", Science, vol. 343, No. 6166, Jan. 3, 2014, 80-84.
Wang, et al., "One-Step Generation of Mice Carrying Mutations in Multiple Genes by CRISPR/Cas-Mediated Genome Engineering", Cell, vol. 153, No. 4, May 9, 2013, 910-918.
Wu, et al., "Genome-Wide Binding of the CRISPR Endonuclease Cas9 in Mammalian Cells", Nature Biotechnology, vol. 32, No. 7, Jul. 2014, 670-676.
Xie, "RNA-Guided Genome Editing in Plants Using a CRISPR-Cas System", Molecular Plant, vol. 6, No. 6, Nov. 2013, 1975-1983.
Xu, et al., "Gene Targeting Using the Agrobacterium tumefaciens-mediated CRISPR-Cas System in Rice", Rice, vol. 7, No. 5, 2014, 1-4.
Xu, et al., "Sequence Determinants of Improved CRISPR SgRNA Design", Genome Research, vol. 25, No. 8, Aug. 2015, 1147-1157.
Zetsche, et al., "A split-Cas9 architecture for inducible genome editing and transcription modulation", Nature biotechnology, vol. 33, No. 2, 2015, 139-142.
Zetsche, et al., "Cpf1 is a Single RNA-Guided Endonuclease of a Class 2 CRISPR-Cas System", Cell, vol. 163, Sep. 25, 2015, 759-771.
Zhang, et al., "Structure-Based prediction of Protein-Protein Interactions on a Genome-Wide Scale", Nature, vol. 490, No. 7421, Oct. 25, 2012, 556-560.
Zhou, et al., "Exploiting SNPs for Biallelic CRISPR Mutations in the Outcrossing Woody Perennial Populus Reveals 4-coumarate:CoA ligase Specificity and Redundancy", New Phytologist, vol. 208, 2015, 298-301.
International Search Report dated Apr. 24, 2017, which issued during prosecution of International Application No. PCT/US2016/038234.
International Preliminary Report on Patentability and Written Opinion of the International Searching Authority dated Dec. 19, 2017, which issued during prosecution of International Application No. PCT/US2016/038234.
Bhang, et al. "Studying clonal dynamics in response to cancer therapy using high-complexity barcoding" Nature Medicine, 2015, 21(5):440-448, including Online Methods.
Cong, et al. "Multiplex Genome Engineering Using CRISPR-Cas Systems" Science, 2013, 339:819-823.
Cong, et al, "Supplementary Material: Multiplex Genome Engineering Using CRISPR-Cas Systems" Science Express, Jan. 3, 2013. http://www.sciencemag.org/content/full/science.1231143/DC1.
Heckl, et al. "Toward Whole-Transcriptome Editing with CRISPR-Cas9" Molecular Cell, 2015, 58:560-562.
Konermann, et al. "Genome-scale transcriptional activation by an engineered CRISPR-Cas9 complex" Nature, 2015, 517:583-588, including Methods.
Konermann, et al. "Optical control of mammalian endogenous transcription and epigenetic states" Nature, 2013, DOI: 10.1038/nature12466, including Methods.
Mali, et al., "Barcoding cells using cell-surface programmable DNA-binding domains", Nature Methods, 2013, 10(5):403-406, including Online Methods.
Mali, et al, "CAS9 transcriptional activators for target specificity screening and paired nickases for cooperative genome engineering" nature biotechnology, 2013, 31(9):833-838, including Online Methods.
Mali, et al. "Supplementary Information: Use of adjacent sgRNA:Cas9 complexes for transcriptional activation and genome engineering" Nature Biotechnoly, doi:10.1037/nbt.2675, 2013.
Mali, et al. "RNA-Guided Human Genome engineering Via Cas9" Science, 2013, 339:823-826, DOI: 10.1126/Science.1232033.
Mali, et al. "Supplementary Materials for-RNA-Guided Human Genome Engineering Via Cas9" Science, 2013, www.sciencemag.org/cgi/content/full/science.1232033/DC1.
Porter, et al. "Lentiviral and targeted cellular barcoding reveals ongoing clonal dynamics of cell lines in vitro and in vivo" Genome Biology, 2014, 15(5):R75, http://genomebiology.com/2014/15/R75.

\* cited by examiner

FIG. 3 barcode 1
TCAATTATACACTATCTCCTaggGCGGATCGGCTTCGTATATAaggCGTGGGGTTGCCTCGGAAagg barcode 2
CACGGAGCCAGTCCCCATGCCCGGaggACATAAATCTATGATGGCTTaggCTTAGGTCCTATGTGCGCAAagg barcode 3
AGCGGCCAGACAGTGCGTCCCaggGATATGAAACCACGGGCTGACaggATGCATCTAATATAACGAGAagg

FIG. 4A-1

```
                    taactagggaacccactgcttaagcctcaat    910
                    ▨▨▨▨▨ 6 LTR ▨▨▨▨▨
                    ctagcagtggcgcccgaacagggacttgaaa    1040
                    ▷ 5 LTR ▷
                    attttgactagcggaggctagaaggagagag    1170
                    ░░░░░░ Psi ░░░░░░
                    atatagtatgggcaagcagggagctagaacg    1300

FROM FIG.4A-1       atcattatataatacagtagcaaccctctat    1430
                    gctgatcttcagacctggaggaggagatatg    1560
                    gaaaaagagcagtgggaataggagctttgt     1690
                    agaacaatttgctgagggctattgaggcgca    1820
                    ttggggttgctctggaaaactcatttgcacc    1950
                    acaagcttaatacactccttaattgaagaat    2080
                    taaaattattcataatgatagtaggaggctt    2210
                    gggacccgacaggcccgaaggaatagaagaa    2340
```

FROM FIG.4A-2 tttttaaaagaaaaggggggattgggggtac 2470
cPPT agggacagcagagatccagtttggttaatta 2600 gatccgccaccatggtgagcaagggcgagga 2730
mCherry
KOZAK ccgcccctacgagggcacccagaccgccaag 2860
mCherry atccccgactacttgaagctgtccttcccg 2990
mCherry tgaagctgcgcggcaccaacttcccctccga 3120
mCherry

FROM FIG.4A-3

FROM FIG.4B-1 acggcgccctgaagggcgagatcaagcagaggctgaagctgaaggacggcggccactacgacgct 3250
mCherry caagttggacatcacctcccacaacgaggactacaccatcgtggaacagtacgaacgcgccgagg 3380
mCherry ctgtgccttctagttgccagccatctgttgtttgccccctcccccgtgccttccttgaccctggaa 3510
bGHpA tcattctattctggggggtggggtggggcaggacagcaaggggaggattgggaagacaatagca 3640
bGHpA ggcagagcgcacatcgcccacagtccccgagaagttggggggaggggtcggcaattgatccgtg 3770
EFS gagggtggggagaaccgtatataagtgcagtagtcgccgtgaacgttctttttcgcaacgggtt 3900
EFS cgcgacgacgtccccaggccgtacgcaccctcgccgccgcgttcgccgactacccgccacgcg 4030
PUROMYCIN gcgtcggctcgacatcggcaaggtgtgggtcgcggacgacggcgccgccgtggcggtctggacc 4160
PUROMYCIN ccgttcccggctggccggcagcaacagatggaaggcctcctggcgccgcaccggcccaaggagc 4290
PUROMYCIN

FROM FIG.4B-1 ccgcgtggttcctggccaccgtcggagtctcgcccgaccaccagggcaagggtctgggcagcgcc

PUROMYCIN gccccgcaacctcccttctacgagcggctcggcttcaccgtcaccgccgacgtcgaggtgcccg

PUROMYCIN ggtaatcaacctctggatcacaaaatttgtgaaagattgactggtattcttaactatgttgctcc

WPRE tcatttctcctccttgtataaatcctggttgctgtctctttatgaggagttgtggcccgttgtc

WPRE cacctgtcagctcctttccgggactttcgctttccccctccctattgccacggcggaactcatcg

WPRE tggggaaatcatcgtcctttccttggctgctcgcctgtgttgccacctggattctgcgcgggac

WPRE ctctgcggcctcttccgcgtcttcgccttcgccctcagacgagtcggatctccctttgggccgcc

WPRE agcagctaccaatgctgattgtgcctggctagaagcacaagaggaggaggaggtgggttttccag

FROM FIG.4B-2

```
gtcgtgctccccggagtggaggcggccgagcgcgccgggtgccgccttcctggagacctccgc   4420
                              PUROMYCIN
aaggaccgcgcacctggtgcatgacccgcaagcccggtgcctgagaattcgatatcaagcttatc   4550
           PUROMYCIN
tttacgctatgtggatacgctgctttaatgcctttgtatcatgctattgcttcccgtatggctt   4680
                              WPRE
aggcaacgtggcgtggtgtgcactgtgtttgctgacgcaacccccactggttggggcattgccac   4810
                              WPRE
ccgcctgccttgcccgctgctggacaggggctcggctgttgggcactgacaattccgtggtgttg   4940
                              WPRE
gtccttctgctacgtcccttcggccctcaatccagcggaccttcctttcccgcggcctgctgcgg   5070
                              WPRE
tccccgcatcgataccgtcgacctcgagacctagaaaaacatggagcaatcacaagtagcaatac   5200
  WPRE
tcacacctcaggtacctttaagaccaatgacttacaaggcagctgtagatcttagccactttta   5330
```

FROM FIG.4B-3

FIG. 4B-4 ctctgcggcctcttccgcgtcttcgccttcgccctcagacgagtcggatctccctttgggccgcctcc

WPRE agcagctaccaatgctgattgtgcctggctagaagcacaagaggaggaggaggtgggtttccagtca aaagaaaaggggggactggaagggctaattcactcccaacgaagacaagatatccttgatctgtggat atccactgacctttggatggtgctacaagctagtaccagttgagcaagagaaggtagaagaagccaat agaagtattagagtggaggtttgacagccgcctagcatttcatcacatggcccgagagctgcatccgg aaccactgcttaagcctcaataaagcttgccttgagtgcttcaagtagtgtgtgcccgtctgttgtg

3' LTR cccgtttaaacccgctgatcagcctcgactgtgccttctagttgccagccatctgttgtttgcccctc

FROM FIG.4C-1 ccgcatcgataccgtcgacctcgagacctagaaaaacatggagcaatcacaagtagcaatac 5200

WPRE cacctcaggtacctttaagaccaatgacttacaaggcagctgtagatcttagccactttta 5330 ctaccacacacaaggctacttccctgattggcagaactacacaccagggccagggatcagat 5460 gaaggagagaacaccgcttgttacaccctgtgagcctgcatgggatggatgacccggagag 5590 actgtactgggtctctctggttagaccagatctgagcctgggagctctctggctaactaggg 5720

⬅ 3' LTR tgactctggtaactagagatccctcagacccttttagtcagtgtggaaaatctctagcaggg 5850

3' LTR ➡ cccgtgccttccttgacctggaaggtgccactcccactgtcctttcctaataaaatgagg 5980

SEQUENCE LISTING

```
<160> NUMBER OF SEQ ID NOS: 76

<210> SEQ ID NO 1
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 1
nnnnnnnnnn nnnnnnnnnn ngg                                              23

<210> SEQ ID NO 2
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other

<400> SEQUENCE: 2
nnnnnnnnnn nnngg                                                       15

<210> SEQ ID NO 3
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other

<400> SEQUENCE: 3
nnnnnnnnnn nnnnnnnnnn ngg                                              23

<210> SEQ ID NO 4
```

```
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other

<400> SEQUENCE: 4
nnnnnnnnnn nngg                                                       14

<210> SEQ ID NO 5
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(22)
<223> OTHER INFORMATION: a, c, t, g, unknown or other

<400> SEQUENCE: 5
nnnnnnnnnn nnnnnnnnnn nnagaaw                                         27

<210> SEQ ID NO 6
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(14)
<223> OTHER INFORMATION: a, c, t, g, unknown or other

<400> SEQUENCE: 6
nnnnnnnnnn nnnnagaaw                                                  19

<210> SEQ ID NO 7
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
```

```
<222> LOCATION: (21)..(22)
<223> OTHER INFORMATION: a, c, t, g, unknown or other

<400> SEQUENCE: 7
nnnnnnnnnn nnnnnnnnnn nnagaaw                                    27

<210> SEQ ID NO 8
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(13)
<223> OTHER INFORMATION: a, c, t, g, unknown or other

<400> SEQUENCE: 8
nnnnnnnnnn nnnagaaw                                              18

<210> SEQ ID NO 9
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 9
nnnnnnnnnn nnnnnnnnnn nggng                                      25

<210> SEQ ID NO 10
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(12)
<223> OTHER INFORMATION: a, c, t or g
<220> FEATURE:
<221> NAME/KEY: modified_base
<222> LOCATION: (13)..(13)
<223> OTHER INFORMATION: a, c, t, g, unknown or other
<220> FEATURE:
<221> NAME/KEY: modified_base
<222> LOCATION: (16)..(16)
<223> OTHER INFORMATION: a, c, t, g, unknown or other

<400> SEQUENCE: 10
```
nnnnnnnnnn nnnggng                                                          17

<210> SEQ ID NO 11
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t or g
<220> FEATURE:
<221> NAME/KEY: modified_base
<222> LOCATION: (21)..(21)
<223> OTHER INFORMATION: a, c, t, g, unknown or other
<220> FEATURE:
<221> NAME/KEY: modified_base
<222> LOCATION: (24)..(24)
<223> OTHER INFORMATION: a, c, t, g, unknown or other

<400> SEQUENCE: 11
nnnnnnnnnn nnnnnnnnnn nggng                                                 25

<210> SEQ ID NO 12
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(11)
<223> OTHER INFORMATION: a, c, t or g
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: modified_base
<222> LOCATION: (15)..(15)
<223> OTHER INFORMATION: a, c, t, g, unknown or other

<400> SEQUENCE: 12
nnnnnnnnnn nnggng                                                           16

<210> SEQ ID NO 13
<211> LENGTH: 137
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 13
nnnnnnnnnn nnnnnnnnnn gttttttgtac tctcaagatt tagaaataaa tcttgcagaa          60
gctacaaaga taaggcttca tgccgaaatc aacaccctgt cattttatgg cagggtgttt         120
tcgttattta atttttt                                                        137

<210> SEQ ID NO 14
<211> LENGTH: 123

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 14
nnnnnnnnnn nnnnnnnnnn gttttttgtac tctcagaaat gcagaagcta caaagataag    60
gcttcatgcc gaaatcaaca ccctgtcatt ttatggcagg gtgttttcgt tatttaattt   120
ttt                                                                 123

<210> SEQ ID NO 15
<211> LENGTH: 110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 15
nnnnnnnnnn nnnnnnnnnn gttttttgtac tctcagaaat gcagaagcta caaagataag    60
gcttcatgcc gaaatcaaca ccctgtcatt ttatggcagg gtgttttttt              110

<210> SEQ ID NO 16
<211> LENGTH: 102
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (1)..(20)
<223> OTHER INFORMATION: a, c, t, g, unknown or other

<400> SEQUENCE: 16
nnnnnnnnnn nnnnnnnnnn gttttagagc tagaaatagc aagttaaaat aaggctagtc    60
cgttatcaac ttgaaaaagt ggcaccgagt cggtgctttt tt                     102

<210> SEQ ID NO 17
<211> LENGTH: 88
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 17
nnnnnnnnnn nnnnnnnnnn gttttagagc tagaaatagc aagttaaaat aaggctagtc    60
cgttatcaac ttgaaaaagt gttttttt                                       88
```

-continued

<210> SEQ ID NO 18
<211> LENGTH: 76
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, t, g, unknown or other

<400> SEQUENCE: 18
nnnnnnnnnn nnnnnnnnnn gttttagagc tagaaatagc aagttaaaat aaggctagtc    60
cgttatcatt tttttt                                                   76

<210> SEQ ID NO 19
<211> LENGTH: 20
<212> TYPE: DNA
<213> ORGANISM: Homo sapiens

<400> SEQUENCE: 19
gagtccgagc agaagaagaa                                               20

<210> SEQ ID NO 20
<211> LENGTH: 20
<212> TYPE: DNA
<213> ORGANISM: Homo sapiens

<400> SEQUENCE: 20
gagtcctagc aggagaagaa                                               20

<210> SEQ ID NO 21
<211> LENGTH: 20
<212> TYPE: DNA
<213> ORGANISM: Homo sapiens

<400> SEQUENCE: 21
gagtctaagc agaagaagaa                                               20

<210> SEQ ID NO 22
<211> LENGTH: 7
<212> TYPE: PRT
<213> ORGANISM: Simian virus 40

<400> SEQUENCE: 22

Pro Lys Lys Lys Arg Lys Val
1               5

<210> SEQ ID NO 23
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"

<400> SEQUENCE: 23

Lys Arg Pro Ala Ala Thr Lys Lys Ala Gly Gln Ala Lys Lys Lys Lys
1               5                   10                  15

<210> SEQ ID NO 24
<211> LENGTH: 9

```
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 24

Pro Ala Ala Lys Arg Val Lys Leu Asp
1               5

<210> SEQ ID NO 25
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 25

Arg Gln Arg Arg Asn Glu Leu Lys Arg Ser Pro
1               5                   10

<210> SEQ ID NO 26
<211> LENGTH: 38
<212> TYPE: PRT
<213> ORGANISM: Homo sapiens

<400> SEQUENCE: 26

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 27
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 27

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 28
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 28

Val Ser Arg Lys Arg Pro Arg Pro
1               5
```

<210> SEQ ID NO 29
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 29

Pro Pro Lys Lys Ala Arg Glu Asp
1               5

<210> SEQ ID NO 30
<211> LENGTH: 8
<212> TYPE: PRT
<213> ORGANISM: Homo sapiens

<400> SEQUENCE: 30

Pro Gln Pro Lys Lys Lys Pro Leu
1               5

<210> SEQ ID NO 31
<211> LENGTH: 12
<212> TYPE: PRT
<213> ORGANISM: Mus musculus

<400> SEQUENCE: 31

Ser Ala Leu Ile Lys Lys Lys Lys Lys Met Ala Pro
1               5                   10

<210> SEQ ID NO 32
<211> LENGTH: 5
<212> TYPE: PRT
<213> ORGANISM: Influenza virus

<400> SEQUENCE: 32

Asp Arg Leu Arg Arg
1               5

<210> SEQ ID NO 33
<211> LENGTH: 7
<212> TYPE: PRT
<213> ORGANISM: Influenza virus

<400> SEQUENCE: 33

Pro Lys Gln Lys Lys Arg Lys
1               5

<210> SEQ ID NO 34
<211> LENGTH: 10
<212> TYPE: PRT
<213> ORGANISM: Hepatitis delta virus

<400> SEQUENCE: 34

Arg Lys Leu Lys Lys Lys Ile Lys Lys Leu
1               5                   10

<210> SEQ ID NO 35
<211> LENGTH: 10
<212> TYPE: PRT
<213> ORGANISM: Mus musculus

<400> SEQUENCE: 35

```
Arg Glu Lys Lys Lys Phe Leu Lys Arg Arg
1               5                   10

<210> SEQ ID NO 36
<211> LENGTH: 20
<212> TYPE: PRT
<213> ORGANISM: Homo sapiens

<400> SEQUENCE: 36

Lys Arg Lys Gly Asp Glu Val Asp Gly Val Asp Glu Val Ala Lys Lys
1               5                   10                  15

Lys Ser Lys Lys
            20

<210> SEQ ID NO 37
<211> LENGTH: 17
<212> TYPE: PRT
<213> ORGANISM: Homo sapiens

<400> SEQUENCE: 37

Arg Lys Cys Leu Gln Ala Gly Met Asn Leu Glu Ala Arg Lys Thr Lys
1               5                   10                  15

Lys

<210> SEQ ID NO 38
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Gly Gly Ser Gly
1

<210> SEQ ID NO 39
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Gly Gly Gly Ser
1

<210> SEQ ID NO 40
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Gly Gly Gly Ser Gly Gly Gly Ser Gly Gly Gly Ser
1               5                   10

<210> SEQ ID NO 41
<211> LENGTH: 7
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Ala Glu Ala Ala Ala Lys Ala
1               5

<210> SEQ ID NO 42
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Gly Gly Gly Gly Ser Gly Gly Gly Gly Ser Gly Gly Gly Gly Ser
1               5                   10                  15

<210> SEQ ID NO 43
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 44
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 45
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gly Gly Gly Gly Ser Gly Gly Gly Gly Ser Gly Gly Gly Gly Ser Gly
1               5                   10                  15
```

```
Gly Gly Gly Ser Gly Gly Gly Ser Gly Gly Gly Ser Gly Gly
        20                  25                  30

Gly Gly Ser Gly Gly Gly Ser Gly Gly Gly Ser Gly Gly
        35                  40                  45

Gly Ser Gly Gly Gly Ser Gly Gly Gly Ser
    50                  55                  60

<210> SEQ ID NO 46
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46

Gly Gly Gly Gly Ser
1               5

<210> SEQ ID NO 47
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Gly Gly Gly Gly Ser Gly Gly Gly Gly Ser
1               5                   10

<210> SEQ ID NO 48
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gly Gly Gly Gly Ser Gly Gly Gly Gly Ser Gly Gly Gly Gly Ser Gly
1               5                   10                  15

Gly Gly Gly Ser
        20

<210> SEQ ID NO 49
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Gly Gly Gly Ser Gly Gly Gly Gly Ser Gly Gly Gly Gly Ser Gly
1               5                   10                  15

Gly Gly Gly Ser Gly Gly Gly Gly Ser
        20                  25

<210> SEQ ID NO 50
<211> LENGTH: 35
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser
        35

<210> SEQ ID NO 51
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser
        35                  40

<210> SEQ ID NO 52
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Ser Gly Gly
            35                  40                  45

Gly Ser
    50

<210> SEQ ID NO 53
<211> LENGTH: 55
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
```

```
                20                  25                  30
Gly Gly Ser Gly Gly Gly Ser Gly Gly Gly Ser Gly Gly Gly
        35                  40                  45
Gly Ser Gly Gly Gly Gly Ser
        50                  55

<210> SEQ ID NO 54
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Ser Gly Ser Glu Thr Pro Gly Thr Ser Glu Ser Ala Thr Pro Glu Ser
1               5                   10                  15

<210> SEQ ID NO 55
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Met Lys Ile Ile Glu Gln Leu Pro Ser Ala
1               5                   10

<210> SEQ ID NO 56
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Val Arg His Lys Leu Lys Arg Val Gly Ser
1               5                   10

<210> SEQ ID NO 57
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Val Pro Phe Leu Leu Glu Pro Asp Asn Ile Asn Gly Lys Thr Cys
1               5                   10                  15

<210> SEQ ID NO 58
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58
```

```
Gly His Gly Thr Gly Ser Thr Gly Ser Gly Ser Ser
1               5                   10

<210> SEQ ID NO 59
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Met Ser Arg Pro Asp Pro Ala
1               5

<210> SEQ ID NO 60
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Gly Ser Ala Gly Ser Ala Ala Gly Ser Gly Glu Phe
1               5                   10

<210> SEQ ID NO 61
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Ser Gly Ser Glu Thr Pro Gly Thr Ser Glu Ser Ala
1               5                   10

<210> SEQ ID NO 62
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gly Gly Ser Met
1

<210> SEQ ID NO 63
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Ser Gly Ser Glu Thr Pro Gly Thr Ser Glu Ser Ala Thr Pro Glu Gly
1               5                   10                  15
```

<210> SEQ ID NO 64
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 64
guuuuagagc ua                                                          12

<210> SEQ ID NO 65
<211> LENGTH: 10506
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 65

| | |
|---|---|
| gtcgacggat cgggagatct cccgatcccc tatggtgcac tctcagtaca atctgctctg | 60 |
| atgccgcata gttaagccag tatctgctcc ctgcttgtgt gttggaggtc gctgagtagt | 120 |
| gcgcgagcaa aatttaagct acaacaaggc aaggcttgac cgacaattgc atgaagaatc | 180 |
| tgcttagggt taggcgtttt cgctgcttc gcgatgtacg ggccagatat acgcgttgac | 240 |
| attgattatt gactagttat taatagtaat caattacggg gtcattagtt catagcccat | 300 |
| atatggagtt ccgcgttaca taacttacgg taaatggccc gcctggctga ccgcccaacg | 360 |
| acccccgccc attgacgtca ataatgacgt atgttcccat agtaacgcca atagggactt | 420 |
| tccattgacg tcaatgggtg gagtatttac ggtaaactgc ccacttggca gtacatcaag | 480 |
| tgtatcatat gccaagtacg ccccctattg acgtcaatga cggtaaatgg cccgcctggc | 540 |
| attatgccca gtacatgacc ttatgggact ttcctacttg gcagtacatc tacgtattag | 600 |
| tcatcgctat taccatggtg atgcggtttt ggcagtacat caatgggcgt ggatagcggt | 660 |
| ttgactcacg gggatttcca agtctccacc ccattgacgt caatgggagt ttgttttggc | 720 |
| accaaaatca acgggacttt ccaaaatgtc gtaacaactc cgccccattg acgcaaatgg | 780 |
| gcggtaggcg tgtacggtgg gaggtctata taagcagcgc gttttgcctg tactgggtct | 840 |
| ctctggttag accagatctg agcctgggag ctctctggct aactagggaa cccactgctt | 900 |
| aagcctcaat aaagcttgcc ttgagtgctt caagtagtgt gtgcccgtct gttgtgtgac | 960 |
| tctggtaact agagatccct cagacccttt tagtcagtgt ggaaaatctc tagcagtggc | 1020 |
| gcccgaacag ggacttgaaa gcgaaaggga accagagga gctctctcga cgcaggactc | 1080 |
| ggcttgctga agcgcgcacg gcaagaggcg aggggcggcg actggtgagt acgccaaaaa | 1140 |
| ttttgactag cggaggctag aaggagagag atgggtgcga gagcgtcagt attaagcggg | 1200 |
| ggagaattag atcgcgatgg gaaaaaattc ggttaaggcc agggggaaag aaaaaatata | 1260 |
| aattaaaaca tatagtatgg gcaagcaggg agctagaacg attcgcagtt aatcctggcc | 1320 |
| tgttagaaac atcagaaggc tgtagacaaa tactgggaca gctacaacca tcccttcaga | 1380 |
| caggatcaga agaacttaga tcattatata atacagtagc aaccctctat tgtgtgcatc | 1440 |
| aaaggataga gataaaagac accaaggaag ctttagacaa gatagaggaa gagcaaaaca | 1500 |

```
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctggggatt   1920
tggggttgct ctggaaaact catttgcacc actgctgtgc cttggaatgc tagttggagt   1980
aataaatctc tggaacagat tggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aaggggggat   2460
tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta gctagctagg tcttgaaagg agtgggaatt ggctccggtg   2640
cccgtcagtg ggcagagcgc acatcgccca cagtccccga aagttggggg gaggggtcg   2700 gcaattgatc cggtgcctag agaaggtggc gcggggtaaa ctgggaaagt gatgtcgtgt   2760
actggctccg ccttttttccc gagggtgggg gagaaccgta tataagtgca gtagtcgccg   2820
tgaacgttct ttttcgcaac gggtttgccg ccagaacaca ggaccggttc tagagcgctg   2880
ccaccatgtt ccaaaagctc aaacgtcacc tccaatcaca agggtggctt cgcaggatcg   2940
tttgtacagg cagtggagag ggcagaggaa gtctgctcac ctgcggcgac gtcgaggaga   3000
atcctggccc agtgagcaag ggcgaggagc tgttcaccgg ggtggtgccc atcctggtcg   3060
agctggacgg cgacgtaaac ggccacaagt tcagcgtgtc cggcgagggc gagggcgatg   3120
ccacctacgg caagctgacc ctgaagttca tctgcaccac cggcaagctg cccgtgccct   3180
ggcccaccct cgtgaccacc ctgacctacg gcgtgcagtg cttcagccgc taccccgacc   3240
acatgaagca gcacgacttc ttcaagtccg ccatgcccga aggctacgtc caggagcgca   3300
ccatcttctt caaggacgac ggcaactaca agacccgcgc cgaggtgaag ttcgagggcg   3360
acaccctggt gaaccgcatc gagctgaagg gcatcgactt caaggaggac ggcaacatcc   3420
tggggcacaa gctggagtac aactacaaca gccacaacgt ctatatcatg gccgacaagc   3480
agaagaacgg catcaaggtg aacttcaaga tccgccacaa catcgaggac ggcagcgtgc   3540
agctcgccga ccactaccag cagaacaccc ccatcggcga cggccccgtg ctgctgcccg   3600
acaaccacta cctgagcacc cagtccgccc tgagcaaaga ccccaacgag aagcgcgatc   3660
acatggtcct gctggagttc gtgaccgccg ccgggatcac tctcggcatg gacgagctct   3720
acaagtaata taaccggat ccggcgcaac aaacttctct ctgctcaaac aagccggcga   3780
cgtcgaagag aatcctgggc cggtgtccaa gggcgaggaa gataacatgg ccatcatcaa   3840
ggagttcatg aggtttaagg tccacatgga gggttcagtc aatggccacg agttcgagat   3900
```

```
tgaaggcgag ggcgagggcc gccccuacga agggacacag acggcgaaat tgaaggtgac   3960
caaaggcggg ccattgccct tcgcatggga catcttgtcc cctcagttta tgtatgcag    4020 caaggcctat gttaagcacc ccgctgatat cccggactac ttgaagctgt cctttccaga   4080
ggggtttaaa tgggagcgcg ttatgaattt cgaagacgga ggagtggtta cggtgacgca   4140
ggactcatcc ctgcaggacg gagaatttat atataaggtt aagttgagag cacaaactt    4200 cccaagcgac ggccctgtga tgcagaagaa aacaatgggg tgggaagctt ccagcgagcg   4260
catgtacccc gaagatggcg ccctcaaggg cgagataaag caaggctga aacttaagga    4320 cggcggtcat tacgacgcgg aggtcaagac aacttacaag gctaaaaaac ccgttcagtt   4380
gcctggggct tacaatgtta atatcaaact tgacatcaca agccacaatg aagactatac   4440
gatcgtggag cagtatgaac gagcggaagg caggcactca acgggggga tggacgagct    4500 ttacaagggc agtggggagg gcagaggaag tctgctaaca tgcggtgacg tcgaggagaa   4560
tcctggccca atgaccgagt acaagcccac ggtgcgcctc gccacccgcg acgacgtccc   4620
cagggccgta cgcaccctcg ccgccgcgtt cgccgactac cccgccacgc gccacaccgt   4680
cgatccggac cgccacatcg agcgggtcac cgagctgcaa gaactcttcc tcacgcgcgt   4740
cgggctcgac atcggcaagg tgtgggtcgc ggacgacggc gccgccgtgg cggtctggac   4800
cacgccggag agcgtcgaag cggggcggt gttcgccgag atcggcccgc gcatggccga    4860
gttgagcggt tcccggctgg ccgcgcagca acagatggaa ggcctcctgg cgccgcaccg   4920
gcccaaggag cccgcgtggt tcctggccac cgtcggagtc tcgcccgacc accagggcaa   4980
gggtctgggc agcgccgtcg tgctccccgg agtggaggcg gccgagcgcg ccggggtgcc   5040
cgccttcctg gagacctccg cgccccgcaa cctccccttc tacgagcggc tcggcttcac   5100
cgtcaccgcc gacgtcgagg tgcccgaagg accgcgcacc tggtgcatga cccgcaagcc   5160
cggtgcctga taagaattcg atatcaagct tatcggtaat caacctctgg attacaaaat   5220
ttgtgaaaga ttgactggta ttcttaacta tgttgctcct tttacgctat gtggatacgc   5280
tgctttaatg cctttgtatc atgctattgc ttcccgtatg ctttcatttt ctcctcctt    5340 gtataaatcc tggttgctgt ctctttatga ggagttgtgg cccgttgtca ggcaacgtgg   5400
cgtggtgtgc actgtgtttg ctgacgcaac ccccactggt tggggcattg ccaccacctg   5460
tcagctcctt tccgggactt tcgctttccc cctccctatt gccacggcgg aactcatcgc   5520
cgcctgcctt gcccgctgct ggacaggggc tcggctgttg ggcactgaca attccgtggt   5580
gttgtcgggg aaatcatcgt cctttccttg gctgctcgcc tgtgttgcca cctggattct   5640
gcgcgggacg tccttctgct acgtcccttc ggccctcaat ccagcggacc ttccttcccg   5700
cggcctgctg ccggctctgc ggcctcttcc gcgtcttcgc cttcgccctc agacgagtcg   5760
gatctccctt tgggccgcct ccccgcatcg ataccgtcga cctcgagacc tagaaaaaca   5820
tggagcaatc acaagtagca atacagcagc taccaatgct gattgtgcct ggctagaagc   5880
acaagaggag gaggaggtgg gttttccagt cacacctcag gtacctttaa gaccaatgac   5940
ttacaaggca gctgtagatc ttagccactt tttaaaagaa aaggggggac tggaagggct   6000
aattcactcc caacgaagac aagatatcct tgatctgtgg atctaccaca cacaaggcta   6060
cttccctgat tggcagaact acacaccagg gccagggatc agatatccac tgacctttgg   6120
atggtgctac aagctagtac cagttgagca agagaaggta gaagaagcca atgaaggaga   6180
gaacacccgc ttgttacacc ctgtgagcct gcatgggatg gatgacccgg agagagaagt   6240
```

```
attagagtgg aggtttgaca gccgcctagc atttcatcac atggcccgag agctgcatcc    6300
ggactgtact gggtctctct ggttagacca gatctgagcc tgggagctct ctggctaact    6360
agggaaccca ctgcttaagc ctcaataaag cttgccttga gtgcttcaag tagtgtgtgc    6420
ccgtctgttg tgtgactctg gtaactagag atccctcaga ccctttttagt cagtgtggaa    6480
aatctctagc agggcccgtt taaacccgct gatcagcctc gactgtgcct tctagttgcc    6540
agccatctgt tgtttgcccc tcccccgtgc cttccttgac cctggaaggt gccactccca    6600
ctgtcctttc ctaataaaat gaggaaattg catcgcattg tctgagtagg tgtcattcta    6660
ttctgggggg tggggtgggg caggacagca agggggagga ttgggaagac aatagcaggc    6720
atgctgggga tgcggtgggc tctatggctt ctgaggcgga agaaccagc tggggctcta     6780
gggggtatcc ccacgcgccc tgtagcggcg cattaagcgc ggcgggtgtg gtggttacgc    6840
gcagcgtgac cgctacactt gccagcgccc tagcgcccgc tcctttcgct ttcttccctt    6900
cctttctcgc cacgttcgcc ggctttcccc gtcaagctct aaatcggggg ctccctttag    6960
ggttccgatt tagtgcttta cggcacctcg accccaaaaa acttgattag ggtgatggtt    7020
cacgtagtgg gccatcgccc tgatagacgg ttttttcgccc tttgacgttg gagtccacgt    7080
tctttaatag tggactcttg ttccaaactg gaacaacact caaccctatc tcggtctatt    7140
cttttgattt ataagggatt ttgccgattt cggcctattg gttaaaaaat gagctgattt    7200
aacaaaaatt taacgcgaat taattctgtg gaatgtgtgt cagttagggt gtggaaagtc    7260
cccaggctcc ccagcaggca gaagtatgca aagcatgcat ctcaattagt cagcaaccag    7320
gtgtggaaag tccccaggct ccccagcagg cagaagtatg caaagcatgc atctcaatta    7380
gtcagcaacc atagtcccgc ccctaactcc gcccatcccg ccctaactc cgcccagttc    7440
cgcccattct ccgccccatg gctgactaat ttttttatt tatgcagagg ccgaggccgc    7500
ctctgcctct gagctattcc agaagtagtg aggaggcttt tttggaggcc taggcttttg    7560
caaaaagctc ccgggagctt gtatatccat tttcggatct gatcagcacg tgttgacaat    7620
taatcatcgg catagtatat cggcatagta taatacgaca aggtgaggaa ctaaaccatg    7680
gccaagttga ccagtgccgt tccggtgctc accgcgcgcg acgtcgccgg agcggtcgag    7740
ttctggaccg accggctcgg gttctcccgg gacttcgtgg aggacgactt cgccggtgtg    7800
gtccgggacg acgtgaccct gttcatcagc gcggtccagg accaggtggt gccggacaac    7860
accctggcct gggtgtgggt gcgcggcctg gacgagctgt acgccgagtg gtcggaggtc    7920
gtgtccacga cttccgggga cgcctccggg ccggccatga ccgagatcgg cgagcagccg    7980
tgggggcggg agttcgccct gcgcgacccg gccggcaact gcgtgcactt cgtggccgag    8040
gagcaggact gacacgtgct acgagatttc gattccaccg ccgccttcta tgaaaggttg    8100
ggcttcggaa tcgttttccg gacgccggc tggatgatcc tccagcgcgg ggatctcatg     8160
ctggagttct tcgcccaccc caacttgttt attgcagctt ataatggtta caaataaagc    8220
aatagcatca caaatttcac aaataaagca ttttttttcac tgcattctag ttgtggtttg    8280
tccaaactca tcaatgtatc ttatcatgtc tgtataccgt cgacctctag ctagagcttg    8340
gcgtaatcat ggtcatagct gtttcctgtg tgaaattgtt atccgctcac aattccacac    8400
aacatacgag ccggaagcat aaagtgtaaa gcctggggtg cctaatgagt gagctaactc    8460
acattaattg cgttgcgctc actgcccgct ttccagtcgg gaaacctgtc gtgccagctg    8520
cattaatgaa tcggccaacg cgcggggaga ggcggtttgc gtattgggcg ctcttccgct    8580
tcctcgctca ctgactcgct gcgctcggtc gttcggctgc ggcgagcggt atcagctcac    8640
```

| | |
|---|---|
| tcaaaggcgg taatacggtt atccacagaa tcagggata acgcaggaaa gaacatgtga | 8700 |
| gcaaaaggcc agcaaaaggc caggaaccgt aaaaaggccg cgttgctggc gttttccat | 8760 |
| aggctccgcc ccctgacga gcatcacaaa atcgacgct caagtcagag gtggcgaaac | 8820 |
| ccgacaggac tataaagata ccaggcgttt ccccctggaa gctccctcgt gcgctctcct | 8880 |
| gttccgaccc tgccgcttac cggatacctg tccgcctttc tcccttcggg aagcgtggcg | 8940 |
| ctttctcata gctcacgctg taggtatctc agttcggtgt aggtcgttcg ctccaagctg | 9000 |
| ggctgtgtgc acgaaccccc cgttcagccc gaccgctgcg ccttatccgg taactatcgt | 9060 |
| cttgagtcca acccggtaag acacgactta tcgccactgg cagcagccac tggtaacagg | 9120 |
| attagcagag cgaggtatgt aggcggtgct acagagttct tgaagtggtg gcctaactac | 9180 |
| ggctacacta gaagaacagt atttggtatc tgcgctctgc tgaagccagt taccttcgga | 9240 |
| aaaagagttg gtagctcttg atccggcaaa caaaccaccg ctggtagcgg tggtttttt | 9300 |
| gtttgcaagc agcagattac gcgcagaaaa aaaggatctc aagaagatcc tttgatcttt | 9360 |
| tctacggggt ctgacgctca gtggaacgaa aactcacgtt aagggatttt ggtcatgaga | 9420 |
| ttatcaaaaa ggatcttcac ctagatcctt ttaaattaaa aatgaagttt taaatcaatc | 9480 |
| taaagtatat atgagtaaac ttggtctgac agttaccaat gcttaatcag tgaggcacct | 9540 |
| atctcagcga tctgtctatt tcgttcatcc atagttgcct gactccccgt cgtgtagata | 9600 |
| actacgatac gggagggctt accatctggc cccagtgctg caatgatacc gcgagaccca | 9660 |
| cgctcaccgg ctccagattt atcagcaata aaccagccag ccggaagggc cgagcgcaga | 9720 |
| agtggtcctg caactttatc cgcctccatc cagtctatta attgttgccg ggaagctaga | 9780 |
| gtaagtagtt cgccagttaa tagtttgcgc aacgttgttg ccattgctac aggcatcgtg | 9840 |
| gtgtcacgct cgtcgtttgg tatggcttca ttcagctccg gttcccaacg atcaaggcga | 9900 |
| gttacatgat cccccatgtt gtgcaaaaaa gcggttagct ccttcggtcc tccgatcgtt | 9960 |
| gtcagaagta agttggccgc agtgttatca ctcatggtta tggcagcact gcataattct | 10020 |
| cttactgtca tgccatccgt aagatgcttt tctgtgactg gtgagtactc aaccaagtca | 10080 |
| ttctgagaat agtgtatgcg gcgaccgagt tgctcttgcc cggcgtcaat acgggataat | 10140 |
| accgcgccac atagcagaac tttaaaagtg ctcatcattg gaaaacgttc ttcggggcga | 10200 |
| aaactctcaa ggatcttacc gctgttgaga tccagttcga tgtaacccac tcgtgcaccc | 10260 |
| aactgatctt cagcatcttt tactttcacc agcgtttctg ggtgagcaaa aacaggaagg | 10320 |
| caaaatgccg caaaaaaggg aataagggcg acacggaaat gttgaatact catactcttc | 10380 |
| ctttttcaat attattgaag catttatcag ggttattgtc tcatgagcgg atacatattt | 10440 |
| gaatgtattt agaaaaataa acaaataggg gttccgcgca catttccccg aaaagtgcca | 10500 |
| cctgac | 10506 |

<210> SEQ ID NO 66
<211> LENGTH: 10027
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 66

| | |
|---|---|
| ctgtactggg tctctctggt tagaccagat ctgagcctgg gagctctctg gctaactagg | 60 |

```
gaacccactg cttaagcctc aataaagctt gccttgagtg cttcaagtag tgtgtgcccg    120
tctgttgtgt gactctggta actagagatc cctcagaccc ttttagtcag tgtggaaaat    180
ctctagcagt ggcgcccgaa cagggacttg aaagcgaaag gaaaccaga ggagctctct    240 cgacgcagga ctcggcttgc tgaagcgcgc acggcaagag gcgaggggcg gcgactggtg    300
agtacgccaa aattttgac tagcggaggc tagaaggaga gagatgggtg cgagagcgtc    360
agtattaagc gggggagaat tagatcgcga tgggaaaaaa ttcggttaag gccaggggga    420 aagaaaaat ataattaaa acatatagta tgggcaagca gggagctaga acgattcgca    480
gttaatcctg gcctgttaga aacatcagaa ggctgtagac aaatactggg acagctacaa    540
ccatcccttc agacaggatc agaagaactt agatcattat ataatacagt agcaaccctc    600
tattgtgtgc atcaaaggat agagataaaa gacaccaagg aagctttaga caagatagag    660
gaagagcaaa acaaaagtaa gaccaccgca cagcaagcgg ccgctgatct tcagacctgg    720
aggaggagat atgagggaca attggagaag tgaattatat aaatataaag tagtaaaaat    780
tgaaccatta ggagtagcac ccaccaaggc aaagagaaga gtggtgcaga gagaaaaaag    840
agcagtggga ataggagctt tgttccttgg gttcttggga gcagcaggaa gcactatggg    900
cgcagcgtca atgacgctga cggtacaggc cagacaatta ttgtctggta tagtgcagca    960
gcagaacaat ttgctgaggg ctattgaggc gcaacagcat ctgttgcaac tcacagtctg   1020
gggcatcaag cagctccagg caagaatcct ggctgtggaa agatacctaa aggatcaaca   1080
gctcctgggg atttggggtt gctctggaaa actcatttgc accactgctg tgccttggaa   1140
tgctagttgg agtaataaat ctctggaaca gatttggaat cacacgacct ggatggagtg   1200
ggacagagaa attaacaatt acacaagctt aatacactcc ttaattgaag aatcgcaaaa   1260
ccagcaagaa aagaatgaac aagaattatt ggaattagat aaatgggcaa gtttgtggaa   1320
ttggtttaac ataacaaatt ggctgtggta tataaaatta ttcataatga tagtaggagg   1380
cttggtaggt ttaagaatag ttttttgctgt actttctata gtgaatagag ttaggcaggg   1440
atattcacca ttatcgtttc agacccacct cccaaccccg aggggacccg acaggcccga   1500
aggaatagaa gaagaaggtg gagagagaga cagagacaga tccattcgat tagtgaacgg   1560
atcggcactg cgtgcgccaa ttctgcagac aaatggcagt attcatccac aattttaaaa   1620 gaaaagggg gattgggggg tacagtgcag gggaaagaat agtagacata atagcaacag   1680
acatacaaac taaagaatta caaaaacaaa ttacaaaaat tcaaaatttt cgggtttatt   1740
acagggacag cagagatcca gtttggttaa ttagctagtc tagaaataaa atatctttat   1800
tttcattaca tctgtgtgtt ggttttttgt gtgaatcgat agtactaaca tacgctctcc   1860
atcaaaacaa aacgaaacaa aacaaactag caaaataggc tgtccccagt gcaagtgcag   1920
gtgccagaac atttctctgc tagcgagacg ctcagactca gacgtctcag gtaggcgtgt   1980
acggtgggag gcctatataa gcagagctcg tttagtgaac cgtcgatcg cctggaggat   2040 ccgccaccat ggtgtccaag gcgaggaag ataacatggc catcatcaag gagttcatga   2100
ggtttaaggt ccacatggag ggttcagtca atggccacga gttcgagatt gaaggcgagg   2160
gcgagggccg cccctacgaa gggacacaga cggcgaaatt gaaggtgacc aaaggcgggc   2220
cattgccctt cgcatgggac atcttgtccc ctcagtttat gtatggcagc aaggcctatg   2280
ttaagcaccc cgctgatatc ccggactact gaagctgtc cttccagag gggtttaaat   2340 gggagcgcgt tatgaatttc gaagacggag gagtggttac ggtgacgcag gactcatccc   2400
tgcaggacgg agaatttata tataaggtta agttgagagg cacaaacttc ccaagcgacg   2460
```

```
gccctgtgat gcagaagaaa acaatggggt gggaagcttc cagcgagcgc atgtaccccg   2520
aagatggcgc cctcaagggc gagataaagc aaaggctgaa acttaaggac ggcggtcatt   2580
acgacgcgga ggtcaagaca acttacaagg ctaaaaaacc cgttcagttg cctggggctt   2640
acaatgttaa tatcaaactt gacatcacaa gccacaatga agactatacg atcgtggagc   2700
agtatgaacg agcggaaggc aggcactcaa cgggggggat ggacgagctt tacaagtaac   2760
tagagctcgc tgatcagcct cgactgtgcc ttctagttgc cagccatctg ttgtttgccc   2820
ctcccccgtg ccttccttga ccctggaagg tgccactccc actgtccttt cctaataaaa   2880
tgaggaaatt gcatcgcatt gtctgagtag gtgtcattct attctggggg gtggggtggg   2940
gcaggacagc aaggggagg attgggaaga caatagcagg catgctgggg aagctcgagt    3000
aggtcttgaa aggagtggga attggctccg gtgcccgtca gtgggcagag cgcacatcgc   3060
ccacagtccc cgagaagttg gggggagggg tcggcaattg atccggtgcc tagagaaggt   3120
ggcgcggggt aaactgggaa agtgatgtcg tgtactggct ccgcctttt cccgagggtg    3180 ggggagaacc gtatataagt gcagtagtcg ccgtgaacgt tcttttcgc aacgggtttg    3240 ccgccagaac acaggaccgg tgccaccatg accgagtaca agcccacggt gcgcctcgcc   3300
acccgcgacg acgtccccag ggccgtacgc accctcgccg ccgcgttcgc cgactacccc   3360
gccacgcgcc acaccgtcga tccggaccgc cacatcgagc gggtcaccga gctgcaagaa   3420
ctcttcctca cgcgcgtcgg gctcgacatc ggcaaggtgt gggtcgcgga cgacggcgcc   3480
gccgtggcgg tctggaccac gccggagagc gtcgaagcgg gggcggtgtt cgccgagatc   3540
ggcccgcgca tggccgagtt gagcggttcc cggctggccg cgcagcaaca gatggaaggc   3600
ctcctggcgc cgcaccggcc caaggagccc gcgtggttcc tggccaccgt cggagtctcg   3660
cccgaccacc agggcaaggg tctgggcagc gccgtcgtgc tccccggagt ggaggcggcc   3720
gagcgcgccg gggtgcccgc cttcctggag acctccgcgc cccgcaacct ccccttctac   3780
gagcggctcg gcttcaccgt caccgccgac gtcgaggtgc ccgaaggacc gcgcacctgg   3840
tgcatgaccc gcaagcccgg tgcctgagaa ttcgatatca agcttatcgg taatcaacct   3900
ctggattaca aaatttgtga agattgact ggtattctta actatgttgc tccttttacg    3960
ctatgtggat acgctgcttt aatgccttg tatcatgcta ttgcttcccg tatggctttc    4020
attttctcct ccttgtataa atcctggttg ctgtctcttt atgaggagtt gtggcccgtt   4080
gtcaggcaac gtggcgtggt gtgcactgtg tttgctgacg caaccccac tggttggggc    4140 attgccacca cctgtcagct cctttccggg actttcgctt tccccctccc tattgccacg   4200
gcggaactca tcgccgcctg ccttgcccgc tgctggacag gggctcggct gttgggcact   4260
gacaattccg tggtgttgtc ggggaaatca tcgtcctttc cttggctgct cgcctgtgtt   4320
gccacctgga ttctgcgcgg gacgtccttc tgctacgtcc cttcggccct caatccagcg   4380
gaccttcctt cccgcggcct gctgccggct ctgcggcctc ttccgcgtct tcgccttcgc   4440
cctcagacga gtcggatctc cctttgggcc gcctccccgc atcgataccg tcgacctcga   4500
gacctagaaa acatggagc aatcacaagt agcaatacag cagctaccaa tgctgattgt    4560
gcctggctag aagcacaaga ggaggaggag gtgggttttc cagtcacacc tcaggtacct   4620
ttaagaccaa tgacttacaa ggcagctgta gatcttagcc acttttaaa agaaaagggg    4680 ggactggaag ggctaattca ctcccaacga agacaagata tccttgatct gtggatctac   4740
cacacacaag gctacttccc tgattggcag aactacacac cagggccagg gatcagatat   4800
```

```
ccactgacct ttggatggtg ctacaagcta gtaccagttg agcaagagaa ggtagaagaa      4860
gccaatgaag gagagaacac ccgcttgtta caccctgtga gcctgcatgg gatggatgac      4920
ccggagagag aagtattaga gtggaggttt gacagccgcc tagcatttca tcacatggcc      4980
cgagagctgc atccggactg tactgggtct ctctggttag accagatctg agcctgggag      5040
ctctctggct aactagggaa cccactgctt aagcctcaat aaagcttgcc ttgagtgctt      5100
caagtagtgt gtgcccgtct gttgtgtgac tctggtaact agagatccct cagaccctt       5160 tagtcagtgt ggaaaatctc tagcagggcc cgtttaaacc cgctgatcag cctcgactgt      5220
gccttctagt tgccagccat ctgttgtttg cccctccccc gtgccttcct tgaccctgga      5280
aggtgccact cccactgtcc tttcctaata aaatgaggaa attgcatcgc attgtctgag      5340
taggtgtcat tctattctgg ggggtggggt ggggcaggac agcaaggggg aggattggga     5400
agacaatagc aggcatgctg gggatgcggt gggctctatg gcttctgagg cggaaagaac      5460
cagctggggc tctaggggt atccccacgc gccctgtagc ggcgcattaa gcgcggcggg      5520
tgtggtggtt acgcgcagcg tgaccgctac acttgccagc gccctagcgc ccgctccttt      5580
cgctttcttc ccttcctttc tcgccacgtt cgccggcttt cccgtcaag ctctaaatcg       5640 ggggctccct ttagggttcc gatttagtgc tttacggcac ctcgacccca aaaaacttga     5700
ttagggtgat ggttcacgta gtgggccatc gccctgatag acggttttc gccctttgac      5760 gttgagtcc acgttcttta atagtggact cttgttccaa actggaacaa cactcaaccc      5820
tatctcggtc tattctttg atttataagg gattttgccg atttcggcct attggttaaa      5880
aaatgagctg atttaacaaa aatttaacgc gaattaattc tgtggaatgt gtgtcagtta      5940
gggtgtggaa agtccccagg ctccccagca ggcagaagta tgcaaagcat gcatctcaat      6000
tagtcagcaa ccaggtgtgg aaagtcccca ggctccccag caggcagaag tatgcaaagc      6060
atgcatctca attagtcagc aaccatagtc cgcccctaa ctccgcccat cccgcccta       6120 actccgccca gttccgccca ttctccgccc catggctgac taattttt tatttatgca        6180 gaggccgagg ccgcctctgc ctctgagcta ttccagaagt agtgaggagg cttttttgga      6240
ggcctaggct tttgcaaaaa gctcccggga gcttgtatat ccattttcgg atctgatcag      6300
cacgtgttga caattaatca tcggcatagt atatcggcat agtataatac gacaaggtga     6360
ggaactaaac catggccaag ttgaccagtg ccgttccggt gctcaccgcg gcgacgtcg       6420 ccggagcggt cgagttctgg accaccggc tcgggttctc ccggacttc gtggaggacg       6480 acttcgccgg tgtggtccgg gacgacgtga ccctgttcat cagcgcggtc caggaccagg      6540
tggtgccgga caaccctg gcctgggtgt gggtgcgcgg cctggacgag ctgtacgccg        6600
agtggtcgga ggtcgtgtcc acgaacttcc gggacgcctc cggccgggcc atgaccgaga      6660
tcggcgagca gccgtggggg cgggagttcg ccctgcgcga cccggccggc aactgcgtgc      6720
acttcgtggc cgaggagcag gactgacacg tgctacgaga tttcgattcc accgccgcct      6780
tctatgaaag gttgggcttc ggaatcgttt tccgggacgc cggctggatg atcctccagc      6840
gcggggatct catgctggag ttcttcgccc accccaactt gtttattgca gcttataatg      6900
gttacaaata aagcaatagc atcacaaatt tcacaataa agcattttt tcactgcatt       6960 ctagttgtgg tttgtccaaa ctcatcaatg tatcttatca tgtctgtata ccgtcgacct      7020
ctagctagag cttggcgtaa tcatggtcat agctgtttcc tgtgtgaaat tgttatccgc      7080
tcacaattcc acacaacata cgagccggaa gcataaagtg taaagcctgg ggtgcctaat      7140
gagtgagcta actcacatta attgcgttgc gctcactgcc cgctttccag tcgggaaacc      7200
```

```
tgtcgtgcca gctgcattaa tgaatcggcc aacgcgcggg gagaggcggt ttgcgtattg   7260
ggcgctcttc cgcttcctcg ctcactgact cgctgcgctc ggtcgttcgg ctgcggcgag   7320
cggtatcagc tcactcaaag gcggtaatac ggttatccac agaatcaggg gataacgcag   7380
gaaagaacat gtgagcaaaa ggccagcaaa aggccaggaa ccgtaaaaag gccgcgttgc   7440
tggcgttttt ccataggctc cgcccccctg acgagcatca caaaaatcga cgctcaagtc   7500
agaggtggcg aaacccgaca ggactataaa gataccaggc gtttccccct ggaagctccc   7560
tcgtgcgctc tcctgttccg accctgccgc ttaccggata cctgtccgcc tttctccctt   7620
cgggaagcgt ggcgctttct catagctcac gctgtaggta tctcagttcg gtgtaggtcg   7680
ttcgctccaa gctgggctgt gtgcacgaac cccccgttca gcccgaccgc tgcgccttat   7740
ccggtaacta tcgtcttgag tccaacccgg taagacacga cttatcgcca ctggcagcag   7800
ccactggtaa caggattagc agagcgaggt atgtaggcgg tgctacagag ttcttgaagt   7860
ggtggcctaa ctacggctac actagaagaa cagtatttgg tatctgcgct ctgctgaagc   7920
cagttacctt cggaaaaaga gttggtagct cttgatccgg caaacaaacc accgctggta   7980
gcggtggttt ttttgtttgc aagcagcaga ttacgcgcag aaaaaaagga tctcaagaag   8040
atcctttgat cttttctacg gggtctgacg ctcagtggaa cgaaaactca cgttaaggga   8100
ttttggtcat gagattatca aaaaggatct tcacctagat ccttttaaat taaaaatgaa   8160
gttttaaatc aatctaaagt atatatgagt aaacttggtc tgacagttac caatgcttaa   8220
tcagtgaggc acctatctca gcgatctgtc tatttcgttc atccatagtt gcctgactcc   8280
ccgtcgtgta gataactacg atacgggagg gcttaccatc tggccccagt gctgcaatga   8340
taccgcgaga cccacgctca ccggctccag atttatcagc aataaaccag ccagccggaa   8400
gggccgagcg cagaagtggt cctgcaactt tatccgcctc catccagtct attaattgtt   8460
gccgggaagc tagagtaagt agttcgccag ttaatagttt gcgcaacgtt gttgccattg   8520
ctacaggcat cgtggtgtca cgctcgtcgt ttggtatggc ttcattcagc tccggttccc   8580
aacgatcaag gcgagttaca tgatccccca tgttgtgcaa aaaagcggtt agctccttcg   8640
gtcctccgat cgttgtcaga agtaagttgg ccgcagtgtt atcactcatg gttatggcag   8700
cactgcataa ttctcttact gtcatgccat ccgtaagatg cttttctgtg actggtgagt   8760
actcaaccaa gtcattctga gaatagtgta tgcggcgacc gagttgctct tgcccggcgt   8820
caatacggga taataccgcg ccacatagca gaactttaaa agtgctcatc attggaaaac   8880
gttcttcggg gcgaaaactc tcaaggatct taccgctgtt gagatccagt tcgatgtaac   8940
ccactcgtgc acccaactga tcttcagcat cttttacttt caccagcgtt tctgggtgag   9000
caaaaacagg aaggcaaaat gccgcaaaaa agggaataag ggcgacacgg aaatgttgaa   9060
tactcatact cttcctttt caatattatt gaagcattta tcagggttat tgtctcatga   9120
gcggatacat atttgaatgt atttagaaaa ataaacaaat aggggttccg cgcacatttc   9180
cccgaaaagt gccacctgac gtcgacggat cgggagatct cccgatcccc tatggtgcac   9240
tctcagtaca atctgctctg atgccgcata gttaagccag tatctgctcc ctgcttgtgt   9300
gttggaggtc gctgagtagt gcgcgagcaa aatttaagct acaacaaggc aaggcttgac   9360
cgacaattgc atgaagaatc tgcttagggt taggcgtttt gcgctgcttc gcgatgtacg   9420
ggccagatat acgcgttgac attgattatt gactagttat taatagtaat caattacggg   9480
gtcattagtt catagcccat atatggagtt ccgcgttaca taacttacgg taaatggccc   9540
```

```
gcctggctga ccgcccaacg accccgccc attgacgtca ataatgacgt atgttcccat    9600
agtaacgcca atagggactt tccattgacg tcaatgggtg gagtatttac ggtaaactgc    9660
ccacttggca gtacatcaag tgtatcatat gccaagtacg cccctattg acgtcaatga    9720 cggtaaatgg cccgcctggc attatgccca gtacatgacc ttatgggact ttcctacttg    9780
gcagtacatc tacgtattag tcatcgctat taccatggtg atgcggtttt ggcagtacat    9840
caatgggcgt ggatagcggt ttgactcacg gggatttcca gtctccacc ccattgacgt    9900 caatgggagt ttgttttggc accaaaatca acgggacttt ccaaaatgtc gtaacaactc    9960
cgccccattg acgcaaatgg gcggtaggcg tgtacggtgg gaggtctata taagcagcgc   10020
gttttgc                                                             10027

<210> SEQ ID NO 67
<211> LENGTH: 10505
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360 accccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg cccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca gtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc    1080
ggcttgctga gcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
```

-continued

| | | | | | |
|---|---|---|---|---|---|
| aaagtaagac | caccgcacag | caagcggccg | ctgatcttca | gacctggagg | aggagatatg | 1560 |
| agggacaatt | ggagaagtga | attatataaa | tataaagtag | taaaaattga | accattagga | 1620 |
| gtagcaccca | ccaaggcaaa | gagaagagtg | gtgcagagag | aaaaaagagc | agtgggaata | 1680 |
| ggagctttgt | tccttgggtt | cttgggagca | gcaggaagca | ctatgggcgc | agcgtcaatg | 1740 |
| acgctgacgg | tacaggccag | acaattattg | tctggtatag | tgcagcagca | gaacaatttg | 1800 |
| ctgagggcta | ttgaggcgca | acagcatctg | ttgcaactca | cagtctgggg | catcaagcag | 1860 |
| ctccaggcaa | gaatcctggc | tgtggaaaga | tacctaaagg | atcaacagct | cctgggggatt | 1920 |
| tggggttgct | ctggaaaact | catttgcacc | actgctgtgc | cttggaatgc | tagttggagt | 1980 |
| aataaatctc | tggaacagat | ttggaatcac | acgacctgga | tggagtggga | cagagaaatt | 2040 |
| aacaattaca | caagcttaat | acactcctta | attgaagaat | cgcaaaacca | gcaagaaaag | 2100 |
| aatgaacaag | aattattgga | attagataaa | tgggcaagtt | tgtggaattg | gtttaacata | 2160 |
| acaaattggc | tgtggtatat | aaaattattc | ataatgatag | taggaggctt | ggtaggttta | 2220 |
| agaatagttt | ttgctgtact | ttctatagtg | aatagagtta | ggcagggata | ttcaccatta | 2280 |
| tcgtttcaga | cccacctccc | aaccccgagg | ggacccgaca | ggcccgaagg | aatagaagaa | 2340 |
| gaaggtggag | agagagacag | agacagatcc | attcgattag | tgaacggatc | ggcactgcgt | 2400 |
| gcgccaattc | tgcagacaaa | tggcagtatt | catccacaat | tttaaaagaa | aaggggggat | 2460 |
| tggggggtac | agtgcagggg | aaagaatagt | agacataata | gcaacagaca | tacaaactaa | 2520 |
| agaattacaa | aaacaaatta | caaaaattca | aaattttcgg | gtttattaca | gggacagcag | 2580 |
| agatccagtt | tggttaatta | gctagctagg | tcttgaaagg | agtgggaatt | ggctccggtg | 2640 |
| cccgtcagtg | ggcagagcgc | acatcgccca | cagtccccga | gaagttgggg | ggaggggtcg | 2700 |
| gcaattgatc | cggtgcctag | agaaggtggc | gcggggtaaa | ctgggaaagt | gatgtcgtgt | 2760 |
| actggctccg | cctttttccc | gagggtgggg | agaaccgta | tataagtgca | gtagtcgccg | 2820 |
| tgaacgttct | ttttcgcaac | gggtttgccg | ccagaacaca | ggaccggttc | tagagcgctg | 2880 |
| ccaccatgtc | caaaagctca | aacgtcacct | ccaatcacaa | gggtggcttc | gcaggatcgt | 2940 |
| ttgtacaggc | agtggagagg | gcagaggaag | tctgctcacc | tgcggcgacg | tcgaggagaa | 3000 |
| tcctggccca | gtgagcaagg | gcgaggagct | gttcaccggg | gtggtgccca | tcctggtcga | 3060 |
| gctgacggc | gacgtaaacg | gccacaagtt | cagcgtgtcc | ggcgagggcg | agggcgatgc | 3120 |
| cacctacggc | aagctgaccc | tgaagttcat | ctgcaccacc | ggcaagctgc | ccgtgccctg | 3180 |
| gcccaccctc | gtgaccaccc | tgacctacgg | cgtgcagtgc | ttcagccgct | accccgacca | 3240 |
| catgaagcag | cacgacttct | tcaagtccgc | catgcccgaa | ggctacgtcc | aggagcgcac | 3300 |
| catcttcttc | aaggacgacg | gcaactacaa | gacccgcgcc | gaggtgaagt | tcgagggcga | 3360 |
| caccctggtg | aaccgcatcg | agctgaaggg | catcgacttc | aaggaggacg | gcaacatcct | 3420 |
| ggggcacaag | ctggagtaca | actacaacag | ccacaacgtc | tatatcatgg | ccgacaagca | 3480 |
| gaagaacggc | atcaaggtga | acttcaagat | ccgccacaac | atcgaggacg | gcagcgtgca | 3540 |
| gctcgccgac | cactaccagc | agaacacccc | catcggcgac | ggccccgtgc | tgctgcccga | 3600 |
| caaccactac | ctgagcaccc | agtccgccct | gagcaaagac | cccaacgaga | agcgcgatca | 3660 |
| catggtcctg | ctggagttcg | tgaccgccgc | cgggatcact | ctcggcatgg | acgagctcta | 3720 |
| caagtaataa | taaccggatc | cggcgcaaca | aacttctctc | tgctcaaaca | agccggcgac | 3780 |
| gtcgaagaga | atcctgggcc | ggtgtccaag | ggcgaggaag | ataacatggc | catcatcaag | 3840 |

```
gagttcatga ggtttaaggt ccacatggag ggttcagtca atggccacga gttcgagatt    3900
gaaggcgagg gcgagggccg cccctacgaa gggacacaga cggcgaaatt gaaggtgacc    3960
aaaggcgggc cattgccctt cgcatgggac atcttgtccc ctcagtttat gtatggcagc    4020
aaggcctatg ttaagcaccc cgctgatatc ccggactact tgaagctgtc ctttccagag    4080
gggtttaaat gggagcgcgt tatgaatttc gaagacggag gagtggttac ggtgacgcag    4140
gactcatccc tgcaggacgg agaatttata tataaggtta agttgagagg cacaaacttc    4200
ccaagcgacg gccctgtgat gcagaagaaa acaatggggt gggaagcttc cagcgagcgc    4260
atgtaccccg aagatggcgc cctcaagggc gagataaagc aaaggctgaa acttaaggac    4320
ggcggtcatt acgacgcgga ggtcaagaca acttacaagg ctaaaaaacc cgttcagttg    4380
cctgggcttt acaatgttaa tatcaaactt gacatcacaa gccacaatga agactatacg    4440
atcgtggagc agtatgaacg agcggaaggc aggcactcaa cgggggggat ggacgagctt    4500
tacaagggca gtggggaggg cagaggaagt ctgctaacat gcggtgacgt cgaggagaat    4560 cctgcccaa tgaccgagta caagcccacg gtgcgcctcg ccacccgcga cgacgtcccc    4620
agggccgtac gcaccctcgc cgccgcgttc gccgactacc ccgccacgcg ccacaccgtc    4680
gatccggacc gccacatcga gcgggtcacc gagctgcaag aactcttcct cacgcgcgtc    4740
gggctcgaca tcggcaaggt gtgggtcgcg gacgacggcg ccgccgtggc ggtctggacc    4800
acgccggaga gcgtcgaagc gggggcggtg ttcgccgaga tcggcccgcg catggccgag    4860
ttgagcggtt cccggctggc cgcgcagcaa cagatggaag gcctcctggc gccgcaccgg    4920
cccaaggagc ccgcgtggtt cctggccacc gtcgagtct cgcccgacca ccagggcaag    4980
ggtctgggca gcgccgtcgt gctccccgga gtggaggcgg ccgagcgcgc cggggtgccc    5040
gccttcctgg agacctccgc gccccgcaac ctccccttct acgagcggct cggcttcacc    5100
gtcaccgccg acgtcgaggt gcccgaagga ccgcgcacct ggtgcatgac ccgcaagccc    5160
ggtgcctgat aagaattcga tatcaagctt atcggtaatc aacctctgga ttacaaaatt    5220
tgtgaaagat tgactggtat tcttaactat gttgctcctt ttacgctatg tggatacgct    5280
gctttaatgc ctttgtatca tgctattgct tcccgtatgg ctttcatttt ctcctccttg    5340
tataaatcct ggttgctgtc tctttatgag gagttgtggc ccgttgtcag caacgtggc    5400 gtggtgtgca ctgtgtttgc tgacgcaacc cccactggtt ggggcattgc caccacctgt    5460
cagctccttt ccgggacttt cgctttcccc ctccctattg ccacggcgga actcatcgcc    5520
gcctgccttg cccgctgctg gacaggggct cggctgttgg cactgacaa ttccgtggtg    5580 ttgtcgggga atcatcgtc cttccttgg ctgctcgcct gtgttgccac ctggattctg    5640
cgcgggacgt ccttctgcta cgtcccttcg ccctcaatc cagcgacct tccttcccgc    5700 ggcctgctgc cggctctgcg gcctcttccg cgtcttcgcc ttcgccctca gacgagtcgg    5760
atctcccttt gggccgcctc cccgcatcga taccgtcgac ctcgagacct agaaaaacat    5820
ggagcaatca caagtagcaa tacagcagct accaatgctg attgtgcctg ctagaagca    5880 caagaggagg aggaggtggg ttttccagtc acacctcagg taccttttaag accaatgact    5940 tacaaggcag ctgtagatct tagccacttt ttaaaagaaa agggggggact ggaagggcta    6000 attcactccc aacgaagaca agatatcctt gatctgtgga tctaccacac acaaggctac    6060
ttccctgatt ggcagaacta cacaccaggg ccagggatca gatatccact gacctttgga    6120
tggtgctaca agctagtacc agttgagcaa gagaaggtag aagaagccaa tgaaggagag    6180
aacacccgct tgttacaccc tgtgagcctg catgggatgg atgacccgga gagagaagta    6240
```

```
ttagagtgga ggtttgacag ccgcctagca tttcatcaca tggcccgaga gctgcatccg    6300
gactgtactg ggtctctctg gttagaccag atctgagcct gggagctctc tggctaacta    6360
gggaacccac tgcttaagcc tcaataaagc ttgccttgag tgcttcaagt agtgtgtgcc    6420
cgtctgttgt gtgactctgg taactagaga tccctcagac ccttttagtc agtgtggaaa    6480
atctctagca gggcccgttt aaacccgctg atcagcctcg actgtgcctt ctagttgcca    6540
gccatctgtt gtttgcccct cccccgtgcc ttccttgacc ctggaaggtg ccactcccac    6600
tgtcctttcc taataaaatg aggaaattgc atcgcattgt ctgagtaggt gtcattctat    6660
tctggggggt ggggtggggc aggacagcaa gggggaggat tgggaagaca atagcaggca    6720
tgctggggat gcggtgggct ctatggcttc tgaggcggaa agaaccagct ggggctctag    6780
ggggtatccc cacgcgccct gtagcggcgc attaagcgcg gcgggtgtgg tggttacgcg    6840
cagcgtgacc gctacacttg ccagcgccct agcgcccgct cctttcgctt tcttcccttc    6900
ctttctcgcc acgttcgccg gctttccccg tcaagctcta aatcgggggc tccctttagg    6960
gttccgattt agtgctttac ggcacctcga ccccaaaaaa cttgattagg gtgatggttc    7020
acgtagtggg ccatcgccct gatagacggt ttttcgccct ttgacgttgg agtccacgtt    7080
ctttaatagt ggactcttgt tccaaactgg aacaacactc aaccctatct cggtctattc    7140
ttttgattta agggatttt  tgccgatttc ggcctattgg ttaaaaaatg agctgattta    7200
acaaaaattt aacgcgaatt aattctgtgg aatgtgtgtc agttagggtg tggaaagtcc    7260
ccaggctccc cagcaggcag aagtatgcaa agcatgcatc tcaattagtc agcaaccagg    7320
tgtggaaagt ccccaggctc cccagcaggc agaagtatgc aaagcatgca tctcaattag    7380
tcagcaacca tagtcccgcc cctaactccg cccatcccgc cctaactccg cccagttcc     7440 gcccattctc cgccccatgg ctgactaatt ttttttattt atgcagaggc cgaggccgcc    7500
tctgcctctg agctattcca gaagtagtga ggaggctttt ttggaggcct aggcttttgc    7560
aaaaagctcc cgggagcttg tatatccatt ttcggatctg atcagcacgt gttgacaatt    7620
aatcatcggc atagtatatc ggcatagtat aatacgacaa ggtgaggaac taaaccatgg    7680
ccaagttgac cagtgccgtt ccggtgctca ccgcgcgcga cgtcgccgga gcggtcgagt    7740
tctggaccga ccggctcggg ttctcccggg acttcgtgga ggacgacttc gccggtgtgg    7800
tccgggacga cgtgaccctg ttcatcagcg cggtccagga ccaggtggtg ccggacaaca    7860
ccctggcctg ggtgtgggtg cgcggcctgg acgagctgta cgccgagtgg tcggaggtcg    7920
tgtccacgaa cttccgggac gcctccgggc cggccatgac cgagatcggc gagcagccgt    7980
gggggcggga gttcgccctg cgcgacccgg ccggcaactg cgtgcacttc gtggccgagg    8040
agcaggactg acacgtgcta cgagatttcg attccaccgc cgccttctat gaaaggttgg    8100
gcttcggaat cgttttccgg gacgccggct ggatgatcct ccagcgcggg gatctcatgc    8160
tggagttctt cgcccacccc aacttgttta ttgcagctta taatggttac aaataaagca    8220
atagcatcac aaatttcaca aataaagcat ttttttcact gcattctagt tgtggtttgt    8280
ccaaactcat caatgtatct tatcatgtct gtataccgtc gacctctagc tagagcttgg    8340
cgtaatcatg gtcatagctg tttcctgtgt gaaattgtta tccgctcaca attccacaca    8400
acatacgagc cggaagcata aagtgtaaag cctggggtgc ctaatgagtg agctaactca    8460
cattaattgc gttgcgctca ctgcccgctt tccagtcggg aaacctgtcg tgccagctgc    8520
attaatgaat cggccaacgc gcggggagag gcggtttgcg tattgggcgc tcttccgctt    8580
```

```
cctcgctcac tgactcgctg cgctcggtcg ttcggctgcg gcgagcggta tcagctcact    8640
caaaggcggt aatacggtta tccacagaat caggggataa cgcaggaaag aacatgtgag    8700
caaaaggcca gcaaaaggcc aggaaccgta aaaaggccgc gttgctggcg ttttttccata   8760 ggctccgccc ccctgacgag catcacaaaa atcgacgctc aagtcagagg tggcgaaacc    8820
cgacaggact ataaagatac caggcgtttc ccctggaag ctccctcgtg cgctctcctg    8880
ttccgaccct gccgcttacc ggatacctgt ccgcctttct cccttcggga agcgtggcgc    8940
tttctcatag ctcacgctgt aggtatctca gttcggtgta ggtcgttcgc tccaagctgg    9000
gctgtgtgca cgaaccccc gttcagcccg accgctgcgc cttatccggt aactatcgtc     9060
ttgagtccaa cccggtaaga cacgacttat cgccactggc agcagccact ggtaacagga    9120
ttagcagagc gaggtatgta ggcggtgcta cagagttctt gaagtggtgg cctaactacg    9180
gctacactag aagaacagta tttggtatct gcgctctgct gaagccagtt accttcggaa    9240
aaagagttgg tagctcttga tccggcaaac aaaccaccgc tggtagcggt ggtttttttg    9300
tttgcaagca gcagattacg cgcagaaaaa aaggatctca agaagatcct ttgatctttt    9360
ctacggggtc tgacgctcag tggaacgaaa actcacgtta agggattttg gtcatgagat    9420
tatcaaaaag gatcttcacc tagatccttt taaattaaaa atgaagtttt aaatcaatct    9480
aaagtatata tgagtaaact tggtctgaca gttaccaatg cttaatcagt gaggcaccta    9540
tctcagcgat ctgtctattt cgttcatcca tagttgcctg actccccgtc gtgtagataa    9600
ctacgatacg ggagggctta ccatctggcc ccagtgctgc aatgataccg cgagacccac    9660
gctcaccggc tccagattta tcagcaataa accagccagc cggaagggcc gagcgcagaa    9720
gtggtcctgc aactttatcc gcctccatcc agtctattaa ttgttgccgg gaagctagag    9780
taagtagttc gccagttaat agtttgcgca acgttgttgc cattgctaca ggcatcgtgg    9840
tgtcacgctc gtcgtttggt atggcttcat tcagctccgg ttcccaacga tcaaggcgag    9900
ttacatgatc ccccatgttg tgcaaaaaag cggttagctc cttcggtcct ccgatcgttg    9960
tcagaagtaa gttggccgca gtgttatcac tcatggttat ggcagcactg cataattctc   10020
ttactgtcat gccatccgta agatgctttt ctgtgactgg tgagtactca accaagtcat   10080
tctgagaata gtgtatgcgg cgaccgagtt gctcttgccc ggcgtcaata cgggataata   10140
ccgcgccaca tagcagaact ttaaaagtgc tcatcattgg aaaacgttct cggggcgaa    10200 aactctcaag gatcttaccg ctgttgagat ccagttcgat gtaacccact cgtgcaccca   10260
actgatcttc agcatctttt actttcacca gcgtttctgg gtgagcaaaa acaggaaggc   10320
aaaatgccgc aaaaaaggga ataagggcga cacggaaatg ttgaatactc atactcttcc   10380 ttttcaata ttattgaagc atttatcagg gttattgtct catgagcgga tacatatttg     10440
aatgtattta gaaaaataaa caaatagggg ttccgcgcac atttccccga aaagtgccac   10500
ctgac                                                                10505
```

<210> SEQ ID NO 68
<211> LENGTH: 10504
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 68

```
gtcgacggat cgggagatct cccgatcccc tatggtgcac tctcagtaca atctgctctg    60
```

```
atgccgcata gttaagccag tatctgctcc ctgcttgtgt gttggaggtc gctgagtagt    120
gcgcgagcaa aatttaagct acaacaaggc aaggcttgac cgacaattgc atgaagaatc    180
tgcttagggt taggcgtttt gcgctgcttc gcgatgtacg ggccagatat acgcgttgac    240
attgattatt gactagttat taatagtaat caattacggg gtcattagtt catagcccat    300
atatggagtt ccgcgttaca taacttacgg taaatggccc gcctggctga ccgcccaacg    360
acccccgccc attgacgtca ataatgacgt atgttcccat agtaacgcca atagggactt    420
tccattgacg tcaatgggtg gagtatttac ggtaaactgc ccacttggca gtacatcaag    480
tgtatcatat gccaagtacg cccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagaccctt tagtcagtgt ggaaaatctc tagcagtggc   1020
gcccgaacag ggacttgaaa gcgaaaggga accagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctgggatt   1920 tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
```

```
gcgccaattc tgcagacaaa tggcagtatt catccacaat tttaaaagaa aaggggggat    2460 tgggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta gctagctagg tcttgaaagg agtgggaatt ggctccggtg    2640
cccgtcagtg ggcagagcgc acatcgccca cagtccccga gaagttgggg ggaggggtcg    2700
gcaattgatc cggtgcctag agaaggtggc gcggggtaaa ctgggaaagt gatgtcgtgt    2760
actggctccg cctttttccc gagggtgggg gagaaccgta tataagtgca gtagtcgccg    2820
tgaacgttct ttttcgcaac gggttttgccg ccagaacaca ggaccggttc tagagcgctg    2880
ccaccatgcc aaaagctcaa acgtcacctc caatcacaag ggtggcttcg caggatcgtt    2940
tgtacaggca gtggagaggg cagaggaagt ctgctcacct gcggcgacgt cgaggagaat    3000
cctggcccag tgagcaaggg cgaggagctg ttcaccgggg tggtgcccat cctggtcgag    3060
ctggacggcg acgtaaacgg ccacaagttc agcgtgtccg gcgagggcga gggcgatgcc    3120
acctacggca agctgaccct gaagttcatc tgcaccaccg gcaagctgcc cgtgccctgg    3180
cccaccctcg tgaccaccct gacctacggc gtgcagtgct tcagccgcta ccccgaccac    3240
atgaagcagc acgacttctt caagtccgcc atgcccgaag gctacgtcca ggagcgcacc    3300
atcttcttca aggacgacgg caactacaag acccgcgccg aggtgaagtt cgagggcgac    3360
accctggtga accgcatcga gctgaagggc atcgacttca aggaggacgg caacatcctg    3420
gggcacaagc tggagtacaa ctacaacagc cacaacgtct atatcatggc cgacaagcag    3480
aagaacggca tcaaggtgaa cttcaagatc cgccacaaca tcgaggacgg cagcgtgcag    3540
ctcgccgacc actaccagca gaacaccccc atcggcgacg gccccgtgct gctgcccgac    3600
aaccactacc tgagcaccca gtccgccctg agcaaagacc ccaacgagaa gcgcgatcac    3660
atggtcctgc tggagttcgt gaccgccgcc gggatcactc tcggcatgga cgagctctac    3720
aagtaataat aaccggatcc ggcgcaacaa acttctctct gctcaaacaa gccgcgacg    3780 tcgaagagaa tcctgggccg gtgtccaagg gcgaggaaga taacatggcc atcatcaagg    3840
agttcatgag gtttaaggtc cacatggagg gttcagtcaa tggccacgag ttcgagattg    3900
aaggcgaggg cgagggccgc ccctacgaag ggacacagac ggcgaaattg aaggtgacca    3960
aaggcggggc attgcccttc gcatgggaca tcttgtcccc tcagtttatg tatggcagca    4020
aggcctatgt taagcacccc gctgatatcc cggactactt gaagctgtcc tttccagagg    4080
ggtttaaatg ggagcgcgtt atgaatttcg aagacggagg agtggttacg gtgacgcagg    4140
actcatccct gcaggacgga gaatttatat ataaggttaa gttgagaggc acaaacttcc    4200
caagcgacgg ccctgtgatg cagaagaaaa caatgggggtg ggaagcttcc agcgagcgca    4260
tgtaccccga agatggcgcc ctcaagggcg agataaagca aaggctgaaa cttaaggacg    4320
gcggtcatta cgacgcggag gtcaagacaa cttacaaggc taaaaaaccc gttcagttgc    4380
ctggggctta caatgttaat atcaaacttg acatcacaag ccacaatgaa gactatacga    4440
tcgtggagca gtatgaacga gcggaaggca ggcactcaac gggggggatg gacgagcttt    4500
acaagggcag tggggagggc agaggaagtc tgctaacatg cggtgacgtc gaggagaatc    4560
ctggcccaat gaccgagtac aagcccacgg tgcgcctcgc cacccgcgac gacgtcccca    4620
gggccgtacg caccctcgcc gccgcgttcg ccgactaccc cgccacgcgc cacaccgtcg    4680
atccggaccc ccacatcgag cgggtcaccg agctgcaaga actcttcctc acgcgcgtcg    4740
ggctcgacat cggcaaggtg tgggtcgcgg acgacggcgc cgccgtggcg gtctggacca    4800
```

```
cgccggagag cgtcgaagcg ggggcggtgt tcgccgagat cggcccgcgc atggccgagt    4860
tgagcggttc ccggctggcc gcgcagcaac agatggaagg cctcctggcg ccgcaccggc    4920
ccaaggagcc cgcgtggttc ctggccaccg tcggagtctc gcccgaccac cagggcaagg    4980
gtctgggcag cgccgtcgtg ctccccggag tggaggcggc cgagcgcgcc ggggtgcccg    5040
ccttcctgga gacctccgcg ccccgcaacc tccccttcta cgagcggctc ggcttcaccg    5100
tcaccgccga cgtcgaggtg cccgaaggac cgcgcacctg gtgcatgacc cgcaagcccg    5160
gtgcctgata agaattcgat atcaagctta tcggtaatca acctctggat tacaaaattt    5220
gtgaaagatt gactggtatt cttaactatg ttgctccttt tacgctatgt ggatacgctg    5280
ctttaatgcc tttgtatcat gctattgctt cccgtatggc tttcattttc tcctccttgt    5340
ataaatcctg gttgctgtct ctttatgagg agttgtggcc cgttgtcagg caacgtggcg    5400
tggtgtgcac tgtgtttgct gacgcaaccc ccactggttg gggcattgcc accacctgtc    5460
agctcctttc cgggactttc gctttccccc tccctattgc cacggcggaa ctcatcgccg    5520
cctgccttgc ccgctgctgg acaggggctc ggctgttggg cactgacaat tccgtggtgt    5580
tgtcggggaa atcatcgtcc tttccttggc tgctcgcctg tgttgccacc tggattctgc    5640
gcgggacgtc cttctgctac gtcccttcgg ccctcaatcc agcggacctt ccttcccgcg    5700
gcctgctgcc ggctctgcgg cctcttccgc gtcttcgcct tcgccctcag acgagtcgga    5760
tctcccttg ggccgcctcc ccgcatcgat accgtcgacc tcgagaccta gaaaaacatg    5820
gagcaatcac aagtagcaat acagcagcta ccaatgctga ttgtgcctgg ctagaagcac    5880
aagaggagga ggaggtgggt tttccagtca cacctcaggt acctttaaga ccaatgactt    5940
acaaggcagc tgtagatctt agccactttt taaaagaaaa gggggactg aagggctaa     6000
ttcactccca acgaagacaa gatatccttg atctgtggat ctaccacaca caaggctact    6060
tccctgattg gcagaactac acaccagggc cagggatcag atatccactg acctttggat    6120
ggtgctacaa gctagtacca gttgagcaag agaaggtaga agaagccaat gaaggagaga    6180
acacccgctt gttacaccct gtgagcctgc atgggatgga tgacccggag agagaagtat    6240
tagagtggag gtttgacagc cgcctagcat ttcatcacat ggcccgagag ctgcatccgg    6300
actgtactgg gtctctctgg ttagaccaga tctgagcctg ggagctctct ggctaactag    6360
ggaacccact gcttaagcct caataaagct tgccttgagt gcttcaagta gtgtgtgccc    6420
gtctgttgtg tgactctggt aactagagat ccctcagacc cttttagtca gtgtggaaaa    6480
tctctagcag ggcccgttta aacccgctga tcagcctcga ctgtgccttc tagttgccag    6540
ccatctgttg tttgccctc ccccgtgcct tccttgaccc tggaaggtgc cactcccact    6600
gtcctttcct aataaaatga ggaaattgca tcgcattgtc tgagtaggtg tcattctatt    6660
ctggggggtg gggtggggca ggacagcaag ggggaggatt gggaagacaa tagcaggcat    6720
gctggggatg cggtgggctc tatgcttcct gaggcggaaa gaaccagctg gggctctagg    6780
gggtatcccc acgcgccctg tagcggcgca ttaagcgcgg cgggtgtggt ggttacgcgc    6840
agcgtgaccg ctacacttgc cagcgcccta gcgcccgctc ctttcgcttt cttcccttcc    6900
tttctcgcca cgttcgccgg ctttccccgt caagctctaa atcgggggct ccctttaggg    6960
ttccgattta gtgctttacg gcacctcgac cccaaaaaac ttgattaggg tgatggttca    7020
cgtagtgggc catcgccctg atagacggtt tttcgccctt tgacgttgga gtccacgttc    7080
tttaatagtg gactcttgtt ccaaactgga acaacactca accctatctc ggtctattct    7140
```

```
tttgatttat aagggatttt gccgatttcg gcctattggt taaaaaatga gctgatttaa    7200
caaaaattta acgcgaatta attctgtgga atgtgtgtca gttagggtgt ggaaagtccc    7260
caggctcccc agcaggcaga agtatgcaaa gcatgcatct caattagtca gcaaccaggt    7320
gtggaaagtc cccaggctcc ccagcaggca gaagtatgca aagcatgcat ctcaattagt    7380
cagcaaccat agtcccgccc ctaactccgc ccatcccgcc cctaactccg cccagttccg    7440
cccattctcc gccccatggc tgactaattt tttttattta tgcagaggcc gaggccgcct    7500
ctgcctctga gctattccag aagtagtgag gaggcttttt tggaggccta ggcttttgca    7560
aaaagctccc gggagcttgt atatccattt tcggatctga tcagcacgtg ttgacaatta    7620
atcatcggca tagtatatcg gcatagtata atacgacaag gtgaggaact aaaccatggc    7680
caagttgacc agtgccgttc cggtgctcac cgcgcgcgac gtcgccggag cggtcgagtt    7740
ctggaccgac cggctcgggt tctcccggga cttcgtggag gacgacttcg ccggtgtggt    7800
ccggacgac gtgaccctgt tcatcagcgc ggtccaggac caggtggtgc cggacaacac    7860
cctgcctgg gtgtgggtgc gcggcctgga cgagctgtac gccgagtggt cggaggtcgt    7920
gtccacgaac ttccgggacg cctccgggcc ggccatgacc gagatcggcg agcagccgtg    7980
ggggcgggag ttcgccctgc gcgacccggc cggcaactgc gtgcacttcg tggccgagga    8040
gcaggactga cacgtgctac gagatttcga ttccaccgcc gccttctatg aaaggttggg    8100
cttcggaatc gttttccggg acgccggctg atgatcctc cagcgcgggg atctcatgct    8160
ggagttcttc gcccacccca acttgtttat tgcagcttat aatggttaca aataaagcaa    8220
tagcatcaca aatttcacaa ataaagcatt ttttttcactg cattctagtt gtggtttgtc    8280
caaactcatc aatgtatctt atcatgtctg tataccgtcg acctctagct agagcttggc    8340
gtaatcatgg tcatagctgt ttcctgtgtg aaattgttat ccgctcacaa ttccacacaa    8400
catacgagcc ggaagcataa agtgtaaagc ctggggtgcc taatgagtga gctaactcac    8460
attaattgcg ttgcgctcac tgcccgcttt ccagtcggga aacctgtcgt gccagctgca    8520
ttaatgaatc ggccaacgcg cggggagagg cggtttgcgt attgggcgct cttccgcttc    8580
ctcgctcact gactcgctgc gctcggtcgt tcggctgcgg cgagcggtat cagctcactc    8640
aaaggcggta atacggttat ccacagaatc aggggataac gcaggaaaga acatgtgagc    8700
aaaaggccag caaaaggcca ggaaccgtaa aaaggccgcg ttgctggcgt ttttccatag    8760
gctccgcccc cctgacgagc atcacaaaaa tcgacgctca agtcagaggt ggcgaaaccc    8820
gacaggacta taaagatacc aggcgtttcc ccctggaagc tccctcgtgc gctctcctgt    8880
tccgaccctg ccgcttaccg gatacctgtc cgcctttctc ccttcgggaa gcgtggcgct    8940
ttctcatagc tcacgctgta ggtatctcag ttcggtgtag tcgttcgct ccaagctggg    9000
ctgtgtgcac gaaccccccg ttcagcccga ccgctgcgcc ttatccggta actatcgtct    9060
tgagtccaac ccggtaagac acgacttatc gccactggca gcagccactg gtaacaggat    9120
tagcagagcg aggtatgtag gcggtgctac agagttcttg aagtggtggc ctaactacgg    9180
ctacactaga agaacagtat ttggtatctg cgctctgctg aagccagtta ccttcggaaa    9240
aagagttggt agctcttgat ccggcaaaca aaccaccgct ggtagcggtg gtttttttgt    9300
ttgcaagcag cagattacgc gcagaaaaaa aggatctcaa gaagatcctt tgatcttttc    9360
tacggggtct gacgctcagt ggaacgaaaa ctcacgttaa gggattttgg tcatgagatt    9420
atcaaaaagg atcttcacct agatcctttt aaattaaaaa tgaagtttta aatcaatcta    9480
aagtatatat gagtaaactt ggtctgacag ttaccaatgc ttaatcagtg aggcacctat    9540
```

```
ctcagcgatc tgtctatttc gttcatccat agttgcctga ctccccgtcg tgtagataac    9600
tacgatacgg gagggcttac catctggccc cagtgctgca atgataccgc gagacccacg    9660
ctcaccggct ccagatttat cagcaataaa ccagccagcc ggaagggccg agcgcagaag    9720
tggtcctgca actttatccg cctccatcca gtctattaat tgttgccggg aagctagagt    9780
aagtagttcg ccagttaata gtttgcgcaa cgttgttgcc attgctacag gcatcgtggt    9840
gtcacgctcg tcgtttggta tggcttcatt cagctccggt tcccaacgat caaggcgagt    9900
tacatgatcc cccatgttgt gcaaaaaagc ggttagctcc ttcggtcctc cgatcgttgt    9960
cagaagtaag ttggccgcag tgttatcact catggttatg gcagcactgc ataattctct   10020
tactgtcatg ccatccgtaa gatgcttttc tgtgactggt gagtactcaa ccaagtcatt   10080
ctgagaatag tgtatgcggc gaccgagttg ctcttgcccg gcgtcaatac gggataatac   10140
cgcgccacat agcagaactt taaaagtgct catcattgga aaacgttctt cggggcgaaa   10200
actctcaagg atcttaccgc tgttgagatc cagttcgatg taacccactc gtgcacccaa   10260
ctgatcttca gcatctttta ctttcaccag cgtttctggg tgagcaaaaa caggaaggca   10320
aaatgccgca aaaagggaa taaggcgac acggaaatgt tgaatactca tactcttcct   10380
ttttcaatat tattgaagca tttatcaggg ttattgtctc atgagcggat acatatttga   10440
atgtatttag aaaaataaac aaataggggt tccgcgcaca tttccccgaa aagtgccacc   10500
tgac                                                                10504

<210> SEQ ID NO 69
<211> LENGTH: 10522
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 69
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360 accccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt tgttttggc     720 accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
```

```
tctggtaact agagatccct cagacccttt tagtcagtgt ggaaaatctc tagcagtggc      1020
gcccgaacag ggacttgaaa gcgaaaggga aaccagagga gctctctcga cgcaggactc      1080
ggcttgctga agcgcgcacg gcaagaggcg aggggcggcg actggtgagt acgccaaaaa      1140
ttttgactag cggaggctag aaggagagag atgggtgcga gagcgtcagt attaagcggg      1200
ggagaattag atcgcgatgg gaaaaaattc ggttaaggcc agggggaaag aaaaaatata      1260
aattaaaaca tatagtatgg gcaagcaggg agctagaacg attcgcagtt aatcctggcc      1320
tgttagaaac atcagaaggc tgtagacaaa tactgggaca gctacaacca tcccttcaga      1380
caggatcaga agaacttaga tcattatata atacagtagc aaccctctat tgtgtgcatc      1440
aaaggataga gataaaagac accaaggaag ctttagacaa gatagaggaa gagcaaaaca      1500
aaagtaagac caccgcacag caagcggccg ctgatcttca gacctggagg aggagatatg      1560
agggacaatt ggagaagtga attatataaa tataaagtag taaaaattga accattagga      1620
gtagcaccca ccaaggcaaa gagaagagtg gtgcagagag aaaaaagagc agtgggaata      1680
ggagctttgt tccttgggtt cttggagca gcaggaagca ctatgggcgc agcgtcaatg      1740
acgctgacgg tacaggccag acaattattg tctggtatag tgcagcagca gaacaatttg      1800
ctgagggcta ttgaggcgca acagcatctg ttgcaactca cagtctgggg catcaagcag      1860
ctccaggcaa gaatcctggc tgtggaaaga tacctaaagg atcaacagct cctgggaatt      1920
tggggttgct ctggaaaact catttgcacc actgctgtgc cttggaatgc tagttggagt      1980
aataaatctc tggaacagat ttggaatcac acgacctgga tggagtggga cagagaaatt      2040
aacaattaca caagcttaat acactcctta attgaagaat cgcaaaacca gcaagaaaag      2100
aatgaacaag aattattgga attagataaa tgggcaagtt tgtggaattg gtttaacata      2160
acaaattggc tgtggtatat aaaattattc ataatgatag taggaggctt ggtaggttta      2220
agaatagttt ttgctgtact ttctatagtg aatagagtta ggcagggata ttcaccatta      2280
tcgtttcaga cccacctccc aaccccgagg ggacccgaca ggcccgaagg aatagaagaa      2340
gaaggtggag agagagacag agacagatcc attcgattag tgaacggatc ggcactgcgt      2400
gcgccaattc tgcagacaaa tggcagtatt catccacaat tttaaaagaa aagggggggat      2460 tgggggggtac agtgcagggg aaagaatagt agacataata gcaacagaca tacaaactaa      2520
agaattacaa aaacaaatta caaaaattca aaattttcgg gtttattaca gggacagcag      2580
agatccagtt tggttaatta gctagctagg tcttgaaagg agtgggaatt ggctccggtg      2640
cccgtcagtg ggcagagcgc acatcgccca cagtccccga aagttgggg ggagggggtcg      2700 gcaattgatc cggtgcctag agaaggtggc gcggggtaaa ctgggaaagt gagtcgtgta      2760
ctggctccgc ctttttcccg agggtggggg agaaccgtat ataagtgcag tagtcgccgt      2820
gaacgttctt tttcgcaacg ggtttgccgc cagaacacag gaccggttaa tagtgagtag      2880
tagtaagtga taatagaaat tgccaccatg agctcaaacg tcacctccaa tcacaagggt      2940
ggcttctcca attgtacagg cagtggagag ggcagaggaa gtctgctcac ctgcggcgac      3000
gtcgaggaga atcctggccc agtcagcaag ggcgaggagc tgttcaccgg ggtggtgccc      3060
atcctggtcg agctggacgg cgacgtcaac ggccacaagt tcagcgtgtc cggcgagggc      3120
gaaggcgacg ccacctacgg aaagctcact ctcaagttca tctgcaccac aggcaagctg      3180
cccgtgccct ggcccaccct cgtcaccacc ctcacctacg gcgtgcagtg cttcagccgc      3240 tacccccgacc acctcaagca gcacgacttc ttcaagtccg ctatgcccga aggctacgtc      3300
caggagcgca ccatcttctt caaggacgac ggcaactaca agacccgcgc cgaggtcaag      3360
```

```
ttcgagggcg acaccctggt caaccgcatc gagctcaagg gcatcgactt caaggaggac   3420
ggcaacatcc tggggcacaa gctggagtac aactacaaca gccacaacgt ctatatcatg   3480
gccgacaagc agaagaacgg catcaaggtc aacttcaaga tccgccacaa catcgaggac   3540
ggcagcgtgc agctcgccga ccactaccag cagaacaccc ccatcggcga cggccccgtg   3600
ctgctgcccg acaaccacta cctcagcacc cagtccgccc tcagcaaaga ccccaacgag   3660
aagcgcgatc acatggtcct gctggagttc gtcaccgccg ccgggatcac tctcggcatg   3720
gacgagctct acaagtaata taaccggat ccggcgcaac aaacttctct ctgctcaaac   3780
aagccggcga cgtcgaagag aatcctgggc cgaccgagta caagcccacg gtgcgcctcg   3840
ctacccgcga cgacgtcccc agggctgtcc gcaccctcgc cgctgcgttc gccgactacc   3900
ccgctacgcg ccacaccgtc gatccggacc gccacatcga gcgggtcacc gaactgcaag   3960
aactcttcct cacgcgcgtc gggctcgaca tcggcaaggt gtgggtcgcg gacgacggcg   4020
ccgctgtggc ggtctggacc acacggaga gcgtcgaagc gggtgcggtg ttcgccgaga   4080
tcggtccgcg catggccgag ctcagcggtt cccggctggc cgcgcagcaa cagatggaag   4140
gtctcctggc gccgcaccgg cccaaggagc ctgcgtggtt cctggccacc gtcggagtct   4200
cgcccgacca ccaaggcaag ggtctgggca gcgccgtcgt gctccccgga gtggaggcgg   4260
cagagcgtgc tggagtgccc gccttcctgg agacctccgc gccccgcaac ctcccttttct   4320
acgagcggct cggcttcacc gtcaccgcag acgtcgaggt gccagaagga cctcgcacct   4380
ggtgtctcac ccgcaagccc ggtgcccgta cgggcagtgg ggagggcaga ggaagtctgc   4440
taacctgcgg tgacgtcgag gagaatcctg gcccagtgtc caagggcgag gaagataaca   4500
tggccatcat caaggagttc atgaggttta aggtccacat ggagggttca gtcaatggcc   4560
acgagttcga gattgaaggc gagggcgagg gccgccccta cgaagggaca cagacggcga   4620
aattgaaggt gaccaaggc gggccattgc ccttcgcatg gacatcttg tcccctcagt   4680
ttatgtatgg cagcaaggcc tatgttaagc accccgctga tatcccggac tacttgaagc   4740
tgtccttttcc agagggtttt aaatgggagc gcgttatgaa tttcgaagac ggaggagtgg   4800
ttacggtgac gcaggactca tccctgcagg acggagaatt tatatataag gttaagttga   4860
gaggcacaaa cttcccaagc gacggccctg tgatgcagaa gaaaacaatg gggtgggaag   4920
cttccagcga gcgcatgtac cccgaagatg gcgccctcaa gggcgagata aagcaaaggc   4980
tgaaacttaa ggacggcggt cattacgacg cggaggtcaa gacaacttac aaggctaaaa   5040
aacccgttca gttgcctggg gcttacaatg ttaatatcaa acttgacatc acaagccaca   5100
atgaagacta tacgatcgtg gagcagtatg aacgagcgga aggcaggcac tcaacggggg   5160
ggatggacga gctttacaag taataataag aattcgatat caagcttatc ggtaatcaac   5220
ctctggatta caaaatttgt gaaagattga ctggtattct taactatgtt gctccttttta   5280
cgctatgtgg atacgctgct ttaatgcctt tgtatcatgc tattgcttcc cgtatggctt   5340
tcattttctc ctccttgtat aaatcctggt tgctgtctct ttatgaggag ttgtggcccg   5400
ttgtcaggca acgtggcgtg gtgtgcactg tgtttgctga cgcaaccccc actggttggg   5460
gcattgccac cacctgtcag ctcctttccg ggactttcgc tttccccctc cctattgcca   5520
cggcggaact catcgccgcc tgccttgccc gctgctggac aggggctcgg ctgttgggca   5580
ctgacaattc cgtggtgttg tcggggaaat catcgtcctt ccttggctg ctcgcctgtg   5640
ttgccacctg gattctgcgc gggacgtcct tctgctacgt cccttcggcc ctcaatccag   5700
```

```
cggaccttcc ttcccgcggc ctgctgccgg ctctgcggcc tcttccgcgt cttcgccttc    5760
gccctcagac gagtcggatc tccctttggg ccgcctcccc gcatcgatac cgtcgacctc    5820
gagacctaga aaacatgga gcaatcacaa gtagcaatac agcagctacc aatgctgatt    5880
gtgcctggct agaagcacaa gaggaggagg aggtgggttt tccagtcaca cctcaggtac    5940
ctttaagacc aatgacttac aaggcagctg tagatcttag ccacttttta aaagaaaagg    6000
ggggactgga agggctaatt cactcccaac gaagacaaga tatccttgat ctgtggatct    6060
accacacaca aggctacttc cctgattggc agaactacac accagggcca gggatcagat    6120
atccactgac ctttggatgg tgctacaagc tagtaccagt tgagcaagag aaggtagaag    6180
aagccaatga aggagagaac acccgcttgt tacaccctgt gagcctgcat gggatggatg    6240
acccggagag agaagtatta gagtggaggt ttgacagccg cctagcattt catcacatgg    6300
cccgagagct gcatccggac tgtactgggt ctctctggtt agaccagatc tgagcctggg    6360
agctctctgg ctaactaggg aacccactgc ttaagcctca ataaagcttg ccttgagtgc    6420
ttcaagtagt gtgtgcccgt ctgttgtgtg actctggtaa ctagagatcc ctcagaccct    6480
tttagtcagt gtggaaaatc tctagcaggg cccgttaaa cccgctgatc agcctcgact    6540
gtgccttcta gttgccagcc atctgttgtt tgccctcccc ccgtgccttc cttgaccctg    6600
gaaggtgcca ctcccactgt cctttcctaa taaaatgagg aaattgcatc gcattgtctg    6660
agtaggtgtc attctattct ggggggtggg gtggggcagg acagcaaggg ggaggattgg    6720
gaagacaata gcaggcatgc tggggatgcg gtgggctcta tggcttctga ggcggaaaga    6780
accagctggg gctctagggg gtatccccac gcgccctgta gcggcgcatt aagcgcggcg    6840
ggtgtggtgg ttacgcgcag cgtgaccgct acacttgcca gcgccctagc gcccgctcct    6900
ttcgctttct tcccttcctt tctcgccacg ttcgccggct ttccccgtca gctctctaaat    6960 cggggggctcc ctttagggtt ccgatttagt gctttacggc acctcgaccc caaaaaactt    7020
gattagggtg atggttcacg tagtgggcca tcgccctgat agacggtttt tcgccctttg    7080
acgttggagt ccacgttctt taatagtgga ctcttgttcc aaactggaac aacactcaac    7140
cctatctcgg tctattcttt tgatttataa gggattttgc cgatttcggc ctattggtta    7200
aaaaatgagc tgatttaaca aaaatttaac gcgaattaat tctgtggaat gtgtgtcagt    7260
tagggtgtga aaagtcccca ggctccccag caggcagaag tatgcaaagc atgcatctca    7320
attagtcagc aaccaggtgt ggaaagtccc caggctcccc agcaggcaga agtatgcaaa    7380
gcatgcatct caattagtca gcaaccatag tcccgcccct aactccgccc atcccgcccc    7440
taactccgcc cagttccgcc cattctccgc cccatggctg actaattttt tttatttatg    7500
cagaggccga ggccgcctct gcctctgagc tattccagaa gtagtgagga ggcttttttg    7560
gaggcctagg cttttgcaaa aagctcccgg gagcttgtat atccattttc ggatctgatc    7620
agcacgtgtt gacaattaat catcggcata gtatatcggc atagtataat acgacaaggt    7680
gaggaactaa accatggcca agttgaccag tgccgttccg gtgctcaccg cgcgcgacgt    7740
cgccggagcg gtcgagttct ggaccgaccg gctcgggttc tcccgggact tcgtggagga    7800
cgacttcgcc ggtgtggtcc gggacgacgt gaccctgttc atcagcgcgg tccaggacca    7860
ggtggtgccg gacaacaccc tggcctgggt gtgggtgcgc ggcctggacg agctgtacgc    7920
cgagtggtcg gaggtcgtgt ccacgaactt ccgggacgcc tccggccggg ccatgaccga    7980
gatcggcgag cagccgtggg ggcgggagtt cgccctgcgc gacccggccg gcaactgcgt    8040
gcacttcgtg gccgaggagc aggactgaca cgtgctacga gatttcgatt ccaccgccgc    8100
```

```
cttctatgaa aggttgggct tcggaatcgt tttccgggac gccggctgga tgatcctcca   8160
gcgcggggat ctcatgctgg agttcttcgc ccacccaac ttgtttattg cagcttataa    8220
tggttacaaa taaagcaata gcatcacaaa tttcacaaat aaagcatttt tttcactgca   8280
ttctagttgt ggtttgtcca aactcatcaa tgtatcttat catgtctgta taccgtcgac   8340
ctctagctag agcttggcgt aatcatggtc atagctgttt cctgtgtgaa attgttatcc   8400
gctcacaatt ccacacaaca tacgagccgg aagcataaag tgtaaagcct ggggtgccta   8460
atgagtgagc taactcacat taattgcgtt gcgctcactg cccgctttcc agtcgggaaa   8520
cctgtcgtgc cagctgcatt aatgaatcgg ccaacgcgcg gggagaggcg gtttgcgtat   8580
tgggcgctct tccgcttcct cgctcactga ctcgctgcgc tcggtcgttc ggctgcggcg   8640
agcggtatca gctcactcaa aggcggtaat acggttatcc acagaatcag gggataacgc   8700
aggaaagaac atgtgagcaa aaggccagca aaaggccagg aaccgtaaaa aggccgcgtt   8760
gctggcgttt ttccataggc tccgcccccc tgacgagcat cacaaaaatc gacgctcaag   8820
tcagaggtgg cgaaacccga caggactata aagataccag gcgtttcccc ctggaagctc   8880
cctcgtgcgc tctcctgttc cgaccctgcc gcttaccgga tacctgtccg cctttctccc   8940
ttcgggaagc gtggcgcttt ctcatagctc acgctgtagg tatctcagtt cggtgtaggt   9000
cgttcgctcc aagctgggct gtgtgcacga accccccgtt cagcccgacc gctgcgcctt   9060
atccggtaac tatcgtcttg agtccaaccc ggtaagacac gacttatcgc cactggcagc   9120
agccactggt aacaggatta gcagagcgag gtatgtaggc ggtgctacag agttcttgaa   9180
gtggtggcct aactacggct acactagaag aacagtattt ggtatctgcg ctctgctgaa   9240
gccagttacc ttcggaaaaa gagttggtag ctcttgatcc ggcaaacaaa ccaccgctgg   9300
tagcggtggt ttttttgttt gcaagcagca gattacgcgc agaaaaaaag gatctcaaga   9360
agatcctttg atcttttcta cggggtctga cgctcagtgg aacgaaaact cacgttaagg   9420
gattttggtc atgagattat caaaaaggat cttcacctag atcctttttaa attaaaaatg   9480 aagttttaaa tcaatctaaa gtatatatga gtaaacttgg tctgacagtt accaatgctt   9540
aatcagtgag gcacctatct cagcgatctg tctatttcgt tcatccatag ttgcctgact   9600
ccccgtcgtg tagataacta cgatacggga gggcttacca tctggcccca gtgctgcaat   9660
gataccgcga gacccacgct caccggctcc agatttatca gcaataaacc agccagccgg   9720
aagggccgag cgcagaagtg gtcctgcaac tttatccgcc tccatccagt ctattaattg   9780
ttgccgggaa gctagagtaa gtagttcgcc agttaatagt ttgcgcaacg ttgttgccat   9840
tgctacaggc atcgtggtgt cacgctcgtc gtttggtatg gcttcattca gctccggttc   9900
ccaacgatca aggcgagtta catgatcccc catgttgtgc aaaaaagcgg ttagctcctt   9960
cggtcctccg atcgttgtca gaagtaagtt ggccgcagtg ttatcactca tggttatggc  10020
agcactgcat aattctctta ctgtcatgcc atccgtaaga tgcttttctg tgactggtga  10080
gtactcaacc aagtcattct gagaatagtg tatgcggcga ccgagttgct cttgcccggc  10140
gtcaatacgg gataataccg cgccacatag cagaacttta aaagtgctca tcattggaaa  10200
acgttcttcg gggcgaaaac tctcaaggat cttaccgctg ttgagatcca gttcgatgta  10260
acccactcgt gcacccaact gatcttcagc atcttttact ttcaccagcg tttctgggtg  10320
agcaaaaaca ggaaggcaaa atgccgcaaa aaagggaata agggcgacac ggaaatgttg  10380
aatactcata ctcttccttt ttcaatatta ttgaagcatt tatcagggtt attgtctcat  10440
```

```
gagcggatac atatttgaat gtatttagaa aaataaacaa ataggggttc cgcgcacatt    10500
tccccgaaaa gtgccacctg ac                                            10522
```

<210> SEQ ID NO 70
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70

```
tcaattatac actatctcct aggggggatc ggcttcgtat ataaggcgtg gggttggcct    60
cgcgaaagg                                                            69
```

<210> SEQ ID NO 71
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71

```
cacgagcagt cccatgccgg aggacataaa tctatgatgg cttaggctta ggtcctatgt    60
gcgcaaagg                                                            69
```

<210> SEQ ID NO 72
<211> LENGTH: 69
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72

```
agcgccagac agtgcgtccc agggatatga aaccacggct gacaggatgc atctaatata    60
acgagaaagg                                                           69
```

<210> SEQ ID NO 73
<211> LENGTH: 5460
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 73

```
gcggtaggcg tgtacggtgg gaggtctata taagcagcgc gttttgcctg tactgggtct    60
ctctggttag accagatctg agcctgggag ctctctggct aactagggaa cccactgctt   120
aagcctcaat aaagcttgcc ttgagtgctt caagtagtgt gtgcccgtct gttgtgtgac   180
tctggtaact agagatccct cagacccttt tagtcagtgt ggaaaatctc tagcagtggc   240
gcccgaacag ggacttgaaa gcgaaaggga accagagga gctctctcga cgcaggactc   300
ggcttgctga agcgcgcacg gcaagaggcg aggggcggcg actggtgagt acgccaaaaa   360
ttttgactag cggaggctag aaggagagag atgggtgcga gagcgtcagt attaagcggg   420
ggagaattag atcgcgatgg gaaaaaattc ggttaaggcc agggggaaag aaaaaatata   480
```

```
aattaaaaca tatagtatgg gcaagcaggg agctagaacg attcgcagtt aatcctggcc    540
tgttagaaac atcagaaggc tgtagacaaa tactgggaca gctacaacca tcccttcaga    600
caggatcaga agaacttaga tcattatata atacagtagc aaccctctat tgtgtgcatc    660
aaaggataga gataaaagac accaaggaag ctttagacaa gatagaggaa gagcaaaaca    720
aaagtaagac caccgcacag caagcggccg ctgatcttca gacctggagg aggagatatg    780
agggacaatt ggagaagtga attatataaa tataaagtag taaaaattga accattagga    840
gtagcaccca ccaaggcaaa gagaagagtg gtgcagagag aaaaaagagc agtgggaata    900
ggagctttgt tccttgggtt cttgggagca gcaggaagca ctatgggcgc agcgtcaatg    960
acgctgacgg tacaggccag acaattattg tctggtatag tgcagcagca gaacaatttg   1020
ctgagggcta ttgaggcgca acagcatctg ttgcaactca cagtctgggg catcaagcag   1080
ctccaggcaa gaatcctggc tgtggaaaga tacctaaagg atcaacagct cctggggatt   1140
tggggttgct ctggaaaact catttgcacc actgctgtgc cttggaatgc tagttggagt   1200
aataaatctc tggaacagat ttggaatcac acgacctgga tggagtggga cagagaaatt   1260
aacaattaca caagcttaat acactcctta attgaagaat cgcaaaacca gcaagaaaag   1320
aatgaacaag aattattgga attagataaa tgggcaagtt tgtggaattg gtttaacata   1380
acaaattggc tgtggtatat aaaattattc ataatgatag taggaggctt ggtaggttta   1440
agaatagttt ttgctgtact ttctatagtg aatagagtta ggcagggata ttcaccatta   1500
tcgtttcaga cccacctccc aaccccgagg ggacccgaca ggcccgaagg aatagaagaa   1560
gaaggtggag agagagacag agacagatcc attcgattag tgaacggatc ggcactgcgt   1620
gcgccaattc tgcagacaaa tggcagtatt catccacaat tttaaaagaa aaggggggat   1680
tggggggtac agtgcagggg aaagaatagt agacataata gcaacagaca tacaaactaa   1740
agaattacaa aaacaaatta caaaaattca aaattttcgg gtttattaca gggacagcag   1800
agatccagtt tggttaatta gctagcgaga cgctcagact cagacgtctc aggtaggcgt   1860
gtacggtggg aggcctatat aagcagagct cgtttagtga accgtcagat cgcctggagg   1920
atccgccacc atggtgagca agggcgagga ggataacatg gccatcatca aggagttcat   1980
gcgcttcaag gtgcacatgg agggctccgt gaacggccac gagttcgaga tcgagggcga   2040
gggcgagggc cgcccctacg agggcaccca gaccgccaag ctgaaggtga ccaagggtgg   2100
ccccctgccc ttcgcctggg acatcctgtc ccctcagttc atgtacggct ccaaggccta   2160
cgtgaagcac cccgccgaca tccccgacta cttgaagctg tccttccccg agggcttcaa   2220
gtgggagcgc gtgatgaact tcgaggacgg cggcgtggtg accgtgaccc aggactcctc   2280
cctgcaggac ggcgagttca tctacaaggt gaagctgcgc ggcaccaact cccctccga    2340 cggccccgta atgcagaaga gaccatggg ctgggaggcc tcctccgagc ggatgtaccc   2400
cgaggacggc gccctgaagg gcgagatcaa gcagaggctg aagctgaagg acggcggcca   2460
ctacgacgct gaggtcaaga ccacctacaa ggccaagaag cccgtgcagc tgcccggcgc   2520
ctacaacgtc aacatcaagt tggacatcac ctcccacaac gaggactaca ccatcgtgga   2580
acagtacgaa cgcgccgagg ccgccactc caccggcggc atggacgagc tgtacaagta   2640
actagagctc gctgatcagc ctcgactgtg ccttctagtt gccagccatc tgttgtttgc   2700
ccctcccccg tgccttcctt gaccctggaa ggtgccactc ccactgtcct ttcctaataa   2760
aatgaggaaa ttgcatcgca ttgtctgagt aggtgtcatt ctattctggg gggtggggtg   2820
```

| | |
|---|---|
| gggcaggaca gcaaggggga ggattgggaa gacaatagca ggcatgctgg ggaagctcga | 2880 |
| gtaggtcttg aaaggagtgg gaattggctc cggtgcccgt cagtgggcag agcgcacatc | 2940 |
| gcccacagtc cccgagaagt tggggggagg ggtcggcaat tgatccggtg cctagagaag | 3000 |
| gtggcgcggg gtaaactggg aaagtgatgt cgtgtactgg ctccgccttt ttcccgaggg | 3060 |
| tgggggagaa ccgtatataa gtgcagtagt cgccgtgaac gttcttttc gcaacgggtt | 3120 |
| tgccgccaga acacaggtct agagccacca tgaccgagta caagcccacg gtgcgcctcg | 3180 |
| ccacccgcga cgacgtcccc agggccgtac gcaccctcgc cgccgcgttc gccgactacc | 3240 |
| ccgccacgcg ccacaccgtc gatccggacc gccacatcga gcgggtcacc gagctgcaag | 3300 |
| aactcttcct cacgcgcgtc gggctcgaca tcggcaaggt gtgggtcgcg gacgacggcg | 3360 |
| ccgccgtggc ggtctggacc acgcggaga gcgtcgaagc gggggcggtg ttcgccgaga | 3420 |
| tcggcccgcg catggccgag ttgagcggtt cccggctggc cgcgcagcaa cagatggaag | 3480 |
| gcctcctggc gccgcaccgg cccaaggagc ccgcgtggtt cctggccacc gtcggagtct | 3540 |
| cgccccgacca ccagggcaag ggtctgggca gcgccgtcgt gctccccgga gtggaggcgg | 3600 |
| ccgagcgcgc cggggtgccc gccttcctgg agacctccgc gccccgcaac ctccccttct | 3660 |
| acgagcggct cggcttcacc gtcaccgccg acgtcgaggt gcccgaagga ccgcgcacct | 3720 |
| ggtgcatgac ccgcaagccc ggtgcctgag aattcgatat caagcttatc ggtaatcaac | 3780 |
| ctctggatta caaaatttgt gaaagattga ctggtattct taactatgtt gctccttta | 3840 |
| cgctatgtgg atacgctgct ttaatgcctt tgtatcatgc tattgcttcc cgtatggctt | 3900 |
| tcattttctc ctccttgtat aaatcctggt tgctgtctct ttatgaggag ttgtggcccg | 3960 |
| ttgtcaggca acgtggcgtg gtgtgcactg tgtttgctga cgcaacccc actggttggg | 4020 |
| gcattgccac cacctgtcag ctcctttccg ggactttcgc tttccccctc cctattgcca | 4080 |
| cggcggaact catcgccgcc tgccttgccc gctgctggac aggggctcgg ctgttgggca | 4140 |
| ctgacaattc cgtggtgttg tcggggaaat catcgtcctt tccttggctg ctcgcctgtg | 4200 |
| ttgccacctg gattctgcgc gggacgtcct tctgctacgt cccttcggcc ctcaatccag | 4260 |
| cggaccttcc ttcccgcggc ctgctgccgg ctctgcggcc tcttccgcgt cttcgccttc | 4320 |
| gccctcagac gagtcggatc tccctttggg ccgcctcccc gcatcgatac cgtcgacctc | 4380 |
| gagacctaga aaacatgga gcaatcacaa gtagcaatac agcagctacc aatgctgatt | 4440 |
| gtgcctggct agaagcacaa gaggaggagg aggtgggttt tccagtcaca cctcaggtac | 4500 |
| ctttaagacc aatgacttac aaggcagctg tagatcttag ccacttttta ctctgcggcc | 4560 |
| tcttccgcgt cttcgccttc gccctcagac gagtcggatc tccctttggg ccgcctcccc | 4620 |
| gcatcgatac cgtcgacctc gagacctaga aaacatgga gcaatcacaa gtagcaatac | 4680 |
| agcagctacc aatgctgatt gtgcctggct agaagcacaa gaggaggagg aggtgggttt | 4740 |
| tccagtcaca cctcaggtac ctttaagacc aatgacttac aaggcagctg tagatcttag | 4800 |
| ccactttta aagaaaagg ggggactgga agggctaatt cactcccaac gaagacaaga | 4860 |
| tatccttgat ctgtggatct accacacaca aggctacttc cctgattggc agaactacac | 4920 |
| accagggcca gggatcagat atccactgac ctttggatgg tgctacaagc tagtaccagt | 4980 |
| tgagcaagag aaggtagaag aagccaatga aggagagaac accgcttgt tacaccctgt | 5040 |
| gagcctgcat gggatggatg acccggagag agaagtatta gagtggaggt ttgacagccg | 5100 |
| cctagcattt catcacatgg cccgagagct gcatccggag tgtactgggt ctctctggtt | 5160 |
| agaccagatc tgagcctggg agctctctgg ctaactaggg aacccactgc ttaagcctca | 5220 |

```
ataaagcttg ccttgagtgc ttcaagtagt gtgtgcccgt ctgttgtgtg actctggtaa      5280
ctagagatcc ctcagaccct tttagtcagt gtggaaaatc tctagcaggg cccgtttaaa      5340
cccgctgatc agcctcgact gtgccttcta gttgccagcc atctgttgtt tgcccctccc      5400
ccgtgccttc cttgaccctg gaaggtgcca ctcccactgt cctttcctaa taaaatgagg      5460

<210> SEQ ID NO 74
<211> LENGTH: 106
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 74
gtaagtgata atagaaattg ccaccatgag ctcaaacgtc acctccaatc acaagggtgg        60
cttctccaat tgtacaggca gtggagaggg cagaggaagt ctgctc                      106

<210> SEQ ID NO 75
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 75

Val Ser Asp Asn
1

<210> SEQ ID NO 76
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 76

Met Ser Ser Asn Val Thr Ser Asn His Lys Gly Gly Phe Ser Asn Cys
1               5                   10                  15

Thr Gly Ser Gly Glu Gly Arg Gly Ser Leu Leu
            20                  25
```

CELL SORTING

RELATED APPLICATIONS AND INCORPORATION BY REFERENCE

This application is a continuation-in-part application of international patent application Serial No. PCT/US2016/038234 filed Jun. 17, 2016, which published as PCT Publication No. WO2016/205745 on Dec. 22, 2016 and which claims priority and benefit of U.S. provisional application Ser. No. 62/181,704 filed Jun. 18, 2015.

Mention is made of: US provisional patent applications: 62/055,460 and 62/055,487 each filed Sep. 25, 2014. Reference is made to: US provisional patent applications: 62/087,475 and 62/087,546 each filed Dec. 4, 2014. Reference is also made to concurrently-filed application Ser. No. 62/181,687 filed Jun. 18, 2015, and concurrently-filed application Ser. No. 62/181,690 filed Jun. 18, 2015.

All documents or applications cited therein during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under grant number MH100706 awarded by the National Institutes of Health. The government has certain rights in the invention.

SEQUENCE LISTING

The instant application contains a sequence listing which has been submitted electronically in ASCII format and is hereby incorporated by reference in its entirety. Said ASCII copy, created on Oct. 6, 2016, is named 47627_99_2018_SL.txt and k 99,716 bytes in size.

FIELD OF THE INVENTION

The present invention generally relates to the delivery, engineering and optimization of systems, methods and compositions used for the control of gene expression involving sequence targeting, such as genome perturbation or gene-editing, that relate to Clustered Regularly Interspaced Short Palindromic Repeats (CRISPR) and components thereof.

In particular, the present invention relates to the preparation, testing, and application of CRISPR-Cas activator systems in methods and compositions for cell sorting.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that are affordable, easy to set up, scalable, and amenable to targeting multiple positions within the eukaryotic genome.

Targeted, rapid, and efficient genome editing using the RNA-guided Cas9 system is enabling the systematic interrogation of genetic elements in a variety of cells and organisms and holds enormous potential as next-generation gene therapies (Hsu, Lander, & Zhang, 2014). In contrast to other DNA targeting systems based on zinc-finger proteins (ZFPs) (Klug, 2010) and transcription activator-like effectors (TALEs) (Boch & Bonas, 2010), which rely on protein domains to confer DNA-binding specificity, Cas9 forms a complex with a small guide RNA that directs the enzyme to its DNA target via Watson-Crick base pairing. Consequently, the system is simple and fast to design and requires only the production of a short oligonucleotide to direct DNA binding to any locus.

The type II microbial CRISPR (clustered regularly interspaced short palindromic repeats) system (Chylinski, Makarova, Charpentier, & Koonin, 2014), which is the simplest among the three known CRISPR types (Barrangou & Marraffini, 2014; Gasiunas, Sinkunas, & Siksnys, 2014; Wiedenheft, Sternberg, & Doudna, 2012), consists of the CRISPR-associated (Cas) genes and a series of non-coding repetitive elements (direct repeats) interspaced by short variable sequences (spacers). These short approximate 30 bp spacers are often derived from foreign genetic elements such as phages and conjugating plasmids, and they constitute the basis for an adaptive immune memory of those invading elements (Barrangou et al., 2007). The corresponding sequences on the phage genomes and plasmids are called protospacers, and each protospacer is flanked by a short protospacer-adjacent motif (PAM), which plays a critical role in the target search and recognition mechanism of Cas9. The CRISPR array is transcribed and processed into short RNA molecules known as CRISPR RNAs (crRNA) that, together with a second short trans-activating RNA (tracrRNA) (Deltcheva et al., 2011), complex with Cas9 to facilitate target recognition and cleavage (Deltcheva et al., 2011; Garneau et al., 2010). Additionally, the crRNA and tracrRNA can be fused into a single guide RNA (sgRNA) to facilitate Cas9 targeting (Jinek et al., 2012).

The Cas9 enzyme from *Streptococcus pyogenes* (SpCas9), which requires a 5'-NGG PAM (Mojica, Diez-Villasenor, Garcia-Martinez, & Almendros, 2009), has been widely used for genome editing applications (Hsu et al., 2014). In order to target any desired genomic locus of interest that fulfills the PAM requirement, the enzyme can be "programmed" merely by altering the 20-bp guide sequence of the sgRNA. Additionally, the simplicity of targeting lends itself to easy multiplexing such as simultaneous editing of several loci by including multiple sgRNAs (Cong et al., 2013; Wang et al., 2013).

Like other designer nucleases, Cas9 facilitates genome editing by inducing double-strand breaks (DSBs) at its target site, which in turn stimulates endogenous DNA damage repair pathways that lead to edited DNA: homology directed repair (HDR), which requires a homologous template for recombination but repairs DSBs with high fidelity, and non-homologous end-joining (NHEJ), which functions without a template and frequently produces insertions or deletions (indels) as a consequence of repair. Exogenous HDR templates can be designed and introduced along with Cas9 and sgRNA to promote exact sequence alteration at a target locus; however, this process typically occurs only in dividing cells and at low efficiency.

Certain applications—e.g. therapeutic genome editing in human stem cells—demand editing that is not only efficient, but also highly specific. Nucleases with off-target DSB activity could induce undesirable mutations with potentially deleterious effects, an unacceptable outcome in most clinical settings. The remarkable ease of targeting Cas9 has enabled extensive off-target binding and mutagenesis studies employing deep sequencing (Fu et al., 2013; Hsu et al., 2013; Pattanayak et al., 2013) and chromatin immunoprecipitation (ChIP) in human cells (Kuscu, Arslan, Singh, Thorpe, & Adli, 2014; Wu et al., 2014). As a result, an increasingly complete picture of the off-target activity of the enzyme is emerging. Cas9 will tolerate some mismatches between its guide and a DNA substrate, a characteristic that depends strongly on the number, position (PAM proximal or distal) and identity of the mismatches. Off-target binding and cleavage may further depend on the organism being edited, the cell type, and epigenetic contexts.

These specificity studies, together with direct investigations of the catalytic mechanism of Cas9, have stimulated homology- and structure-guided engineering to improve its targeting specificity. The wild-type enzyme makes use of two conserved nuclease domains, HNH and RuvC, to cleave DNA by nicking the sgRNA-complimentary and non-complimentary strands, respectively. A "nickase" mutant (Cas9n) can be generated by alanine substitution at key catalytic residues within these domains—SpCas9 D10A inactivates RuvC (Jinek et al., 2012), while N863A has been found to inactivate HNH (Nishimasu et al., 2014). Though an H840A mutation was also reported to convert Cas9 into a nicking enzyme, this mutant has reduced levels of activity in mammalian cells compared with N863A (Nishimasu et al., 2014).

Because single stranded nicks are generally repaired via the non-mutagenic base-excision repair pathway (Dianov & Hubscher, 2013), Cas9n mutants can be leveraged to mediate highly specific genome engineering. A single Cas9n-induced nick can stimulate HDR at low efficiency in some cell types, while two nicking enzymes, appropriately spaced and oriented at the same locus, effectively generate DSBs, creating 3' or 5' overhangs along the target as opposed to a blunt DSB as in the wild-type case (Mali et al., 2013; Ran et al., 2013). The on-target modification efficiency of the double-nicking strategy is comparable to wild-type, but indels at predicted off-target sites are reduced below the threshold of detection by Illumina deep sequencing (Ran et al., 2013).

SUMMARY OF THE INVENTION

The analysis of genetically heterogeneous cell populations is complicated by the fact that many biological assays are destructive, making it difficult to isolate cells with particular properties for further study and use. For example, cells originating from a patient tumor may carry different mutations and chromosomal arrangements, leading to different properties, e.g., resistance to chemotherapy. Techniques such as RNA and protein analysis may reveal key signatures of resistant cells, e.g., an aberrant epigenetic state, but destroy the cells, thus precluding further experiments on the same cells.

Traditionally, this limitation has been circumvented in dividing cell populations by isolating individual cells, e.g., in a multiwell plate, expanding the cells, and splitting the cells for downstream use. However, this process is laborious (each cell must be handled individually), slow (typically a month to expand cells), and low throughput. Furthermore, many cell types are not amenable to expansion from single cells, which may cause cell death or profound changes to cell physiology.

Recently, methods to introduce unique DNA barcodes into a cell population have partially alleviated this difficulty. Barcoded cells are expanded, split into parallel selection-based assays, and after each assay barcodes are counted by next-generation sequencing (Nolan-Stevaux et al. 2013, PLoS ONE 8(6): e67316; and Bhang et al., Nature Medicine May 2015, Vol. 21:5, 440-448). These methods do not allow for determining gene and protein expression of the cells before drug treatment and do not allow for recovering a pure population of cells of interest before treatment. As such, these methods do not address the goal of retrieving particular sub-populations (such as the descendants of an initial resistant cell), and is limited to selection-based assays with a simple readout obtainable by counting barcodes as a proxy for cells.

Surprisingly, Applicants' invention provides a method to recover cells containing specific DNA barcodes from a heterogeneous population. It will be appreciated that the present methods may relate to sorting cells, but that this also equally applies to methods of separating cells or to methods of isolating cells.

In one aspect, the present invention provides a polynucleotide sequence comprising one or more DNA barcodes, the or each DNA barcode comprising a target sequence designed to be recognized by a CRISPR-Cas guide and a PAM sequence of a CRISPR-Cas complex; and a sequence encoding a selection marker or reporter under the control of or operably linked to a suitable promoter.

In another aspect, the present invention provides a viral vector comprising a polynucleotide sequence comprising one or more DNA barcodes, the or each DNA barcode comprising a target sequence designed to be recognized by a CRISPR-Cas guide and a PAM sequence of a CRISPR-Cas complex; and a sequence encoding a selection marker or reporter under the control of or operably linked to a suitable promoter.

In one embodiment, the polynucleotide sequence as herein described, comprises two or more selection markers or reporters under the control of or operably linked to the suitable promoter, wherein the two or more selection markers or reporters are in frame or out of frame within an open reading frame. In an embodiment, one marker is in frame and one marker is out of frame. The barcode may be configured such that introducing an insertion or deletion in said barcode creates a frameshift in said open reading frame, whereby two or more selection markers or reporters are activated or inactivated. In a preferred embodiment, one marker or reporter is activated and one marker or reporter is inactivated. Not being bound by a theory, the specificity of recovery of a specific cell is increased by sorting cells based on more than one marker or reporter.

In another aspect, the present invention provides a polynucleotide sequence encoding a CRISPR-Cas enzyme and a selection marker or reporter. In some embodiments, the CRISPR-Cas enzyme is a Cas9 enzyme. In some embodiments, the CRISPR-Cas enzyme is a catalytically inactive CRISPR-Cas enzyme, optionally a dead or diminished nuclease activity-Cas9 enzyme. In some embodiments, the Cas9 comprises mutations at D10 and N863 in SpCas9, D10 or N580 in SaCas9 or corresponding mutations in orthologs. In aspect, the present invention provides a viral vector comprising said polynucleotide sequence encoding a CRISPR-Cas enzyme and a selection marker or reporter.

In another aspect, the present invention provides a polynucleotide sequence as herein described, wherein the CRISPR-Cas enzyme further comprises a functional domain.

In another aspect, the present invention provides a polynucleotide sequence comprising:
  guide RNA, optionally sgRNA, that recognizes the target sequence in the DNA barcode of claim 1;
  a sequence encoding one or more adaptor proteins, each adaptor protein comprising at least one functional domain, optionally wherein the functional domain comprises a transcriptional activator; and
  a sequence encoding a selection marker or reporter.

In another aspect, the present invention provides a viral vector comprising provides a polynucleotide sequence comprising:
  guide RNA, optionally sgRNA, that recognizes the target sequence in the DNA barcode of claim 1;
  a sequence encoding one or more adaptor proteins, each adaptor protein comprising at least one functional domain, optionally wherein the functional domain comprises a transcriptional activator; and
  a sequence encoding a selection marker or reporter.

In some embodiments, the viral vector described herein is a retroviral vector, optionally a lentivirus, or an AAV vector.

In another aspect, the present invention provides a kit comprising one or two or three or more of the polynucleotide sequences described herein.

In an aspect, provided is a method of sorting one or more cells of interest from a mixed population of cells, the one or more cells of interest comprising a DNA barcode of interest, and the remaining cells in the population each comprising at least another DNA barcode or lacking a barcode, the cells comprising a CRISPR-Cas enzyme and one or more DNA barcodes, the or each DNA barcode comprising:
  a target recognizable by a CRISPR-Cas guide RNA;
  a PAM sequence for the CRISPR-Cas enzyme; and
  a selection marker or reporter under the control of (operably linked to) a suitable promoter;
the method comprising:
a. providing the mixed population of cells, including the one or more cells of interest;
b. providing a CRISPR-Cas guide RNA specific for the DNA barcode of interest and comprising a transcriptional activator;
c. delivering the CRISPR-Cas guide RNA to the population of cells so as to form a CRISPR-Cas complex in the one or more cells of interest,
the CRISPR-Cas complex comprising the CRISPR-Cas enzyme complexed with the CRISPR-Cas guide RNA and the DNA barcode of interest, thereby activating transcription (expression?) of the selection marker or reporter, comprised within the DNA barcode of interest, by the transcriptional activator comprised within the CRISPR-Cas guide RNA; and
d. separating the cells that express said selection marker or reporter from the remaining cells within the population that do not express said selection marker or reporter.

In an aspect, the one or both of the CRISPR-Cas enzyme and/or the CRISPR-Cas guide RNA comprise a functional domain, which is preferably a transcriptional activator. As such, in an aspect, provided is a method of sorting one or more cells of interest from a mixed population of cells, the one or more cells of interest comprising a DNA barcode of interest, and the remaining cells in the population each comprising at least other DNA barcode, the cells comprising a CRISPR-Cas enzyme comprising a transcriptional activator and one or more DNA barcodes, the or each DNA barcode comprising:
  a target recognizable by a CRISPR-Cas guide RNA;
  a PAM sequence for the CRISPR-Cas enzyme; and
  a selection marker or reporter under the control of (operably linked to) a suitable promoter;
the method comprising:
a. providing the mixed population of cells, including the one or more cells of interest;
b. providing a CRISPR-Cas guide RNA specific for the DNA barcode of interest;
c. delivering the CRISPR-Cas guide RNA to the population of cells so as to form a CRISPR-Cas complex in the one or more cells of interest,
the CRISPR-Cas complex comprising the CRISPR-Cas enzyme complexed with the CRISPR-Cas guide RNA and the DNA barcode of interest, thereby activating transcription (expression?) of the selection marker or reporter, comprised within the DNA barcode of interest, by the transcriptional activator comprised within the CRISPR-Cas guide RNA; and
d. separating the cells that express said selection marker or reporter from the remaining cells within the population that do not express said selection marker or reporter.

In an aspect, provided is a method of sorting one or more cells or nucleic acid molecules of interest from a mixed population of cells or nucleic acid molecules, the one or more cells or nucleic acid molecules of interest comprising a DNA barcode of interest, and optionally the remaining cells or nucleic acid molecules in the population each comprising at least another DNA barcode or lacking a barcode, the cells or nucleic acid molecules comprising a CRISPR-Cas enzyme and one or more DNA barcodes, the or each DNA barcode comprising:
  a target recognizable by a CRISPR-Cas guide RNA;
  a PAM sequence for the CRISPR-Cas enzyme; and
  a selection marker or reporter under the control of (operably linked to) a suitable promoter;
the method comprising:
a. providing the mixed population of cells or nucleic acid molecules, including the one or more cells or nucleic acid molecules of interest;
b. providing a CRISPR-Cas guide RNA specific for the DNA barcode of interest;
c. delivering the CRISPR-Cas guide RNA to the population of cells or nucleic acid molecules so as to form a CRISPR-Cas complex in the one or more cells of interest or with or one or more nucleic acid molecules of interest,
the CRISPR-Cas complex comprising the CRISPR-Cas enzyme complexed with the CRISPR-Cas guide RNA and the DNA barcode of interest, wherein said CRISPR enzyme creates a targeted insertion or deletion in the barcode of interest, wherein the insertion or deletion creates a frameshift within an open reading frame of a selection marker or reporter, thereby activating or inactivating function;

and d. separating the cells that express said selection marker or reporter or nucleic acid molecules that include the selection marker or reporter from the remaining cells or nucleic acid molecules within the population that do not express or include said selection marker or reporter.

In some embodiments, the method further comprises delivering the CRISPR-Cas enzyme to the cells so as to provide the mixed population of cells, including the one or more cells of interest, with the CRISPR-Cas enzyme.

In some embodiments, the method further comprises delivering the DNA barcodes, including the DNA barcode of interest, to the cells so as to provide the mixed population of cells, including the one or more cells of interest, with DNA barcodes.

In some embodiments, the cells of interest comprising a phenotype of interest. In some embodiments, the phenotype of interest is resistance to a drug or treatment of interest. In some embodiments, the phenotype of interest is susceptibility to a drug or treatment of interest.

In some embodiments, the cells of interest, and/or the remaining cells in the population of cells, are mammalian cells. In some embodiments, the cells of interest, and/or the remaining cells in the population of cells, are cancer cells.

In certain embodiments, cancer cells may be sorted using the compositions and methods described herein. A heterogeneous population of cancer cells may be transformed or transduced with the barcode constructs or vectors of the present invention to obtain a population of cancer cells, each with a single barcode reporter construct. The cancer cells may be expanded and the pool of expanded cells may be assayed, for example for drug resistance. Upon determination of enriched barcodes, optionally in individual cells, the cells may be recovered from a recovery pool of the expanded cells for further analysis. Not being bound by a theory, a single cell type may be assayed for resistance to a plurality of drugs by repeating the method of assaying and recovery of the cells, thus identifying cells with multiple resistance.

In some embodiments, the cells of interest, and/or the remaining cells in the population of cells, have been the subject of genome engineering or modification at a particular locus.

In some embodiments, the cells of interest, and/or the remaining cells in the population of cells, are a heterogeneous population of cells.

In some embodiments, the selection marker or reporter is a luminescent or fluorescent marker and, optionally, the cells of interest are separated by FACS.

In some embodiments, the selection marker or reporter confers drug resistance to the cells of interest and, optionally, the cells of interest are separate upon provision of said drug to the mixed population of cells.

In some embodiments, the selection marker or reporter is a surface protein and, optionally, the cells of interest are separated by FACS or magnetic sorting.

In some embodiments, the method further comprises testing cells that express the selection marker or reporter to confirm said cells are desired and/or testing cells that do not express the selection marker or reporter to confirm said cells are undesired.

In some embodiments, the method is non-destructive in respect of the cells of interest or the remaining cells of the mixed population.

In some embodiments, the population is a mixed population of cells of interest and the remaining cells. In some embodiments, recovery (or separation) of the cells of interest from the remaining cells is achieved through use of a Cas9 activator system (2: Konermann et al. 2014). In some embodiments, the Cas9 activator system is programmed to recognize (via the guide RNA).

In some embodiments, the Cas9 activator system comprises a CRISPR-Cas guide RNA that recruits a CRISPR-Cas enzyme to target the specific barcodes. In other words, the guide sequence of the guide RNA is programmed or generated to match and select for the DNA barcode of interest. All the DNA barcodes are typically operably linked to a selection marker or reporter.

One or both of the CRISPR-Cas enzyme and/or the CRISPR-Cas guide RNA comprise a functional domain, which is preferably a transcriptional activator.

In an alternative embodiment, one or both of the CRISPR-Cas enzyme and/or the CRISPR-Cas guide RNA comprise a functional domain, which is preferably a transcriptional repressor. In some embodiments, a repressor or nuclease could be used to disrupt expression of a negative selection marker. In some embodiments, the negative selection marker is conditional. In some embodiments, the negative selection marker is Cytosine deaminase.

The CRISPR-Cas complex comprises the CRISPR-Cas enzyme, the CRISPR-Cas guide RNA specific for the DNA barcode of interest, and said DNA barcode of interest. This CRISPR-Cas complex only forms in the presence of the DNA barcode of interest and so only in the cell or cells of interest bearing (comprising) that DNA barcode of interest.

Formation of the CRISPR-Cas complex effectively recruits a transcriptional activator to the DNA barcode of interest. As such, formation of the CRISPR-Cas complex leads to expression of the selection marker or reporter marker. Thus, the cells of interest can be separated from the remaining cells.

In some embodiments, the DNA barcodes are preferably introduced into the population via a cassette. In an aspect, provided is such a cassette.

The cassette comprises unique barcodes and a selection marker or reporter. In some embodiments, the selection marker or reporter is preferably a fluorescent protein. In some embodiments, the selection marker or reporter preferably confers antibiotic resistance. In some embodiments, the selection marker or reporter is preferably a luciferase protein. In some embodiments, one or more selection markers or reporters are provided, either multiple copies of the same selection marker or reporter, or a combination of different selection markers or reporters. In some embodiments the selection marker or reporter can be that which provides identification or selection based on binding or chemical reaction, such as an antigen or antibody, that may be further labeled so as to provide color or a magnetic bead.

In some embodiments, the cassette is preferably integrated into the population of cells, which is preferably heterogeneous.

In some embodiments, cells of interest containing one or more specific DNA barcodes of interest are preferably selected for by introducing a Cas9 activator system comprising a CRISPR-Cas enzyme and a CRISPR-Cas guide RNA, preferably a sgRNA, targeting one or more sequences within the barcode.

In some embodiments, selection is completed by traditional means, such as fluorescently-activated flow sorting (FACS), drug selection, or affinity purification via a surface epitope, depending on the selection marker or reporter.

In some embodiments, the method is applied to cell populations with natural heterogeneity, such as cancer cells.

In some embodiments, the method is applied to cell populations with engineered heterogeneity, such as cells modified through genome engineering.

The transcriptional activator may be VP64, p65, HSF1 or any combination thereof can be used, see Konermann et al. 2014. The transcriptional activator is a functional domain and preferred examples of functional domains are provided herein, noting that transcriptional activators are preferred.

Guidance is provided below in respect of guide length (the spacer or guide sequence). In some embodiments, for Sp, optimal guide length can vary as low as is necessary to achieve activation 10, 11, 12, 13, 14, 15 or 16 nucleotides in the case of dead guides. For example, this may be as low as 10 nucleotides, although it is also preferred in some embodiments to use a 'tru-guide', e.g., 17-nucleotides or a length corresponding thereto; and in some embodiments, for Sa, the optimal guide length may be 20 or 21 or 22 or 23 or 24 nucleotides in length (Ran 2015). In some embodiments, the CRISPR/Cas guide RNA may be a dead guide, preferably with a guide sequence of at least 10, 11, 12, 13, 14, 15 or 16 nucleotides, preferably in combination with an active CRISPR-Cas enzyme, preferably a Cas9 with nuclease (cutting) activity. This can be useful when, for example, as initial perturbation to produce heterogeneity requires a CRISPR-Cas enzyme (preferably a cas9) nuclease, or when follow-up engineering of sorted cells requires such a nuclease.

Also provided is a host cell or cell line. This may be an in vivo, ex vivo or in vitro host cell or cell line. The host cell or cell line may, in some embodiments, comprise or have been modified by the composition or enzyme according to the present invention. Also provided are progeny of said host cell or cell line. In some embodiments, the cells of the host cell, cell line or progeny are stem cells or a stem cell line. Methods, products and uses described herein may be used for non-therapeutic purposes. Furthermore, any of the methods described herein may be applied in vitro and ex vivo.

In relation to the guides in general, but specifically in respect of the sgRNA and the CRISPR complex formed therewith, it is preferable that the guide has one or more of the following features. In some embodiments, the tracr sequence has one or more hairpins and is 30 or more nucleotides in length, more preferably 40 or more nucleotides in length, or more preferably 50 or more nucleotides in length. In some embodiments, the guide sequence is between 10 to 30 nucleotides in length. In some embodiments, the CRISPR/Cas enzyme is a Type II Cas9 enzyme. In some embodiments, the tracr sequence has one or more hairpins and is 30 or more nucleotides in length, more preferably 40 or more nucleotides in length, or more preferably 50 or more nucleotides in length, the guide sequence is between 10 to 30 nucleotides in length and the CRISPR/Cas enzyme is a Type II Cas9 enzyme.

In aspect, the present invention provides a cell population resulting from any of the methods described herein.

In aspect, the present invention provides a library of cells from any of the methods as herein described.

In aspect, the present invention provides a cell or cell line of the methods as herein described.

In aspect, the present invention provides a library, for example an oligonucleotide library, comprising two or more of the polynucleotides as herein described.

In aspect, the present invention provides an expression cassette comprising one or more of the polynucleotides as herein described.

In aspect, the present invention provides a delivery cassette comprising one or more of the polynucleotides as herein described.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 3: Sample barcode sequences: the lower case letters are PAMs for SpCas9, and the uppercase letters are 20 ntd stretches representing target sequences for the guide RNA. Figure discloses SEQ ID NOS 70-72, respectively, in order of appearance.

FIG. 4A1-4C2: Barcode construct example sequence: barcode sequences (such as shown in FIG. 3) can be cloned into the vector via BsmBI sites. Figure discloses SEQ ID NO: 73.

FIG. 7: Example double stranded DNA sequence that can be targeted by a nuclease to 3 overlapping sgRNA barcodes, labeled sg_0, sg_1 and sg_2. The amino acid sequence of the protein translated from the in frame open reading frame is shown below. This construct can be used for multiplex retrieval of all 3 barcodes. Figure discloses SEQ ID NOS 74-76, respectively, in order of appearance.

DETAILED DESCRIPTION OF THE INVENTION

Figure 1:
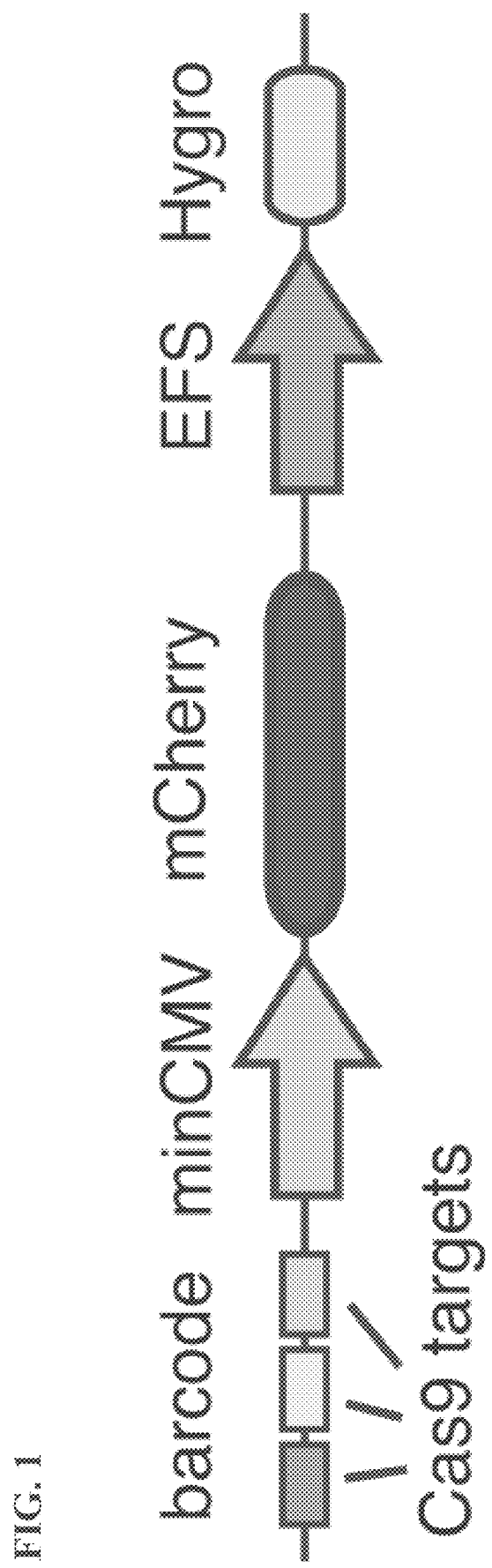
FIG. 1: Barcode construct containing 3 Cas9 targets. The DNA barcode is shown on the left, with a minCMV minimal promoter and an mCherry fluorescent reporter; together with a first drug selection marker (Hygro, inferring resistance to Hygromycin) under the control of an EFS promoter.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 6/10/14; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055,484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 14, PROTECTED GUIDE RNAS (PGRNAS); U.S. application 62/096,708, 24 Dec. 14, PROTECTED GUIDE RNAS (PGRNAS); U.S. application 62/091,462, 12 Dec. 14, DEAD GUIDES FOR CRISPR TRANSCRIPTION FACTORS; U.S. application 62/096,324, 23 Dec. 14, DEAD GUIDES FOR CRISPR TRANSCRIPTION FAC- TORS; U.S. application 62/091,456, 12 Dec. 14, ESCORTED AND FUNCTIONALIZED GUIDES FOR CRISPR-CAS SYSTEMS; U.S. application 62/091,461, 12 Dec. 14, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 14, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 14, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 14, RNA-TARGETING SYSTEM; U.S. application 62/096,656, 24 Dec. 14, CRISPR HAVING OR ASSOCIATED WITH DESTABILIZATION DOMAINS; U.S. application 62/096,697, 24 Dec. 14, CRISPR HAVING OR ASSOCIATED WITH AAV; U.S. application 62/098,158, 30 Dec. 14, ENGINEERED CRISPR COMPLEX INSERTIONAL TARGETING SYSTEMS; U.S. application 62/151,052, 22 Apr. 15, CELLULAR TARGETING FOR EXTRACELLULAR EXOSOMAL REPORTING; U.S. application 62/054,490, 24 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 14, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 14, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 14, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 14, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 14, FUNCTIONAL SCREENING WITH OPTIMIZED FUNCTIONAL CRISPR-CAS SYSTEMS; U.S. application 62/055,487, 25 Sep. 14, FUNCTIONAL SCREENING WITH OPTIMIZED FUNCTIONAL CRISPR-CAS SYSTEMS; U.S. application 62/087,546, 4 Dec. 14, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 14, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science Feb. 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4):910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463):472-6. doi: 10.1038/Nature 12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure™, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014);

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh 00, Barcena C, Hsu P D, Habib N, Gootenberg J S, Nishimasu H, Nureki O, Zhang F., Nature. January 29; 517(7536):583-8 (2015);

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520 (7546):186-91 (2015);

Shalem et al., "High-throughput functional genomics using CRISPR-Cas9," Nature Reviews Genetics 16, 299-311 (May 2015);

Xu et al., "Sequence determinants of improved CRISPR sgRNA design," Genome Research 25, 1147-1157 (August 2015);

Parnas et al., "A Genome-wide CRISPR Screen in Primary Immune Cells to Dissect Regulatory Networks," Cell 162, 675-686 (Jul. 30, 2015);

Ramanan et al., CRISPR/Cas9 cleavage of viral DNA efficiently suppresses hepatitis B virus," Scientific Reports 5:10833. doi: 10.1038/srep10833 (Jun. 2, 2015);

Nishimasu et al., Crystal Structure of *Staphylococcus aureus* Cas9," Cell 162, 1113-1126 (Aug. 27, 2015);

Zetsche et al., "Cpfl Is a Single RNA-Guided Endonuclease of a Class 2 CRISPR-Cas System," Cell 163, 1-13 (Oct. 22, 2015);

Shmakov et al., "Discovery and Functional Characterization of Diverse Class 2 CRISPR-Cas Systems," Molecular Cell 60, 1-13 (Available online Oct. 22, 2015);

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knock-out (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 Å° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Zetsche et al. (2015) reported the characterization of Cpf1, a putative class 2 CRISPR effector. It was demonstrated that Cpf1 mediates robust DNA interference with features distinct from Cas9. Identifying this mechanism of interference broadens our understanding of CRISPR-Cas systems and advances their genome editing applications.

Shmakov et al. (2015) reported the characterization of three distinct Class 2 CRISPR-Cas systems. The effectors of two of the identified systems, C2c1 and C2c3, contain RuvC like endonuclease domains distantly related to Cpf1. The third system, C2c2, contains an effector with two predicted HEPN RNase domains.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, Calif.), SOAP (available at soap.genomics.org.cn), and Maq (available at maq.source-forge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10-30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form MMMMMMMMNNNNNNNNNNNNXGG (SEQ ID NO: 1) where NNNNNNNNNNNNXGG (SEQ ID NO: 2) (N is A, G, T, or C; and X can be anything) has a single occurrence in the genome. A unique target sequence in a genome may include an S. pyogenes Cas9 target site of the form MMMMMMMMMNNNNNNNNNNNXGG (SEQ ID NO: 3) where NNNNNNNNNNNXGG (SEQ ID NO: 4) (N is A, G, T, or C; and X can be anything) has a single occurrence in the genome. For the S. thermophilus CRISPR1 Cas9, a unique target sequence in a genome may include a Cas9 target site of the form MMMMMMMMNNNNNNNNNNNNXXAGAAW (SEQ ID NO: 5) where NNNNNNNNNNNNXXAGAAW (SEQ ID NO: 6) (N is A, G, T, or C; X can be anything; and W is A or T) has a single occurrence in the genome. A unique target sequence in a genome may include an S. thermophilus CRISPR1 Cas9 target site of the form MMMMMMMMMNNNNNNNNNNNXXAGAAW (SEQ ID NO: 7) where NNNNNNNNNNNXXAGAAW (SEQ ID NO: 8) (N is A, G, T, or C; X can be anything; and W is A or T) has a single occurrence in the genome. For the S. pyogenes Cas9, a unique target sequence in a genome may include a Cas9 target site of the form MMMMMMMMNNNNNNNNNNNNXGGXG (SEQ ID NO: 9) where NNNNNNNNNNNNXGGXG (SEQ ID NO: 10) (N is A, G, T, or C; and X can be anything) has a single occurrence in the genome. A unique target sequence in a genome may include an S. pyogenes Cas9 target site of the form MMMMMMMMMNNNNNNNNNNNXGGXG (SEQ ID NO: 11) where NNNNNNNNNNNXGGXG (SEQ ID NO: 12) (N is A, G, T, or C; and X can be anything) has a single occurrence in the genome. In each of these sequences "M" may be A, G, T, or C, and need not be considered in identifying a sequence as unique. In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and PA Carr and GM Church, 2009, Nature Biotechnology 27(12): 1151-62).

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgttttgtactctcaagatt-taGAAAtaaatcttgcagaagctacaaagataa ggcttcatgccgaaat-caacaccctgtcattttatggcagggtgttttcgttatttaaTTTTTT (SEQ ID NO: 13); (2) NNNNNNNNNNNNNNNNNNNNgttttgtactctcaGAA Atgcagaagctacaaagataaggcttcatgccg aaatcaacaccctgtcattt-tatggcagggtgttttcgttatttaaTTTTTT (SEQ ID NO: 14); (3) NNNNNNNNNNNNNNNNNNNNgttttgtactctca GAAAtgcagaagctacaaagataaggcttcatgccg aaatcaacaccctgt-cattttatggcagggtgtTTTTTT (SEQ ID NO: 15); (4) NNNNNNNNNNNNNNNNNNNNgttt-tagagctaGAAAtagcaagttaaaataaggctagtccgttatcaactt gaaaaagtggcaccgagtcggtgcTTTTTT (SEQ ID NO: 16); (5) NNNNNNNNNNNNNNNNNNNNgttt-tagagctaGAAATAGcaagttaaaataaggctagtccgttatcaac ttgaaaaagtgTTTTTTT (SEQ ID NO: 17); and (6)

NNNNNNNNNNNNNNNNNNNNNgttt-tagagctagAAATAGcaagttaaaataaggctagtccgttatcaTTTTTTT (SEQ ID NO: 18). In some embodiments, sequences (1) to (3) are used in combination with Cas9 from S. thermophilus CRISPR1. In some embodiments, sequences (4) to (6) are used in combination with Cas9 from S. pyogenes. In some embodiments, the tracr sequence is a separate transcript from a transcript comprising the tracr mate sequence.

In some embodiments, candidate tracrRNA may be subsequently predicted by sequences that fulfill any or all of the following criteria: 1. sequence homology to direct repeats (motif search in Geneious with up to 18-bp mismatches); 2. presence of a predicted Rho-independent transcriptional terminator in direction of transcription; and 3. stable hairpin secondary structure between tracrRNA and direct repeat. In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the direct repeat and tracrRNA.

For minimization of toxicity and off-target effect, it may be important to control the concentration of CRISPR enzyme mRNA and guide RNA delivered. Optimal concentrations of CRISPR enzyme mRNA and guide RNA can be determined by testing different concentrations in a cellular or non-human eukaryote animal model and using deep sequencing the analyze the extent of modification at potential off-target genomic loci. For example, for the guide sequence targeting 5'-GAGTCCGAGCAGAAGAAGAA-3' (SEQ ID NO: 19) in the EMX1 gene of the human genome, deep sequencing can be used to assess the level of modification at the following two off-target loci, 1: 5'-GAGTCCTAGCAGGAGAAGAA-3' (SEQ ID NO: 20) and 2: 5'-GAGTCTAAGCAGAAGAAGAA-3' (SEQ ID NO: 21). The concentration that gives the highest level of on-target modification while minimizing the level of off-target modification should be chosen for in vivo delivery. Alternatively, to minimize the level of toxicity and off-target effect, CRISPR enzyme nickase mRNA (for example S. pyogenes Cas9 with the D10A mutation) can be delivered with a pair of guide RNAs targeting a site of interest. The two guide RNAs need to be spaced as follows. Guide sequences and strategies to minimize toxicity and off-target effects can be as in WO 2014/093622 (PCT/US2013/074667).

The CRISPR system is derived advantageously from a type II CRISPR system. In some embodiments, one or more elements of a CRISPR system is derived from a particular organism comprising an endogenous CRISPR system, such as Streptococcus pyogenes. In preferred embodiments of the invention, the CRISPR system is a type II CRISPR system and the Cas enzyme is Cas9, which catalyzes DNA cleavage. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof.

In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from S. pyogenes converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred. Orthologs of SpCas9 can be used in the practice of the invention. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 (S. pyogenes Cas9) or saCas9 (S. aureus Cas9). StCas9" refers to wild type Cas9 from S. thermophilus, the protein sequence of which is given in the SwissProt database under accession number G3ECR1. Similarly, S. pyogenes Cas9 or spCas9 is included in SwissProt under accession number Q99ZW2. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR locus in Streptococcus pyogenes. However, it will be appreciated that this invention includes many more Cas9s from other species of microbes, such as SpCas9, SaCa9, St1Cas9 and so forth. Enzymatic action by Cas9 derived from Streptococcus pyogenes or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon. The CRISPR system: small RNA-guided defence in bacteria and archaea, Mole Cell 2010, January 15; 37(1): 7. The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. A pre-crRNA array consisting of a single spacer flanked by two direct repeats (DRs) is also encompassed by the term "tracr-mate sequences"). In certain embodiments, Cas9 may be constitutively present or inducibly present or conditionally present or administered or delivered. Cas9 optimization may be used to enhance function or to develop new functions, one can generate chimeric Cas9 proteins. And Cas9 may be used as a generic DNA binding protein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 22); the NLS from nucleoplasmin (e.g. the nucleoplasmin bipartite NLS with the sequence KRPAATKKAGQAKKKK (SEQ ID NO: 23)); the c-myc NLS having the amino acid sequence PAAKRVKLD (SEQ ID NO: 24) or RQRRNELKRSP (SEQ ID NO: 25); the hRNPA1 M9 NLS having the sequence NQSSNFGPMKGGNFGGRSSGPYGGGGQYFAKPRNQGGY (SEQ ID NO: 26); the sequence RMRIZFKNKGKDTAELRRRRVEVS- VELRKAKKDEQILKRRNV (SEQ ID NO: 27) of the IBB domain from importin-alpha; the sequences VSRKRPRP (SEQ ID NO: 28) and PPKKARED (SEQ ID NO: 29) of the myoma T protein; the sequence PQPKKKPL (SEQ ID NO: 30) of human p53; the sequence SALIKKKKKMAP (SEQ ID NO: 31) of mouse c-abl IV; the sequences DRLRR (SEQ ID NO: 32) and PKQKKRK (SEQ ID NO: 33) of the influenza virus NS1; the sequence RKLKKKIKKL (SEQ ID NO: 34) of the Hepatitis virus delta antigen; the sequence REKKKFLKRR (SEQ ID NO: 35) of the mouse Mx1 protein; the sequence KRKGDEVDGVDEVAKKKSKK (SEQ ID NO: 36) of the human poly(ADP-ribose) polymerase; and the sequence RKCLQAGMNLEARKTKK (SEQ ID NO: 37) of the steroid hormone receptors (human) glucocorticoid. In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein. Only sgRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity. Since Cas9n and Cas9H840A nick opposite strands of DNA, substitution of Cas9n with Cas9H840A with a given sgRNA pair should have resulted in the inversion of the overhang type; but no indel formation is observed as with Cas9H840A indicating that Cas9H840A is a CRISPR enzyme substantially lacking all DNA cleavage activity (which is when the DNA cleavage activity of the mutated enzyme is about no more than 25%, 10%, 5%, 1%, 0.1%, 0.01%, or less of the DNA cleavage activity of the non-mutated form of the enzyme; whereby an example can be when the DNA cleavage activity of the mutated form is nil or negligible as compared with the non-mutated form, e.g., when no indel formation is observed as with Cas9H840A in the eukaryotic system in contrast to the biochemical or prokaryotic systems). Nonetheless, a pair of sgRNAs that will generate a 5' overhang with Cas9n should in principle generate the corresponding 3' overhang instead, and double nicking. Therefore, sgRNA pairs that lead to the generation of a 3' overhang with Cas9n can be used with another mutated Cas9 to generate a 5' overhang, and double nicking. Accordingly, in some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Or, RNA(s) of the CRISPR System can be delivered to a transgenic Cas9 animal or mammal, e.g., an animal or mammal that constitutively or inducibly or conditionally expresses Cas9; or an animal or mammal that is otherwise expressing Cas9 or has cells containing Cas9, such as by way of prior administration thereto of a vector or vectors that code for and express in vivo Cas9. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter. Delivery vehicles, vectors, particles, nanoparticles, formulations and components thereof for expression of one or more elements of a CRISPR system are as used in the foregoing documents, such as WO 2014/093622 (PCT/US2013/074667). In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding a CRISPR enzyme, such as a Cas protein. CRISPR enzyme or CRISPR enzyme mRNA or CRISPR guide RNA or RNA(s) can be delivered separately; and advantageously at least one of these is delivered via a nanoparticle complex. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA. Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA. Additional administrations of CRISPR enzyme mRNA and/or guide RNA might be useful to achieve the most efficient levels of genome modification.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence. In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell. The break created by the CRISPR complex can be repaired by a repair processes such as the error prone non-homologous end joining (NHEJ) pathway or the high fidelity homology-directed repair (HDR). During these repair process, an exogenous polynucleotide template can be introduced into the genome sequence. In some methods, the HDR process is used modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome. Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer. The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function. The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence. An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp. In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996). In a method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template. In other embodiments, this invention provides a method of modifying expression of a polynucleotide in a eukaryotic cell. The method comprises increasing or decreasing expression of a target polynucleotide by using a CRISPR complex that binds to the polynucleotide. In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA).

The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). The tareget can be a control element or a regulatory element or a promoter or an enhancer or a silencer. The promoter may, in some embodiments, be in the region of +200 bp or even +1000 bp from the TTS. In some embodiments, the regulatory region may be an enhancer. The enhancer is typically more than +1000 bp from the TTS. More in particular, expression of eukaryotic protein-coding genes generally is regulated through multiple cis-acting transcription-control regions. Some control elements are located close to the start site (promoter-proximal elements), whereas others lie more distant (enhancers and silencers) Promoters determine the site of transcription initiation and direct binding of RNA polymerase II. Three types of promoter sequences have been identified in eukaryotic DNA. The TATA box, the most common, is prevalent in rapidly transcribed genes. Initiator promoters infrequently are found in some genes, and CpG islands are characteristic of transcribed genes. Promoter-proximal elements occur within ~200 base pairs of the start site. Several such elements, containing up to ~20 base pairs, may help regulate a particular gene. Enhancers, which are usually ~100-200 base pairs in length, contain multiple 8- to 20-bp control elements. They may be located from 200 base pairs to tens of kilobases upstream or downstream from a promoter, within an intron, or downstream from the final exon of a gene. Promoter-proximal elements and enhancers may be cell-type specific, functioning only in specific differentiated cell types. However, any of these regions can be the target sequence and are encompassed by the concept that the target can be a control element or a regulatory element or a promoter or an enhancer or a silencer.

Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence) Examples of PAM sequences are given in the examples section below, and the skilled person will be able to identify further PAM sequences for use with a given CRISPR enzyme. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention. In one aspect, the invention provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

Indeed, in any aspect of the invention, the CRISPR complex may comprise a CRISPR enzyme complexed with a guide sequence hybridized to a target sequence, wherein said guide sequence may be linked to a tracr mate sequence which in turn may hybridize to a tracr sequence.

The invention relates to the engineering and optimization of systems, methods and compositions used for the control of gene expression involving sequence targeting, such as genome perturbation or gene-editing, that relate to the CRISPR-Cas system and components thereof. In advantageous embodiments, the Cas enzyme is Cas9. An advantage of the present methods is that the CRISPR system minimizes or avoids off-target binding and its resulting side effects. This is achieved using systems arranged to have a high degree of sequence specificity for the target DNA.

The tracr sequence may be referred to as the tracrRNA. In some embodiments, it may be at least 30, at least 40 or at least 50 nucleotides in length. In relation to a CRISPR-Cas complex or system preferably, the tracr sequence has one or more hairpins and is 30 or more nucleotides in length, 40 or more nucleotides in length, or 50 or more nucleotides in length; the guide sequence is between 10 to 30 nucleotides in length, the CRISPR/Cas enzyme is a Type II Cas9 enzyme.

One guide with a first aptamer/RNA-binding protein pair can be linked or fused to an activator, whilst a second guide with a second aptamer/RNA-binding protein pair can be linked or fused to a repressor. The guides are for different targets (loci), so this allows one gene to be activated and one repressed. For example, the following schematic shows such an approach:

Guide 1-MS2 aptamer - - - MS2 RNA-binding protein - - - VP64 activator; and
Guide 2-PP7 aptamer - - - PP7 RNA-binding protein - - - SID4x repressor.

In an aspect, provided is a non-naturally occurring or engineered composition comprising:

I. two or more CRISPR-Cas system polynucleotide sequences comprising (a) a first CRISPR-Cas guide RNA sequence capable of hybridizing to a first target sequence in a polynucleotide locus which is comprised within a first DNA barcode of interest as described herein, (b) a CRISPR-Cas guide RNA guide sequence capable of hybridizing to a second target sequence in a polynucleotide locus which is comprised within a second DNA barcode of interest as described herein, (c) a tracr mate sequence, and (d) a tracrRNA sequence, and II. a CRISPR-Cas enzyme (preferably a Type II Cas9 enzyme) or a second polynucleotide sequence encoding it as described herein, wherein one or both of the CRISPR-Cas enzyme and/or the CRISPR-Cas guide RNA comprise a functional domain, which is preferably a transcriptional activator, wherein when transcribed, the first and the second tracr mate sequences hybridize to the first and second tracrRNA sequences respectively and the first and the second guide sequences direct sequence-specific binding of a first and a second CRISPR complex to the first and second target sequences respectively, wherein the first CRISPR-Cas complex comprises the CRISPR-Cas enzyme complexed with (1) the first CRISPR-Cas guide RNA sequence that is hybridizable to the first target sequence in the first DNA barcode of interest, and (2) the first tracr mate sequence that is hybridized to the first tracrRNA sequence, wherein the second CRISPR-Cas complex comprises the CRISPR-Cas enzyme complexed with (1) the second CRISPR-Cas guide RNA sequence that is hybridizable to the second target sequence in the second DNA barcode of interest, and (2) the second tracr mate sequence that is hybridized to the second tracrRNA sequence, and wherein the formation of the first and second CRISPR-Cas complexes directs transcriptional activation of a first or a second selection marker or reporter, preferably both.

In an aspect, the CRISPR-Cas enzyme is a dead Cas, preferably a dead Cas9 (dCas9). A dual dCas9 approach is favoured. In some embodiments, the dCas9 may comprising mutations at D10 and N863 in SpCas9, D10 or N580 in SaCas9 or corresponding mutations in orthologs. Other examples are known in the art.

Optimal overhang lengths are described herein for use with dual dead Cas9s, but range from 1 to 10, 20, 30, 40, 50, 60, 70, 80, 90, or 100, such as 1 to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides on each 3' overhanging end. The offset between the 5' end of each of guide pair is, in some embodiments 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 nucleotides. Ranges of around 15-60, 16-60, 17-60, 18-60, 19-60, 20-60, 21-60, 22-60, 23-60, 24-60, 25-60, 15-55, 16-55, 17-55, 18-55, 19-55, 20-55, 21-55, 22-55, 23-55, 24-, 25-55, 35-60, 15-40, 16-40, 17-40, 18-40, 19-40, 20-40, 21-40, 22-40, 23-40, 24-40, 25-40, 15-45, 16-45, 17-45, 18-45, 19-45, 20-45, 21-45, 22-45, 23-45, 24-45, 25-45, 30-50, 35-55, and especially 35-45 are also preferred in some embodiments.

In an aspect, the present cell populations are host cells or cell lines and may have been modified by or comprising the CRISPR-Cas compositions, systems or modified enzymes. The present populations may include stem cells. In an aspect, provided are progeny of the present populations (including the cells of interest) thereof. In an aspect, methods of cellular therapy are provided, where, for example, a single cell or a population of cells is separated, optionally cultured, and is then re-introduced (sampled cells) or introduced (cultured cells) into the organism. Stem cells, whether embryonic or induced pluripotent or totipotent stem cells, are also particularly preferred in this regard. But, of course, in vivo embodiments are also envisaged. Inventive methods can further comprise delivery of templates, such as repair templates, which may be dsODN or ssODN. Delivery of templates may be via the cotemporaneous or separate from delivery of any or all the CRISPR enzyme, guide, tracr mate or tracrRNA and via the same delivery mechanism or different. In some embodiments, it is preferred that the template is delivered together with the guide, tracr mate and/or tracrRNA and, preferably, also the CRISPR enzyme. An example may be an AAV vector where the CRISPR enzyme is SaCas9 (with the N580 mutation).

In some embodiments, one or more functional domains are associated with an adaptor protein, for example as used with the modified guides of Konnerman et al. (Nature 517, 583-588, 29 Jan. 2015). A functional domain can be a functional domain associated with the CRISPR enzyme or a functional domain associated with the adaptor protein. In some embodiments, the one or more functional domains is an NLS (Nuclear Localization Sequence) or an NES (Nuclear Export Signal). In some embodiments, the one or more functional domains is a transcriptional activation domain comprises VP64, p65, MyoD1, HSF1, RTA, SET7/9 and a histone acetyltransferase. Other references herein to activation (or activator) domains in respect of those associated with the CRISPR enzyme include any known transcriptional activation domain and specifically VP64, p65, MyoD1, HSF1, RTA, SET7/9 or a histone acetyltransferase. In some embodiments, the one or more functional domains is a transcriptional repressor domain. In some embodiments, the transcriptional repressor domain is a KRAB domain. In some embodiments, the transcriptional repressor domain is a NuE domain, NcoR domain, SID domain or a SID4X domain. In some embodiments, the one or more functional domains have one or more activities comprising methylase activity, demethylase activity, transcription activation activity, transcription repression activity, transcription release factor activity, histone modification activity, RNA cleavage activity, DNA cleavage activity, DNA integration activity or nucleic acid binding activity. Histone modifying domains are also preferred in some embodiments. Exemplary histone modifying domains are discussed below. Transposase domains, HR (Homologous Recombination) machinery protein so that upon binding of the CRISPR enzyme to the sgRNA and target, the functional domain is in a spatial orientation allowing for the functional domain to function in its attributed function. In an aspect the invention provides a composition as herein discussed wherein the one or more functional domains is attached to the CRISPR enzyme or adaptor protein via a linker, optionally a GlySer linker. Endogenous transcriptional repression is often mediated by chromatin modifying enzymes such as histone methyltransferases (HMTs) and deacetylases (HDACs). Repressive histone effector domains are known and an exemplary list is provided below. In the exemplary table, preference was given to proteins and functional truncations of small size to facilitate efficient viral packaging (for instance via AAV). In general, however, the domains may include HDACs, histone methyltransferases (HMTs), and histone acetyltransferase (HAT) inhibitors, as well as HDAC and HMT recruiting proteins. The functional domain may be or include, in some embodiments, HDAC Effector Domains, HDAC Recruiter Effector Domains, Histone Methyltransferase (HMT) Effector Domains, Histone Methyltransferase (HMT) Recruiter Effector Domains, or Histone Acetyltransferase Inhibitor Effector Domains.

TABLE 1

HDAC Effector Domains

| Subtype/Complex | Name | Substrate (if known) | Modification (if known) | Organism | Full size (aa) | Selected truncation (aa) | Final size (aa) | Catalytic domain |
|---|---|---|---|---|---|---|---|---|
| HDAC I | HDAC8 | — | — | X. laevis | 325 | 1-325 | 325 | 1-272: HDAC |
| HDAC I | RPD3 | — | — | S. cerevisiae | 433 | 19-340 (Vannier) | 322 | 19-331: MAC |
| MAC IV | MesoLo4 | — | — | M. loti | 300 | 1-300 (Gregoretti) | 300 | — |
| HDAC IV | HDAC11 | — | — | H. sapiens | 347 | 1-347 (Gao) | 347 | 14-326: HDAC |
| HD2 | HDT1 | — | — | A. thaliana | 245 | 1-211 (Wu) | 211 | — |
| SIRT I | SIRT3 | H3K9Ac H4K16Ac H3K56Ac | — | H. sapiens | 399 | 143-399 (Scher) | 257 | 126-382: SIRT |
| SIRT I | HST2 | — | — | C. albicans | 331 | 1-331 (Hnisz) | 331 | — |
| SIRT I | CobB | — | — | E. coli (K12) | 242 | 1-242 (Landry) | 742 | — |
| SIRT I | HST2 | — | — | S. cerevisiae | 357 | 8-298 (Wilson) | 291 | — |
| SIRT III | STRT5 | H4K8Ac H4K16Ac | — | H. sapiens | 310 | 37-310 (Gertz) | 274 | 41-309: SIRT |
| SIRT III | Sir2A | — | — | P. falciparum | 273 | 1-273 (Zhu) | 273 | 19-273: SIRT |
| SIRT IV | SIRT6 | H3K9Ae H3K56Ac | — | H. sapiens | 355 | 1-289 (Tennen) | 289 | 35-274: SIRT | domains, recombinase domains, and/or integrase domains are also preferred as the present functional domains. In some embodiments, DNA integration activity includes HR machinery domains, integrase domains, recombinase domains and/or transposase domains. Histone acetyltransferases are preferred in some embodiments. In some embodiments, the DNA cleavage activity is due to a nuclease. In some embodiments, the nuclease comprises a Fok1 nuclease. In some embodiments, the one or more functional domains is attached to the CRISPR enzyme so that upon binding to the sgRNA and target the functional domain is in a spatial orientation allowing for the functional domain to function in its attributed function. In some embodiments, the one or more functional domains is attached to the adaptor Accordingly, the repressor domains of the present invention may be selected from histone methyltransferases (HMNTs), histone deacetylases (HIDACs), histone acetyltransferase (HAT) inhibitors, as well as THDAC and HMNT recruiting proteins. The THDAC domain may be any of those in the table above, namely: HIDAC8, RPD3, MesoLo4, THDAC11, HIDT1, STRT3, HST2, CobB, HST2, SIRT5, Sir2A, or SIRT6.

In some embodiment, the functional domain may be a THDAC Recruiter Effector Domain. Preferred examples include those in the Table below, namely MeCP2, MBD2b, Sin3a, NcoR, SALL1, RCOR1. NcoR is exemplified in the present Examples and, although preferred, it is envisaged that others in the class will also be useful.

TABLE 2

Table of HDAC Recruiter Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| Sin3a | MeCP2 | — | — | R. norvegicus | 492 | 207-492 (Nan) | 286 | — |
| Sin3a | MBD2b | — | — | H. sapiens | 262 | 45-262 (Boeke) | 218 | — |
| Sin3a | Sin3a | — | — | H. sapiens | 1273 | 524-851 (Laherty) | 328 | 627-829: HDAC1 interaction |
| NcoR | NcoR | — | — | H. sapiens | 2440 | 420-488 (Zhang) | 69 | — |
| NuRD | SALL1 | — | — | M. musculus | 1322 | 1-93 (Lauberth) | 93 | — |
| CoREST | RCOR1 | — | — | H. sapiens | 482 | 81-300 (Gu, Ouyang) | 220 | — |

In some embodiment, the functional domain may be a Methyltransferase (tyT) Effector Domain. Preferred examples include those in the Table below, namely NUE, vSET, EHMT2/G9A, SUV39H1, dim-5, KYP, SUVR4, SET4, SET1, SETD8, and TgSET8. NUE is exemplified in the present Examples and, although preferred, it is envisaged that others in the class will also be useful.

TABLE 3

Table of Histone Methyltransferase (HMT) Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| SET | NUE | H2B, H3, H4 | — | C. trachomatis | 219 | 1-219 (Pennini) | 219 | — |
| SET | vSET | — | H3K27me3 | P. bursaria chlorella virus | 119 | 1-119 (Mujtaba) | 119 | 4-112: SET2 |
| SUV39 family | EHMT2/ G9A | H1.4K2, H3K9, H3K27 | H3K9me1/2, H1K25me1 | M. musculus | 1263 | 969-1263 (Tachibana) | 295 | 1025-1233: preSET, SET, postSET |
| SUV39 | SUV39H1 | — | H3K9me2/3 | H. sapiens | 412 | 79-412 (Snowden) | 334 | 172-412: preSET, SET, postSET |
| Suvar3-9 | dim-5 | — | H3K9me3 | N. crassa | 331 | 1-331 (Rathert) | 331 | 77-331: preSET, SET, postSET |
| Suvar3-9 (SUVH subfamily) | KYP | — | H3K9me1/2 | A. thaliana | 624 | 335-601 (Jackson) | 267 | — |
| Suvar3-9 (SUVR subfamily) | SUVR4 | H3K9me1 | H3K9me2/3 | A. thaliana | 492 | 180-492 (Thorstensen) | 313 | 192-462: preSET, SET, postSET |
| Suvar4-20 | SET4 | — | H4K20me3 | C. elegans | 288 | 1-288 (Vielle) | 288 | — |
| SET8 | SET1 | — | H4K20me1 | C. elegans | 242 | 1-242 (Vielle) | 242 | — |
| SET8 | SETD8 | — | H4K20me1 | H. sapiens | 393 | 185-393 (Couture) | 209 | 256-382: SET |
| SET8 | TgSET8 | — | H4K20me1/ 2/3 | T. gondii | 1893 | 1590-1893 (Sautel) | 304 | 1749-1884: SET |

In some embodiment, the functional domain may be a Histone Methyltransferase (HMT) Recruiter Effector Domain. Preferred examples include those in the Table below, namely Hp1a, PHF19, and NIPP1.

readout by e.g. RNAseq or microarray. This would allow for the identification of likely candidate genes involved in the disease phenotype. Such candidate genes could be useful as novel drug targets.

TABLE 4

Table of Histone Methyltransferase (HMT) Recruiter Effector Domains

| Subtype/Complex | Name | Substrate (if known) | Modification (if known) | Organism | Full size (aa) | Selected truncation (aa) | Final size (aa) | Catalytic domain |
|---|---|---|---|---|---|---|---|---|
| — | Hp1a | — | H3K9me3 | *M. musculus* | 191 | 73-191 | 119 (Hathaway) | 121-179: chromoshadow |
| — | PHF19 | — | H3K27me3 | *H. sapiens* | 580 | (1-250) + GGSG linker (SEQ ID NO: 38) + (500-580) | 335 (Ballaré) | 163-250: PHD2 |
| — | NIPP1 | — | H3K27me3 | *H. sapiens* | 351 | 1-329 (Jin) | 329 | 310-329: EED |

In some embodiment, the functional domain may be Histone Acetyltransferase Inhibitor Effector Domain. Preferred examples include SET/TAF-103 listed in the Table below.

Histone acetyltransferase (HAT) inhibitors are mentioned herein. However, an alternative in some embodiments is for the one or more functional domains to comprise an acetyltransferase, preferably a histone acetyltransferase. These are

TABLE 5

Table of Histone Acetyltransferase Inhibitor Effector Domains

| Subtype/Complex | Name | Substrate (if known) | Modification (if known) | Organism | Full size (aa) | Selected truncation (aa) | Final size (aa) | Catalytic domain |
|---|---|---|---|---|---|---|---|---|
| — | SET/TAF-1β | — | — | *M. musculus* | 289 | 1-289 (Cervoni) | 289 | — |

It is also preferred to target endogenous (regulatory) control elements (such as enhancers and silencers) in addition to a promoter or promoter-proximal elements. Thus, the invention can also be used to target endogenous control elements (including enhancers and silencers) in addition to targeting of the promoter. These control elements can be located upstream and downstream of the transcriptional start site (TSS), starting from 200 bp from the TSS to 100 kb away. Targeting of known control elements can be used to activate or repress the gene of interest. In some cases, a single control element can influence the transcription of multiple target genes. Targeting of a single control element could therefore be used to control the transcription of multiple genes simultaneously. Targeting of putative control elements on the other hand (e.g. by tiling the region of the putative control element as well as 200 bp up to 100 kB around the element) can be used as a means to verify such elements (by measuring the transcription of the gene of interest) or to detect novel control elements (e.g. by tiling 100 kb upstream and downstream of the TSS of the gene of interest). In addition, targeting of putative control elements can be useful in the context of understanding genetic causes of disease. Many mutations and common SNP variants associated with disease phenotypes are located outside coding regions. Targeting of such regions with either the activation or repression systems described herein can be followed by readout of transcription of either a) a set of putative targets (e.g. a set of genes located in closest proximity to the control element) or b) whole-transcriptome useful in the field of epigenomics, for example in methods of interrogating the epigenome. Methods of interrogating the epigenome may include, for example, targeting epigenomic sequences. Targeting epigenomic sequences may include the guide being directed to an epigenomic target sequence. Epigenomic target sequence may include, in some embodiments, include a promoter, silencer or an enhancer sequence.

Use of a functional domain linked to a CRISPR-Cas enzyme as described herein, preferably a dead-Cas, more preferably a dead-Cas9, to target epigenomic sequences can be used to activate or repress promoters, silencer or enhancers.

Examples of acetyltransferases are known but may include, in some embodiments, histone acetyltransferases. In some embodiments, the histone acetyltransferase may comprise the catalytic core of the human acetyltransferase p300 (Gerbasch & Reddy, Nature Biotech 6 April 2015).

In some preferred embodiments, the functional domain is linked to a dead-Cas9 enzyme to target and activate epigenomic sequences such as promoters or enhancers. One or more guides directed to such promoters or enhancers may also be provided to direct the binding of the CRISPR enzyme to such promoters or enhancers.

The term "associated with" is used here in relation to the association of the functional domain to the CRISPR enzyme or the adaptor protein. It is used in respect of how one molecule 'associates' with respect to another, for example between an adaptor protein and a functional domain, or between the CRISPR enzyme and a functional domain. In the case of such protein-protein interactions, this association may be viewed in terms of recognition in the way an antibody recognizes an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit. Alternatively, this may essentially be viewed as binding between two molecules or direct linkage, such as a fusion protein. In any event, the fusion protein may include a linker between the two subunits of interest (i.e. between the enzyme and the functional domain or between the adaptor protein and the functional domain). Thus, in some embodiments, the CRISPR enzyme or adaptor protein is associated with a functional domain by binding thereto. In other embodiments, the CRISPR enzyme or adaptor protein is associated with a functional domain because the two are fused together, optionally via an intermediate linker.

Attachment of a functional domain or fusion protein can be via a linker, e.g., a flexible glycine-serine (GlyGlyGly-Ser) (SEQ ID NO: 39) or (GGGS)3 (SEQ ID NO: 40) or a rigid alpha-helical linker such as (Ala(GluAlaAlaAlaLys)Ala) (SEQ ID NO: 41). Linkers such as (GGGGS)3 (SEQ ID NO: 42) are preferably used herein to separate protein or peptide domains. (GGGGS)3 (SEQ ID NO: 42) is preferable because it is a relatively long linker (15 amino acids). The glycine residues are the most flexible and the serine residues enhance the chance that the linker is on the outside of the protein. (GGGGS)6 (SEQ ID NO: 43) (GGGGS)9 (SEQ ID NO: 44) or (GGGGS)12 (SEQ ID NO: 45) may preferably be used as alternatives. Other preferred alternatives are (GGGGS)1 (SEQ ID NO: 46), (GGGGS)2 (SEQ ID NO: 47), (GGGGS)4 (SEQ ID NO: 48), (GGGGS)5 (SEQ ID NO: 49), (GGGGS)7 (SEQ ID NO: 50), (GGGGS)8 (SEQ ID NO: 51), (GGGGS)10 (SEQ ID NO: 52), or (GGGGS)11 (SEQ ID NO: 53). Alternative linkers are available, but highly flexible linkers are thought to work best to allow for maximum opportunity for the 2 parts of the Cas9 to come together and thus reconstitute Cas9 activity. One alternative is that the NLS of nucleoplasmin can be used as a linker. For example, a linker can also be used between the Cas9 and any functional domain. Again, a (GGGGS)3 linker (SEQ ID NO: 42) may be used here (or the 6 (SEQ ID NO: 43), 9 (SEQ ID NO: 44), or 12 (SEQ ID NO: 45) repeat versions therefore) or the NLS of nucleoplasmin can be used as a linker between Cas9 and the functional domain. For example, Fok1 nuclease domains may be fused to a catalytically inactive Cas9. Fok1 is a homodimeric enzyme, requiring two copies of the Fok1 monomer to form an active enzyme. The Fok1 domain can be fused to the N-terminus or the C-terminus of Cas9. Fusion to the N-terminus provides superior activity, since the N-terminus protrudes beyond the RuvC domain of Cas9, which interacts with the sgRNA:DNA duplex formed by Cas9; therefore, N-terminal fusion allows greater flexibility for Fok1 activity in the combined protein. Nuclear localisation signal(s) may also be provided, and are located for example N-terminal to the Fok1 domain.

Target sites, defined by the presence of a PAM sequence and regions complementary to the selected sgRNA, can be up to 50 nucleotides apart, for example between 5 and 43 nucleotides apart, for instance about 15 or about 25 nucleotides apart, in order for cleavage to occur; however, the exact length of the spacer in between cleavage sites is dependent on the linker length selected. The domains may be linked using any suitable linker, but for example are linked using one or more copies of the sequence Gly-Gly-Ser (GSS). For example, 1, 2, 3, 4, 5, 6, 8 or more copies may be used. Other potential linkers include SGSETPGTSESATPES (SEQ ID NO: 54), MKIIEQLPSA (SEQ ID NO: 55), VRHKLKRVGS (SEQ ID NO: 56), VPFLLEPDNINGKTC (SEQ ID NO: 57), GHGTGSTGSGSS (SEQ ID NO: 58), MSRPDPA (SEQ ID NO: 59), GSAGSAAGSGEF (SEQ ID NO: 60), SGSETPGTSESA (SEQ ID NO: 61), GGSM (SEQ ID NO: 62) and SGSETPGTSESATPEGGSGGS (SEQ ID NO: 63), as well as multiples thereof. The linkers should be sufficiently long and flexible to permit the Fok1 domains to align with the DNA for optimal cleavage, which is believed to be 1.5 to 2.5 helical turns apart. NLS is in turn linked to the Fok1 domain via a linker, which may be GGS or a multiple thereof. The guide RNAs which target the Cas9/Fok1 fusion to the DNA to be cleaved should be oriented such that the PAM is distal to the cleaved spacer in both instances. This means that the sgRNA molecules will align in opposite orientations along the DNA strand to be cleaved. This provides a further level of specificity, since PAM sequences need to be present in the correct orientation in target DNA. For example, see Guilinger et al., (2014) Nature Biotechnology 32:577. In another embodiment, the inserted domain may comprise an intein domain which excises to reconstitute the activity of one or more domains of Cas9, and is subject to influence from an external activator or repressor.

Because the specificity of Cas9 is imperfect, with off-target effects being observable in many instances in the absence of suitable precautions being taken, techniques which increase the on target/off target cleavage ratio of Cas9 are advantageous. The use of Fok1-dCas9 fusions, as well as small-molecule regulated split Cas9 approaches (Zetsche, B., Volz, S. E. & Zhang, F. Nat. Biotechnol. 33, 139-142 (2015)) and truncated guide RNAs (Fu, Y., Sander, J. D., Reyon, D., Cascio, V. M. & Joung, J. K. Nat. Biotechnol. 32, 279-284 (2014)), paired Cas9 nickases (Ran, F. A. et al. Cell 154, 1380-1389 (2013); Mali, P. et al. Nat. Biotechnol. 31, 833-838 (2013)) can increase the specificity of Cas9 by proportionally reducing the level of off-target enzyme activity, compared to on-target activity. In one embodiment, an intein domain can be used to regulate the activity of a modified Cas9 enzyme. Inteins are protein domains which can be inserted into heterologous proteins such that they undergo splicing to excise themselves from their integration site, splicing together the remaining segments of the heterologous protein. A wide variety of inteins is known in the art; an extensive database of inteins is available (Perler, F. B. (2002). InBase, the Intein Database. Nucleic Acids Res. 30, 383-384). Inteins that undergo protein splicing only in the presence of 4-hydroxytamoxifen (4-HT) are known (Buskirk, A. R., Ong, Y. C., Gartner, Z. J. & Liu, D. R. Proc. Natl. Acad. Sci. USA 101, 10505-10510 (2004)). These inteins were developed by inserting the human estrogen receptor ligand-binding domain into the *M. tuberculosis* RecA intein and evolving the resulting inactive fusion protein into a conditionally active intein that requires the presence of 4-HT. Subsequent evolution at 37° C. yielded a second-generation intein, 37R3-2, with improved splicing properties in mammalian cells (Peck, S. H., Chen, I. & Liu, D. R. Chem. Biol. 18, 619-630 (2011)). The 37R3-2 intein has been inserted into Cas9 at a location that disrupts Cas9 activity until protein splicing has taken place, which results in conditionally active Cas9 nucleases that are active only in the presence of 4-HT (Davis et al., Nature Chemical Biology (2015) doi: 10.1038/nchembio.1793).

The domain may be inserted at any suitable site, including for example at Ala127, Thr146, Ser219, Thr333, Thr519, Cys574, Ser1006 and/or Ser1159. Preferred insertion points include Ser219 and Cys574. Intein-modified Cas9 exhibits an on-target cleavage activity similar to wild-type Cas9 in the presence of 4-HT. However, on-target/off-target indel modification ratios for intein-Cas9 fusions are on average sixfold higher and as much as 25-fold higher than those of wild-type Cas9. In some embodiments, it may be necessary to further engineer the intein domain to prevent activation by endogenous potential activators, such as steroids. For example, 37R3-2 is susceptible to activation by endogenous β-estradiol. In order to minimize activation by unwanted signals, the intein can be further modified and/or evolved to resist activation except by the intended activator. For example, a mutation in the estrogen receptor ligand-binding domain (G521R) renders the domain more specific for 4-HT. This mutation slightly reduces affinity for 4-HT but almost abolishes affinity for β-estradiol. In a further example, the intein may be photosensitive, with protein splicing induced by light treatment. In one example, a photocaged cysteine amino acid residue can be genetically introduced into a *Nostoc punctiforme* (Npu) DnaE intein. A light-induced photochemical reaction can to reactivate the intein and trigger protein splicing (Wen et al., J. Am. Chem. Soc., (2015), 137 (6), pp 2155-2158). Such an approach permits optical control of gene editing by Cas9. Inteins may also be used to provide temporal control of Cas9 activity, effectively allowing the user to switch Cas9 activity on or off at will, by administering an activator such as 4-HT. Alternatively, inteins may be used to make Cas9 responsive to endogenous signals which are under the control of other processes in a cell or organism.

In some embodiments, the invention may involve allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized or hybridizable to a target sequence within said target polynucleotide, wherein said guide sequence is linked to a tracr mate sequence which in turn hybridizes to a tracr sequence. In some embodiments, phenotypic alteration may be preferably the result of genome modification when a genetic disease is targeted, especially in methods of therapy and preferably where a repair template is provided to correct or alter the phenotype. In some embodiments diseases that may be targeted or investigated by the present sorting method include those concerned with disease-causing splice defects. In some embodiments, cellular targets (populations) include Hemopoietic Stem/Progenitor Cells (CD34+); Human T cells; and Eye (retinal cells)—for example photoreceptor precursor cells. In some embodiments disease targets also include: cancer; Sickle Cell Anemia (based on a point mutation); HBV, HIV; Beta-Thalassemia; and ophthalmic or ocular disease—for example Leber Congenital Amaurosis (LCA)-causing Splice Defect. In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized or hybridizable to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention.

In any aspect, the CRISPR complex may comprise a CRISPR enzyme complexed with a guide sequence hybridized or hybridizable to a target sequence, wherein said guide sequence may be linked to a tracr mate sequence which in turn may hybridize to a tracr sequence.

Modifying the target: As described herein elsewhere, it will also be apparent that in certain embodiments "modified", "altered", "manipulated" or like terms corresponds to alterations of target loci such as the activation or repression of the transcription of a gene, methylation or demethylation of CpG sites and the like, which may not require point mutations, deletions, substitutions, or insertions of one or more nucleotides at target loci. Furthermore as described herein elsewhere, it will also be apparent that reference to a CRISPR-Cas enzyme as "altering" or "modifying" or "manipulating" one or more target polynucleotide loci encompasses direct alteration or modification, e.g. via the catalytic activity of the enzyme itself but also indirect alteration or modification, e.g. via a catalytic activity associated with the CRISPR-Cas enzyme such as a heterologous functional domain, e.g. a transcriptional activation domain or e.g. via a catalytic activity of one or more heterologous functional domains associated with the guide RNA via a protein-binding aptamer, e.g. a transcriptional activation domain. In addition, as it will be appreciated it is intended that the one or more target polynucleotide loci which are "altered" or "modified" by the action of the CRISPR-Cas enzyme may be comprised in or adjacent the polynucleotide sequence complementary to the guide sequence portion of a guide RNA, e.g. in embodiments wherein the alteration or modification is effected by the catalytic activity of the CRISPR-Cas enzyme itself, e.g. cleavage of DNA by the nuclease activity of the CRISPR-Cas enzyme. However, also encompassed are embodiments wherein one or more target loci to be "altered" or "modified" are at a location distinct from the sequence complementary to the guide sequence portion of the guide RNA, e.g. in embodiments wherein the alteration or modification is effected via a heterologous functional domain associated with the CRISPR-Cas enzyme and/or guide RNA, e.g. activation or repression of the transcription of a gene. As such, "alteration" or "modification" (or analogous terms) of a target locus means via direct or indirect action of the CRISPR-Cas enzyme, and furthermore the "target locus" to be altered or modified and the "target sequence" which is complementary to the guide sequence portion of the guide RNA may or may not be the same. Thus, any of the herein described improved functionalities of a CRISPR enzyme may be made to any CRISPR enzyme, such as a Cas9 enzyme. Cas9 enzymes described herein are derived e.g. from Cas9 enzymes from *S. pyogenes* and *S. aureus*. However, it will be appreciated that any of the functionalities described herein may be engineered into Cas9 enzymes from other orthologs, including chimeric enzymes comprising fragments from multiple orthologs. In some embodiments, the ortholog is *Staphylococcus aureus* so that the Cas9 is that from or derived from *Staphylococcus aureus* (referred to as SaCas9). In some embodiments, the *Staphylococcus aureus* is *Staphylococcus aureus* subspecies *aureus*. Guidance is provided below in respect of guide length (the spacer or guide sequence). In some embodiments, for Sp, optimal guide length can vary and be as low as a 'tru-guide', e.g., 17-nucleotides Fu, et al. Nature biotechnology 31, 822-826 (2013). In some embodiments, for Sa, the optimal guide length may be 19, 20 or 21 or 22 or 23 or 24 nucleotides in length (Ran 2015). Orthologs can be selected using, various techniques, including Homology modelling. Homology modelling: Corresponding residues, domains, regions etc in Cas9 orthologs can be identified by the methods of Zhang et al., 2012 (Nature; 490(7421): 556-60) and Chen et al., 2015 (PLoS Comput Biol; 11(5): e1004248). These two groups describe a computational protein-protein interaction (PPI) method to predict interactions mediated by domain-motif interfaces. PrePPI (Predicting PPI), a structure based PPI prediction method, combines structural evidence with non-structural evidence using a Bayesian statistical framework. The method involves taking a pair a query proteins and using structural alignment to identify structural representatives that correspond to either their experimentally determined structures or homology models. Structural alignment is further used to identify both close and remote structural neighbours by considering global and local geometric relationships. Whenever two neighbors of the structural representatives form a complex reported in the Protein Data Bank, this defines a template for modelling the interaction between the two query proteins. Models of the complex are created by superimposing the representative structures on their corresponding structural neighbour in the template. See Dey et al., 2013 (Prot Sci; 22: 359-66).

With respect to use of the CRISPR-Cas system generally, mention is made of the documents, including patent applications, patents, and patent publications cited throughout this disclosure as embodiments of the invention can be used as in those documents. CRISPR-Cas system(s) (e.g., single or multiplexed) can be used in conjunction with recent advances in crop genomics. Such CRISPR-Cas system(s) can be used to perform efficient and cost effective plant gene or genome interrogation or editing or manipulation—for instance, for rapid investigation and/or selection and/or interrogations and/or comparison and/or manipulations and/or transformation of plant genes or genomes; e.g., to create, identify, develop, optimize, or confer trait(s) or characteristic(s) to plant(s) or to transform a plant genome. There can accordingly be improved production of plants, new plants with new combinations of traits or characteristics or new plants with enhanced traits. Such CRISPR-Cas system(s) can be used with regard to plants in Site-Directed Integration (SDI) or Gene Editing (GE) or any Near Reverse Breeding (NRB) or Reverse Breeding (RB) techniques. With respect to use of the CRISPR-Cas system in plants, mention is made of the University of Arizona website "CRISPR-PLANT" (www.genome.arizona.edu/crispr/) (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR/Cas system," Plant Methods 2013, 9:39 (doi:10.1186/1746-4811-9-39); Brooks, "Efficient gene editing in tomato in the first generation using the CRISPR/Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR/Cas system," Cell Research (2013) 23:1229-1232. doi: 10.1038/cr.2013.114; published online 20 Aug. 2013; Xie, "RNA-guided genome editing in plants using a CRISPR-Cas system," Mol Plant. 2013 November; 6(6):1975-83. doi: 10.1093/mp/sst119. Epub 2013 Aug. 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial Populus reveals 4-coumarate: CoA ligase specificity and Redundancy," New Phytologist (2015) (Forum) 1-4 (available online only at www.newphytologist.com); Caliando et al, "Targeted DNA degradation using a CRISPR device stably carried in the host genome, NATURE COMMUNICATIONS 6:6989, DOI: 10.1038/ncomms7989, www.nature.com/naturecommunications DOI: 10.1038/ncomms7989; U.S. Pat. No. 6,603,061—*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics: advances and applications," Nat Rev Genet. 2011 Dec. 29; 13(2):85-96; each of which is incorporated by reference herein including as to how herein embodiments may be used as to plants. Accordingly, reference herein to animal cells may also apply, mutatis mutandis, to plant cells unless otherwise apparent.

SAM SCREENING: US provisional patent applications: 62/055,460 and 62/055,487 each filed Sep. 25, 2014 and US provisional patent applications: 62/087,475 and 62/087,546 each filed Dec. 4, 2014 and concurrently-filed application serial no. Not Yet Assigned filed Jun. 18, 2015, and concurrently-filed application serial no. Not Yet Assigned filed Jun. 18, 2015, each hereby incorporated herein by reference, with respect to the instant invention, all relate to a screening method known as SAM. In SAM, the modified sgRNA are modified such that once the sgRNA forms a CRISPR complex (i.e. CRISPR enzyme binding to sgRNA and target) the adapter proteins bind and, the functional domain (see, e.g., discussion herein of functional domains for functional domains that may be used in SAM) on the adapter protein is positioned in a spatial orientation which is advantageous for the attributed function to be effective. For example, if the functional domain is a transcription activator (e.g. VP64 or p65), the transcription activator is placed in a spatial orientation which allows it to affect the transcription of the target. Likewise, a transcription repressor will be advantageously positioned to affect the transcription of the target and a nuclease (e.g. Fok1) will be advantageously positioned to cleave or partially cleave the target. The skilled person will understand that modifications to the sgRNA which allow for binding of the adapter+functional domain but not proper positioning of the adapter+functional domain (e.g. due to steric hindrance within the three dimensial structure of the CRISPR complex) are modifications which are not intended. The one or more modified sgRNA may be modified at the tetra loop, the stem loop 1, stem loop 2, or stem loop 3, as described herein, preferably at either the tetra loop or stem loop 2, and most preferably at both the tetra loop and stem loop 2. As explained herein the functional domains may be, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). In some cases it is advantageous that additionally at least one NLS is provided. In some instances, it is advantageous to position the NLS at the N terminus. When more than one functional domain is included, the functional domains may be the same or different. The sgRNA may be designed to include multiple binding recognition sites (e.g.

aptamers) specific to the same or different adapter protein. The sgRNA may be designed to bind to the promoter region −1000-+1 nucleic acids upstream of the transcription start site (i.e. TSS), preferably −200 nucleic acids. This positioning improves functional domains which affect gene activation (e.g. transcription activators) or gene inhibition (e.g. transcription repressors). The modified sgRNA may be one or more modified sgRNAs targeted to one or more target loci (e.g. at least 1 sgRNA, at least 2 sgRNA, at least 5 sgRNA, at least 10 sgRNA, at least 20 sgRNA, at least 30 sg RNA, at least 50 sgRNA) comprised in a composition. Further, the CRISPR enzyme with diminished nuclease activity is most effective when the nuclease activity is inactivated (e.g. nuclease inactivation of at least 70%, at least 80%, at least 90%, at least 95%, at least 97%, or 100% as compared with the wild type enzyme; or to put in another way, a Cas9 enzyme or CRISPR enzyme having advantageously about 0% of the nuclease activity of the non-mutated or wild type Cas9 enzyme or CRISPR enzyme (i.e., "dead"), or no more than about 3% or about 5% or about 10% of the nuclease activity of the non-mutated or wild type Cas9 enzyme or CRISPR enzyme). This is possible by introducing mutations into the RuvC and HNH nuclease domains of the SpCas9 and orthologs thereof. For example utilizing mutations in a residue selected from the group consisting of D10, E762, H840, N854, N863, or D986 and more preferably introducing one or more of the mutations selected from the group consisting of D10A, E762A, H840A, N854A, N863A or D986A. A preferable pair of mutations is D10A with H840A, more preferable is D10A with N863A of SpCas9 and orthologs thereof. In some embodiments, N580A according to SaCas9 protein, may be used, as discussed herein. The inactivated CRISPR enzyme may have associated (e.g. via fusion protein) one or more functional domains, like for example as described herein for the modified sgRNA adaptor proteins, including for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). Preferred domains are Fok1, VP64, P65, HSF1, MyoD1. In the event that Fok1 is provided, it is advantageous that multiple Fok1 functional domains are provided to allow for a functional dimer and that sgRNAs are designed to provide proper spacing for functional use (Fok1) as specifically described in Tsai et al. Nature Biotechnology, Vol. 32, Number 6, June 2014). The adaptor protein may utilize known linkers to attach such functional domains. In some cases it is advantageous that additionally at least one NLS is provided. In some instances, it is advantageous to position the NLS at the N terminus. When more than one functional domain is included, the functional domains may be the same or different. In general, the positioning of the one or more functional domain on the inactivated CRISPR enzyme is one which allows for correct spatial orientation for the functional domain to affect the target with the attributed functional effect. For example, if the functional domain is a transcription activator (e.g. VP64 or p65), the transcription activator is placed in a spatial orientation which allows it to affect the transcription of the target. Likewise, a transcription repressor will be advantageously positioned to affect the transcription of the target, and a nuclease (e.g. Fok1) will be advantageously positioned to cleave or partially cleave the target. This may include positions other than the N-/C-terminus of the CRISPR enzyme. Due to crystal structure experiments, the Applicant has identified that positioning the functional domain in the Rec domain, the Rec2 domain, the HNH domain, or the PI domain of the SpCas9 protein or any ortholog corresponding to these domains is advantageous. Positioning of the functional domains to the Rec1 domain or the Rec2 domain, of the SpCas9 protein or any ortholog corresponding to these domains, in some instances may be preferred. Positioning of the functional domains to the Rec domain at position 553, Rec domain at 575, the Rec2 domain at any position of 175-306 or replacement thereof, the HNH domain at any position of 715-901 or replacement thereof, or the PI domain at position 1153 of the SpCas9 protein or any ortholog corresponding to these domains, in some instances may be preferred. Fok1 functional domain may be attached at the N terminus. When more than one functional domain is included, the functional domains may be the same or different. The adaptor protein may be any number of proteins that binds to an aptamer or recognition site introduced into the modified sgRNA and which allows proper positioning of one or more functional domains, once the sgRNA has been incorporated into the CRISPR complex, to affect the target with the attributed function. As explained in detail in this application such may be coat proteins, preferably bacteriophage coat proteins. The functional domains associated with such adaptor proteins (e.g. in the form of fusion protein) may include, for example, one or more domains from the group consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g. light inducible). Preferred domains are Fok1, VP64, P65, HSF1, MyoD1. In the event that the functional domain is a transcription activator or transcription repressor it is advantageous that additionally at least an NLS is provided and preferably at the N terminus. When more than one functional domain is included, the functional domains may be the same or different. The adaptor protein may utilize known linkers to attach such functional domains. Thus, the modified sgRNA, the inactivated CRISPR enzyme (with or without functional domains), and the binding protein with one or more functional domains, may each individually be comprised in a composition and administered to a host individually or collectively. Alternatively, these components may be provided in a single composition for administration to a host. Delivery may be performed as herein described e.g., via viral vectors known to the skilled person or described herein for delivery to a host (e.g. lentiviral vector, adenoviral vector, AAV vector). As explained herein, use of different selection markers (e.g. for lentiviral sgRNA selection) and concentration of sgRNA (e.g. dependent on whether multiple sgRNAs are used) may be advantageous for eliciting an improved effect. On the basis of this concept, several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g. gene activation of lincRNA and identification of function; gain-of-function modeling; loss-of-function modeling; identification of non-coding RNA or possible regulatory elements, establish cell lines and transgenic animals for optimization and screening purposes). The practice of SAM in the current invention comprehends the use of the compositions of the current invention to establish and utilize conditional or inducible CRISPR transgenic cell/animals. (See, e.g., Platt et al., Cell (2014), dx.doi.org/10.1016/j.cell.2014.09.014, or PCT patent publications cited herein, such as WO 2014/093622 (PCT/US2013/074667), which are not believed prior to the present invention or application). For example, the target cell comprises CRISPR enzyme (e.g. Cas9) conditionally or inducibly (e.g. in the form of Cre dependent constructs) and/or the adapter protein conditionally or inducibly and, on expression of a vector introduced into the target cell, the vector expresses that which induces or gives rise to the condition of CRISPR enzyme (e.g. Cas9) expression and/or adaptor expression in the target cell. By applying the teaching and compositions of the current invention with the known method of creating a CRISPR complex, inducible genomic events affected by functional domains are also an aspect of the current invention. One more example of this is the creation of a CRISPR knock-in/conditional transgenic animal (e.g. mouse comprising e.g. a Lox-Stop-polyA-Lox(LSL) cassette) and subsequent delivery of one or more compositions providing one or more modified sgRNA (e.g. −200 nucleotides to TSS of a target gene of interest for gene activation purposes) as described herein (e.g. modified sgRNA with one or more aptamers recognized by coat proteins, e.g. MS2), one or more adapter proteins as described herein (MS2 binding protein linked to one or more VP64) and means for inducing the conditional animal (e.g. Cre recombinase for rendering Cas9 expression inducible). Alternatively, the adaptor protein may be provided as a conditional or inducible element with a conditional or inducible CRISPR enzyme to provide an effective model for screening purposes, which advantageously only requires minimal design and administration of specific sgRNAs for a broad number of applications.

In an aspect of SAM there is the provision of a method of screening for gain of function (GOF) or loss of function (LOF) or for screen non-coding RNAs or potential regulatory regions (e.g. enhancers, repressors) comprising the cell line of as herein-discussed or cells of the model herein-discussed containing or expressing Cas9 and introducing a composition as herein-discussed into cells of the cell line or model, whereby the sgRNA includes either an activator or a repressor, and monitoring for GOF or LOF or non-coding RNAs or potential regulatory regions respectively as to those cells as to which the introduced sgRNA includes an activator or as to those cells as to which the introduced sgRNA includes a repressor. The screening of the instant invention is referred to as a SAM screen. In an aspect of SAM can be provision of a library, wherein gene function of one or more gene products is altered by said targeting; or wherein as to gene function there is gain of function; or wherein as to gene function there is change of function; or wherein as to gene function there is reduced function; or wherein the screen is for non-coding RNAs or potential regulatory regions (e.g. enhancers, repressors). In an aspect of SAM is the provision of a library as herein discussed, wherein said targeting results in a knockout of gene function. In an aspect the invention provides a library as herein discussed, wherein the targeting is of about 100 or more sequences. In an aspect of SAM is the provision of a library, wherein the targeting is of about 1000 or more sequences. In an aspect of SAM is the provision of a library as herein discussed, wherein the targeting is of about 20,000 or more sequences. In an aspect of SAM is the provision of a library as herein discussed, wherein the targeting is of the entire genome. In an aspect of SAM is the provision of a library as herein discussed, wherein the targeting is of a panel of target sequences focused on a relevant or desirable pathway. In an aspect of SAM is the provision of a library as herein discussed, wherein the pathway is an immune pathway. In an aspect of SAM is the provision of a library as herein discussed, wherein the pathway is a cell division pathway. In an aspect of SAM is the provision of a library as herein discussed, wherein the alteration of gene function comprises: introducing into each cell in the population of cells a vector system of one or more vectors comprising an engineered, non-naturally occurring CRISPR-Cas system comprising I. a Cas protein, and II. one or more guide RNAs, wherein components I and II may be same or on different vectors of the system, integrating components I and II into each cell, wherein the guide sequence targets a unique gene in each cell, wherein the Cas protein is operably linked to a regulatory element, wherein when transcribed, the guide RNA comprising the guide sequence directs sequence-specific binding of a CRISPR-Cas system to a target sequence in the genomic loci of the unique gene, inducing cleavage of the genomic loci by the Cas protein, and confirming different mutations in a plurality of unique genes in each cell of the population of cells thereby generating a mutant cell library. In an aspect of SAM is the provision of a library as herein discussed, wherein the one or more vectors are plasmid vectors. In an aspect of SAM is the provision of a library as herein discussed, wherein the regulatory element is an inducible promoter. In an aspect the invention provides a library as herein discussed, wherein the inducible promoter is a doxycycline inducible promoter. In an aspect the invention provides a library as herein discussed wherein the confirming of different mutations is by whole exome sequencing. In an aspect the invention provides a library as herein discussed, wherein the mutation is achieved in 100 or more unique genes. In an aspect of SAM is the provision of a library as herein discussed, wherein the t mutation is achieved in 1000 or more unique genes. In an aspect of SAM is the provision of a library as herein discussed, wherein the mutation is achieved in 20,000 or more unique genes. In an aspect of SAM is the provision of a library as herein discussed, wherein the mutation is achieved in the entire genome. In an of SAM is the provision of a library as herein discussed, wherein the alteration of gene function is achieved in a plurality of unique genes which function in a particular physiological pathway or condition. In an aspect of SAM is the provision of a library as herein discussed, wherein the pathway or condition is an immune pathway or condition. In an aspect of SAM is the provision of a library as herein discussed, wherein the pathway or condition is a cell division pathway or condition. In an aspect of SAM is the provision of a library as herein discussed, wherein a first adaptor protein is associated with a p65 domain and a second adaptor protein is associated with a HSF1 domain. In an aspect of SAM is the provision of a library as herein discussed, wherein each a CRISPR-Cas complex has at least three functional domains, at least one of which is associated with the CRISPR enzyme and at least two of which are associated with sgRNA. In an aspect of SAM is the provision of a library as herein discussed, wherein the alteration in gene function is a knockout mutation. In an aspect of SAM is the provision of a method for functional screening genes of a genome in a pool of cells ex vivo or in vivo comprising the administration or expression of a library comprising a plurality of CRISPR-Cas system guide RNAs (sgRNAs) and wherein the screening further comprises use of a CRISPR enzyme, wherein the CRISPR complex is modified to comprise a heterologous functional domain. In an aspect of SAM is the provision of a method for screening a genome comprising the administration to a host or expression in a host in vivo of a library as herein as to SAM. In an aspect of SAM is the provision of a method as herein discussed further comprising an activator administered to the host or expressed in the host. In an aspect of SAM is the provision of a method as herein discussed wherein the activator is attached to a CRISPR enzyme. In an aspect of SAM is the provision of a method as herein discussed wherein the activator is attached to the N terminus or the C terminus of the CRISPR enzyme. In an aspect of SAM is the provision of a method wherein the activator is attached to a sgRNA loop. In an aspect of SAM is the provision of a method as herein discussed further comprising a repressor administered to the host or expressed in the host. In an aspect of SAM is the provision of a method as herein discussed, wherein the screening comprises affecting and detecting gene activation, gene inhibition, or cleavage in the locus. In an aspect of SAM is the provision of a method, wherein the host is a eukaryotic cell. In an aspect of SAM is the provision of a method as herein discussed, wherein the host is a mammalian cell. In an aspect of SAM is the provision of a method as herein discussed, wherein the host is a non-human eukaryote. In an aspect of SAM is the provision of a method as herein discussed, wherein the non-human eukaryote is a non-human mammal. In an aspect of SAM is the provision of a method as herein discussed, wherein the non-human mammal is a mouse. In an aspect of SAM is the provision of a method as herein discussed comprising the delivery of the CRISPR-Cas complexes or component(s) thereof or nucleic acid molecule(s) coding therefor, wherein said nucleic acid molecule(s) are operatively linked to regulatory sequence(s) and expressed in vivo. In an aspect the invention provides a method as herein discussed wherein the expressing in vivo is via a lentivirus, an adenovirus, or an AAV. In an aspect of SAM is the provision of a method as herein discussed wherein the delivery is via a particle, a nanoparticle, a lipid or a cell penetrating peptide (CPP).

In some aspects a SAM screen comprises having a functional screen wherein a library of guide RNAs targeting multiple sites is introduced into the genome(s), e.g., each genome, of a population of cells. The guide RNA has at least a loop like MS2 that recruits a functional domain, like an activator protein domain. From the sequence of the different guide RNAs the skilled person can determine which gene is activated or repressed in cells that show some gain or loss of function or one can ascertain whether there is non-coding RNA or a putative regulatory region. See also Konermann et al (2014).

The analysis of genetically heterogeneous cell populations is complicated by the fact that many biological assays are destructive, making it difficult to isolate cells with particular properties for further study and use. For example, cells originating from a patient tumor may carry different mutations and chromosomal arrangements, leading to different properties, e.g., resistance to chemotherapy. Techniques such as RNA and protein analysis may reveal key signatures of resistant cells, e.g., an aberrant epigenetic state, but destroy the cells, thus precluding further experiments on the same cells. Traditionally, this limitation has been circumvented in dividing cell populations by isolating individual cells, e.g., in a multiwell plate, expanding the cells, and splitting the cells for downstream use. However, this process is laborious (each cell must be handled individually), slow (typically a month to expand cells), and low throughput. Furthermore, many cell types are not amenable to expansion from single cells, which may cause cell death or profound changes to cell physiology. Recently, the introduction of unique DNA barcodes into a cell population has partially alleviated this difficulty. Barcoded cells are expanded, split into parallel selection-based assays, and after each assay barcodes are counted by next-generation sequencing (Nolan-Stevaux, Olivier et al. "Measurement of cancer cell growth heterogeneity through lentiviral barcoding identifies clonal dominance as a characteristic of in vivo tumor engraftment." *PloS one* 8.6 (2013)). However, this does not address the goal of retrieving particular subpopulations (such as the descendants of an initial resistant cell), and is limited to selection-based assays with a simple readout obtainable by counting barcodes as a proxy for cells. The instant invention involves a novel use of SAM to separate barcoded cells or other barcoded nucleic acid molecules. The inventive technique recovers cells containing specific barcodes from a heterogeneous population by programming a Cas9 activator (Konermann, Silvana et al. "Genome-scale transcriptional activation by an engineered CRISPR-Cas9 complex." *Nature* (2014)). to target the specific barcodes, leading to expression of a selection marker. A cassette including unique barcodes, followed by a selection marker (e.g., fluorescent protein, antibiotic resistance, luciferase protein), is integrated into the heterogenous population of interest. Cells containing specific barcodes are selected for by introducing a Cas9 activator and sgRNA targeting sequences within the barcode. Selection is completed by traditional means, such as fluorescently-activated flow sorting (FACS) or drug selection. The method can be applied to cell populations with natural heterogeneity, such as cancer cells, or engineered heterogeneity, such as cells modified through genome engineering.

The present invention may include barcoding. Barcoding may be performed based on any of the compositions or methods disclosed in patent publication WO 2014047561 A1, Compositions and methods for labeling of agents, incorporated herein in its entirety. In certain embodiments barcoding uses an error correcting scheme (T. K. Moon, Error Correction Coding: Mathematical Methods and Algorithms (Wiley, New York, ed. 1, 2005)).

The term "barcode" as used herein, refers to any unique, non-naturally occurring, nucleic acid sequence that may be used to identify the originating source of a nucleic acid fragment. Such barcodes may be sequences including but not limited to, TTGAGCCT, AGTTGCTT, CCAGTTAG, ACCAACTG, GTATAACA, CAGGAGCC, or any combination thereof. In certain embodiments of the present invention, barcodes may be at least 20, 30, 40, 50, 60, 70, 80, 90, 100, 150, 200, preferably about 70 base pairs in length. Although it is not necessary to understand the mechanism of an invention, it is believed that the barcode sequence provides a high-quality individual read of a barcode associated with a viral vector, shRNA, or cDNA such that multiple species can be sequenced together.

DNA barcoding is also a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" Proc. Natl. Acad. Sci. U.S.A. 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" African Invertebrates 51(2): 413-421 (2010); and Seberg et al., "How many loci does it take to DNA barcode a crocus?"

PLoS One 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" Frontiers in Zoology 6:16 (2009).

It has been suggested that a desirable locus for DNA barcoding should be standardized so that large databases of sequences for that locus can be developed. Most of the taxa of interest have loci that are sequencable without species-specific PCR primers. CBOL Plant Working Group, "A DNA barcode for land plants" PNAS 106(31):12794-12797 (2009). Further, these putative barcode loci are believed short enough to be easily sequenced with current technology. Kress et al., "DNA barcodes: Genes, genomics, and bioinformatics" PNAS 105(8):2761-2762 (2008). Consequently, these loci would provide a large variation between species in combination with a relatively small amount of variation within a species. Lahaye et al., "DNA barcoding the floras of biodiversity hotspots" Proc Natl Acad Sci USA 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit 1 (CO1) gene was proposed as a potential 'barcode'. As of 2009, databases of CO1 sequences included at least 620,000 specimens from over 58,000 species of animals, larger than databases available for any other gene. Ausubel, J., "A botanical macroscope" Proceedings of the National Academy of Sciences 106(31):12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

Additionally other barcoding designs and tools have been described (see e.g., Birrell et al., (2001) Proc. Natl Acad. Sci. USA 98, 12608-12613; Giaever, et al., (2002) Nature 418, 387-391; Winzeler et al., (1999) Science 285, 901-906; and Xu et al., (2009) Proc Natl Acad Sci USA. February 17; 106(7):2289-94). Barcoding may be performed based on any of the compositions or methods disclosed in patent publication WO 2014047561 A1, Compositions and methods for labeling of agents, incorporated herein in its entirety (bead that includes a barcode sequence); see also Klein et al., "Droplet Barcoding for Single-Cell Transcriptomics Applied to Embryonic Stem Cells," 2015, Cell 161, 1187-1201 (May 21, 2015) dx.doi.org/10.1016/j.cell.2015.04.044; Macosko et al., "Highly Parallel Genome-wide Expression Profiling of Macosko et al., Cell 161, 1202-1214 (May 21, 2015) dx.doi.org/10.1016/j.cell.2015.05.002; and International patent application number PCT/US2015/049178, published as WO2016/040476 on Mar. 17, 2016.

Methodology for cell sorting: In one embodiment, the method comprises the following steps:
1. Barcode the cell population of interest using a lentiviral barcode delivery vector at low multiplicity of infection (MOI) and subsequent selection of the population for transformed cells.
2. Expand the population of cells through a number of cell divisions, in this case 4 is advantageous, and split the cells into a test population and a recovery population.
3. Optionally, the recovery population are preserved cryogenically.
4. Assay the test population by exposing the cells to different drug regimes over a period of time, in this case several weeks.
5. Determine the barcodes present in cells of interest in the test population (e.g. those cells that have a survival or growth advantage when exposed to drug), across multiple replicates (replicates are obtained e.g. by splitting the cell population into separate subpopulations during assay growth).
6. Generate guides for recruiting Cas9 activators. The guides target the barcodes of interest. The guides are generated by cloning matching sgRNAs into an adeno-associated virus (AAV) Cas9 activator vector.
7. Deliver the guides and Cas9 activators targeting the barcodes of interest to the recovery population, activating the selection marker.
8. Isolate the cells containing barcodes of interest by a selection protocol, e.g., FACS based on mCherry expression.
9. Cells are isolated corresponding to individual barcodes of interest.

As an optional step in addition to or in replacement of step 9 above:
10. Cells are isolated corresponding to subsets of barcodes of interest. If a subset of cells is isolated and analyzed, e.g., by single-cell gene expression profiling, the exact barcode corresponding to each analyzed cell is determined by identifying a transcribed barcode present in the Cas9-targetable selection marker, e.g., a barcode encoded by synonymous mutation.

Generating Constructs: The following is prepared in the practice of the invention:
1. Barcode Construct and Barcode delivery vector;
2. Cas9 activator and delivery vector; and
3. Guide Construct(s) and delivery vector.

Barcode Construct: In general barcode constructs are known, but until the instant invention none were designed for use with the CRISPR-Cas system. A DNA construct for the barcode may be designed based on the following. The barcode comprises:
I. A barcode sequence following one or more, preferably all, of the following rules:
   a. That may be from 20-200 bp long
   b. That may contains one or multiple subsequences targetable by Cas9, and a CRISPR RNA target sequence (e.g., a CRISPR-Cas9 complex) and includes a PAM (e.g., NGG for SpCas9) so as to be targeted
   c. That may be designed according to rules that enhance Cas9 activator specificity or activity, including restrictions on GC content, homopolymer stretches, maximal orthogonality among targets, and/or reduced or essentially none nuclease activity d. That may be synthesized as individual oligonucleotides, oligonucleotides containing degenerate bases, or a library of oligonucleotides synthesized on an array
e. That may be handled individually or as a pooled library II. Activatable promoter or enhancer following one or more, preferably all, of the following rules:
a. That may be placed before or after the barcode sequence
b. That may be placed before or after the selection marker
c. That may contain an inducible element (e.g., Tet promoter compatible with IPTG induction)
d. That may be a constitutive native promoter with low baseline activity
e. That may be a constitutive synthetic promoter with low baseline activity (e.g., minCMV)

III. Cas9-targetable first selection marker following one or more, preferably all, of the following rules:
a. That may be an antibiotic resistance gene (e.g, Pac conferring puromycin resistance)
b. That may be a fluorescent reporter (e.g., mCherry)
c. That may be a luminescent reporter (e.g., luciferase)
d. That may contain a unique barcode in part of the RNA transcript, possibly encoded through synonymous mutations, to be used in matching RNA-seq data (e.g., single cell gene expression profiling) to the originating cell.

In the present invention, as shown in FIG. 1 (from left to right): the DNA barcode is provided, with a minCMV minimal promoter and an mCherry fluorescent reporter; together with a first drug selection marker (Hygro, inferring resistance to Hygromycin) under the control of an EFS promoter. FIG. 3 shows some barcode sequences, where the lower case letters are PAMs for SpCas9, and the uppercase letters are 20 nucleotide stretches representing target sequences for the guide RNA.

In another embodiment, vectors that activate a selection marker may include a barcode designed to be cut by a CRISPR-Cas system, as described herein. The present invention advantageously allows for the isolation and culturing of subpopulations of cells with stable phenotypes of interest by targeting a DNA barcode. Applicants have unexpectedly determined that the barcodes of the present invention can be maintained in cell subpopulation progeny and that the phenotypes remain stable after greater than 15 divisions. The present invention also provides high specificity for recovery of rare subpopulations of cells of interest, such that gene expression and protein analysis may be performed on the cells before testing for a phenotype. Vectors encoding previously described selection markers may be modified for use in the present invention. Vectors used in the present invention minimally require a library of unique barcodes containing CRISPR target sequences that are incorporated into the vector, such that individual cells will each have a single unique barcode after delivery of the vectors to a population of cells. Roark et al., Ramakrishna et al., and Kim et al., used out of frame fluorescent protein surrogate vectors in order to enrich for cells that express a TALEN or CRISPR nuclease and have nuclease-induced mutations (tools.thermofisher.com/content/sfs/posters/Use-of-surrogate-reporter-vectors-to-enrich-for-CRISPR-and-TALEN-modified-cells.pdf, Nature Communications 5, Article number: 3378 doi:10.1038/ncomms4378; and Nature Methods 8, 941-943 (2011)). Kuhar et al., describes fluorescent traffic light reporters as a means to determine the repair pathway used after a double stranded break introduced in the reporter (Nucleic Acids Research, 2014, Vol. 42, No. 1 e4). All of the vectors described were used to determine a readout or phenotype in response to a nuclease, whereas the present invention uses CRISPR to isolate specific cells of a single subtype with an inherent phenotype unrelated to genome modification.

Figure 2:
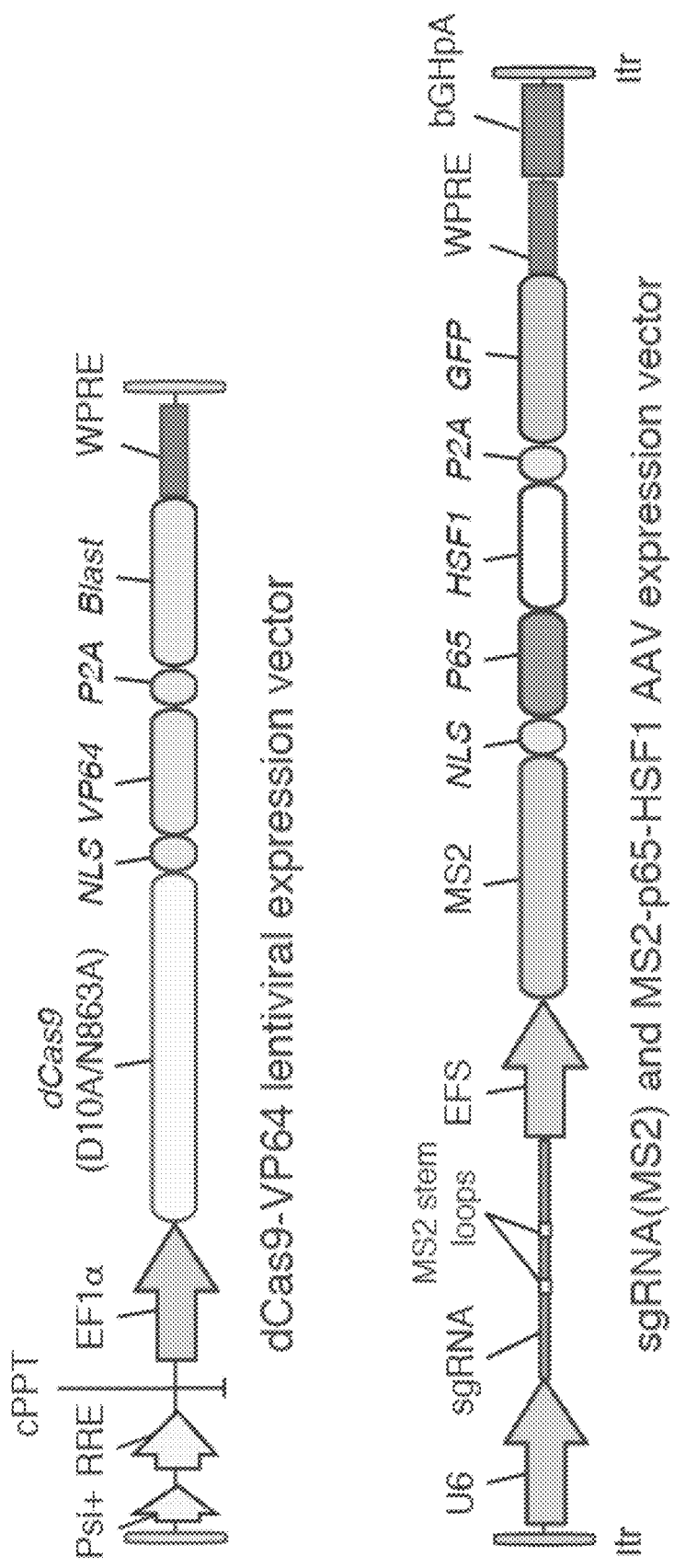
FIG. 2: Activator constructs design: showing dead Cas9 from *S. pyogenes* (comprising double mutant D10A and N863A) under the EF1alpha promoter, together with an NLS (nuclear localization signal), VP64 transcriptional activator, the P2A self cleaving peptide, a second drug selection marker (Blast, inferring resistance to Blasticidin) and the Woodchuck regulatory element (WPRE) to improve expression levels from a retrovirus (such as a lentivirus as sued in this example).
Figure 4A-1:
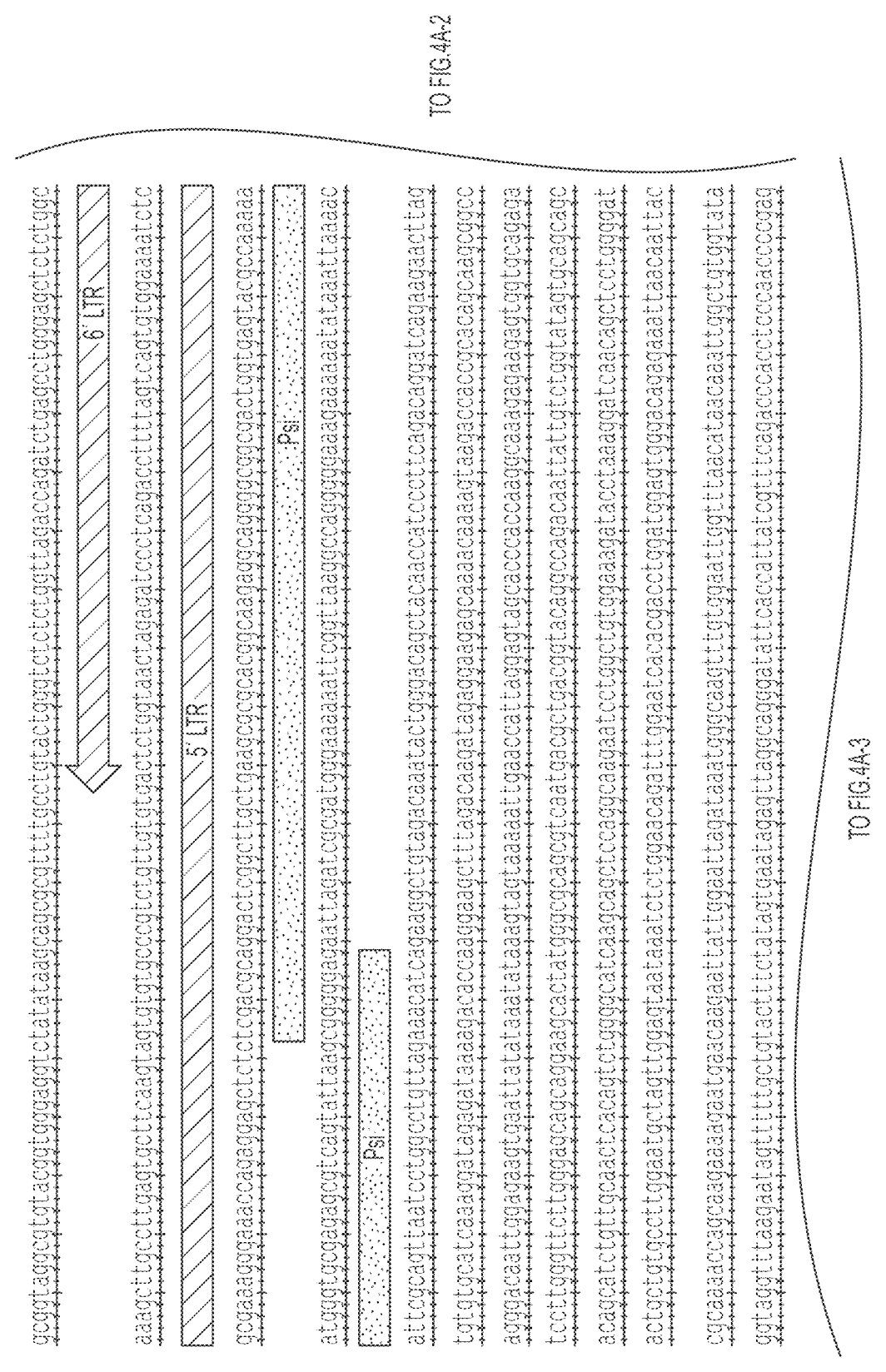
Figure 4A-3:
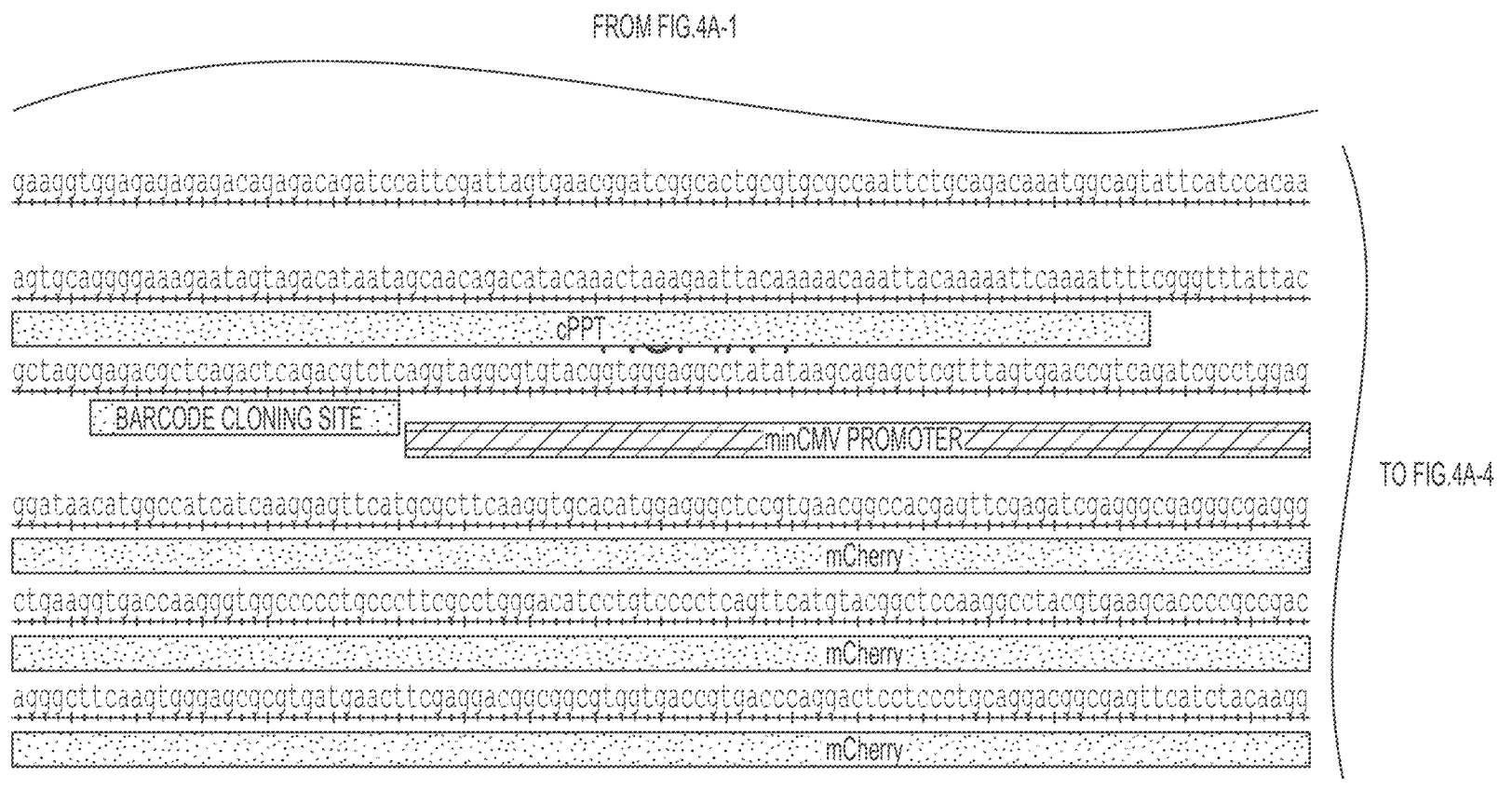
Figure 4B-1:
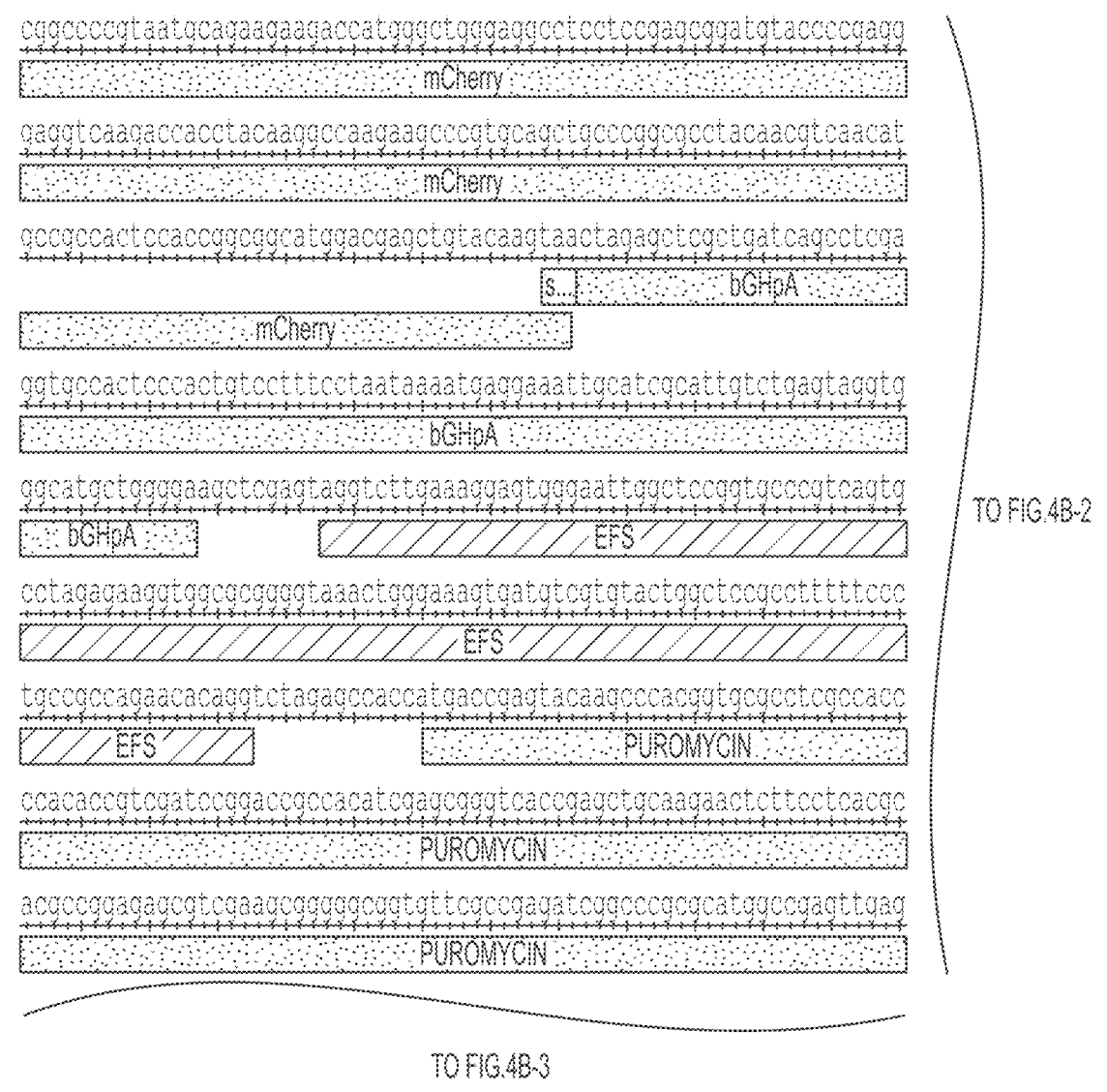
Figure 6:
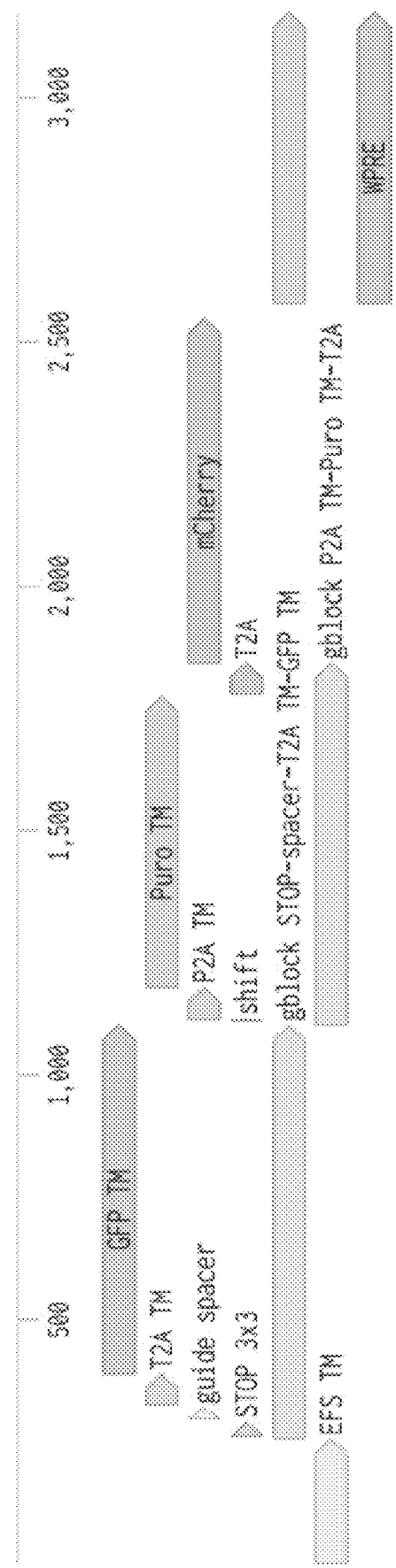
FIG. 6: Nuclease construct design showing an open reading frame with multiple reporters and a guide spacer. The construct is designed to activate and/or deactivate the reporters by shifting the open reading frame. The frameshift is the result of an insert or deletion by Cas9 targeting.

The Barcode delivery vector can be any herein-discussed vector. The Barcode delivery vector comprises a vector to deliver the single barcodes, described above, to cells in the initial cell population. This vector as exemplified herein can comprises a lentiviral backbone encoding a second selection marker. The lentiviral backbone may be advantageous as lentivirus is an integrating virus and it can thus deliver the barcode in an integrating manner; and hence other integrating vectors may be considered for Barcode delivery. This second selection marker is different from first or other selection marker(s) used in the method to assist with sorting. The vector is used to introduce barcodes at low MOI. This is followed by selection to ensure a high fraction of cells with single integration events. FIGS. 4 and 6 show a barcode construct example sequence. FIG. 4 shows barcode construct sequences (such as shown in FIG. 3) cloned into the vector via BsmBI sites. Cas9 activators: An exemplified activator vector design is shown in FIG. 2. Here, the Cas9 transcriptional activator dCas9-VP64 is used (see top of FIG. 2). A separate guide construct is provided, although the guide and the Cas9 transcriptional activator are used in combination, they may be delivered separately. The Cas9 transcriptional activator can be constitutively expressed by the cells. The guide construct exemplified comprises MS2-P65-HSF1. The guide sequence in the sgRNA targets, i.e. hybridizes to, the selected barcode, se the bottom of FIG. 3. Here, sgRNAs targeting the selected barcode and containing MS2 loops integrated at tetraloop and stemloop2 (as previously described by Konermann et al (2014)) are used with MS2-activator (adaptor protein) fusions. Alternative functionalized guides and Cas9s with transcriptional effector (functional) domains are of course within the ambit of the invention, with it noted that domains as herein discussed can be used in the practice of the invention.

Vector for delivery of Cas9 transcriptional activator: The vector can be any herein discussed vector and can be delivered in any manner herein discussed, and is exemplified as nucleic acid molecule(s) encoding dCas9-VP64 packaged into a lentiviral vector and can be selected via any suitable antibiotic or color selection system, such as blasticidin. The cells of interest can be transduced with this vector at different stages of the method (e.g. at the same time as the barcodes or after the assay and sequencing of enriched barcodes).

Guide(s) and delivery vector: The guide(s) and delivery vector(s) can be any vector and/or delivery system herein discussed, and is exemplified as the MS2-P65-HSF1 activator component packaged together with an sgRNA targeting the desired barcode into an AAV plasmid. The purpose of using AAV is that it does not integrate into the genome and therefore provides transient expression in dividing cells. This allows for efficient activation and sorting of the target population followed by loss of activation. This leaves the cells unperturbed for either follow-up sorting with a separate barcode or further experiments. Alternatively, these components could be delivered via transient transfection, electroporation, nucleofection or other viral vectors.

Delivery generally: The CRISPR-Cas enzyme, preferably Cas9, can be delivered into a cell as a protein. The CRISPR-Cas enzyme can be delivered into the cell as a protein or as a nucleotide sequence encoding it. Delivery to the cell as a protein may include delivery of a Ribonucleoprotein (RNP) complex, where the protein is complexed with the CRISPR-Cas guide RNA. Vector delivery, e.g., plasmid, viral delivery: The CRISPR enzyme, for instance a Cas9, and/or any of the present RNAs, for instance a guide RNA, can be delivered using any suitable vector, e.g., plasmid or viral vectors, such as adeno associated virus (AAV), lentivirus, adenovirus or other viral vector types, or combinations thereof. Cas9 and one or more guide RNAs can be packaged into one or more vectors, e.g., plasmid or viral vectors. In an embodiment herein the delivery is via an adenovirus, which may be at a single dose containing at least $1\times10^5$ particles (also referred to as particle units, pu) of adenoviral vector. In an embodiment herein, the dose preferably is at least about $1\times10^6$ particles (for example, about $1\times10^6$-$1\times10^{12}$ particles), more preferably at least about $1\times10^7$ particles, more preferably at least about $1\times10^8$ particles (e.g., about $1\times10^8$-$1\times10^{11}$ particles or about $1\times10^8$-$1\times10^{12}$ particles), and most preferably at least about $1\times10^0$ particles (e.g., about $1\times10^9$-$1\times10^{10}$ particles or about $1\times10^9$-$1\times10^{12}$ particles), or even at least about $1\times10^{10}$ particles (e.g., about $1\times10^{10}$-$1\times10^{12}$ particles) of the adenoviral vector. Alternatively, the dose comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ articles). Thus, the dose may contain a single dose of adenoviral vector with, for example, about $1\times10^6$ particle units (pu), about $2\times10^6$ pu, about $4\times10^6$ pu, about $1\times10^7$ pu, about $2\times10^7$ pu, about $4\times10^7$ pu, about $1\times10^8$ pu, about $2\times10^8$ pu, about $4\times10^8$ pu, about $1\times10^9$ pu, about $2\times10^9$ pu, about $4\times10^9$ pu, about $1\times10^{10}$ pu, about $2\times10^{10}$ pu, about $4\times10^{10}$ pu, about $1\times10^{11}$ pu, about $2\times10^{11}$ pu, about $4\times10^{11}$ pu, about $1\times10^{12}$ pu, about $2\times10^{12}$ pu, or about $4\times10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses. In an embodiment herein, the delivery is via an AAV. In an embodiment herein, the AAV dose is generally in the range of concentrations of from about $1\times10^5$ to $1\times10^{50}$ genomes AAV, from about $1\times10^8$ to $1\times10^{20}$ genomes AAV, from about $1\times10^{10}$ to about $1\times10^{16}$ genomes, or about $1\times10^{11}$ to about $1\times10^{16}$ genomes AAV. In an embodiment herein the delivery is via a plasmid. In such plasmid compositions, suitable quantities of plasmid DNA in plasmid compositions can be from about 0.1 to about 2 mg, or from about 1 g to about 10 μg per 70 kg individual. Plasmids of the invention will generally comprise (i) a promoter; (ii) a sequence encoding a CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector. In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention. Indeed, RNA delivery is a useful method of in vivo delivery. It is possible to deliver Cas9 and gRNA (and, for instance, HR repair template) into cells using liposomes or nanoparticles. Thus delivery of the CRISPR enzyme, such as a Cas9 and/or delivery of the RNAs of the invention may be in RNA form and via microvesicles, liposomes or nanoparticles. For example, Cas9 mRNA and gRNA can be packaged into liposomal particles for delivery in vivo. Liposomal transfection reagents such as lipofectamine from Life Technologies and other reagents on the market can effectively deliver RNA molecules into the liver. Means of delivery of RNA also preferred include delivery of RNA via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Vitamin E (α-tocopherol) may be conjugated with CRISPR Cas and delivered along with high density lipoprotein (HDL), for example in a similar manner as was done by Uno et al. (HUMAN GENE THERAPY 22:711-719 (June 2011)) for delivering short-interfering RNA (siRNA). Zou et al. ((HUMAN GENE THERAPY 22:465-475 (April 2011)) describes a method of lentiviral-mediated delivery of short-hairpin RNAs targeting PKC7 for in vivo gene silencing. Adeno associated virus (AAV): Cas9 and one or more guide RNA can be delivered using adeno associated virus (AAV), lentivirus, adenovirus or other plasmid or viral vector types; see, e.g., U.S. Pat. Nos. 8,454,972, 8,404,658 and 5,846,946. AAV has a packaging limit of 4.5 or 4.75 Kb. This means that Cas9 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

TABLE 6

| Species | Cas9 Size |
| --- | --- |
| Corynebacter diphtheria | 3252 |
| Eubacterium ventriosum | 3321 |
| Streptococcus pasteurianus | 3390 |
| Lactobacillus farciminis | 3378 |
| Sphaerochaeta globus | 3537 |
| Azospirillum B510 | 3504 |
| Gluconacetobacter diazotrophicus | 3150 |

TABLE 6-continued

| Species | Cas9 Size |
|---|---|
| Neisseria cinerea | 3246 |
| Roseburia intestinalis | 3420 |
| Parvibaculum lavamentivorans | 3111 |
| Staphylococcus aureus | 3159 |
| Nitratifractor salsuginis DSM 16511 | 3396 |
| Campylobacter lari CF89-12 | 3009 |
| Streptococcus thermophilus LMD-9 | 3396 |

These species are therefore, in general, preferred Cas9 species; SaCas9 and SpCas9 are presently preferred. As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

TABLE 7

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 2 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

Lentivirus: Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types. Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids: 5 μg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum. These methods use serum during cell culture, but serum-free methods are preferred. Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50 ul of DMEM overnight at 4 C. They were then aliquoted and immediately frozen at −80° C. In another embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas system of the present invention. In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention. Concerning Lentiviral vectors, see also US Patent Publication No. 20120295960 and U.S. Pat. Nos. 7,303,910 and 7,351,585; US Patent Publication Nos. 20060281180, 20090007284, US20110117189; US20090017543; US20070054961, US20100317109; US Patent Publication Nos. US20110293571; US20110293571, US20040013648, US20070025970, US20090111106 and U.S. Pat. No. 7,259,015.

RNA delivery: RNA delivery: The CRISPR enzyme, for instance a Cas9, and/or any of the present RNAs, for instance a guide RNA, can also be delivered in the form of RNA. Cas9 mRNA can be generated using in vitro transcription. For example, Cas9 mRNA can be synthesized using a PCR cassette containing the following elements: T7_promoter-kozak sequence (GCCACC)-Cas9-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

Nanoparticles: In general, a "nanoparticle" is a particle and can refer to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm. Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention. Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants. CRISPR enzyme mRNA and guide RNA may be delivered simultaneously using nanoparticles or lipid envelopes; see, e.g., Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1); Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199); Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93; US patent application 20110293703; US Patent Publication No. 20130302401. Lipid nanoparticles (LNPs) are also contemplated; see, e.g., Coelho et al., N Engl J Med 2013; 369:819-29; Tabernero et al., Cancer Discovery, April 2013, Vol. 3, No. 4, pages 363-470; Rosin et al, Molecular Therapy, vol. 19, no. 12, pages 1286-2200, December 2011). Spherical Nucleic Acid (SNA™) constructs and other nanoparticles (particularly gold nanoparticles) are also contemplated; see, e.g., Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192. Concerning construction of self-assembling nanoparticles with RNA; see, e.g., Schiffelers et al., Nucleic Acids Research, 2004, Vol. 32, No. 19; Bartlett et al. PNAS, Sep. 25, 2007, vol. 104, no. 39; Davis et al. Nature, Vol 464, 15 Apr. 2010; U.S. Pat. Nos. 8,709,843; 6,007,845; 5,855,913; 5,985,309; 5,543,158; WO2012135025 (also published as US20120251560); James E. Dahlman and Carmen Barnes et al. Nature Nanotechnology (2014) published online 11 May 2014, doi:10.1038/nnano.2014.84).

Particle delivery systems and/or formulations: Several types of particle delivery systems and/or formulations are known to be useful in a diverse spectrum of biomedical applications. In general, a particle is defined as a small object that behaves as a whole unit with respect to its transport and properties. Particles are further classified according to diameter Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm. As used herein, a particle delivery system/formulation is defined as any biological delivery system/formulation which includes a particle in accordance with the present invention. A particle in accordance with the present invention is any entity having a greatest dimension (e.g. diameter) of less than 100 microns (m). In some embodiments, inventive particles have a greatest dimension of less than 10 m. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm. Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry(MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, concerning particles, methods of making and using them and measurements thereof. Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

Exosomes: Exosomes, nano-vesicles that transport RNAs and proteins, are contemplated; see, e.g. Alvarez-Erviti et al. 2011, Nat Biotechnol 29: 341; El-Andaloussi et al. Nature Protocols 7, 2112-2126(2012); Wahlgren et al. Nucleic Acids Research, 2012, Vol. 40, No. 17 e130.

Liposomes: Liposomes are contemplated. Liposomes are spherical vesicle structures composed of a uni- or multilamellar lipid bilayer surrounding internal aqueous compartments and a relatively impermeable outer lipophilic phospholipid bilayer; see, e.g., Spuch and Navarro, Journal of Drug Delivery, vol. 2011, Article ID 469679, 12 pages, 2011. doi:10.1155/2011/469679; cshprotocols.cshlp.org/content/2010/4/pdb.prot5407.long (Trojan Horse liposomes also known as Molecular Trojan Horses); Morrissey et al., Nature Biotechnology, Vol. 23, No. 8, August 2005) (stable nucleic-acid-lipid particle (SNALP)); Zimmerman et al., Nature Letters, Vol. 441, 4 May 2006); Li, Gene Therapy (2012) 19, 775-780); Geisbert et al., Lancet 2010; 375: 1896-905; Judge, J. Clin. Invest. 119:661-673 (2009); Barros and Gollob, Advanced Drug Delivery Reviews 64 (2012) 1730-1737; Semple et al., Nature Biotechnology, Volume 28 Number 2 Feb. 2010, pp. 172-177.

Other Lipids: Other cationic lipids, such as amino lipid 2,2-dilinoleyl-4-dimethylaminoethyl-[1,3]-dioxolane (DLin-KC2-DMA) may be utilized to encapsulate CRISPR-Cas or components thereof or nucleic acid molecule(s) coding therefor; see e.g., Jayaraman, Angew. Chem. Int. Ed. 2012, 51, 8529-8533; Kormann et al. "Expression of therapeutic proteins after delivery of chemically modified mRNA in mice: Nature Biotechnology, Volume:29, Pages: 154-157 (2011); Novobrantseva, Molecular Therapy-Nucleic Acids (2012) 1, e4; doi:10.1038/mtna.2011.3); U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 1766035; 1519714; 1781593 and 1664316). The CRISPR Cas system or components thereof or nucleic acid molecule(s) coding therefor may be delivered encapsulated in PLGA Microspheres such as that further described in US published applications 20130252281 and 20130245107 and 20130244279 (assigned to Moderna Therapeutics); Schrum et al., Delivery and Formulation of Engineered Nucleic Acids, US published application 20120251618. See also Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161 (2):523-36; US Patent Publication No. 20050019923; US Patent Publication No. 20050019923; Bioactive Polymers, US published application 20080267903.

Supercharged proteins: Supercharged proteins are contemplated too and are a class of engineered or naturally occurring proteins with unusually high positive or negative net theoretical charge and may be employed in delivery of CRISPR Cas system(s) or component(s) thereof or nucleic acid molecule(s) coding therefor; see, e.g., Lawrence et al., 2007, Journal of the American Chemical Society 129, 10110-10112); Akinc et al., 2010, Nat. Biotech. 26, 561-569; McNaughton et al., 2009, Proc. Natl. Acad. Sci. USA 106, 6111-6116; Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012).

Packaging and Promoters generally: Ways to package Cas9 coding nucleic acid molecules, e.g., DNA, into vectors, e.g., viral vectors, to mediate genome modification in vivo include:

To achieve NHEJ-mediated gene knockout:
Single virus vector:
    Vector containing two or more expression cassettes:
    Promoter-Cas9 coding nucleic acid molecule-terminator
    Promoter-gRNA1-terminator
    Promoter-gRNA2-terminator
    Promoter-gRNA(N)-terminator (up to size limit of vector)
Double virus vector:
    Vector 1 containing one expression cassette for driving the expression of Cas9
    Promoter-Cas9 coding nucleic acid molecule-terminator
    Vector 2 containing one more expression cassettes for driving the expression of one or more guide RNAs
    Promoter-gRNA1-terminator
    Promoter-gRNA(N)-terminator (up to size limit of vector).

To mediate homology-directed repair.
In addition to the single and double virus vector approaches described above, an additional vector is used to deliver a homology-direct repair template.

The promoter used to drive Cas9 coding nucleic acid molecule expression can include:

AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cas9.

For ubiquitous expression, can use promoters: CMV, CAG, CBh, PGK, SV40, Ferritin heavy or light chains, etc.

For brain or other CNS expression, can use promoters: Synapsin I for all neurons, CaMKIIalpha for excitatory neurons, GAD67 or GAD65 or VGAT for GABAergic neurons, etc.

For liver expression, can use Albumin promoter.
For lung expression, can use SP-B.
For endothelial cells, can use ICAM.
For hematopoietic cells can use IFNbeta or CD45.
For Osteoblasts can use OG-2.
The promoter used to drive guide RNA can include:
Pol III promoters such as U6 or H1
Use of Pol II promoter and intronic cassettes to express gRNA Nucleic acids, amino acids and proteins, Regulatory sequences, Vectors, etc: Nucleic acids, amino acids and proteins: The invention uses nucleic acids to bind target DNA sequences. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. As used herein the term "wild type" is a term of the art understood by skilled persons and means the typical form of an organism, strain, gene or characteristic as it occurs in nature as distinguished from mutant or variant forms. A "wild type" can be a base line. As used herein the term "variant" should be taken to mean the exhibition of qualities that have a pattern that deviates from what occurs in nature. The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. "Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately-stringent washing conditions are selected to be about 15 to 30° C. lower than the $T_m$. Highly permissive (very low stringency) washing conditions may be as low as 50° C. below the $T_m$, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C. "Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. As used herein, the term "domain" or "protein domain" refers to a part of a protein sequence that may exist and function independently of the rest of the protein chain. As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% identical or share identity to the capping region amino acid sequences provided herein. Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p387). Examples of other software than may perform sequence comparisons include, but are not limited to, the BLAST package (see Ausubel et al., 1999 Short Protocols in Molecular Biology, 4$^{th}$ Ed.—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174 (2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" Comput. Appl. Biosci. 9: 745-756) (Taylor W. R. (1986) "The classification of amino acid conservation" J. Theor. Biol. 119; 205-218). Conservative substitutions may be made, for example according to the table below which describes a generally accepted Venn diagram grouping of amino acids.

TABLE 8

| Set | Sub-set | | |
|---|---|---|---|
| Hydrophobic | FWYHKMILVAGC | Aromatic | FWYH |
| | | Aliphatic | ILV |
| Polar | WYHKREDCSTNQ | Charged | HKRED |
| | | Positively charged | HKR |
| | | Negatively charged | ED |
| Small | VCAGSPTND | Tiny | AGS |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of E. coli DNA polymerase, and reverse transcriptase. A preferred amplification method is PCR.

In certain aspects the invention involves vectors. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects of the invention relate to bicistronic vectors for chimeric RNA and Cas9. Bicistronic expression vectors for chimeric RNA and Cas9 are preferred. In general and particularly in this embodiment Cas9 is preferably driven by the CBh promoter. The chimeric RNA may preferably be driven by a Pol III promoter, such as a U6 promoter. Ideally the two are combined. The chimeric guide RNA typically consists of a 20 bp guide sequence (Ns) and this may be joined to the tracr sequence (running from the first "U" of the lower strand to the end of the transcript). The tracr sequence may be truncated at various positions as indicated.

The guide and tracr sequences are separated by the tracr-mate sequence, which may be GUUUUAGAGCUA (SEQ ID NO: 64). This may be followed by the loop sequence GAAA as shown. Both of these are preferred examples. Applicants have demonstrated Cas9-mediated indels at the human EFMX and PVALB loci by SURVEYOR assays. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (sgRNA). The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced into a cell by nucleofection.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET lid (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast *Saccharomyces cerivisae* include pYepSecl (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei*, *Streptococcus pyogenes*, *Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochem. Biophys. Acta 1307: 26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum*, *Pyrobaculum*, *Sulfolobus*, *Archaeoglobus*, *Haloarcula*, *Methanobacterium*, *Methanococcus*, *Methanosarcina*, *Methanopyrus*, *Pyrococcus*, *Picrophilus*, *Thermoplasma*, *Corynebacterium*, *Mycobacterium*, *Streptomyces*, *Aquifex*, *Porphyromonas*, *Chlorobium*, *Thermus*, *Bacillus*, *Listeria*, *Staphylococcus*, *Clostridium*, *Thermoanaerobacter*, *Mycoplasma*, *Fusobacterium*, *Azarcus*, *Chromobacterium*, *Neisseria*, *Nitrosomonas*, *Desulfovibrio*, *Geobacter*, *Myxococcus*, *Campylobacter*, *Wolinella*, *Acinetobacter*, *Erwinia*, *Escherichia*, *Legionella*, *Methylococcus*, *Pasteurella*, *Photobacterium*, *Salmonella*, *Xanthomonas*, *Yersinia*, *Treponema*, and *Thermotoga*.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, which is hereby incorporated by reference in its entirety.

The practice of the present invention employs, unless otherwise indicated, conventional techniques of immunology, biochemistry, chemistry, molecular biology, microbiology, cell biology, genomics and recombinant DNA, which are within the skill of the art. See MOLECULAR CLONING: A LABORATORY MANUAL, 2nd edition (1989) (Sambrook, Fritsch and Maniatis); MOLECULAR CLONING: A LABORATORY MANUAL, 4th edition (2012) (Green and Sambrook); CURRENT PROTOCOLS IN MOLECULAR BIOLOGY (1987) (F. M. Ausubel, et al. eds.); the series METHODS IN ENZYMOLOGY (Academic Press, Inc.); PCR 2: A PRACTICAL APPROACH (1995) (M. J. MacPherson, B. D. Hames and G. R. Taylor eds.); ANTIBODIES, A LABORATORY MANUAL (1988) (Harlow and Lane, eds.); ANTIBODIES A LABORATORY MANUAL, 2nd edition (2013) (E. A. Greenfield ed.); and ANIMAL CELL CULTURE (1987) (R. I. Freshney, ed.).

The practice of the present invention employs, unless otherwise indicated, conventional techniques for generation of genetically modified mice. See Marten H. Hofker and Jan van Deursen, TRANSGENIC MOUSE METHODS AND PROTOCOLS, 2nd edition (2011).

Kits: In one aspect, the invention provides kits containing any one or more of the elements disclosed in the above methods and compositions. Elements may be provided individually or in combinations, and may be provided in any suitable container, such as a vial, a bottle, or a tube. In some embodiments, the kit includes instructions in one or more languages, for example in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allows to provide all elements of the systems of the invention.

The present invention advantageously provides for isolating and culturing subpopulations of cells with interesting, stable phenotypes by targeting a DNA barcode. The present invention is especially advantageous when the subpopulations are rare (<1%) at timepoints of interest (e.g., resistant cells before adding drug). Applicants have also unexpectedly determined that the subpopulations have a stable phenotype and behave reproducibly after >15 divisions+freeze-thaw.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1 Cas9-Targetable Barcodes for Efficient Isolation of Clonal Sub-Populations The analysis of genetically heterogeneous cell populations is complicated by the fact that many biological assays are destructive, making it difficult to isolate cells with particular properties for further study and use. For example, cells originating from a patient tumor may carry different mutations and chromosomal arrangements, leading to different properties, e.g., resistance to chemotherapy. Techniques such as RNA and protein analysis may reveal key signatures of resistant cells, e.g., an aberrant epigenetic state, but destroy the cells, thus precluding further experiments on the same cells. Traditionally, this limitation has been circumvented in dividing cell populations by isolating individual cells, e.g., in a multiwell plate, expanding the cells, and splitting the cells for downstream use. However, this process is laborious (each cell must be handled individually), slow (typically a month to expand cells), and low throughput. Furthermore, many cell types are not amenable to expansion from single cells, which may cause cell death or profound changes to cell physiology. Recently, the introduction of unique DNA barcodes into a cell population has partially alleviated this difficulty. Barcoded cells are expanded, split into parallel selection-based assays, and after each assay barcodes are counted by next-generation sequencing (Nolan-Stevaux, Olivier et al. "Measurement of cancer cell growth heterogeneity through lentiviral barcoding identifies clonal dominance as a characteristic of in vivo tumor engraftment." *PLoS one* (8)6 (2013)). However, this does not address the goal of retrieving particular subpopulations (such as the descendants of an initial resistant cell), and is limited to selection-based assays with a simple readout obtainable by counting barcodes as a proxy for cells. The inventive technique recovers cells containing specific barcodes from a heterogeneous population by programming a Cas9 activator (Konermann, Silvana et al. "Genome-scale transcriptional activation by an engineered CRISPR-Cas9 complex." *Nature* (2014)). to target the specific barcodes, leading to expression of a selection marker. A cassette including unique barcodes, followed by a selection marker (e.g., fluorescent protein, antibiotic resistance, luciferase protein), is integrated into the heterogeneous population of interest. Cells containing specific barcodes are selected for by introducing a Cas9 activator and sgRNA targeting sequences within the barcode. Selection is completed by traditional means, such as fluorescently-activated flow sorting (FACS) or drug selection. The method can be applied to cell populations with natural heterogeneity, such as cancer cells, or engineered heterogeneity, such as cells modified through genome engineering.

Methodology: The method comprises the following steps:
1. Barcode the cell population of interest using a lentiviral barcode delivery vector at low multiplicity of infection (MOI) and subsequent selection of the population for transformed cells.
2. Expand the population of cells through a number of cell divisions, in this case 4 is advantageous, and split the cells into a test population and a recovery population.
3. Optionally, the recovery population is preserved cryogenically.
4. Assay the test population by exposing the cells to different drug regimes over a period of time, in this case several weeks.
5. Determine the barcodes present in cells of interest in the test population (e.g. those cells that have a survival or growth advantage when exposed to drug), across multiple replicates (replicates are obtained e.g. by splitting the cell population into separate subpopulations during assay growth).
6. Generate guides for recruiting Cas9 activators. The guides target the barcodes of interest. The guides are generated by cloning matching sgRNAs into an adeno-associated virus (AAV) Cas9 activator vector.
7. Deliver the guides and Cas9 activators targeting the barcodes of interest to the recovery population, activating the selection marker.
8. Isolate the cells containing barcodes of interest by a selection protocol, e.g., FACS based on mCherry expression.
9. Cells are isolated corresponding to individual barcodes of interest.

As an optional step in addition to or in replacement of step 9 above:
10. Cells are optionally isolated corresponding to subsets of barcodes of interest. If a subset of cells is isolated and analyzed, e.g., by single-cell gene expression profiling, the exact barcode corresponding to each analyzed cell may be determined by identifying a transcribed barcode present in the Cas9-targetable selection marker, e.g., a barcode encoded by synonymous mutation.

Generating Constructs: The following may be prepared in the practice of the invention:
A. Barcode Construct and Barcode delivery vector;
B. Cas9 activator and delivery vector; and
C. Guide Construct(s) and delivery vector.

Barcode Construct: In general barcode constructs are known, but until the instant invention none were designed for use with the CRISPR-Cas system. A DNA construct for the barcode is designed based on the following. The barcode comprises three components:
I. A barcode sequence
II. Activatable promoter or enhancer
III. Cas9-targetable first selection marker Each of these three components is designed based on one or more of the rules set out below.
I. A barcode sequence is designed based on one or more of the following rules:
   a. from 20-200 bp long
   b. contains one or multiple subsequences targetable by Cas9, and a CRISPR RNA target sequence (e.g., a CRISPR-Cas9 complex) and includes a PAM (e.g., NGG for SpCas9) so as to be targeted
   c. designed according to rules that enhance Cas9 activator specificity or activity, including restrictions on GC content, homopolymer stretches, maximal orthogonality among targets, and/or reduced or essentially none nuclease activity
   d. synthesized as individual oligonucleotides, oligonucleotides containing degenerate bases, or a library of oligonucleotides synthesized on an array
   e. That handled individually or as a pooled library
II. Activatable promoter or enhancer is designed based on one or more of the following rules:
   a. placed before or after the barcode sequence
   b. placed before or after the selection marker
   c. contains an inducible element (e.g., Tet promoter compatible with IPTG induction)
   d. a constitutive native promoter with low baseline activity
   e. a constitutive synthetic promoter with low baseline activity (e.g., minCMV)
III. Cas9-targetable first selection marker is designed based on one or more of the following rules:
   a. an antibiotic resistance gene (e.g, Pac conferring puromycin resistance)
   b. a fluorescent reporter (e.g., mCherry)
   c. a luminescent reporter (e.g., luciferase)
   d. a unique barcode in part of the RNA transcript, possibly encoded through synonymous mutations, to be used in matching RNA-seq data (e.g., single cell gene expression profiling) to the originating cell.

An additional alternative methodology comprises the following steps:
1. Prepare cells with stably integrated universal components for barcoding system, e.g., Cas9. These components may not need to be present in the cells that are initially assayed; they could be added just before recovery. For example, if a Cas9 lentivirus is used, integration (and potential for functional disruption) can be delayed until after the barcoded population is phenotyped. Cas9 integration will not produce a barcode phenotype. Before recovery the cells can be expanded to ~100 cells/barcode followed by a MOI~1 integration (or no integration).
2. Barcode cells using a high-complexity lentivirus pool at low MOI. Expand and split into replicate assays so that the probability of an assay containing at least one cell with a given barcode is high (calculated as 1−exp(#cells/#assays)). Early cell division and splitting cells into replicate assays will be stochastic, contributing to variation among final barcode abundance, even under a null model. Enough replicates must be used to overcome this noise for the anticipated effect size (e.g., relative fitness of subpopulation).

3. Optionally, deplete high-background barcodes by FACS or immunopanning against a synthetic surface marker. This is most relevant when the barcode is a Cas9 activator target, and barcodes with low background remain so over time.

4. Split population at timepoints of interest. Expand and freeze. Sequence barcode abundances at some timepoints. Analyze abundances across replicates and conditions to estimate effect size (e.g., differential fitness) and prioritize barcodes for recovery.

5. Recover N barcodes of interest from a population after thawing and expansion. If a single round of selection is used, the population must be expanded and split into N replicates, while minimizing barcode dropout. If two rounds are used, multiple barcodes may be targeted in the first round, depending on the delivery strategy, e.g., if the barcode is an sgRNA, then a string of many baits could be used. Selection may use an antibiotic resistance marker, fluorescent protein, or surface marker depending on the size of population to select, and viability and purity required.

6. Expand and validate isolated subpopulations by sequencing barcodes and/or insertion site. To show functional equivalence, it may be necessary to repeat the original phenotyping experiment with the subpopulation.

Integrated barcode: The barcode must be readily deconvolved by PCR and sequencing. It would be valuable to be able to link barcode and insertion site in one PCR amplicon <800 bp, although this requires a recombination-free PCR. An sgRNA chimeric backbone plus lentiviral 3' LTR is about 350 bp in length, so this may be used with a "reverse" barcode. A short promoter (EFS) in the antisense direction plus lentiviral 3' LTR is about 500 bp, which may be too long to prepare a high complexity sequencing library of integration sites.

It may also be desirable for the barcode to appear in poly-adenylated transcripts visible in population/single-cell RNA-seq datasets. Some library construction methods (e.g., drop-seq) will only capture 3' barcodes.

AAV can be used for efficient, titratable delivery of transgene up to ~4.7 kb in length. High titer lentivirus holds ~8 kb and will stably integrate with a preference for the 5' region of transcribed genes. Both infect a wide range of cells, with exceptions. Transfection of plasmid is not desirable due to low efficiency, chemical perturbation, and inability to titer proportionally in many cell types.

Forward/reverse barcoding: Cas9-based barcoding could be implemented in a "reverse" direction, where the cellular barcode is an sgRNA. The target for an activator or nuclease reporter could be delivered transiently (e.g., as AAV), with multiple copies per cell. Multiple targets could be included per reporter (e.g., tandem baits), potentially increasing the efficiency of isolating subpopulations, although this will automatically require a second round of deconvolution. In this embodiment, one selection reagent can be applied to the whole population, minimizing dropout. The benefit is greater if interested in more barcodes (>8).

This approach can also allow combining multiple Cas9 modalities in separate selection rounds. For example, an activator with high sensitivity but low specificity can be followed by a nuclease with lower sensitivity but high specificity, using the same sgRNA(MS2) for both steps.

Barcode implementations and trade-offs:

SAM activator: 3xbait-minP-selection+lenti-dCas9-VP64+AAV-sgRNA(MS2)-MS2-activators. Strategies to decrease background transcription:

can use self-inactivating (SIN) lentivirus, with minimal transcription from LTR add 5' polyA (promega pL4.10 design), may require inverting cassette for titer add 5' insulator place bait at least 300 bp into virus in order to minimize genomic off-target space.

Nuclease reporter: Encoding an on/off switch in the DNA sequence rather than the transcriptional context can provide a reporter with much lower background. Off-target effects could also be reduced as Cas9 nuclease is more specific than the dCas9 activator. However, sensitivity will be decreased due to the requirement for an indel of the correct type (for a random frameshift, total indel efficiency is 1/3).

In the present example, as shown in FIG. 1 (from left to right): the DNA barcode is provided, with a minCMV minimal promoter and an mCherry fluorescent reporter; together with a first drug selection marker (Hygro, inferring resistance to Hygromycin) under the control of an EFS promoter. FIG. 3 shows some barcode sequences, where the lower case letters are PAMs for SpCas9, and the uppercase letters are 20 ntd stretches representing target sequences for the guide RNA.

Barcode delivery vector: A vector is provided to deliver the single barcodes, described above, to cells in the initial cell population. This comprises a lentiviral backbone encoding a second selection marker. This second selection marker is different from first or other selection marker(s) used in the method to assist with sorting. The vector is used to introduce barcodes at low MOI. This is followed by selection to ensure a high fraction of cells with single integration events. FIG. 4 shows a barcode construct example sequence, where barcode sequences (such as shown in FIG. 3) cloned into the vector via BsmBI sites.

Cas9 activators: The activator vector design is shown in FIG. 2. Here, the Cas9 transcriptional activator dCas9-VP64 is used, see top of FIG. 2. A separate guide construct is provided, although the guide and the Cas9 transcriptional activator are used here in combination, they may be delivered separately. The Cas9 transcriptional activator can be constitutively expressed by the cells. The guide construct used comprises MS2-P65-HSF1. The guide sequence in the sgRNA targets, i.e. hybridizes to, the selected barcode, see the bottom of FIG. 3. Here, sgRNAs targeting the selected barcode and containing MS2 loops integrated at tetraloop and stemloop2 (as previously described by Konermann et al (2014)) are used with MS2-activator (adaptor protein) fusions. Vector for delivery of Cas9 transcriptional activator: dCas9-VP64 is packaged into a lentiviral vector and can be selected via blasticidin. The cells of interest can be transduced with this vector at different stages of the method (e.g. at the same time as the barcodes or after the assay and sequencing of enriched barcodes). Guide(s) and delivery vector: The MS2-P65-HSF1 activator component is packaged together with an sgRNA targeting the desired barcode into an AAV plasmid. The purpose and benefit of using AAV is that it does not integrate into the genome and therefore provides transient expression in dividing cells. This allows for efficient activation and sorting of the target population followed by loss of activation. This leaves the cells unperturbed for either follow-up sorting with a separate barcode or further experiments. Alternatively, these components are delivered via transient transfection, electroporation, nucleofection or other viral vectors.

Figure 5:
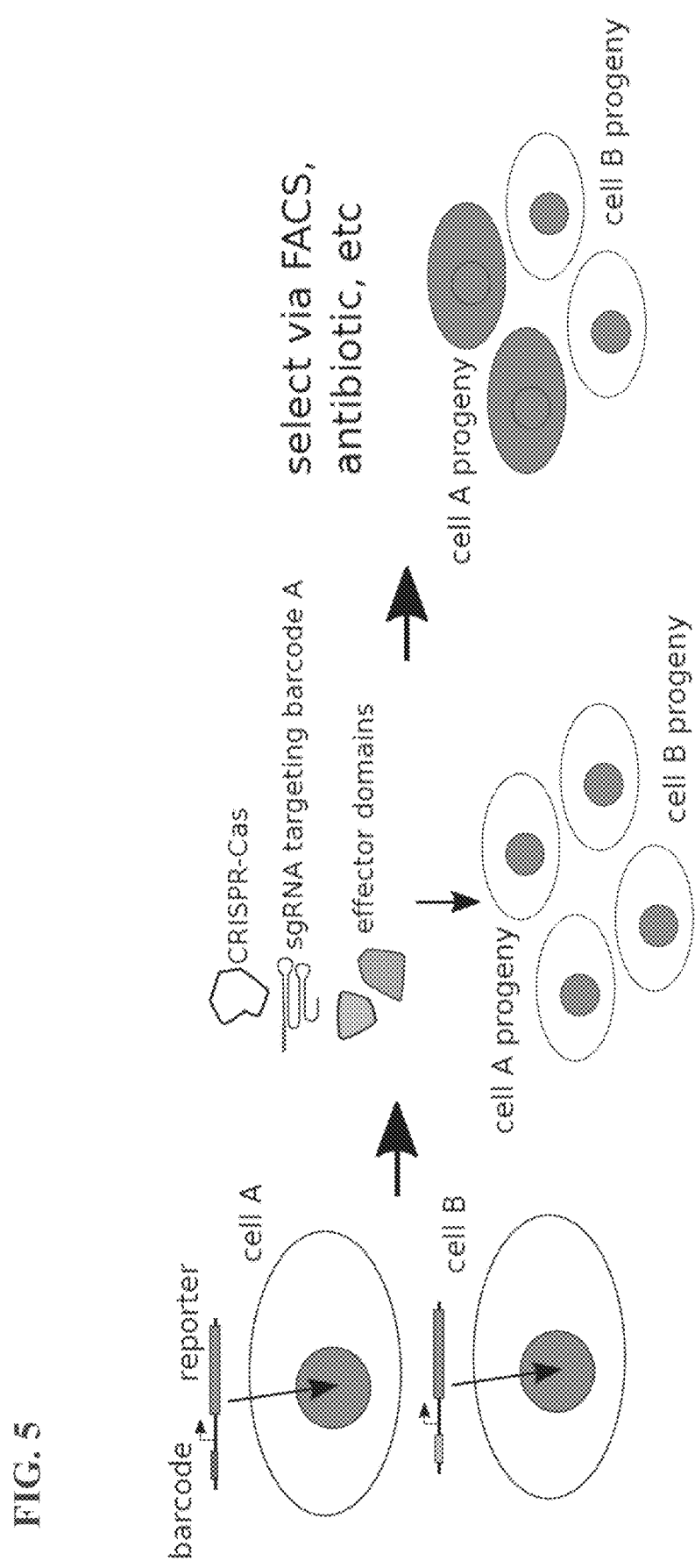
FIG. 5: Representation of a CRISPR-Cas complex of the invention comprising the CRISPR-Cas enzyme, the CRISPR-Cas guide RNA and the DNA barcode of interest.

FIG. 5 depicts an activation strategy. Cell A is selected for by using a guide RNA targeting the barcode of the reporter present in cell A. An effector domain bound to the sgRNA through MS2 binding activates expression of the reporter in cell A. Cell A and its progeny are then sorted by FACS or antibiotic resistance.

There are multiple strategies for barcoding cells and retrieving cells containing specific barcodes using an RNA-directed protein. In addition to the above activator strategy, Applicants have demonstrated highly specific barcode activation using a catalytically active Cas9, where creating a double-strand break that is repaired by error-prone pathways results in an insertion or deletion, creating a frameshift within an open reading frame that activates and/or deactivates multiple reporters. FIG. 6 depicts an exemplary embodiment of a frameshift reporter containing a barcode sequence to be activated by a targeted nuclease. Components of the reporter include a) EFS, constitutive mammalian promoter; b) STOP 3×3, encodes stop codons in all 3 reading frames to suppress upstream translation; c) guide spacer, contains the barcode-specific sequence (for CRISPR/Cas9, this includes a 3' NGG PAM); d) T2A TM, self-cleaving 2A linker, silent nucleotide substitutions to remove ATG start codons; e) GFP™, contains silent and amino acid substitutions to remove ATG start codons; f) shift of 2 bp, changing downstream reading frame; g) P2A TM, similar to T2A TM but derived from different 2A linker; h) Puro™, contains silent substitutions to remove ATG start codons (applying puromycin before barcode targeting selects for cells expressing the Puro-mCherry frame, not the GFP frame); i) T2A, nucleotide sequence silently modified from T2A TM to avoid lentiviral recombination; and k) mCherry fluorescent reporter.

The reporter may also include any of the following. (A) An upstream ORF embedded in a bait sequence. Targeting the ORF leads to an indel, causing translation to shift to the downstream reporter ORF. The ATG start codon should be preceded by an RCC Kozak sequence, limiting the complexity in the critical PAM-proximal bases. Cryptic start/stop codons can be avoided by generating the bait with a 3 letter alphabet, e.g., V=A/C/G. An alternate bait could be encoded in the antisense direction, at the complexity cost of fixing two additional bases (antisense PAM). Enhanced nonsense mediated decay (NMD) may result from termination far upstream of an exon-exon junction. (B) A bicistronic out-of-frame reporter switches translation from GFP to mCherry if a +2/−1 indel occurs in a bait region after the start codon. Multiple baits could be placed in tandem. The bases around the cut site could be designed based on existing indel datasets to bias repair towards a +2/−1 indel. The 2A sequences match the frame of the subsequent reporter. (C) Mutate splice acceptor, switching cells from GFP to RFP.

Figure 7:
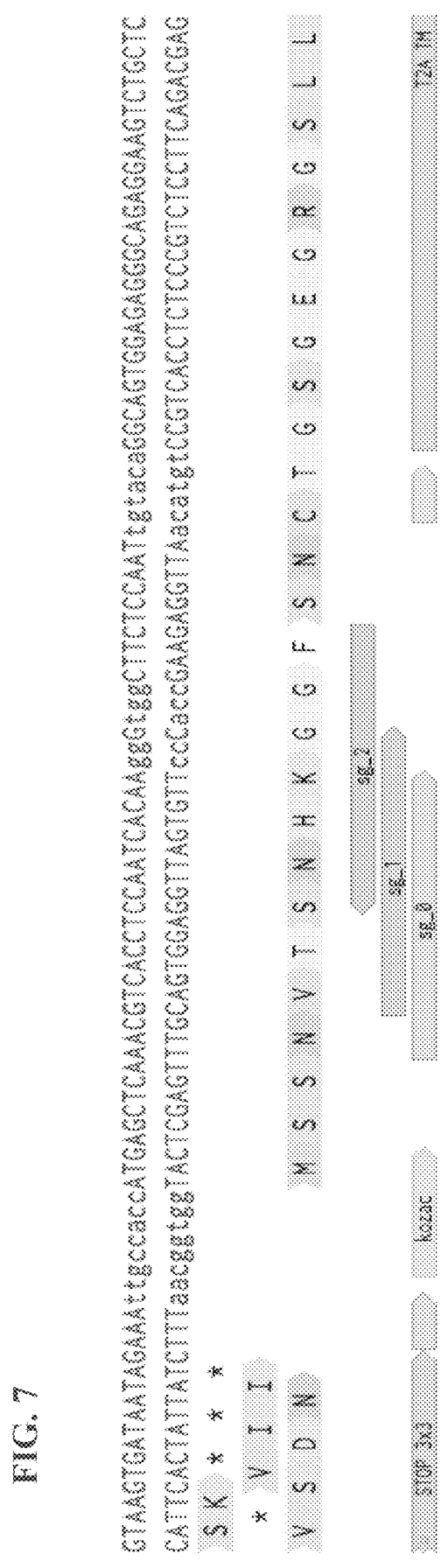

FIG. 7 depicts a double stranded DNA sequence that can be targeted by a nuclease to 3 overlapping sgRNA barcodes, labeled sg_0, sg_1 and sg_2. The amino acid sequence of the protein translated from the in frame open reading frame is shown below. This construct can be used for multiplex retrieval of all 3 barcodes.

Figure 8:
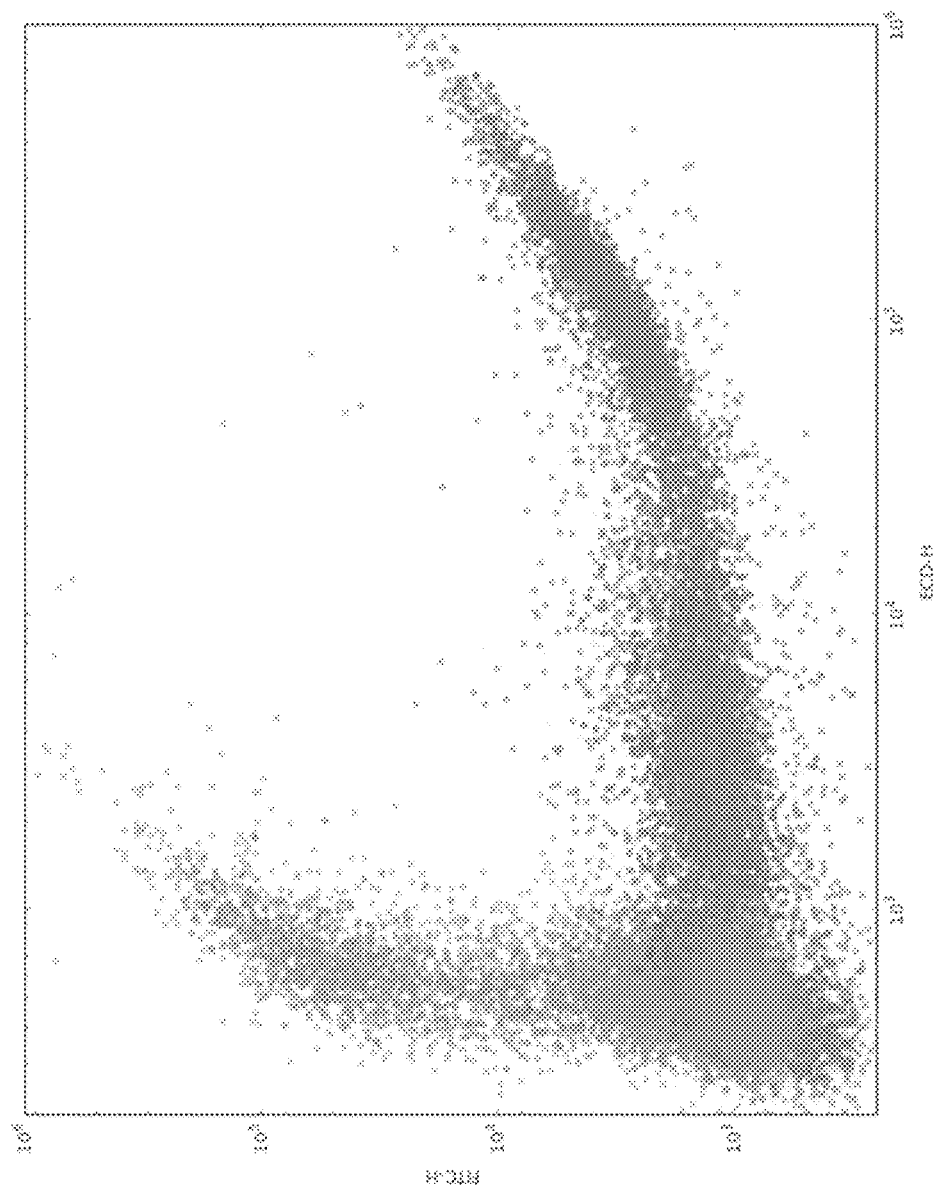
FIG. 8: FACS experiment using FR3 and FR5 reporters (see Table 9) cloned with 0, 1, and 2 bp deletions at a Cas9 targeting site (FR3-5, MOI ~0.3).
Figure 9:
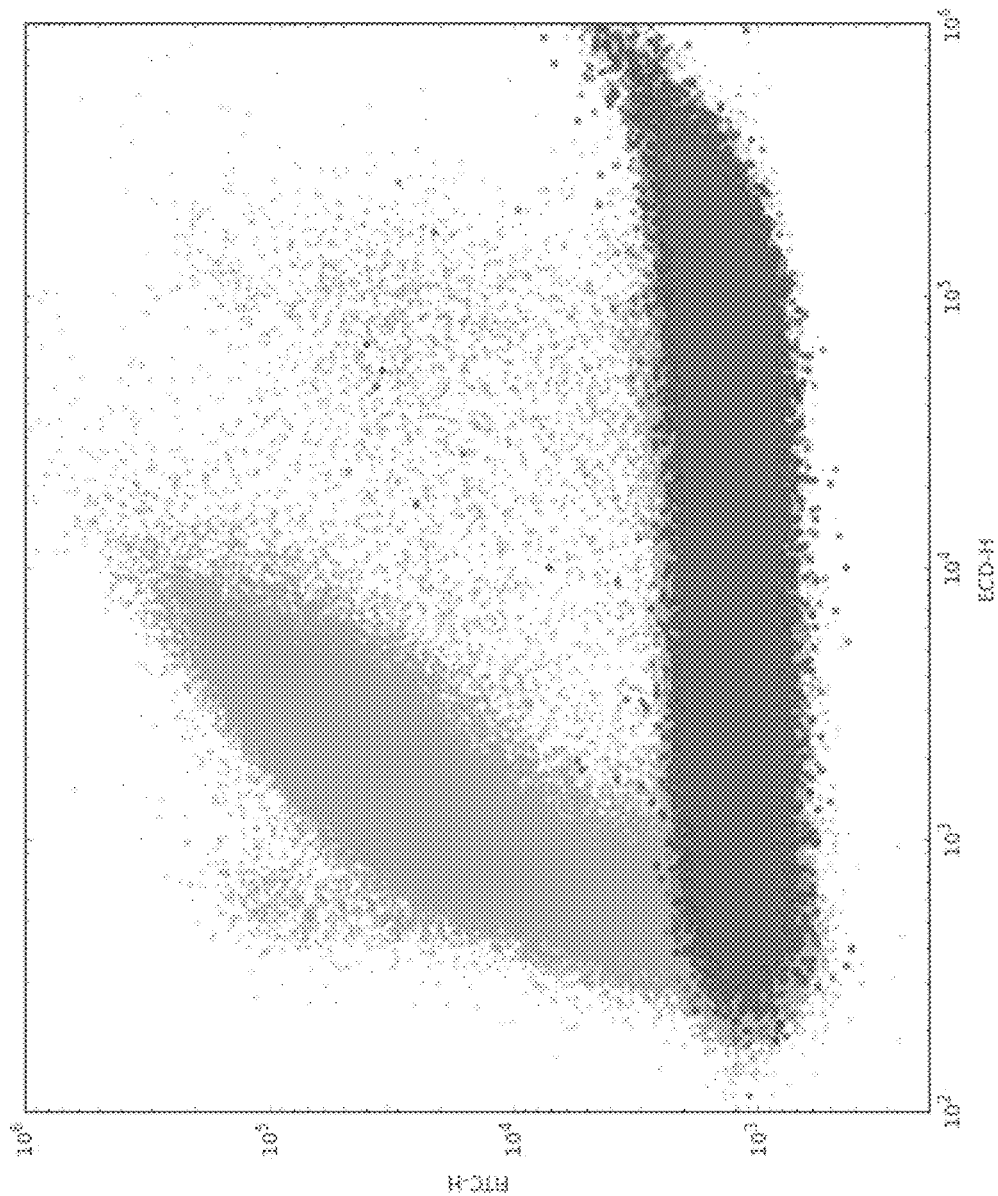
FIG. 9: FACS experiment using the FR5 reporter showing pre-activation of cells after 12d Puro selection (MOI 0.1 (3 uL) and 1.0 (27 uL)). 50K points are shown.
Figure 10:
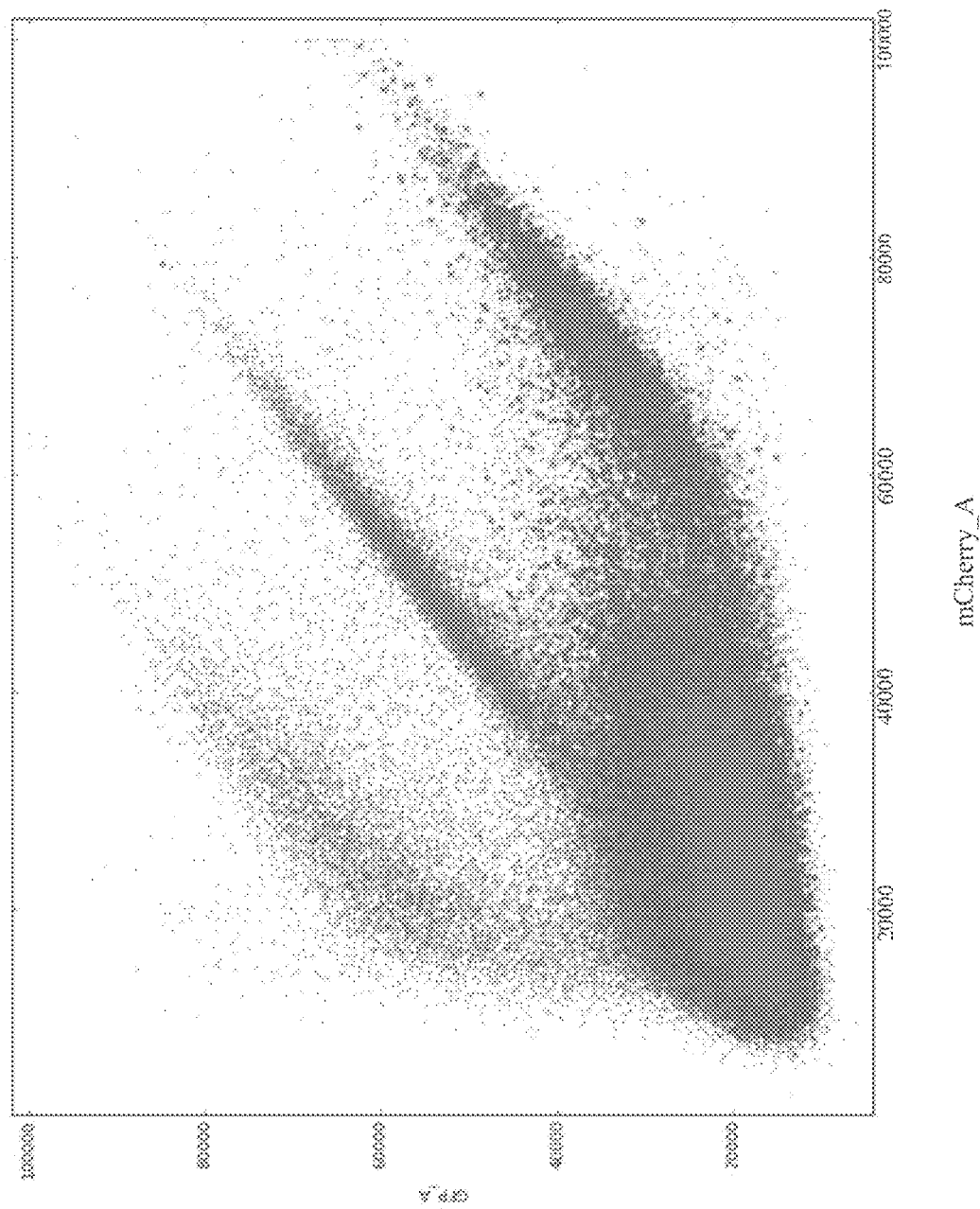
FIG. 10: FACS experiment showing no activation of GFP with 7 day treatment with a non-targeting sgRNA.
Figure 11:
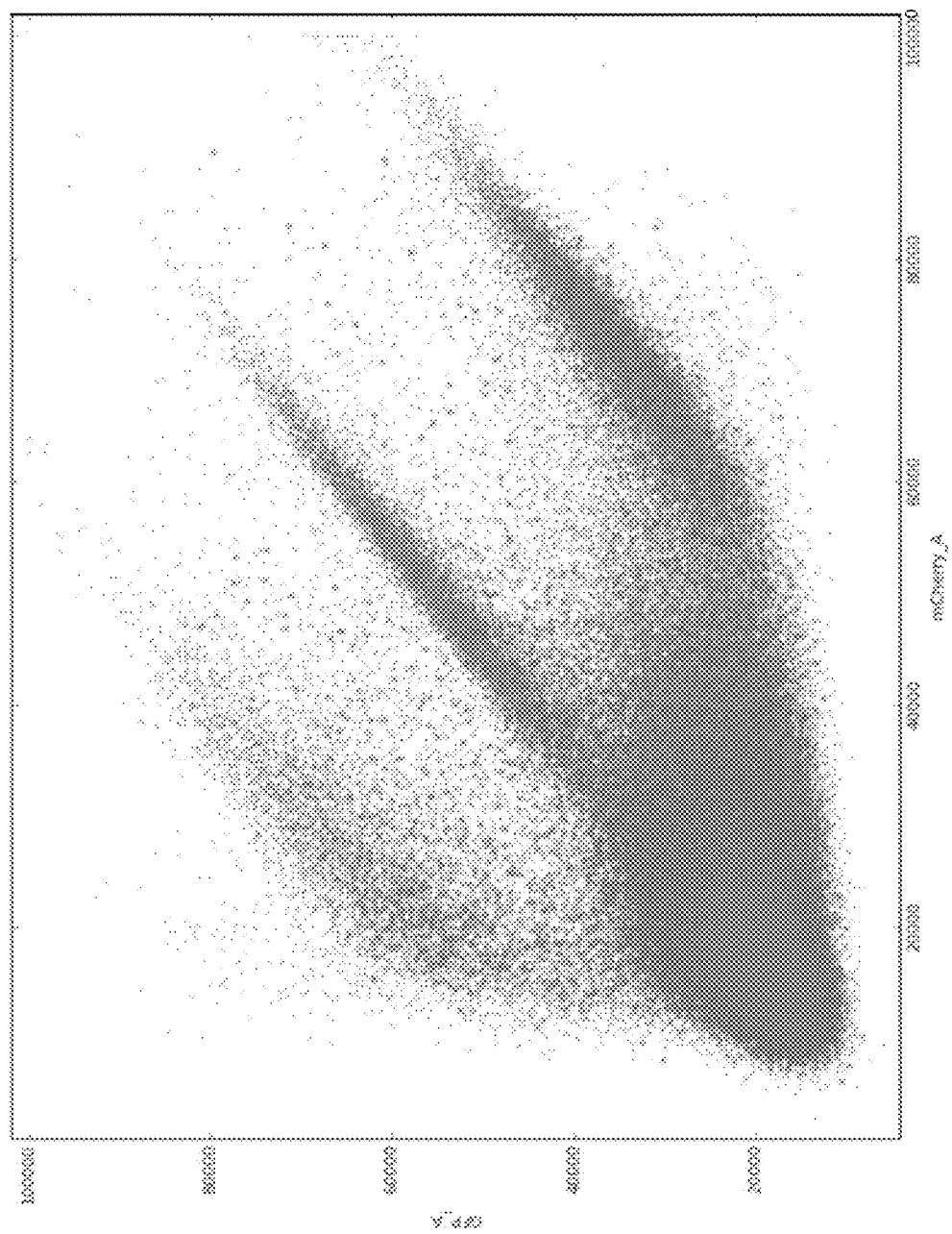
FIG. 11: FACS experiment showing activation of GFP with 7 day treatment with a barcode targeting sgRNA.
Figure 12:
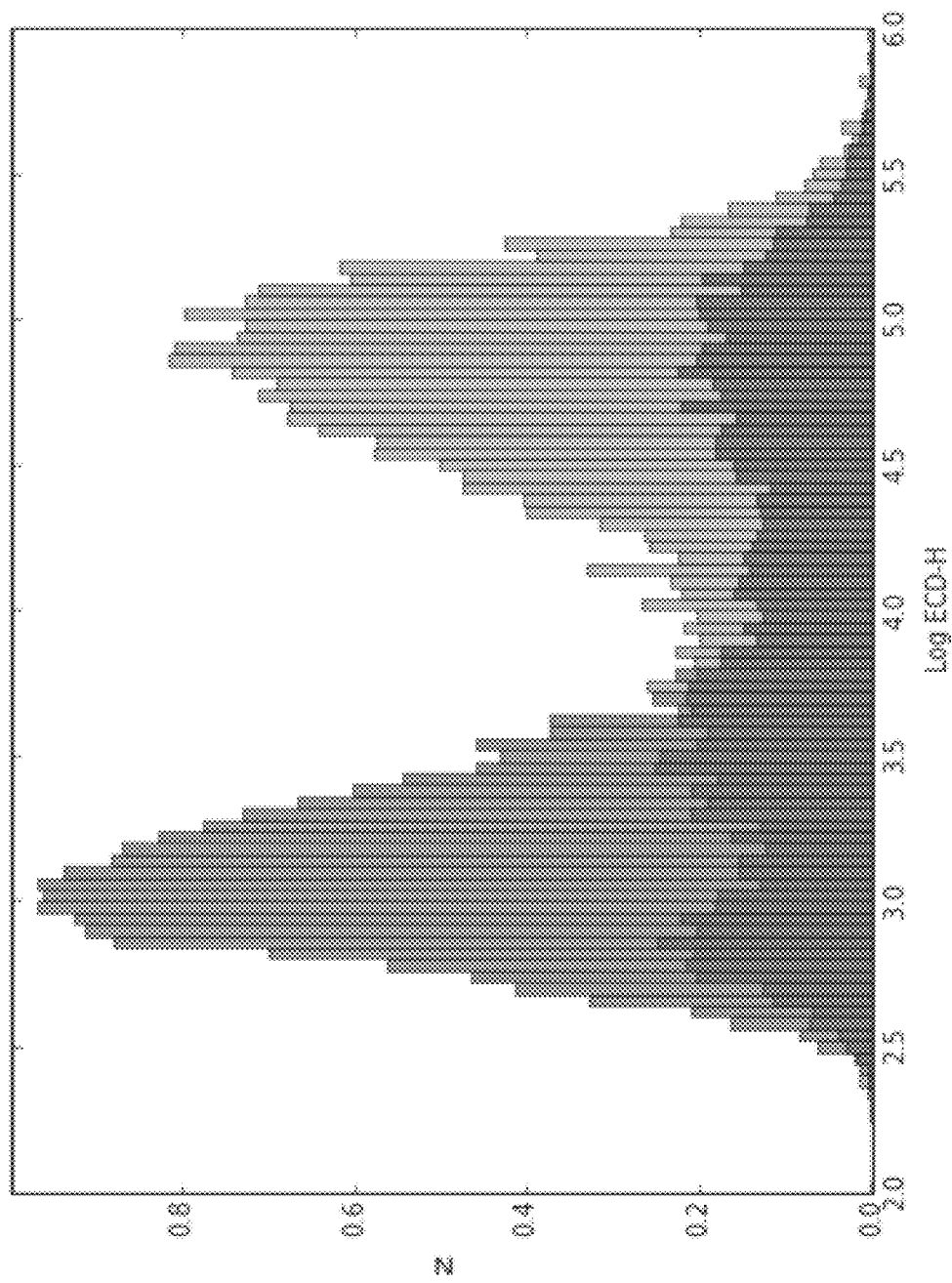
FIG. 12: Histogram of FACS experiment showing mCherry expression under selection with puromycin and with no puromycin.

FIGS. 8 to 12 show the characterization of the frameshift reporters for use in sorting and isolating culture subpopulations. FIG. 8 depicts a control FACS experiment using FR3 and FR5 reporters (see Table 1) cloned with 0, 1, and 2 bp deletions at a Cas9 targeting site. The reporters were introduced at a MOI of ~0.3. One reporter was used to show eGFP expression from the constructs and the other was used to show mCherry expression from the reporter. The experiment shows that the constructs strongly express either eGFP or mCherry depending on the deletion. FIG. 9 depicts a control FACS experiment using the FR5 reporter showing pre-activation of cells after 12d Puro selection for two MOI (MOI 0.1 (3 uL) and 1.0 (27 uL)). Shown are 50K points. FIG. 12 depicts a histogram of a control FACS experiment showing mCherry expression under selection with puromycin or with no puromycin. The experiments shows that the reporter exclusively expresses mCherry under puromycin selection and that puromycin is effective for selecting clones with the reporter. FIG. 10 depicts a FACS experiment showing cells with the reporter construct treated with a non-targeting sgRNA. The cells show no activation of GFP with a 7 day treatment with the non-targeting sgRNA showing high specificity and no background activation. FIG. 11 depicts a FACS experiment showing activation of GFP with a 7 day treatment with a barcode targeting sgRNA. The results show that activation of GFP and inactivation of mCherry in response to a targeting sgRNA is highly specific, thus allowing for the isolation of a pure subpopulation of cells with the barcode of interest. Applicants could sort cells based on simultaneous inactivation of mCherry and activation of eGFP. This highly specific signature was resolvable by FACS with a specificity of at least 1 activated cell in 1000 non-activated cells.

Sequences of exemplary vectors as described in the present invention are shown in Table 6.

TABLE 9

Vectors lenti-fr-target_0_f3-t2a-egfp-p2a-mcherry-t2a-puro
(SEQ ID NO: 65)
GTCGACGGATCGGGAGATCTCCCGATCCCCTATGGTGCACTCTCAGTACA
ATCTGCTCTGATGCCGCATAGTTAAGCCAGTATCTGCTCCCTGCTTG
TGTGTTGGAGGTCGCTGAGTAGTGCGCGAGCAAAATTTAAGCTACAACAA
GGCAAGGCTTGACCGACAATTGCATGAAGAATCTGCTTAGGGTTAGG
CGTTTTGCGCTGCTTCGCGATGTACGGGCCAGATATACGCGTTGACATTG
ATTATTGACTAGTTATTAATAGTAATCAATTACGGGGTCATTAGTTC
ATAGCCCATATATGGAGTTCCGCGTTACATAACTTACGGTAAATGGCCCG
CCTGGCTGACCGCCCAACGACCCCCGCCCATTGACGTCAATAATGAC
GTATGTTCCCATAGTAACGCCAATAGGGACTTTCCATTGACGTCAATGGG
TGGAGTATTTACGGTAAACTGCCCACTTGGCAGTACATCAAGTGTAT
CATATGCCAAGTACGCCCCCTATTGACGTCAATGACGGTAAATGGCCCGC
CTGGCATTATGCCCAGTACATGACCTTATGGGACTTTCCTACTTGGC
AGTACATCTACGTATTAGTCATCGCTATTACCATGGTGATGCGGTTTTGG
CAGTACATCAATGGGCGTGGATAGCGGTTTGACTCACGGGGATTTCC
AAGTCTCCACCCCATTGACGTCAATGGGAGTTTGTTTTGGCACCAAAATC
AACGGGACTTTCCAAAATGTCGTAACAACTCCGCCCCATTGACGCAA
ATGGGCGGTAGGCGTGTACGGTGGGAGGTCTATATAAGCAGCGCGTTTTG
CCTGTACTGGGTCTCTCTGGTTAGACCAGATCTGAGCCTGGGAGCTC
TCTGGCTAACTAGGGAACCCACTGCTTAAGCCTCAATAAAGCTTGCCTTG
AGTGCTTCAAGTAGTGTGTGCCCGTCTGTTGTGTGACTCTGGTAACT
AGAGATCCCTCAGACCCTTTTAGTCAGTGTGCAAAATCTCTAGCAGTGGC
GCCCGAACAGGGACTTGAAAGCGAAAGGGAAACCAGAGGAGCTCTCT
CGACGCAGGACTCGGCTTGCTGAAGCGCGCACGGCAAGAGGCGAGGGGCG
GCGACTGGTGAGTACGCCAAAAATTTTGACTAGCGGAGGCTAGAAGG
AGAGAGATGGGTGCGAGAGCGTCAGTATTAAGCGGGGGAGAATTAGATCG
CGATGGGAAAAATTCGGTTAAGGCCAGGGGGAAAGAAAAAATATAA
ATTAAAACATATAGTATGGGCAAGCAGGGAGCTAGAACGATTCGCAGTTA
ATCCTGGCCTGTTAGAAACATCAGAAGGCTGTAGACAAATACTGGGA
CAGCTACAACCATCCCTTCAGACAGGATCAGAAGAACTTAGATCATTATA
TAATACAGTAGCAACCCTCTATTGTGTGCATCAAAGGATAGAGATAA
AAGACACCAAGGAAGCTTTAGACAAGATAGAGGAAGAGCAAAACAAAAGT
AAGACCACCGCACAGCAAGCGGCCGCTGATCTTCAGACCTGGAGGAG
GAGATATGAGGGACAATTGGAGAAGTGAATTATATAAATATAAAGTAGTA
AAAATTGAACCATTAGGAGTAGCACCCACCAAGGCAAAGAGAAGAGT
GGTGCAGAGAGAAAAAAGAGCAGTGGGAATAGGAGCTTTGTTCCTTGGGT
TCTTGGGAGCAGCAGGAAGCACTATGGGCGCAGCGTCAATGACGCTG
ACGGTACAGGCCAGACAATTATTGTCTGGTATAGTGCAGCAGCAGAACAA TABLE 9-continued Vectors

```
TTTGCTGAGGGCTATTGAGGCGCAACAGCATCTGTTGCAACTCACAG
TCTGGGGCATCAAGCAGCTCCAGGCAAGAATCCTGGCTGTGGAAAGATAC
CTAAAGGATCAACAGCTCCTGGGGATTTGGGGTTGCTCTGGAAAACT
CATTTGCACCACTGCTGTGCCTTGGAATGCTAGTTGGAGTAATAAATCTC
TGGAACAGATTTGGAATCACACGACCTGGATGGAGTGGGACAGAGAA
ATTAACAATTACACAAGCTTAATACACTCCTTAATTGAAGAATCGCAAAA
CCAGCAAGAAAAGAATGAACAAGAATTATTGGAATTAGATAAATGGG
CAAGTTTGTGGAATTGGTTTAACATAACAAATTGGCTGTGGTATATAAAA
TTATTCATAATGATAGTAGGAGGCTTGGTAGGTTTAAGAATAGTTTT
TGCTCTACTTTCTATAGTGAATAGAGTTAGGCAGGGATATTCACCATTAT
CGTTTCAGACCCCACCTCCCAACCCCGAGGGGACCCGACAGGCCCCA
GGAATAGAAGAAGAAGGTGGAGAGAGAGACAGAGACAGATCCATTCGATT
AGTGAACGGATCGGCACTGCGTGCGCCAATTCTGCAGACAAATGGCA
GTATTCATCCACAATTTTAAAAGAAAAGGGGGATTGGGGGGTACAGTGC
AGGGGAAAGAATAGTAGACATAATAGCAACAGACATACAACTAAAG
AATTACAAAACAAATTACAAAAATTCAAAATTTTCGGGTTTATTACAGG
GACAGCAGAGATCCAGTTTGGTTAATTAGCTAGCTAGGTCTTGAAAG
GAGTGGGAATTGGCTCCGTGCCCGTCAGTGGGCAGAGCGCACATCGCCC
ACAGTCCCCGAGAAGTTGGGGGGAGGGGTCGGCAATTCATCCGGTGC
CTAGAGAAGGTGGCGCGGGTAAACTGGGAAAGTGATGTCGTGTACTGGC
TCCGCCTTTTTCCCGAGGGTGGGGGAGAACCGTATATAAGTGCAGTA
GTCGCCGTGAACGTTCTTTTTCGCAACGGGTTTGCCGCCAGAACACAGGA
CCGGTTCTAGAGCGCTGCCACCATGTTCCAAAAGCTCAAACGTCACC
TCCAATCACAAGGGTGGCTTCGCAGGATCGTTTGTACAGGCAGTGGAGAG
GGCAGAGGAAGTCTGCTCACCTGCGGCGACGTCGAGGAGAATCCTGG
CCCAGTGAGCAAGGGCGAGGAGCTGTTCACCGGGGTGGTGCCCATCCTGG
TCGAGCTGGACGGCGACGTAAACGGCCACAAGTTCAGCGTGTCCGGC
GAGGGCGAGGGCGATGCCACCTACGGCAAGCTGACCCTGAAGTTCATCTG
CACCACCGGCAAGCTGCCCGTGCCCTGGCCCACCCTCGTGACCACCC
TGACCTACGGCGTGCAGTGCTTCAGCCGCTACCCCGACCACATGAAGCAG
CACGACTTCTTCAAGTCCGCCATGCCCGAAGGCTACGTCCACGAGCG
CACCATCTTCTTCAAGGACGACGGCAACTACAAGACCCGCGCCGAGGTGA
AGTTCGAGGGCGACACCCTGGTGAACCGCATCGAGCTGAAGGGCATC
GACTTCAAGGAGGACGGCAACATCCTGGGGCACAAGCTGGAGTACAACTA
CAACAGCCACAACGTCTATATCATGGCCGACAAGCAGAAGAACGGCA
TCAAGGTGAACTTCAAGATCCGCCACAACATCGAGGACGGCAGCGTGCAG
CTCGCCGACCACTACCAGCAGAACACCCCCATCGGCGACGGCCCCGT
GCTGCTGCCCGACAACCACTACCTGAGCACCCAGTCCGCCCTGAGCAAAG
ACCCCAACGAGAAGCGCGATCACATGGTCCTGCTGGAGTTCGTGACC
GCCGCCGGGATCACTCTCGGCATGGACGAGCTCTACAAGTAATAATAACC
GGATCCGGCGCAACAAACTTTCTCTCT6CTCAAACAAGCCGGCGACGT
CGAAGAGAATCCTGGGCCGGTGTCCAAGGGCGAGGAAGATAACATGGCCA
TCATCAAGGAGTTCATGAGGTTTAAGGTCCACATGGAGGGTTCAGTC
AATGGCCACGAGTTCGAGATTGAAGGCGAGGGCGAGGGCCGCCCTACGA
AGGGACACAGACGGCGAAATTGAAGGTGACCAAAGCGGGGCCATTGC
CCTTCGCATGGGACATCTTGTCCCCTCAGTTTATGTATGGCAGCAAGGCC
TATGTTAAGCACCCCGCTGATATCCCGGACTACTTGAAGCTGTCCTT
TCCAGAGGGGTTTAAATGGGAGCGCGTTATGAATTTCGAAGACGCAGGAG
TGGTTACGGTCACGCAGGACTCATCCCTGCAGGACGGAGAATTTATA
TATAAGGTTAAGTTGAGAGGCACAAACTTCCCAAGCGACGGCCCTGTGAT
GCAGAAGAAAACAATGGGGTGGGAAGCTTCCAGCGAGCGCATGTACC
CCGAAGATGGCGCCTCAAGGGCGAGATAAAGCAAAGGCTGAACTTAAG
GACGGCGGTCATTACGACGCGGAGGTCAAGACAACTTACAAGGCTAA
AAAACCCGTTCAGTTGCCTGGGGCTTACAATGTTAATATCAAACTTGACA
TCACAAGCCACAATGAAGACTATACGATCGTGGAGCAGTATGAACGA
GCGGAAGGCAGGCACTCAACGGGGGAGATGGACGAGCTTTACAAGGGCAG
TGGGGAGGGCAGAGGAAGTCTGCTAACATGCGGTGACGTCGAGGAGA
ATCCTGGCCAATGACCGAGTACAAGCCCACGGTGCGCCTCGCCACCCGC
GACGACGTCCCCAGGGCCGTACGCACCCTCGCCGCCGCGTTCGCCGA
CTACCCCGCCACGCGCCACACCGTCGATCCGGACCGCCACATCGAGCGGG
TCACCGAGCTGCAAGACTCTTCCTCACGCGGCGTCGGGCTCGACATC
GGCAAGGTGTGGGTCGCGGACGACGGCGCCGCGTGGCGGTCTGGACCAC
GCCGGAGAGCGTCGAAGCGGGGCGGTGTTCGCCGAGATCGGCCCGC
GCATGGCCGAGTTGAGCGGTTCCCGGCTGGCCGCGCAGCAACAGATGAA
GGCCTCCTGGCGCCGCACCGGCCCAAGGAGCCCGCGTTGGTTCCTGcC
CACCGTCGGAGTCTCGCCGACCACCAGGCAAGGGTCTGGGCAGCGCCG
TCGTGCTCCCGGAGTGGAGGCGGCCGAGCGCGCCGGGGTGCCCGCC
TTCCTGGAGACCTCCGCGCCCCGCAACCTCCCCTTCTACGAGCGGCTCGG
CTTCACCGTCACCGCCGACGTCGAGGTGCCCGAAGGACCGCGCACCT
GGTGCATGACCCGCAAGCCGGTGCCTGATAAGAATTCGATATCAAGCTT
ATCGGTAATCAACCTCTGGATTACAAAATTTGTGAAAGATTGACTGG
TATTCTTAACTATGTTGCTCCTTTTACGCTATGTGGATACGCTGCTTTAA
TGCCTTTGTATCATGCTATTGCTTCCCGTATGGCTTTCATTTTCTCC
TCCTTGTATAAATCCTGGTTGCTGTCTCTTTATGAGGAGTTGTGGCCCGT
TGTCAGGCAACGTGGCGTGGTGTGCACTGTGTTTGCTGACGCAACCC
CCACTGGTTGGGGCATTGCCACCACCTGTCAGCTCCTTTCCGGGACTTTC
GCTTTCCCCCTCCCTATTGCCACGGCGGAACTCATCGCCGCCTGCCT
TGCCCGCTGCTGGACAGGGGCTCGGCTGTTGGGCACTGACAATTCCGTGG
```

```
TGTTGTCGGGGAAATCATCGTCCTTTCCTTGGCTGCTCGCCTGTGTT
GCCACCTGGATTCTGCGCGGGACGTCCTTCTGCTACGTCCCCTTCGGCCCT
CAATCCAGCGGACCTTCCTTCCCGCGGCCTGCTGCCGGCTCTGCGGC
CTCTTCCGCGTCTTCGCCTTCGCCCTCAGACGAGTCGGATCTCCCTTTGG
GCCGCCTCCCCGCATCGATACCGTCGACCTCGAGACCTAGAAAAACA
TGGAGCAACTACAAGTAGCAATACAGCAGCTACCAATGCTGATTGTGCCT
GGCTAGAAGCACAAGAGGAGGAGGAGGTGGGTTTTCCAGTCACACGT
CAGGTACCTTTAAGACCAATGACTTACAAGGCAGCTGTAGATCTTAGCCA
CTTTTTAAAGAAAAGGGGGGACTGGAAGGGCTAATTCACTCCCAAC
GAAGACAAGATATCCTTGATCTGTGGATCTACCACACACAAGGCTACTTC
CCTGATTGGCAGAACTACACACAGGGCCAGGGATCAGATATCCAT
GACCTTTGgATGGTGCTACAAGCTAGTACCAGTTGAGCAAGAGAAGGTAG
AAGAAGCCAATGAAGGAGAACACCCGCTTGTTACACCCTGTGAGC
CTGCATGGGATGGATGACCCGGAGAGAGAAGTATTAGAGTGGAGGTTTGA
CAGCCGCCTAGCATTTCATCACATGGCCCGAGAGCTGCATCCGGACT
GTACTGGGTCTCTCTGGTTAGACCAGATCTGAGCCTGGGAGCTCTCTGGC
TAACTAGGGAACCCACTGCTTAAGCCTCAATAAAGCTTGCCTTGAGT
GCTTCAAGTAGTGTGTGCCCGTCTGTTGTGTGACTCTGGTAACTAGAGAT
CCCTCAGACCCTTTTAGTCAGTGTGGAAAATCTCTAGCAGGGCCCGT
TTAAACCCGCTGATCAGCCTCGACTGTGCCTTCTAGTTGCCAGCCATCTG
TTGTTTGCCCCTCCCCGTGCCTTCCTTGACCCTGGAAGGTGCCACT
CCCACTGTCCTTTCCTAATAAAATGAGGAAATTGCATCGCATTGTCTGAG
TAGGTGTCATTCTATTCTGGGGGGTGGGGTGGGGCAGGACAGCAAGG
GGGAGGATTGGGAAGACAATAGCAGGCATGCTGGGGAGTGCGGTGGGCTCT
ATGGCTTCTGAGGCGGAAAGAACCAGCTGGGGCTCTAGGGGGTATCC
CCACGCGCCCTGTAGCGGCGCATTAAGCGCGGCGGGTGTGGTGGTTACGC
GCAGCGTGACCGCTACACTTGCCAGCGCCCTAGCGCCCGCTCCTTTC
GCTTTCTTCCCTTCCTTTCTCGCCACGTTCGCCGGCTTTCCCCGTCAAGC
TCTAAATCGGGGCTCCCTTTAGGGTTCCGATTTAGTGCTTTACGGC
ACCTCGACCCCAAAAAACTTGATTAGGGTGATGGTTCACGTAGTGGGCCA
TCGCCCTGATAGACGGTTTTTCGCCCTTTGACGTTGGAGTCCACGTT
CTTTAATAGTGGACTCTTGTTCCAAACTGGAACAACACTCAACCCTATCT
CGGTCTATTCTTTTGATTTATAAGGGATTTTGCCGATTTCGGCCTAT
TGGTTAAAAAATGAGCTGATTTAACAAAAATTTAACGCGAATTAATTCTG
TGGAATGTGTGTCAGTTAGGGTGTGGAAAGTCCCCAGGCTCCCCAGC
AGGCAGAAGTATGCAAAGCATGCATCTCAATTAGTCAGCAACCAGGTGTG
GAAAGTCCCCAGGCTCCCCAGCAGGCAGAAGTATGCAAAGCATGCAT
CTCAATTAGTCAGCAACCATAGTCCCGCCCCTAACTCCGCCCATCCCGCC
CCTAACTCCGCCCAGTTCCGCCCATTCTCCGCCCCATGCTGACTAA
TTTTTTTTATTTATGCAGAGGCCGAGGCCGCCTCTGCCTCTGAGCTATTC
CAGAAGTAGTGAGGAGGCTTTTTTGGAGGCCTAGGCTTTTGCAAAAA
GCTCCCGGGAGCTTGTATATCCATTTTCGGATCTGATCAGCACGTGTTGA
CAATTAATCATCGGCATAGTATATCGGCATAGTATAATACGACAAGG
TGAGGAACTAAACCATGGCCAAGTTGACCAGTGCCGTTCCGGTGCTCACC
GCGCGCGACGTCGCCGGAGCGGTCGAGTTCTGGACCGACCGGCTCGG
GTTCTCCCGGGACTTCGTGGAGGACGACTTCGCCGGTGTGGTCGGGACG
ACGTGACCCTGTTCATCAGCGCGGTCCAGGACCAGGTGGTGCCGGAC
AACACCCTGGCCTGGGTGTGGGTGCGCGGCCTGGACGAGCTGTACGCCGA
GTGGTCGGAGGTCGTGTCCACGAACTTCCGGGACGCCTCCGGGCCGG
CCATGACCGAGATCGGCGAGCAGCCGTGGGGGCGGGAGTTCGCCCTGCGC
GACCCGGCCGGCAACTGCGTGCACTTCGTGGCCGAGGAGCAGGACTG
ACACGTGCTACGAGATTTCGATTCCACCGCCGCCTTCTATGAAAGGTTGG
GCTTCGGAATCGTTTTCCGGGACGCCGGCTGGATGATCCTCCAGCGC
GGGGATCTCATGCTGGAGTTCTTCGCCCACCCCAACTTGTTTATTGCAGC
TTATAATGGTTACAAATAAAGCAATAGCATCACAAATTTCACAAATA
AAGCATTTTTTTCACTGCATTCTAGTTGTGGTTTGTCCAAACTCATCAAT
GTATCTTATCATGTCTGTATACCGTCGACCTCTAGCTAGAGCTTGG
GTAATCATGGTCATAGCTGTTTCCTGTGTGAAATTGTTATCCGCTCACAA
TTCCACACAACATACGAGCCGGAAGCATAAAGTGTAAAGCCTGGGGT
GCCTAATGAGTGAGCTAACTCACATTAATTGCGTTGCGCTCACTGCCCGC
TTTCCAGTCGGGAAACCTGTCGTGCCAGCTGCATTAATGAATCGGCC
AACGCGCGGGGAGAGGCGGTTTGCGTATTGGGCGCTCTTCCGCTTCCTCG
CTCACTGACTCGCTGCGCTCGGTCGTTCGGCTGCGGCGAGCGGTATC
AGCTCACTCAAAGGCGGTAATACGGTTATCCACAGAATCAGGGGATAACG
CAGGAAAGAACATGTGAGCAAAAGGCCAGCAAAAGGCCAGGAACCGT
AAAAAGGCCGCGTTGCTGGCGTTTTTCCATAGGCTCCGCCCCCCTGACGA
GCATCACAAAAATCGACGCTCAAGTCAGAGGTGGCGAAACCCGACAG
GACTATAAAGATACCAGGCGTTTCCCCCTGGAAGCTCCCTCGTGCGCTCT
CCTGTTCCGACCCTGCCGCTTACCGGATACCTGTCCGCCTTTCTCCC
TTCGGGAAGCGTGGCGCTTTCTCATAGCTCACGCTGTAGGTATCTCAGTT
CGGTGTAGGTCGTTCGCTCCAAGCTGGGCTGTGTGCACGAACCCCCC
GTTCAGCCCGACCGCTGCGCCTTATCCGGTAACTATCGTCTTGAGTCCAA
CCCGGTAAGACAGCCGACTTATCGCCACTGGCAGCAGCCACTGGTAACA
GGATTAGCAGAGCGAGGTATGTAGGCGGTGCTACAGAGTTCTTGAAGTGG
TGGCCTAACTACGGCTACACTAGAAGAACAGTATTTGGTATCTGCGC
TCTGCTGAAGCCAGTTACCTTCGGAAAAAGAGTTGGTAGCTCTTGATCCG
GCAAACAAACCACCGCTGGTAGCGGTGGTTTTTTTGTTTGCAAGCAG
CAGATTACGCGCAGAAAAAAAGGATCTCAAGAAGATCCTTTGATCTTTTC
```

TABLE 9-continued

Vectors

TACGGGGTCTGACGCTCAGTGGAACGAAAACTCACGTTAAGGGATTT
TGGTCATGAGATTATCAAAAAGGATCTTCACCTAGATCCTTTTAAATTAA
AAATGAAGTTTTAAATCAATCTAAAGTATATATGAGTAAACTTGGTC
TGACAGTTACCAATGCTTAATCAGTGAGGCACCTATCTCAGCGATCTGTC
TATTTCGTTCATCCATAGTTGCCTGACTCCCCGTCGTGTAGATAACT
ACGATACGGGAGGGCTTACCATCTGGCCCCAGTGCTGCAATGATACGCG
AGACCCACGCTCACCGGCTCCAGATTTATCAGCAATAAACCAGCCAG
CCGGAAGGGCCGAGCGCAGAAGTGGTCCTGCAACTTTATCCGCCTCCATC
CAGTCTATTAATTGTTGCCGGGAAGCTAGAGTAAGTAGTTCGCCAGT
TAATAGTTTGCGCAACGTTGTTGCCATTGCTACAGGCATCGTGGTGTCAC
GCTCGTCGTTTGGTATGGCTTCATTCAGCTCCGGTTCCCAACGATCA
AGGCGAGTTACATGATCCCCATGTTGTGCAAAAAAGCGGTTAGCTCCTT
CGGTCCTCCGATCGTTGTCAGAAGTAAGTTGGCCGCAGTGTTATCAC
TCATGGTTATGGCAGCACTGCATAATTCTCTTACTGTCATGCCATCCGTA
AGATGCTTTTCTGTGACTGGTGAGTACTCAACCAAGTCATTCTGAGA
ATAGTGTATGCGGCGACCGAGTTGCTCTTGCCCGGCGTCAATACGGATA
ATACCGCGCCACATAGCAGAACTTTAAAAGTGCTCATCATTGGAAAA
CGTTCTTCGGGGCGAAAACTCTCAAGGATCTTACCGCTGTTGAGATCCAG
TTCGATGTAACCCACTCGTGCACCCAACTGATCTTCAGCATCTTTTA
CTTTCACCAGCGTTTCTGGGTGAGCAAAAACAGGAAGGCAAAATGCCGCA
AAAAAGGGAATAAGGGCGACACGGAAATGTTGAATACTCATACTCTT
CCTTTTTCAATATTATTGAAGCATTTATCAGGGTTATTGTCTCATGAGCG
GATACATATTTGAATGTATTTAGAAAAATAAACAAATAGGGGTTCCG
CGCACATTTCCCCGAAAAGTGCCACCTGAC lenti-tps-bait-minCMV-mcherry-efs-puro
(SEQ ID NO: 66)
CTGTACTGGGTCTCTCTGGTTAGACCAGATCTGAGCCTGGGAGCTCTCTG
GCTAACTAGGGAACCCACTGCTTAAGCCTCAATAAAGCTTGCCTTGA
GTGCTTCAAGTAGTGTGTGCCCGTCTGTTGTGTGACTCTGGTAACTAGAG
ATCCCTCAGACCCTTTTAGTCAGTGTGGAAAATCTCTAGCAGTGGCG
CCCGAACAGGGACTTGAAAGCGAAAGGGAAACCAGAGGAGCTCTCTCGAC
GCAGGACTCGGCTTGCTGAAGCGCGCACGGCAAGAGGCGAGGGGCGG
CGACTGGTGAGTACGCCAAAAATTTTGACTAGCGGAGGCTAGAAGGAGAG
AGATGGGTGCGAGAGCGTCAGTATTAAGCGGGGGAGAATTAGATCGC
GATGGGAAAAAATTCGGTTAAGGCCAGGGGGAAAGAAAAATATAAATTA
AAACATATAGTATGGGCAAGCAGGGAGCTAGAACGATTCGCAGTTAA
TCCTGGCCTGTTAGAAACATCAGAAGGCTGTAGACAAATACTGGGACAGC
TACAACCATCCCTTCAGACAGGATCAGAAGAACTTAGATCATTATAT
AATACAGTAGCAACCCTCTATTGTGTGCATCAAAGGATAGAGATAAAAGA
CACCAAGGAAGCTTTAGACAAGATAGAGGAAGAGCAAAACAAAAGTA
AGACCACCGCACAGCAAGCGGCCGCTGATCTTCAGACCTGGAGGAGGAGA
TATGAGGGACAATTGGAGAAGTGAATTATATAAAYATAAAGTAGTAA
AAATTGAACCATTAGGAGTAGCACCCACCAAGGCAAAGAGAAGAGGTGGTG
CAGAGAGAAAAAGAGCAGTGGGAATAGGAGCTTTGTTCCTTGGGTT
CTTGGGAGCAGCAGGAAGCACTATGGGCGCAGCGTCAATGACGCTGACGG
TACAGGCCAGACAATTATTGTCTGGTATAGTGCAGCAGCAGAACAAT
TTGCTGAGGGCTATTGAGGCGCAACAGCATCTGTTGCAACTCACAGTCTG
GGGCATCAAGCAGCTCCAGGCAAGAATCCTGGCTGTGGAAAGATACC
TAAAGGATCAACAGCTCCTGGGGATTTGGGGTTGCTCTGGAAAACTCATT
TGCACCACTGCTGTGCCTTGGAATGCTAGTTGGAGTAATAAATCTCT
GGAACAGATTTGGAATCACACGACCTGGATGGAGTGGGACAAGAAATTA
ACAATTACACAAGCTTAATACACTCCTTAATTGAAGAATCGCAAAAC
CAGCAAGAAAAGAATGAACAAGAATTATTGGAATTAGATAAATGGGCAAG
TTTGTGGAATTGGTTTAACATAACAAATTGGCTGTGGTATATAAAAT
TATTCATAATGATAGTAGGAGGCTTGGTAGGTTTAAGAATAGTTTTTGCT
GTACTTTCTATAGTGAATAGAGTTAGGCAGGGATATTCACCATTATC
GTTTCAGACCCACCTCCCAACCCCGAGGGGACCCGACAGGCCCGAAGGAA
TAGAAGAAGAAGGTGGAGAGAGAGACAGAGACAGATCCATTCGATTA
GTGAACGGATCGGCACTGCGTGCGCCAATTCTGCAGACAAATGGCAGTAT
TCATCCACAATTTTAAAAGAAAAGGGGGGATTGGGGGGTACAGTGCA
GGGGAAAGAATAGTAGACATAATAGCAACAGACATACAAACTAAAGAATT
ACAAAAACAAATTACAAAAATTCAAAATTTTCGGGTTTATTACAGGG
ACAGCAGAGATCCAGTTTGGTTAATTAGCTAGTCTAGAAATAAAATATCT
TTATTTTCATTACATCTGTGTGTTGGTTTTTTGTGTGAATCGATAGT
ACTAACATACGCTCTCCATCAAAACAAAACGAAACAAAACAAACTAGCAA
AATAGGCTGTCCCCAGTCAAGTCAGGTGCCAGAACATTTCTCTGC
TAGCGAGACGCTCAGACTCAGACGTCTCAGGTAGGCGTGTACGGTGGGAG
GCCTATATAAGCAGAGCTCGTTTAGTGAACCGTCAGATCGCCTGGAG
GATCCGCCACCATGGTGTCCAAGGGCGAGGAAGATAACATGGCCATCATC
AAGGAGTTCATGAGGTTTAAGGTCCACATGGAGGGTTCAGTCAATGG
CCACGAGTTCGAGATTGAAGGCGAGGGCGAGGGCCGCCCCTACGAAGGGA
CACAGACGGCGAAATTGAAGCTGAAAGGCGAGGGCCATTGCCCTTC
GCATGGGACATCTTGTCCCCTCAGTTTATGTATGGCAGCAAGGCCTATGT
TAAGCACCCCGCTGATATCCCGGACTACTTGAAGCTGTCCTTTCCAG
AGGGGTTTAAATGGGAGCGCGTTATGAATTTCGAAGACGGAGGAGTGGTT
ACGGTGACGCAGGACTCATCCCTGCAGGACGGAGAATTTATATATAA
GGTTAAGTTGAGAGGCACAAACTTCCCAAGCGACGGCCCTGTGATGCAGA AGAAAACAATGGGGTGGGAAGCTTCCAGCGAGCGCATGTACCCCGAA
GATGGCGCCCTCAAGGGCGAGATAAAGCAAAGGCTGAAACTTAAGGACGG
CGGTCATTACGACGCGGAGGTCAAGACAACTTACAAGGCTAAAAAAC
CCGTTCAGTTGCCTGGGGCTTACAATGTTAATATCAAACTTGACATCACA
AGCCACAATGAAGACTATACGATCGTGGAGCAGTATGAACGAGCGGA
AGGCAGGCACTCAACGAGGGGGATGGACGAGCTTTACAAGTAACTAGAGC
TCGCTGATCAGCCTCGACTGTGCCTTCTAGTTGCCAGCCATCTGTTG
TTTGCCCCTCCCCCGTGCCTTCCTTGACCCTGGAAGGTGCCACTCCCACT
GTCCTTTCCTAATAAAATGAGGAAATTGCATCGCATTGTCTGAGTAG
GTGTCATTCTATTCTGGGGGTGGGGTGGGGCAGGACAGCAAGGGGGAGG
ATTGGGAAGACAATAGCAGGCATGCTGGGGAAGCTCGAGTAGGTCTT
GAAAGGAGTGGGAATTGGCTCCGGTGCCCGTCAGTGGGCAGAGCGCACAT
CGCCCACAGTCCCCGAGAAGTTGGGGGGAGGGGTCGGCAATTGATCC
GGTGCCTAGAGAAGGTGGCGCGGGGTAAACTGGGAAAGTGATGTCGTGTA
CTGGCTCCGCCTTTTTCCCGAGGGTGGGGGAGAACCGTATATAAGTG
CAGTAGTCGCCGTGAACGTTCTTTTTCGCAACGGGTTTGCCGCCACAACA
CAGGACCGGTGCCACCATGACCGAGTACAAGCCCACGGTGCGCCTCG
CCACCCGCGACGACGTCCCCAGGGCCGTACGCACCCTCGCCGCCGCGTTC
GCCGACTACCCCGCCACGCGCCACACCGTCGATCCGGACCGCCACAT
CGAGCGGGTCACCGAGCTGCAAGACTCTTCCTCACGCGCGTCGGGCTCG
ACATCGGCAAGGTGTGGGTCGCGGACGACGGCGCCGCCGTGGCGGTC
TGGACCACGCCGGAGAGCGTCGAAGCGGGGGCGGTGTTCGCCGAGATCGG
CCCGCGCATGGCCGAGTTGAGCGGTTCCCGGCTGGCCGCGCACCAAC
AGATGGAAGGCCTCCTGGCCGCCGCCGCCGCCCAAGGAGCCCGCTGGTTC
CTGGCCACCGTCGGAGTCTCGCCCGACCACCAGGGCAAGGGTCTGGG
CAGCGCCGTCGTGCTCCCCGGAGTGGAGGCGGCCGAGCGCGCCGGGGTGC
CCGCCTTCCTGGAGACCTCCGCGCCCCGCAACCTCCCCTTCATCGAG
CGGCTCGGCTTCACCGTCACCGCCGACGTCGAGGTGCCCGAAGGACCGCG
CACCTGGTGCATGACCCGCAAGCCCGGTGCCTGAGAATTCGATATCA
AGCTTATCGTAATCAACCTCTGGATTACAAAATTTGTGAAAGATTGACT
GGTATTCTTAACTATGTTGCTCCTTTTACGCTATGTGGATACGCTGC
TTTAATGCCTTTGTATCATGCTATTGCTTCCCGTATGGCTTTCATTTTCT
CCTCCTTGTATAAATCCTGGTTGCTGTCTCTTTATGAGGAGTTGTGG
CCCGTTGTCAGGCAACGTGGCGTGGTGTGCACTGTGTTTGCTGACGCAAC
CCCCACTGGTTGGGGCATTGCCACCACCTGTCAGCTCCTTTCCGGGA
CTTTCGCTTTCCCCCCTCCCTATTGCCACGGCGGAACTCATCGCCGCCTGC
CTTGCCCGCTGCTGGACAGGGGCTCGGCTGTTGGGCACTGACAATTC
CGTGGTGTTGTCGGGGAAATCATCGTCCTTTCCTTGGCTGCTCGCCTGTG
TTGCCACCTGGATTCTGCGCGGGACGTCCTTCTGCTACGTCCCTTCG
GCCCTCAATCCAGCGGACCTTCCTTCCCGCGGCCTGCTGCCGCTGCTCGCG
GCCTCTTCCGCGTCTTCGCCTTCGCCCTCAGACGAGTCGGATCTCCC
TTTGGGCCGCCTCCCCGCATCGATACCGTCGACCTCGAGACCTAGAAAAA
CATGGAGCAATCACAAGTAGCAATACAGCAGCTACCAATGCTGATTG
TGCCTGGCTAGAAGCACAAGAGGAGGAGGAGGTGGGTTTTCCAGTCACAC
CTCAGGTACCTTTAAGACCAATGACTTACAAGGCAGCTGTAGATCTT
AGCCACTTTTTAAAAGAAAAGGGGGGACTGGAAGGGCTAATTCACTCCCA
ACGAAGACAAGATATCCTTGATCTGTGGATCTACCACACACAAGGCT
ACTTCCCTGATTGGCAGAACTACACACCAGGGCCAGGGATCAGATATCCA
CTGACCTTTGGATGGTGCTACAAGCTAGTACCAGTTGAGCAAGAGA
GGTAGAAGAAGCCAATGAAGGAGAGAACACCCGCTTGTTACACCCTGTGA
GCCTGCATGGGATGGATGACCCGGAGAGAGAAGTATTAGAGTGGAGG
TTTGACAGCCGCCTAGCATTTCATCACATGGCCCGAGAGCTGCATCCGGA
CTGTACTGGGTCTCTCTGGTTAGACCAGATCTGAGCCTGGGAGCTCT
CTGGCTAACTAGGGAACCCACTGCTTAAGCCTCAATAAAGCTTGCCTTGA
GTGCTTCAAGTAGTGTGTGCCCGTCTGTTGTGTGACTCTGGTAACTA
GAGATCCCTCAGACCCTTTTAGTCAGTGTGGAAAATCTCTAGCAGGGCCC
GTTTAAACCCGCTGATCAGCCTCGACTGTGCCTTCTAGTTGCCAGCC
ATCTGTTGTTTGCCCCTCCCCGTGCCTTCCTTGACCCTGGAAGGTGCCA
CTCCCACTGTCCTTTCCTAATAAAATGAGGAAATTGCATCGCATTGT
CTGAGTAGGTGTCATTCTATTCTGGGGGTGGGGTGGGGCAGGACAGCAA
GGGGGAGGATTGGGAAGACAATAGCAGGCATGCTGGGGATGCGGTGG
GCTCTATGGCTTCTGAGGCGGAAAGAACCAGCTGGGGCTCTAGGGGGTAT
CCCCACGCGCCCTGTAGCGGCGCATTAAGCGCGGCGGGTGTGGTGGT
TACGCGCAGCGTGACCGCTACACTTGCCAGCGCCCTAGCGCCCGCTCCTT
TCGCTTTCTTCCCTTCCTTTCTCGCCACGTTCGCCGGCTTTCCCCGT
CAAGCTCTAAATCGGGGGCTCCCTTTAGGGTTCCGATTTAGTGCTTTACG
GCACCTCGACCCCAAAAAACTTGATTAGGGTGATGGTTCACGTAGTG
GGCCATCGCCCTGATAGACGGTTTTTCGCCCTTTGACGTTGGAGTCCACG
TTCTTTAATAGTGGACTCTTGTTCCAAACTGGAACAACACTCAACCC
TATCTCGGTCTATTCTTTTGATTTATAAGGGATTTTGCCGATTTCGGCCT
ATTGGTTAAAAAATGAGCTGATTTAACAAAAATTTAACGCGAATTAA
TTCTGTGGAATGTGTGTCAGTTAGGGTGTGGAAAGTCCCCAGGCTCCCA
GCAGGCAGAAGTATGCAAAGCATGCATCTCAATTAGTCAGCAACCAG
GTGTGGAAAGTCCCCAGGCTCCCCAGCAGGCAGAAGTATGCAAAGCATGC
ATCTCAATTAGTCAGCAACCATAGTCCCGCCCCTAACTCCGCCCATC
CCGCCCCTAACTCCGCCCAGTTCCGCCCATTCTCCGCCCCATGGCTGACT
AATTTTTTTTATTTATGCAGAGGCCGAGGCCGCCTCTGCCTCTGAGC
TATTCCAGAAGTAGTGAGGAGGCTTTTTTGGAGGCCTAGGCTTTTGCAAA

TABLE 9-continued

Vectors

```
AAGCTCCCGGGAGCTTGTATATCCATTTTCGGATCTGATCAGCACGT
GTTGACAATTAATCATCGGCATAGTATATCGGCATAGTATAATACGACAA
GGTGAGGAACTAAACCATGGCCAAGTTGACCAGTGCCGTTCCGGTGC
TCACCGCGCGCGACGTCGCCGGAGCGGTCGAGTTCTGGACCGACCGGCTC
GGGTTCTCCCGGGACTTCGTGGAGGACGACTTCGCCGGTGTGGTCCG
GGACGACGTGACCCTGTTCATCAGCGCGGTCCAGGACCAGGTGGTGCGG
ACAACACCCTGGCCTGGGTGTGGGTGCGCGGCCTGGACGAGCTGTAC
GCCGAGTGGTCGGAGGTCGTGTCCACGAACTTCCGGGACGCCTCCGGGCC
GGCCATGACCGAGATCGGCGAGCAGCCGTGGGGCGGGAGTTCGCCC
TGCCCGACCCGGCCGGCAACTGCGTGCACTTCGTGGCCGAGGAGCAGGAC
TGACACGTGCTACGAGATTTCGATTCCACCGCCGCCTTCTATGAAAG
GTTGGGCTTCGGAATCGTTTTCCGGGACGCCGGCTGGATGATCCTCAGC
GCGGGGATCTCATGCTGGAGTTCTTCGCCCACCCCAACTPGTTTATT
GCAGCTTATAATGGTTACAAATAAAGCAATAGCATCACAAATTTCACAAA
TAAAGCATTTTTTCACTGCATTCTAGTTGTGGTTTGTCCAAACTCA
TCAATGTATCTTATCATGTCTGTATACCGTCGACCTCTAGCTAGAGCTTG
GCGTAATCATGGTCATAGCTGTTTCCTGTGTGAAATTGTTATCCGCT
CACAATTCCACACAACATACGAGCGGAAGCATAAAGTGTAAAGCCTGGG
GTGCCTAATGAGTGAGCTAACTCACATTAATTGCGTTGCGCTCACTG
CCCGCTTTCCAGTCGGGAAACCTGTCGTGCCAGCTGCATTAATGAATCGG
CCAACGCGCGGGGAGAGGCGGTTTGCGTATTGGGCGCTCTTCCGCTT
CCTCGCTCACTGACTCGCTGCGCTCGGTCGTTCGGCTGCGGCGAGCGGTA
TCAGCTCACTCAAAGGCGGTAATACGGTTATCCACAGAATCAGGGGA
TAACGCAGGAAAGAACATGTGAGCAAAAGGCCAGCAAAAGGCCAGGAACC
GTAAAAAGGCCGCGTTGCTGGCGTTTTTCCATAGGCTCCGCCCCCCT
GACGAGCATCACAAAAATCGACGCTCAAGTCAGAGGTGGCGAAACCCGAC
AGGACTATAAAGATACCAGGCGTTTCCCCCTGGAAGCTCCCTCGTGC
GCTCTCCTGTTCCGACCCTGCCGCTTACCGGATACCTGTCCGCCTTTCTC
CCTTCGGGAAGCGTGGCGCTTTCTCATAGCTCACGCTGTAGGTATCT
CAGTTCGGTGTAGGTCGTTCGCTCCAAGCTGGGCTGTGTGCACGAACCCC
CCGTTCAGCCCGACCGCTGCGCCTTATCCGGTAACTATCGTCTTGAG
TCCAACCCGGTAAGACACGACTTATCGCCACTGGCAGCAGCCACTGGTAA
CAGGATTAGCAGAGCGAGGTATGTAGGCGGTGCTACAGAGTTCTTGA
AGTGGTGGCCTAACTACGGCTACACTAGAAGAACAGTATTTGGTATCTGC
GCTCTGCTGAAGCCAGTTACCTTCGGAAAAAGAGTTGGTAGCTCTTG
ATCCGGCAAACAAACCACCGCTGGTAGCGGTGGTTTTTTGTTTGCAAGC
AGCAGATTACGCGCAGAAAAAAAGGATCTCAAGAAGATCCTTTGATC
TTTTCTACGGGGTCTGACGCTCAGTGGAACGAAAACTCACGTTAAGGGAT
TTTGGTCATGAGATTATCAAAAAGGATCTTCACCTAGATCCTTTTAA
ATTAAAAATGAAGTTTTAAATCAATCTAAAGTATATATGAGTAAACTTGG
TCTGACAGTTACCAATGCTTAATCAGTGAGGCACCTATCTCAGCGAT
CTGTCTATTTCGTTCATCCATAGTTGCCTGACTCCCCGTCGTGTAGATAA
CTACGATACGGGAGGGCTTACCATCTGGCCCCAGTGCTGCAATGATA
CCGCGAGACCCACGCTCACCGGCTCCAGATTTATCAGCAATAAACCAGCC
AGCCGGAAGGGCCGAGCGCAGAAGTGGTCCTGCAACTTTATCCGCCT
CCATCCAGTCTATTAATTGTTGCCGGGAAGCTAGAGTAAGTAGTTCGCCA
GTTAATAGTTTGCGCAACGTTGTTGCCATTGCTACAGGCATCGTGGT
GTCACGCTCGTCGTTTGGTATGGCTTCATTCAGCTCCGGTTCCCAACGAT
CAAGGCGAGTTACATGATCCCCCATGTTGTGCAAAAAAGCGGTTAGC
TCCTTCGGTCCTCCGATCGTTGTCAGAAGTAAGTTGGCCGCAGTGTTATC
ACTCATGGTTATGGCAGCACTGCATAATTCTCTTACTGTCATGCCAT
CCGTAAGATGCTTTTCTGTGACTGGTGAGTACTCAACCAAGTCATTCTGA
GAATAGTGTATGCGGCGACCGAGTTGCTCTTGCCCGGCGTCAATACG
GGATAATACCGCGCCACATAGCAGAACTTTAAAAGTGCTCATCATTGGAA
AACGTTCTTCGGGGCGAAAACTCTCAAGGATCTTACCGCTGTTGAGA
TCCAGTTCGATGTAACCCACTCGTGCACCCAACTGATCTTCAGCATCTTT
TACTTTCACCAGCGTTTCTGGGTGAGCAAAAACAGGAAGGCAAAATG
CCGCAAAAAAGGGAATAAGGGCGACACGGAAATGTTGAATACTCATACTC
TTCCTTTTTCAATATTATTGAAGCATTTATCAGGGTTATTGTCTCAT
GAGCGGATACATATTTGAATGTATTTAGAAAAATAAACAAATAGGGGTTC
CGCGCACATTTCCCCGAAAAGTGCCACCTGACGTCGACGGATCGGGA
GATCTCCCGATCCCCTATGGTGCACTCTCAGTACAATCTGCTCTGATGCC
GCATAGTTAAGCCAGTATCTGCTCCCTGCTTGTGTGTTGGAGGTCGC
TGAGTAGTGCGCGAGCAAAATTTAAGCTACAACAAGGCAAGGCTTGACCG
ACAATTGCATGAAGAATCTGCTTAGGGTTAGGCGTTTTGCGCTGCTT
CGCGATGTACGGGCCAGATATACGCGTTGACATTGATTATTGACTAGTTA
TTAATAGTAATCAATTACGGGGTCATTAGTTCATAGCCCATATATGG
AGTTCCGCGTTACATAACTTACGGTAAATGGCCCGCCTGGCTGACCGCC
AACGACCCCCGCCCATTGACGTCAATAATGACGTATGTTCCCATAGT
AACGCCAATAGGGACTTTCCATTGACGTCAATGGGTGGAGTATTTACGT
AAACTGCCCACTTGGCAGTACATCAAGTGTATCATATGCCAAGTACG
CCCCCTATTGACGTCAATGACGGTAAATGGCCCGCCTGGCATTATGCCCA
GTACATGACCTTATGGGACTTTCCTACTTGGCAGTACATCTACGTAT
TAGTCATCGCTATTACCATGGTGATGCGGTTTTGGCAGTACATCAATGGG
CGTGGATAGCGGTTTGACTCACGGGGATTTCCAAGTCTCCACCCCAT
```

```
TGACGTCAATGGGAGTTTGTTTTGGCACCAAAATCAACGGGACTTTCCAA
AATGTCGTAACAACTCCGCCCCATTGACGCAAATGGGCGGTAGGCGT
GTACGGTGGGAGGTCTATATAAGCAGCGCGTTTTGC
``` lenti-fr-target_0_f4-t2a-egfp-p2a-mcherry-t2a-puro
(SEQ ID NO: 67)

```
GTCGACGGATCGGGAGATCTCCCGATCCCCTATGGTGCACTCTCAGTACA
ATCTGCTCTGATGCCGCATAGTTAAGCCAGTATCTGCTCCCTGCTTG
TGTGTTGGAGGTCGCTGAGTAGTGCGCGAGCAAAATTTAAGCTACAACAA
GGCAAGGCTTGACCGACAATTGCATGAAGAATCTGCTTAGGGTTAGG
CGTTTTGCGCTGCTTCGCGATGTACGGGCCAGATATACGCGTTGACATTG
ATTATTGACTAGTTATTAATAGTAATCAATTACGGGGTCATTAGTTC
ATAGCCCATATATGGAGTTCCGCGTTACATAACTTACGGTAAATGGCCCG
CCTGGCTGACCGCCCAACGACCCCCGCCCATTGACGTCAATAATGAC
GTATGTTCCCATAGTAACGCCAATAGGGACTTTCCATTGACGTCAATGGG
TGGAGTATTTACGGTAAACTGCCCACTTGGCAGTACATCAAGTGTAT
CATATGCCAAGTACGCCCCCTATTGACGTCAATGACGGTAAATGGCCCGC
CTGGCATTATGCCCAGTACATGACCTTATGGGACTTTCCTACTTGGC
AGTACATCTACGTATTAGTCATCGCTATTACCATGGTGATGCGGTTTTGG
CAGTACATCAATGGGCGTGGATAGCGGTTTGACTCACGGGGATTTCC
AAGTCTCCACCCCATTGACGTCAATGGGAGTTTGTTTTGGCACCAAAATC
AACGGGACTTTCCAAAATGTCGTAACAACTCCGCCCCATTGACGCAA
ATGGGCGGTAGGCGTGTACGGTGGGAGGTCTATATAAGCAGCGCGTTTTG
CCTGTACTGGGTCTCTCTGGTTAGACCAGATCTGAGCCTGGGAGCTC
TCTGGCTAACTAGGGAACCCACTGCTTAAGCCTCAATAAAGCTTGCCTTG
AGTGCTTCAAGTAGTGTGTGCCCGTCTGTTGTGTGACTCTGGTAACT
AGAGATCCTCAGACCCTTTTAGTCAGTGTGGAAAATCTCTAGCAGTGGC
GCCCGAACAGGGACTTGAAAGCGAAAGGGAAACCAGAGGAGCTCTCT
CGACGCAGGACTCGGCTTGCTGAAGCGCGCACGGCAAGAGGCGAGGGGCG
GCGACTGGTGAGTACGCCAAAAATTTTGACTAGCGGAGGCTAGAAGG
AGAGAGATGGGTGCGAGAGCGTCAGTATTAAGCGGGGGAGAATTAGATCG
CGATGGGAAAAAATTCGGTTAAGGCCAGGGGGAAAGAAAAAATATAA
ATTAAAACATATAGTATGGGCAAGCAGGGAGCTAGAACGATTCGCAGTTA
ATCCTGGCCTGTTAGAAACATCAGAAGGCTGTAGACAAATACTGGGA
CAGCTACAACCATCCCTTCAGACAGGATCAGAAGAACTTAGATCATTATA
TAATACAGTAGCAACCCTCTATTGTGTGCATCAAAGGATAGAGATAA
AAGACACCAAGGAAGCTTTAGACAAGATAGAGGAAGAGCAAAACAAAAGT
AAGACCACCGCACAGCAAGCGGCCGCTGATCTTCAGACCTGGAGGAG
GAGATATGAGGGACAATTGGAGAAGTCAATTATATAAATATAAAGTAGTA
AAAATTGAACCATTAGGAGTAGCACCCACCAAGGCAAAGAGAAGAGT
GGTGCAGAGAGAAAAGAGCAGTGGGAATAGGAGCTTTGTTCCTTGGGT
TCTTGGGAGCAGCAGGAAGCACTATGGGCGCAGCGTCAATGACGCTG
ACGGTACAGGCCAGACAATTATTGTCTGGTATAGTGCAGCAGCAGAACAA
TTTGCTGAGGGCTATTGAGGCGCAACAGCATCTGTTGCAACTCACAG
TCTGGGGCATCAAGCAGCTCCAGGCAAGAATCCTGGCTGTGGAAAGATAC
CTAAAGGATCAACAGCTCCTGGGGATTTGGGGTTGCTCTGGAAAACT
CATTTGCACCACTGCTGTGCCTTGGAATGCTAGTTGGAGTAATAAATCTC
TGGAACAGATTTGGAATCACACGACCTGGATGGAGTGGGACAGAGAA
ATTAACAATTACACAAGCTTAATACACTCCTTAATTGAAGAATCGCAAAA
CCAGCAAGAAAAGAATGAACAAGAATTATTGGAATTAGATAAATGGG
CAAGTTTGTGGAATTGGTTTAACATAACAAATTGGCTGTGGTATATAAAA
TTATTCATAATGATAGTAGGAGGCTTGGTAGGTTTAAGAATAGTTTT
TGCTGTACTTTCTATAGTGAATAGAGTTAGGCAGGGATATTCACCATTAT
CGTTTCAGACCCACCTCCCAACCCCGAGGGGACCCGACAGGCCCGAA
GGAATAGAAGAAGAAGGTGGAGAGAGAGACAGAGACAGATCCATTCGATT
AGTGAACGGATCGGCACTGCGTGCGCCATTCTGCAGACAAATGGCA
GTATTCATCCACAATTTTAAAAGAAAAGGGGGGATTGGGGGGTACAGTGC
AGGGGAAAGAATAGTAGACATAATAGCAACAGACATACAAACTAAAG
AATTACAAAAACAAATTACAAAAATTCAAAATTTTCGGGTTTATTACAGG
GACAGCAGAGATCCAGTTTGGTTAATTAGCTAGCTAGGTCTTGAAAG
GAGTGGGAATTGGCTCCGGTGCCCGTCAGTGGGCAGAGCGCACATCGCCC
ACAGTCCCCGAGAAGTTGGGGGGAGGGGTCGGCAATTGATCCGGTGC
CTAGAGAAGGTGGCGCGGGGTAAACTGGGAAAGTGATGTCGTGTACTGGC
TCCGCCTTTTTCCCGAGGGTGGGGGAGAACCGTATATAAGTGCAGTA
GTCGCCGTGAACGTTCTTTTTCGCAACGGGTTTGCCGCCAGAACACAGGA
CCGGTTCTAGAGCGCTGCCACCATGTCCAAAAGCTCAAGTCACCT
CCAATCACAAGGGTGGCTTCGCAGGATCCTTTGTACAGGCAGTGGAGACG
GCAGAGGAAGTCTGCTCACCTGCGGCGACGTCGAGGAGAATCCTGGC
CCAGTGAGCAAGGGCGAGCAGCTGTTCACCGGGGTGGTGCCCATCCTGGT
CGAGCTGGACGGCGACGTAAACGGCCACAAGTTCAGCGTGTCCGGCG
AGGGCGAGGGCGATGCCACCTACGGCAAGCTGACCCTGAAGTTCATCTGC
ACCACCGGCAAGCTGCCCGTGCCCTGGCCCACCCTCGTGACCACCCT
GACCTACGGCGTGCAGTGCTTCAGCCGCTACCCCGACCACATGAAGCAGC
ACGACTTCTTCAAGTCCGCCATGCCCGAAGGCTACGTCCAGGAGCGC
ACCATCTTCTTCAAGGACGACGGCAACTACAAGACCCGCGCCGAGGTGAA
GTTCGAGGGCGACACCCTGGTGAACCGCATCGAGCTGAAGGGCATCG
ACTTCAAGGAGGACGGCAACATCCTGGGGCACAAGCTGGAGTACAACTAC
AACAGCCACAACGTCTATATCATGGCCGACAAGCAGAAGAACGGCAT
```

TABLE 9-continued

Vectors

CAAGGTGAACTTCAAGATCCGCCACAACATCGAGGACGGCAGCGTGCAGC
TCGCCGACCACTACCAGCAGAACACCCCCATCGGCGACGGCCCCGTG
CTGCTGCCCGACAACCACTACCTGAGCACCCAGTCCGCCCTGAGCAAAGA
CCCCAACGAGAAGCGCGATCACATGGTCCTGCTGGAGTTCGTGACCG
CCGCCGGGATCACTCTCGGCATGGACGAGCTCTACAAGTAATAATAACCG
GATCCGGCGCAACAAACTTCTCTGCTGCTCAAACAAGCCGGCGACGTC
GAAGAGAATCCTGGGCCGTGTCCAAGGGCGAGGAAGATAACATGGCCAT
CATCAAGGAGTTCATGAGGTTTAAGGTCCACATGGAGGGTTCAGTCA
ATGGCCACGAGTTCGAGATTGAAGGCGAGGGCGAGGGCCGCCCCTACGAA
GGGACACAGACGGCGAAATTGAAGGTGACCAAAGGCGGGCCATTGCC
CTTCGCATGGGACATCTTGTCCCCTCAGTTTATGTATGGCAGCAAGGCCT
ATGTTAAGCACCCCGCTGATATCCCCGACTACTTGAAGCTGTCCTTT
CCAGAGGGGTTTAAATGGGAGCGCGTTATGAATTTCGAAGACGGAGGAGT
GGTTACGGTGACGCAGGACTCATCCCTGCAGGACGGAGAATTTATAT
ATAAGGTTAAGTTGAGAGGCACAAACTTCCCAAGCGACGACGGCCCTGTGATG
CAGAAGAAAACAATGGGGTGGGAAGCTTCCAGCGAGCGCATGTACCC
CGAAGATGGCGCCCTCAAGGGCGAGATAAAGCAAAGGCTGAAACTTAAGG
ACGGCGGTCATTACGACGCGGAGGTCAAGACAACTTACAAGGCTAAA
AAACCCGTTCAGTTGCCTGGGGCTTACAATGTTAATATCAAACTTGACAT
CACAAGCCACAATGAAGACTATACGATCGTGGAGCAGTATGAACGAG
CGGAAGGCAGGCACTCAACGGGGGGGATGGACGAGCTTTACAAGGGCAGT
GGGGAGGGCAGAGGAAGTCTGCTAACATGCGGTGACGTCGAGGAGAA
TCCTGGCCCAATGACCGAGTACAAGCCCACGGTGCGCCTCGCCACCCGCG
ACGACGTCCCCAGGGCCGTACGCACCCTCCCCGCCGCGTTCGCCGAC
TACCCCGCCACGCGCCACACCGTCGATCCGGACCGCCACATCGAGCGGGT
CACCGAGCTGCAAGAACTCTTCCTCACGCGCGTCGGGCTCGACATCG
GCAAGCTGTGGGTCGCGGACGACGGCGCCGTGGCGGTCTGGACCACG
CCGGAGAGCGTCGAAGCGGGGGCGGTGTTCGCCGAGATCGGCCCGCG
CATGGCCGAGTTGAGCGGTTCCCGGCTGGCCGCGCAGCAACAGATGGAAG
GCCTCCTGGCGCCGCACCGGCCCAAGGAGCCCGCGTGGTTCCTGGCC
ACCGTCGGAGTCTCGCCCGACCACCAGGGCAAGCGCTCGGGCAGCGCCGT
CGTGCTCCCCGCAGTGGAGGCGGCCGAGCGCGCCGGGGTGCCCGCT
TCCTGGAGACCTCCGCGCCCCGCAACCTCCCCTTCTACGAGCGGCTCGGC
TTCACCGTCACCGCCGACGTCGAGGTGCCCGAAGGACCGCGCACCTG
GTGCATGACCCGCAAGCCCGGTGCCTGATAAGAATTCGATATCAAGCTTA
TCGGTAATCAACCTCTGGATTACAAAATTTGTGAAAGATTGACTGGT
ATTCTTAACTATGTTGCTCCTTTTACGCTATGTGGATACGCTGCTTTAAT
GCCTTTGTATCATGCTATTGCTTCCCGTATGGCTTTCATTTTCTCTT
CCTTGTATAAATCCTGGTTGCTGTCTCTTTATGAGGAGTTGTGGCCCGTT
GTCAGGCAACGTGGCGTGGTGTGCACTGTGTTTGCTGACGCAACCCC
CACTGGTTGGGGCATTGCCACCACCTGTCAGCTCCTTTCCGGGACTTTCG
CTTTCCCCCTCCCTATTGCCACGGCGGAACTCATCGCCGCCTGCCTT
GCCCGCTGCTGGACAGGGGCTCGGCTGTTGGGCACTGACAATTCCGTGGT
GTTGTCGGGGAATCATCGTCCTTTCCTTGGCTGCTCGCCTGTGTTG
CCACCTGGATTCTGCGCGGGACGTCCTTCTGCTACGTCCCTTCGGCCCTC
AATCCAGCGGACCTTCCTTCCCGCGGCTGCTGCCGGCTCTGCGGCT
TCTTCCCCGTCTTCGCCTTCGCCCTCAGACGAGTCGGATCTCCCTTTGGG
CCGCCTCCCCGCATCGATACCGTCGACCTCGAGACCTAGAAAACAT
GGAGCAATCACAAGTAGCAATACAGCAGCTACCAATGCTGATTGTGCCTG
GCTAGAAGCACAAGAGGAGGAGGAGGTGGGTTTTCCAGTCACACCTC
AGGTACCTTTAAGACCAATGACTTACAAGGCAGCTGTAGATCTTAGCCAC
TTTTTAAAAGAAAAGGGGGGACTGGAAGGGCTAATTCACTCCCAACG
AAGACAAGATATCCTTGATCTGTGGATCTACCACACACAAGGCTACTTCC
CTGATTGGCAGAACTACACACCAGGGCCAGGGATCAGATATCCACTG
ACCTTTGGATGGTGCTACAAGCTAGTACCAGTTGAGCAAGAGAAGGTAGA
AGAACCCAATGAAGGAGAGAACACCCGCTTGTTACACCCTGTGAGCC
TGCATGGGATGGATGACCCGGAGAGAAGTATTAGAGTGGAGGTTTGAC
AGCCGCCTAGCATTTCATCACATGGCCCGAGAGCTGCATCCGGACTG
TACTCGGTCTCTCTGGTTAGACCAGATCTGACCCTGGGAGCTCTCTGCCT
AACTAGGGAACCCACTGCTTAAGCCTCAATAAAGCTTGCCTTGAGTG
CTTCAAGTAGTGTGTGCCCGTCTGTTGTGTGACTCTGGTAACTAGAGATC
CCTCAGACCCTTTTAGTCAGTGTGGAAAATCTCTAGCAGGGCCCGTT
TAAACCCGCTGATCAGCCTCGACTGTGCCTTCTAGTTGCCAGCCATCTGT
TGTTTGCCCCTCCCCCGTGCCTTCCTTGACCCTGGAAGGTGCCACTC
CCACTGTCCTTTCCTAATAAAATGAGGAAATTGCATCGCATTGTCTGAGT
AGGTGTCATTCTATTCTGGGGGGTGGGGTGGGGCAGGACAGCAAGGG
GCAGGATTGGGAAGACAATAGCAGGCATGCTCGGCATGCGGTGGGCTCTA
TGGCTTCTGAGGCGGAAAGAACCAGCTGGGGCTCTAGGGGGTATCCC
CACGCGCCCTGTAGCGGCGCATTAAGCGCGGCGGGTGTGGTGGTTACGCG
CAGCGTGACCGCTACACTTGCCAGCGCCCTAGCGCCCGCTCCTTTCG
CTTTCTTCCCTTCCTTTCTCGCCACGTTCGCCGGCTTTCCCCGTCAAGCT
CTAAATCGGGGGCTCCCTTTAGGGTTCCGATTTAGTGCTTTACGCCA
CCTCGACCCCAAAAAACTTGATTAGGGTGATGGTTCACGTAGTGGGCCAT
CGCCCTGATAGACGGTTTTTCGCCCTTTGACGTTGGAGTCCACGTTC
TTTAATAGTGGACTCTTGTTCCAAACTGGAACAACACTCAACCCTATCTC
GGTCTATTCTTTTGATTTATAAGGGATTTTGCCGATTTCGGCCTATT
GGTTAAAAAATGAGCTGATTTAACAAAAATTTAACGCGAATTAATTCTGT
GGAATGTGTGTCAGTTAGGGTGTGGAAAGTCCCCAGGCTCCCCAGCA

GGCAGAAGTATGCAAAGCATGCATCTCAATTAGTCAGCAACCAGGTGTGG
AAAGTCCCCAGGCTCCCCAGCAGGCAGAAGTATGCAAAGCATGCATC
TCAATTAGTCAGCAACCATAGTCCCGCCCCTAACTCCGCCCATCCCGCCC
CTAACTCCGCCCAGTTCCGCCCATTCTCCGCCCCATGGCTGACTAAT
TTTTTTTATTTATGCAGAGGCCGAGGCCGCCTCTGCCTCTGAGCTATTCC
AGAAGTAGTGAGGAGGCTTTTTTGGAGGCCTAGGCTTTTGCAAAAG
CTCCCGGGAGCTTGTATATCCATTTTCGGATCTGATCAGCACGTGTTGAC
AATTAATCATCGGCATAGTATATCGGCATAGTATAATACGACAAGGT
GAGGAACTAAACCATGGCCAAGTTGACCAGTGCCGTTCCGGTGCTCACCG
CGCGCGACGTCGCCGGAGCGGTCGAGTTCTGGACCGACCGGCTCGGG
TTCTCCCGGGACTTCGTGGAGGACGACTTCGCCGGTGTGGTCCGGGACGA
CGTGACCCTGTTCATCAGCGCGGTCCAGGACCAGGTGGTGCCGGACA
ACACCCTGGCCTGGGTGTGGGTGCGCGGCCTGGACGAGCTGTACGCCGAG
TGGTCGGAGGTCGTGTCCACGAACTTCCCGGGACGCCTCCGGGCCGGC
CATGACCGAGATCGGCGAGCAGCCGTGGGGGCGGGAGTTCGCCCTGCGCG
ACCCGGCCGGCAACTGCGTGCACTTCGTGGCCGAGGAGCAGGACTGA
CACGTGCTACGAGATTTCGATTCCACCGCCGCCTTCTATGAAAGGTTGGG
CTTCGGAATCGTTTTCCGGGACGCCGGCTGGATGATCCTCCAGCGCG
GGGATCTCATGCTGGAGTTCTTCGCCCACCCCAACTTGTTTATTGCAGCT
TATAATGGTTACAAATAAAGCAATAGCATCACAAATTTCACAAATAA
AGCATTTTTTTCACTGCATTCTAGTTGTGGTTTGTCCAAACTCATCAATG
TATCTTATCATGTCTGTATACCGTCGACCTCTAGCTAGAGCTTGGCG
TAATCATGGTCATAGCTGTTTCCTGTGTGAAATTGTTATCCGCTCACAAT
TCCACACAACATACGAGCCGGAAGCATAAAGTGTAAAGCCTGGGGTG
CCTAATGAGTGAGCTAACTCACATTAATTGCGTTGCGCTCACTGCCCGCT
TTCCAGTCGGGAAACCTGTCGTGCCAGCTGCATTAATGAATCGGCCA
ACGCGCGGGGAGAGGCGGTTTGCGTATTGGGCGCTCTTCCGCTTCCTCGC
TCACTGACTCGCTGCGCTCGGTCGTTCGGCTGCGGCGAGCGGTATCA
GCTCACTCAAAGGCGGTAATACGGTTATCCACAGAATCAGGGGATAACGC
AGGAAAGAACATGTGAGCAAAAGGCCAGCAAAAGGCCAGGAACCGTA
AAAAGGCCGCGTTGCTGGCGTTTTTCCATAGGCTCCGCCCCCCTGACGAG
CATCACAAAAATCGACGCTCAAGTCAGAGGTGGCGAAACCCGACAGG
ACTATAAAGATACCAGGCGTTTCCCCCTGGAAGCTCCCTCGTGCGCTCTC
CTGTTCCGACCCTGCCGCTTACCGGATACCTGTCCGCCTTTCTCCCT
TCGGGAAGCGTGGCGCTTTCTCATAGCTCACGCTGTAGGTATCTCAGTTC
GGTGTAGGTCGTTCGCTCCAAGCTGGGCTGTGTGCACGAACCCCCC
TTCAGCCCGACCGCTGCGCCTTATCCGGTAACTATCGTCTTGAGTCCAAC
CCGGTAAGACACGACTTATCGCCACTGGCAGCAGCCACTGGTAACAG
GATTAGCAGAGCGAGGTATGTAGGCGGTGCTACAGAGTTCTTGAAGTGGT
GGCCTAACTACGGCTACACTAGAAGAACAGTATTTGGTATCTGCGCT
CTGCTGAAGCCAGTTACCTTCGGAAAAAGAGTTGGTAGCTCTTGATCCGG
CAAACAAACCACCGCTGGTAGCGGTGGTTTTTTTGTTTGCAAGCAGC
AGATTACGCGCAGAAAAAAAGGATCTCAAGAAGATCCTTTGATCTTTTCT
ACGGGGTCTGACGCTCAGTGGAACGAAAACTCACGTTAAGGGATTTT
GGTCATGAGATTATCAAAAAGGATCTTCACCTAGATCCTTTTAAATTAAA
AATGAAGTTTTAAATCAATCTAAAGTATATATGAGTAAACTTGGTCT
GACAGTTACCAATGCTTAATCAGTGAGGCACCTATCTCAGCGATCTGTCT
ATTTCGTTCATCCATAGTTGCCTGACTCCCCGTCGTGTAGATAACTA
CGATACGGGAGGGCTTACCATCTGGCCCCAGTGCTGCAATGATACCGCGA
GACCCACGCTCACCGGCTCCAGATTTATCAGCAATAAACCAGCCAGC
CGGAAGGGCCGAGCGCAGAAGTGGTCCTGCAACTTTATCCGCCTCCATCC
AGTCTATTAATTGTTGCCGGGAAGCTAGAGTAAGTAGTTCGCCAGTT
AATAGTTTGCGCAACGTTGTTGCCATTGCTACAGGCATCGTGGTGTCACG
CTCGTCGTTTGGTATGGCTTCATTCAGCTCCGGTTCCCAACGATCAA
GGCGAGTTACATGATCCCCCATGTTGTGCAAAAAAGCGGTTAGCTCCTTC
GGTCCTCCGATCGTTGTCAGAAGTAAGTTGGCCGCAGTGTTATCAT
CATGGTTATGGCAGCACTGCATAATTCTCTTACTGTCATGCCATCCGTAA
GATGCTTTTCTGTGACTGGTGAGTACTCAACCAAGTCATTCTGAGAA
TAGTGTATGCGGCGACCGAGTTGCTCTTGCCCGGCGTCAATACGGGATAA
TACCGCGCCACATAGCAGAACTTTAAAAGTGCTCATCATTGGAAAAC
GTTCTTCGGGGCGAAAACTCTCAAGGATCTTACCGCTGTTGAGATCCAGT
TCGATGTAACCCACTCGTGCACCCAACTGATCTTCAGCATCTTTTAC
TTTCACCAGCGTTTCTGGGTGAGCAAAAACAGGAAGGCAAAATGCCGCAA
AAAAGGGAATAAGGGCGACACGGAAATGTTGAATACTCATACTCTTC
CTTTTTCAATATTATTGAAGCATTTATCAGGGTTATTGTCTCATGAGCGG
ATACATATTTGAATGTATTTAGAAAAATAAACAAATAGGGGTTCCGC
GCACATTTCCCCGAAAAGTGCCACCTGAC lenti-fr-target_0_f5-t2a-egfp-p2a-mcherry-t2a-puro
(SEQ ID NO: 68)
GTCGACGGATCGGGAGATCTCCCGATCCCCTATGGTGCACTCTCAGTACA
ATCTGCTCTGATGCCGCATAGTTAAGCCAGTATCTGCTCCCTGCTTG
TGTGTTGGAGGTCGCTGAGTAGTGCGCGAGCAAAATTTAAGCTACAACAA
GGCAAGGCTTGACCGACAATTGCATGAAGAATCTGCTTAGGGTTAGG
CGTTTTGCGCTGCTTCGCGATGTACGGGCCAGATATACGCGTTGACATTG
ATTATTGACTAGTTATTAATAGTAATCAATTACGGGGTCATTAGTTC
ATAGCCCATATATGGAGTTCCGCGTTACATAACTTACGGTAAATGGCCCG
CCTGGCTGACCGCCCAACGACCCCCGCCCATTGACGTCAATAATGAC TABLE 9-continued Vectors

```
GTATGTTCCCATAGTAACGCCAATAGGGACTTTCCATTGACGTCAATGGG
TGGAGTATTTACGGTAAACTGCCCACTTGGCAGTACATCAAGTGTAT
CATATGCCAAGTACGCCCCCTATTGACGTCAATGACGGTAAATGGCCCGC
CTGGCATTATGCCCAGTACATGACCTTATGGGACTTTCCTACTTGGC
AGTACATCTACGTATTAGTCATCGCTATTACCATGGTGATGCGGTTTTGG
CAGTACATCAATGGGCGTGGATAGCGGTTTGACTCACGGGGATTTCC
AAGTCTCCACCCCATTGACGTCAATGGGAGTTTGTTTTGGCACCAAAATC
AACGGGACTTTCCAAAATGTCGTAACAACTCCGCCCCATTGACGCAA
TCTGGCTAACTAGGGAACCCACTGCTTAAGCCTCAATAAAGCTTGCCTTG
AGTGCTTCAAGTAGTGTGTGCCCGTCTGTTGTGTGACTCTGGTAACT
AGAGATCCCTCAGACCCTTTTAGTCAGTGTGGAAAATCTCTAGCAGTGGC
GCCCGAACAGGGACTTGAAAGCGAAAGGGAAACCAGAGGAGCTCTCT
CGACGCAGGACTCGGCTTGCTGAAGCGCGCACGGCAAGAGGCGAGGGGCG
GCGACTGGTGAGTACGCCAAAAATTTTGACTAGCGGAGGCTAGAAGG
AGACAGATGGGTGCGAGAGCGTCAGTATTAAGCGGGGGAGAATTAGATCG
CGATGGGAAAAATTCGGTTAAGGCCAGGGGGAAAGAAAAAATATAA
ATTAAAACATATAGTATGGGCAAGCAGGGAGCTAGAACGATTCGCAGTTA
ATCCTGGCCTGTTAGAAACATCAGAAGGCTGTAGACAAATACTGGGA
CAGCTACAACCATCCCTTCAGACAGGATCAGAAGAACTTAGATCATTATA
TAATACAGTAGCAACCCTCTATTGTGTGCATCAAAGGATAGAGATAA
AAGACACCAAGGAAGCTTTAGACAAGATAGAGGAAGAGCAAACAAAGT
AAGACCACCGCACAGCAAGCGGCCGCTGATCTTCAGACCTGGAGGAG
GAGATATGAGGGACAATTGGAGAAGTGAATTATATAAATATAAAGTAGTA
AAAATTGAACCATTAGGAGTAGCACCCACCAAGGCAAAGAGAAGAGT
GGTGCAGAGAGAAAAAAGAGCAGTGGGAATAGGAGCTTTGTTCCTTGGGT
TCTTGGGAGCAGCAGGAAGCACTATGGGCGCAGCGTCAATGACGCTG
ACGGTACAGGCCAGACAATTATTGTCTGGTATAGTGCAGCAGCAGAACAA
TTTGCTGAGGGCTATTGAGGCGCAACAGCATCTGTTGCAACTCACAG
TCTGGGGCATCAAGCAGCTCCAGGCAAGAATCCTGGCTGTGGAAAGATAC
CTAAAGGATCAACAGCTCCTGGGGATTTGGGGTTGCTCTGGAAAACT
CATTTGCACCACTGCTGTGCCTTGGAATGCTAGTTGGAGTAATAAATCTC
TGGAACAGATTTGGAATCACACGACCTGGATGGAGTGGGACAGAGAA
ATTAACAATTACACAAGCTTAATACACTCCTTAATTGAAGAATCGCAAAA
CCAGCAAGAAAAGAATGAACAAGAATTATTGGAATTAGATAAATGGG
CAAGTTTGTGGAATTGGTTTAACATAACAAATTGGCTGTGGTATATAAAA
TTATTCATAATGATAGTAGGAGGCTTGGTAGGTTTAAGAATAGTTTT
TGCTGTACTTTCTATAGTGAATAGAGTTAGGCAGGGATATTCACCATTAT
CGTTTCAGACCCACCTCCCAACCCCGAGGGGACCCGACAGGCCCGAA
GGAATAGAAGAAGAAGGTGGAGAGAGAGACAGAGACAGATCCATTCGATT
AGTGAACGGATCGGCACTGCGTGCGCCAATTCTGCAGCAAATGGCA
GTATTCATCCACAATTTTAAAAGAAAAGGGGGGATTGGGGGGTACAGTGC
AGGGGAAAGAATAGTAGACATAATAGCAACAGACATACAAACTAAAG
AATTACAAAAACAAATTACAAAAATTCAAAATTTTCGGGTTTATTACAGG
GACAGCAGAGATCCAGTTTGGTTAATTAGCTAGCTAGGTCTTGAAAG
GAGTGGGAATTGGCTCCGGTGCCCGTCAGTGGGCAGAGCGCACATCGCCC
ACAGTCCCCGAGAAGTTGGGGGAGGGCTCGGCAATTGATCCGGTGC
CTAGAGAAGGTGGCGCGGGGTAAACTGGGAAAGTGATCTCGTGTACTGGC
TCCGCCTTTTTCCCGAGGGTGGGGAGAACCGTATATAAGTGCAGTA
GTCGCCCTGAACGTTCTTTTTCGCAACGGGTTTGCCGCCAGAACACAGGA
CCGGTTCTAGAGCGCTGCCACCATGCCAAAAGCTCAAACGTCACCTC
CAATCACAAGGGTGGCTTCGCAGGATCGTTTGTACAGGCAGTGGAGAGGG
CAGAGGAAGTCTGCTCACCTGCGGCGACGTCGAGGAGAATCCTGGCC
CAGTGAGCAAGGGCGAGGAGCTGTTCACCGGGGTGGTGCCCATCCTGGTC
GAGCTGGACGGCGACGTAAACGGCCACAAGTTCAGCGTGTCCGGCGA
GGGCGAGGGCGATGCCACCTACGGCAAGCTGACCCTGAAGTTCATCTGCA
CCACCGGCAAGCTGCCCGTGCCCTGGCCCACCCTCGTGACCACCCTG
ACCTACGGCGTGCAGTGCTTCAGCCGCTACCCCGACCACATGAAGCAGCA
CGACTTCTTCAAGTCCGCCATGCCCGAAGGCTACGTCCAGGAGCGCA
CCATCTTCTTCAAGGACGACGGCAACTACAAGACCCGCGCCGAGGTGAAG
TTCGAGGGCGACACCCTGGTGAACCGCATCGAGCTGAAGGGCATCGA
CTTCAAGGAGGACGGCAACATCCTGGGGCACAAGCTGGAGTACAACTACA
ACAGCCACAACGTCTATATCATGGCCGACAAGCAGAAGAACGGCATC
AAGGTGAACTTCAAGATCCGCCACAACATCGAGGACGGCAGCGTGCAGCT
CGCCGACCACTACCAGCAGAACACCCCCATCGGCGACGGCCCCGTGC
TGCTGCCCGACAACCACTACCTGAGCACCCAGTCCGCCCTGAGCAAGAC
CCCCAACGAGAAGCGCGATCACATGGTCCTGCTGGAGTTCGTGACCGC
CGCCGGGATCACTCTCGGCATGGACGAGCTCTACAAGTAATAATAACCGG
ATCCGGCGCAACAAACTTCTCTCTGCTCAAACAAGCCGGCGACGTCG
AAGAGAATCCTGGGCCGGTCCAAGGGCGAGGAAGATCAACCTGGGCATC
ATCAAGGAGTTCATGAGGTTTAAGGTCCACATGGAGGGTTCAGTCAA
TGGCCACGAGTTCGAGATTGAAGGCGAGGGCGAGGGCCGCCCCTACGAAG
GGACACAGACGGCGAAATTGAAGGTGACCAAAGGCGGGCCATTGCCC
TTCGCATGGGACTTTGCTCCCCTCAGTTTATGTATGGCAGCAAGGCCTA
TGTTAAGCACCCCGCTGATATCCCGGACTACTTGAAGCTGTCCTTTC
CAGAGGGGTTTAAATGGGAGCGCGTTATGAATTTCGAAGACGGAGGAGTG
GTTACGGTGACGCAGGACTCATCCCTGCAGGACGGAGAATTTATATA
TAAGGTTAAGTTGAGAGGCACAAACTTCCCAAGCGACGGCCCTGTGATGC
AGAAGAAAACAATGGGGTGGGAAGCTTCCAGCGAGCGCATGTACCCC
```

TABLE 9-continued

Vectors

```
GAAGATGGCGCCCTCAAGGGCGAGATAAAGCAAAGGCTGAAACTTAAGGA
CGGCGGTCATTACGACGCGGAGGTCAAGACAACTTACAAGGCTAAAA
AACCCGTTCAGTTGCCTGGGGCTTACAATGTTAATATCAAACTTGACATC
ACAAGCCACAATGAAGACTATACGATCGTGGAGCAGTATGAACGAGC
GGAAGGCAGGCACTCAACGGGGGGATGGACGAGCTTTACAAGGGCAGTG
GGGGAGGCAGAGGAAGTCTGCTAACATGCGGTGACGTCGAGGAGAAT
CCTGGCCCAATGACCGAGTACAAGCCCACGGTGCGCCTCGCCACCCGCGA
CGACGTCCCCAGGGCCGTACGCACCCTCGCCGCCGCGTTCGCCGACT
ACCCCGCCACGCGCCACACCGTCGATCCGGACCGCCACATCGAGCGGGTC
ACCGAGCTGCAAGAACTCTTCCTCACGCGCGTCGGGCTCGACATCGG
CAAGGTGTGGGTCGCGGACGACGGCGCCGCCGTGGCGGTCTGGACCACGC
CGGAGAGCGTCGAAGCGGGGGCGGTGTTCGCCGAGATCGGCCCGCGC
ATGGCCGAGTTGAGCGCGTTCCCGGCTGGCCGCGCAGCAACAGATGGAAGG
CCTCCTGGCGCCGCACCCGGCCCAAGGAGCCCGCGTGGTTCCTGGCCA
CCGTCGGAGTCTCGCCCGACCACCAGGGCAAGGGTCTGGGCAGCGCCGTC
GTGCTCCCCGGAGTGGAGGCGGCCGAGCGCGCCGGGGTGCCCGCCTT
CCTGGAGACCTCCGCGCCCCGCAACCTCCCCTTCTACGAGCGGCTCGGCT
TCACCGTCACCGCCGACGTCGAGGTGCCCGAAGGACCGCGCACCTGG
TGCATGACCCGCAAGCCCGGTGCCTGATAAGAATTCGATATCAAGCTTAT
CGGTAATCAACCTCTGGATTACAAAATTTGTGAAAGATTGACTGGTA
TTCTTAACTATGTTGCTCCTTTTACGCTATGTGGATACGCTGCTTTAATG
CCTTTGTATCATGCTATTGCTTCCCGTATGGCTTTCATTTTCTCCTC
CTTGTATAAATCCTGGTTGCTGTCTCTTTATGAGGAGTTGTGGCCCGTTG
TCAGGCAACGTGGCTGGTGTGCACTGTGTTTGCTGACGCAACCCCC
ACTGGTTGCGGCATTGCCACCACCTGTCAGCTCCTTTCCGGGACTTTCGC
TTTCCCCCTCCCTATTGCCACGGCGGAACTCATCGCCGCCTGCCTTG
CCCGCTGCTGGACAGGGGCTCGGCTGTTGGGCACTGACAATTCCGTGGTG
TTGTCGGGGAAATCATCGTCCTTTCCTTGGCTGCTCGCCTGTGTTGC
CACCTGGATTCTGCGCGGGACGTCCTTCTGCTACGTCCCTTCGGCCCTCA
ATCCAGCGGACCTTCCTTCCCGCGGCCTGCTGCCGGCTCTGCGGCCT
CTTCCGCGTCTTCGCCTTCGCCCTCAGACGAGTCGGATCTCCCTTTGGGC
CGCCTCCCCGCATCGATACCGTCGACCTCGAGACCTAGAAAAACATG
GAGCAATCACAAGTAGCAATACAGCAGCTACCAATGCTGATTGTGCCTGG
CTAGAAGCACAAGAGGAGGAGGAGGTGGGTTTTCCAGTCACACCTCA
GGTACCTTTAAGACCAATGACTTACAAGGCAGCTGTAGATCTTAGCCACT
TTTTAAAAGAAAAAGGGGGGACTGGAAGGGCTAATTCACTCCCAACGA
AGACAAGATATCCTTGATCTGTGGATCTACCACACAAGGCTACTTCCC
TGATTGGCAGAACTACACACCAGGGCCAGGGATCAGATATCCACTGA
CCTTTGGATGGTGCTACAAGCTAGTACCAGTTGAGCAAGAGAAGGTAGAA
GAAGCCAATGAAGGAGAGAACACCCGCTTGTTACACCCTGTGAGCCT
GCATGCGATGGATGACCCGGAGAGAGAAGTATTAGAGTGGAGGTTTGACA
GCCGCCTAGCATTTCATCACATGGCCCGAGAGCTGCATCCGGACTGT
ACTGGGTCTCTCTGGTTAGACCAGATCTGAGCCTGGGAGCTCTCTGGCTA
ACTAGGGAACCCACTGCTTAAGCCTCAATAAAGCTTGCCTTGAGTGC
TTCAAGTAGTGTGTGCCCGTCTGTTGTGTGACTCTGGTAACTAGAGATCC
CTCAGACCCTTTTAGTCAGTGTGGAAAATCTCTAGCAGGGCCCGTTT
AAACCCGCTGATCAGCCTCGACTGTGCCTTCTAGTTGCCAGCCATCTGTT
GTTTGCCCCTCCCCCGTGCCTTCCTTGACCCTGGAAGGTGCCACTCC
CACTGTCCTTTCCTAATAAAATGAGGAAATTGCATCGCATTGTCGAGTA
GGTGTCATTCTATTCTGGGGGGTGGGTGGGGCAGGACAGCAAGGGG
GAGGATTGGGAAGACAATAGCAGGCATGCTGGGGATGCGGTGGGCTCTAT
GGCTTCTGAGGCGGAAAAACAGCTGGGGCTCTAGGGGGTATCCCC
ACGCGCCCTGTAGCGGCGCATTAAGCGCGGCGGGTGTGGTGGTTACGCG
CAGCGTGACCGCTACACTTGCCAGCGCCCTAGCGCCCGCTCCTTTCGC
TTTCTTCCCTTCCTTTCTCGCCACGTTCGCCGGCTTTCCCCGTCAAGCTC
TAAATCGGGGGCTCCCTTTAGGGTTCCGATTTAGTGCTTTACGGCAC
CTCGACCCCAAAAAACTTGATTAGGGTGATGGTTCACGTAGTGGGCCATC
GCCCTGATAGACGGTTTTTCGCCCTTTGACGTTGGAGTCCACGTTCT
TTAATAGTGGACTCTTGTTCCAAACTGGAACAACACTCAACCCTATCTCG
GTCTATTCTTTTGATTTATAAGGGATTTTGCCGATTTCGGCCTATTG
GTTAAAAAATGAGCTGATTTAACAAAAATTTAACGCGAATTAATTCTGTG
GAATGTGTGTCAGTTAGGGTGTGGAAAGTCCCCAGCCTCCCCAGCAG
GCAGAAGTATGCAAAGCATGCATCTCAATTAGTCAGCAACCAGGTGTGGA
AAGTCCCCAGGCTCCCCAGCAGGCAGAAGTATGCAAAGCATGCATCT
CAATTAGTCAGCAACCATAGTCCCGCCCCTAACTCCGCCCATCCCGCCC
TAACTCCGCCCAGTTCCGCCCATTCTCCGCCCCATGGCTGACTAATT
TTTTTTATTTATGCAGAGGCCGAGGCCGCCTCTGCCTCTGAGCTATTCCA
GAAGTAGTGAGGAGGCTTTTTTGGAGGCCTAGGCTTTTGCAAAAAGC
TCCCGGGAGCTTGTATATCCATTTTCGGATCTGATCAGCACGTGTTGACA
ATTAATCATCGGCATAGTATATCGGCATAGTATAATACGACAAGGTG
AGGAACTAAACCATGGCCAAGTTGACCAGTGCCGTTCCGGTGCTCACCGC
GCGCGACGTCGCCGGAGCGGTCGAGTTCTGGACCGACCGGCTCGGGT
TCTCCCGGGACTTCGTGGAGGACGACTTCGCCGGTGTGGTCCGGGACGAC
GTGACCGCTGTTCATCAGCGCGGTCCAGGACCAGGTGGTGCCGGACAA
CACCCTGGCCTGGGTGTGGGTGCGCGGCCTGGACGAGCTGTACGCCGAGT
GGTCGGAGGTCGTGTCCACGAACTTCCGGGACGCCTCCGGGCCGGCC
ATGACCGAGATCGGCGAGCAGCCGTGGGGCGGGAGTTCGCCCTGCGCGA
CCCGGCCGGCAACTGCGTGCACTTCGTGGCCGAGGAGCAGGACTGAC
```

TABLE 9-continued

Vectors

ACGTGCTACGAGATTTCGATTCCACCGCCGCCTTCTATGAAAGGTTGGGC
TTCGGAATCGTTTTCCGGGACGCCGGCTGGATGATCCTCCAGCGCGG
GGATCTCATGCTGGAGTTCTTCGCCCACCCCAACTTGTTTATTGCAGCTT
ATAATGGTTACAAATAAAGCAATAGCATCACAAATTTCACAAATAAA
GCATTTTTTTCACTGCATTCTAGTTGTGGTTTGTCCAAACTCATCAATGT
ATCTTATCATGTCTGTATACCGTCGACCTCTAGCTAGAGCTTGGCGT
AATCATGGTCATAGCTGTTTCCTGTGTGAAATTGTTATCCGCTCACAATT
CCACACAACATACGAGCCGGAAGCATAAAGTGTAAAGCCTGGGGTGC
CTAATGAGTGAGCTAACTCACATTAATTGCGTTGCGCTCACTGCCCGCTT
TCCAGTCGGGAAACCTGTCGTGCCAGCTGCATTAATGAATCGGCCAA
CGCGCGGGGAGAGGCGGTTTGCGTATTGGGCGCTCTTCCGCTTCCTCGCT
CACTGACTCGCTGCGCTCGGTCGTTCGGCTGCGGCGAGCGGTATCAG
CTCACTCAAAGGCGGTAATACGGTTATCCACAGAATCAGGGGATAACGCA
GGAAAGAACATGTGAGCAAAAGGCCAGCAAAAGGCCAGGAACCGTAA
AAAGGCCGCGTTGCTGGCGTTTTTCCATAGGCTCCGCCCCCCTGACGAGC
ATCACAAAAATCGACGCTCAAGTCAGAGGTGGCGAAACCCGACAGGA
CTATAAAGATACCAGGCGTTTCCCCCTGGAAGCTCCCTCGTGCGCTCTCC
TGTTCCGACCCTGCCGCTTACCGGATACCTGTCCGCCTTTCTCCCTT
CGGGAAGCGTGGCGCTTTCTCATAGCTCACGCTGTAGGTATCTCAGTTCG
GTGTAGGTCGTTCGCTCCAAGCTGGGCTGTGTGCACGAACCCCCCGT
TCAGCCCGACCGCTGCGCCTTATCCGGTAACTATCGTCTTGAGTCCAACC
CGGTAAGACACGACTTATCGCCACTGGCAGCAGCCACTGGTAACAGG
ATTAGCAGAGCGAGGTATGTAGGCGGTGCTACAGAGTTCTTGAAGTGGTG
GCCTAACTACGGCTACACTAGAAGAACAGTATTTGGTATCTGCGCTC
TGCTGAAGCCAGTTACCTTCGGAAAAAGAGTTGGTAGCTCTTGATCGGC
AAACAAACCACCGCTGGTAGCGGTGGTTTTTTTGTTTGCAAGCAGCA
GATTACGCGCAGAAAAAAAGGATCTCAACAAGATCCTTTGATCTTTTCTA
CGGGGTCTGACGCTCAGTGGAACGAAAACTCACGTTAAGGGATTTTG
GTCATGAGATTATCAAAAAGGATCTTCACCTAGATCCTTTTAAATTAAA
ATGAAGTTTTAAATCAATCTAAAGTATATATGAGTAAACTTGGTCTG
ACAGTTACCAATGCTTAATCAGTGAGGCACCTATCTCAGCGATCTGTCTA
TTTCGTTCATCCATAGTTGCCTGACTCCCCGTCGTGTAGATAACTAC
GATACGGGAGGGCTTACCATCTGGCCCCAGTGCTGCAATGATACCGCGAG
ACCCACGCTCACCGGCTCCAGATTTATCAGCAATAAACCAGCCAGCC
GGAAGGGCCGAGCGCAGAAGTGGTCCTGCAACTTTATCCGCCTCCATCCA
GTCTATTAATTGTTGCCGGGAAGCTAGAGTAAGTAGTTCGCCAGTTA
ATAGTTTGCGCAACGTTGTTGCCATTGCTACAGGCATCGTGGTGTCACGC
TCGTCGTTTGGTATGGCTTCATTCAGCTCCGGTTCCCAACGATCAAG
GCGAGTTACATGATCCCCCATGTTGTGCAAAAAAGCGGTTAGCTCCTTCG
GTCCTCCGATCGTTGTCAGAAGTAAGTTGGCCGCAGTGTTATCACTC
ATGGTTATGGCAGCACTGCATAATTCTCTTACTGTCATGCCATCCGTAAG
ATGCTTTTCTGTGACTGGTGAGTACTCAACCAAGTCATTCTGAGAAT
AGTGTATGCGGCGACCGAGTTGCTCTTGCCCGGCGTCAATACGGGATAAT
ACCGCGCCACATAGCAGAACTTTAAAAGTGCTCATCATTGGAAAACG
TTCTTCGGGGCGAAAACTCTCAAGGATCTTACCGCTGTTGAGATCCAGTT
CGATGTAACCCACTCGTGCACCCAACTGATCTTCAGCATCTTTTACT
TTCACCAGCGTTTCTGGGTGAGCAAAAACAGGAAGGCAAAATGCCGCAAA
AAAGGGAATAAGGGCGACACGGAAATGTTGAATACTCATACTCTTCC
TTTTTCAATATTATTGAAGCATTTATCAGGGTTATTGTCTCATGAGCGGA
TACATATTTGAATGTATTTAGAAAAATAAACAAATAGGGGTTCCGCG
CACATTTCCCCGAAAAGTGCCACCTGAC tm10-t0-f0-efs-stop-spacer-t2a-gfp-t2a-puro-p2a-
mcherry-lenti
                                              (SEQ ID NO: 69)
GTCGACGGATCGGGAGATCTCCCGATCCCCTATGGTGCACTCTCAGTACA
ATCTGCTCTGATGCCGCATAGTTAAGCCAGTATCTGCTCCCTGCTTG
TGTGTTGGAGGTCGCTGAGTAGTGCGCGAGCAAAATTTAAGCTACAACAA
GGCAAGGCTTGACCGACAATTGCATGAAGAATCTGCTTAGGGTTAGG
CGTTTTGCGCTGCTTCGCGATGTACGGGCCAGATATACGCGTTGACATTG
ATTATTGACTAGTTATTAATAGTAATCAATTACGGGGTCATTAGTTC
ATAGCCCATATATGGAGTTCCGCGTTACATAACTTACGGTAAATGGCCCG
CCTGGCTGACCGCCCAACGACCCCCGCCCATTGACGTCAATAATGAC
GTATGTTCCCATAGTAACGCCAATAGGGACTTTCCATTGACGTCAATGGG
TGGAGTATTTACGGTAAACTGCCCACTTGGCAGTACATCAAGTGTAT
CATATGCCAAGTACGCCCCCTATTGACGTCAATGACGGTAAATGGCCCGC
CTGGCATTATGCCCAGTACATGACCTTATGGGACTTTCCTACTTGGC
AGTACATCTACGTATTAGTCATCGCTATTACCATGGTGATGCGGTTTTGG
CAGTACATCAATGGGCGTGGATAGCGGTTTGACTCACGGGGATTTCC
AAGTCTCCACCCCATTGACGTCAATGGGAGTTTGTTTTGGCACCAAAATC
AACGGGACTTTCCAAAATGTCGTAACAACTCCGCCCCATTGACGCAA
ATGGGCGGTAGGCGTGTACGGTGGGAGGTCTATATAAGCAGCGCGTTTTG
CCTGTACTGGGTCTCTCTGGTTAGACCAGATCTGAGCCTGGGAGCTC
TCGACGCAGGACTCGGCTTGCTGAAGCGCGCACGCAAGAGGCGAGGGGCG
GCGACTGGTGAGTACGCCAAAAATTTTGACTAGCGGAGGCTAGAAGG
AGAGAGATGGGTGCGAGAGCGTCAGTATTAAGCGGCGGAGAATTAGATCG
CGATGGGAAAAATTCGGTTAAGGCCAGGGGAAAGAAAAAATATAAA
ATTAAAACATATAGTATGGGCAAGCAGGGAGCTAGAACGATTCGCAGTTA ATCCTGGCCTGTTAGAAACATCAGAAGGCTGTAGACAAATACTGGGA
CAGCTACAACCATCCCTTCAGACAGGATCAGAAGAACTTAGATCATTATA
TAATACAGTAGCAACCCTCTATTGTGTGCATCAAAGGATAGAGATAA
AAGCACCCAAGGAAGCTTTAGACAAGATAGAGGAAGAGCAAACAAAAGT
AAGACCACCGCACAGCAAGCGGCCGCTGATCTTCAGACCTGGAGGAG
GAGATATGAGGGACAATTGGAGAAGTGAATTATATAAATATAAAGTAGTA
AAAATTGAACCATTAGGAGTAGCACCCACCAAGGCAAAGAGAAGAGT
GGTGCAGAGAGAAAAAGAGCAGTGGGAATAGGAGCTTTGTTCCTTGGGT
TCTTGGGAGCAGCAGGAAGCACTATGGGCGCAGCGTCAATGACGCTG
ACGGTACAGGCCAGACAATTATTGTCTGGTATAGTGCAGCAGCAGAACA
TTTGCTGAGGGCTATTGAGGCGCAACAGCATGTGTTGCAACTCACAG
TCTGGGGCATCAAGCAGCTCCAGGCAAGAATCCTGGCTGTGGAAAGATAC
CTAAAGGATCAACAGCTCCTGGGGATTTGGGGTTGCTCTGGAAAACT
CATTTGCACCACTGCTGTGCCTTGGAATGCTAGTTGGAGTAATAAATCTC
TGGAACAGATTTGGAATCACACGACCTGGATGGAGTGGGACAGAGAA
ATTAACAATTACACAAGCTTAATACACTCCTTAATTGAAGAATCGCAAAA
CCAGCAAGAAAAGAATGAACAAGAATTATTGGAATTAGATAAATGGG
CAAGTTTGTGGAATTGGTTTAACATAACAAATTGGCTGTGGTATATAAAA
TTATTCATAATGATAGTAGGAGGCTTGGTAGGTTTAAGAATAGTTTTT
TGCTGTACTTTCTATAGTGAATAGAGTTAGGCAGGGATATTCACCATTAT
CGTTTCAGACCCACCTCCCAACCCCGAGGGGACCCGACAGGCCCGAA
GGAATAGAAGAAGAAGGTGGAGAGAGAGACAGAGACAGATCCATTCGATT
AGTGAACGGATCGGCACTGCGTGCGCCAATTCTGCAGACAAATGGCA
GTATTCATCCACAATTTTAAAAGAAAAGGGGGGATTGGGGGGTACAGTGC
AGGGGAAAGAATAGTAGACATAATAGCAACAGACATACAAACTAAAG
AATTACAAAAACAAATTACAAAAATTCAAAATTTTCGGGTTTATTACAGG
GACAGCAGAGATCCAGTTTGGTTAATTAGCTAGCTAGGTCTTGAAGA
GAGTGGAATTGGCTCCGGTGCCCGTCAGTGGGCAGAGCGCACATCGCCC
ACAGTCCCCGAGAAGTTGGGGGGAGGGGTCGGCAATTGATCCGGTGC
CTAGAGAAGGTGGCGCGGGGTAAACTGGGAAAGTGAGTCGTGTACTGGCT
CCGCCTTTTTCCCGAGGGTGGGGGAGAACCGTATATAAGTGCAGTAG
TCGCCGTGAACGTTCTTTTTCGCAACGGGTTTGCCGCCAGAACACAGGAC
CGGTAATAGTGAGTAGTAGTAAGGTGATAATAGAAATTGCCACCATG
AGCTCAAACGTCACCTCCAATCACAAGGGTGGCTTCTCCAATTGTACAGG
CAGTGGAGAGGGCAGAGGAAGTCTGCTCACCTGCGGCGACGTCGAGG
AGAATCCTGGCCCAGTCAGCAAGGGCGAGGAGCTGTTCACCGGGGTGGTG
CCCATCCTGGTCGAGCTGGACGGCGACGTCAACGGCCACAAGTTCAG
CGTGTCCGGCGAGGGCGAAGGCGACGCCACCTACGGAAAGCTCACTCTCA
AGTTCATCTGCACCACAGGCAAGCTGCCCGTGCCCTGGCCCACCCTC
GTCACCACCCTCACCTACGGCGTGCAGTGCTTCAGCCGCTACCCCGACCA
CCTCAAGCAGCACGACTTCTTCAAGTCCGCTATGCCCGAAGGCTACG
TCCAGGAGCGCACCATCTTCTTCAAGGACGACGGCAACTACAAGACCCGC
GCCGAGGTCAAGTTCGAGGGCGACACCCTGGTCAACCGCATCGAGCT
CAAGGGCATCGACTTCAAGGAGGACGGCAACATCCTGGGGCACAAGCTGG
AGTACAACTACAACAGCCACAACGTCTATATCATGGCCGACAAGCAG
AAGAACGGCATCAAGGTCAACTTCAAGATCCGCCACAACATCGAGGACGG
CAGCGTGCAGCTCGCCGACCACTACCAGCAGAACACCCCCATCGGCG
ACGGCCCCGTGCTGCTGCCCGACAACCACTACCTGAGCACCCAGTCCGCC
CTCAGCAAAGACCCCAACGAGAAGCGCGATCACATGGTCCTGCTGGA
GTTCGTCACCGCCGCCGGGATCACTCTCGGCATGGACGAGCTGTACAAGT
AATAATAACCGGATCCGGCGCAACAAACTTCTCTCTGCTCAAACAAG
CCGGCGACGTCGAAGAGAATCCTGGCCCGACCGAGTACAAGCCCACGGTG
CGCCTCGCTACCCGCGACGACGTCCCCAGGGCTGTCCGCACCCTCG
CGCTGCGTTCGCCGACTACCCCGCTACGCGCACACCGTCGATCCGGACC
GCCACATCGAGCGGGTCACCGAACTGCAAGAACTCTTCCTCACGCGC
GTCGGGCTCGACATCGGCACCAATAGCGTGGGCTGGGCGGTCATCACTGAT
GGCGGTCTGGACCACCGGAGAGCGTCGAAGCGGGTCGGTGTTCG
CCGAGATCGGTCCGCGCATGGCCGAGCTCAGCGGTTCCCGGCTGGCCGCG
CAGCAACAGATGGAAGGTCTCCTGGCGCCGCACCGGCCCAAGGAGCC
TGCGTGGTTCCTGGCCACCGTCGGAGTCTCGCCCGACCACCAAGGCAAGG
GTCTGGGCAGCGCCGTCGTCGTCGTCCCCGGAGTGGAGGCGGCAGAGCGT
GCTGGAGTGCCGCCTTCCTGGAGACCTCCGCGCCCGCCAACCTCCCTTT
CTACGAGCGGCTCGGCTTCACCGTCACCGCAGACGTCGAGGTGCCAG
AAGGACCTCGCACCTGGTGTCTCACCCGCAAGCCCGGTGCCCGTACGGGC
AGTGGGAGGCGGCAGAGAGCTTGCTAACCTGCGGTGACGTCGAGGA
GAATCCTGGCCCAGTGTCCAAGGGCGAGGAAGATAACATGGCCATCATCA
AGGAGTTCATGAGGTTTAAGGTCCACATGGAGGGTTCAGTCAATGGC
CACGAGTTCGAGATTGAAGGCGAGGGCGAGGGCCGCCCCTACGAAGGGAC
ACAGACGGCCAAGTTGAAGGTGACCAAAGGCGGCCCATTGCCCTTCG
CATGGGACATCTTGTCCCCTCAGTTTATGTATGGCAGCAAGGCCTATGTT
AAGCACCCCGCTGATATCCCCGACTACTTGAAGCTGTCCTTTCCAGA
GGGGTTTAAATGGGAGCGCGTTATGAATTTCGAAGACGGAGGAGTGGTTA
CGGTGACCCAGGACTCATCCCTGCAGGACGGAGAATTTATATATAAG
GTTAAGTTGAGAGGGACCAACTTCCCAAGCGACGGCCCTGTGATGCAGAA
GAAAACAATGGGTTGGGAAGCTTCCAGCCAGCGCATGTACCCCGAAG
ATGGCGCCCTCAAGGGCGAGATAAAGCAAAGGCTGAAACTTAAGGACGGC
GCTCATTACGACGCGGAGGTCAAGACAACTTACAAGGCTAAAAAACC
CGTTCAGTTGCCTGGCCCTTACAATGTTAATATCAAACTTGACATCACAA

TABLE 9-continued

Vectors

```
GCCACAATGAAGACTATACGATCGTGGAGCAGTATCAACGAGCGGAA
GGCAGGCACTCAACGGGGGGGATGGACGAGCTTTACAAGTAATAATAAGA
ATTCGATATCAAGCTTATCGGTAATCAACCTCTGGATTACAAAATTT
GTCAAAGATTGACTGGTATTCTTAACTATGTTGCTCCTTTTACGCTATGT
GGATACGCTGCTTTAATGCCTTTGTATCATGCTATTGCTTCCCGTAT
GGCTTTCATTTTCTCCTCCTTGTATAAATCCTGGTTGCTGTCTCTTTATG
AGGAGTTGTGGCCCGTTGTCAGGCAACGTGGCGTGGTGTGCACTGTG
TTTGCTGACGCAACCCCCACTGGTTGGGGCATTGCCACCACCTGTCAGCT
CCTTTCCGGGACTTTCGCTTTCCCCCTCCCTATTGCCACGGCGGAAC
TCATCGCCGCCTGCCTTGCCCGCTGCTGGACAGGGGCTCGGCTGTTGGGC
ACTGACAATTCCGTGGTGTTGTCGGGGAAATCATCGTCCTTTCCTTG
GCTGCTCGCCTGTGTTGCCACCTGGATTCTGCGCGGGACGTCCTTCTGCT
ACGTCCCTTCGGCCCTCAATCCAGCGGACCTTCCTTCCCGCGGCCTG
CTGCCGGCTCTGCGGCCTCTTCCGCGTCTTCGCCTTCGCCCTCAGACGAG
TCGGATCTCCCTTTGGGCCGCCTCCCCGCATCGATACCGTCGACCTC
GAGACCTAGAAAAACATGGAGCAATCACAAGTAGCAATACAGCAGCTACC
AATGCTGATTGTGCCTGGCTAGAAGCACAAGAGGAGGAGGAGGTGGS
TTTTCCAGTCACACCTCAGGTACCTTTAAGACCAATGACTTACAAGGCAG
CTGTAGATCTTAGCCACTTTTTAAAAGAAAAGGGGGACTGAAGGG
CTAATTCACTCCCAACGAAGACAAGATATCCTTGATCTGTGGATCTACCA
CACACAAGGCTACTTCCCTGATTGGCAGAACTACACACCAGGGCCAG
GGATCAGATATCCACTGACCTTTGGATGGTGCTACAAGCTAGTACCAGTT
GAGCAAGAGAAGGTAGAAGAAGCCAATGAAGGAGAGAACACCCGCTT
GTTACACCCTGTGAGCCTGCATGGGATGGATGACCCGGAGAGAGAAGTAT
TAGAGTGGAGGTTTGACAGCCGCCTAGCATTTCATCACATGGCCCGA
GAGCTGCATCCGGACTGTACTGGGTCTCTCTGGTTAGACCAGATCTGAGC
CTGGGAGCTCTCTGGCTAACTAGGGAACCCACTGCTTAAGCCTCAAT
AAAGCTTGCCTTGAGTGCTTCAAGTAGTGTGTGCCCGTCTGTTGTGTGAC
TCTGGTAACTAGAGATCCCTCAGACCCTTTTAGTCAGTGTGGAAAAT
CTCTAGCAGGGCCCGTTTAAACCCGCTGATCAGCCTCGACTGTGCCTTCT
AGTTGCCAGCCATCTGTTGTTTGCCCCTCCCCCGTGCCTTCCTTGAC
CCTGGAAGGTGCCACTCCCACTGTCCTTTCCTAATAAAATGAGGAAATTG
CATCGCATTGTCTGAGTAGGTGTCATTCTATTCTGGGGGTGGGGTG
GGGCAGGACAGCAAGGGGGAGGATTGGGAAGACAATAGCAGGCATGCTGG
GGATGCGGTGGGCTCTATGGCTTCTGAGGCGGAAAGAACCAGCTGGG
GCTCTAGCGGGTATCCCCACGCGCCCTGTAGCGGCGCATTAAGCGCGGCG
GGTGTGGTGGTTACGCGCAGCGTGACCGCTACACTTGCCAGCGCCCT
AGCGCCCGCTCCTTTCGCTTTCTTCCCTTCCTTTCTCGCCACGTTCGCCG
GCTTTCCCCGTCAAGCTCTAAATCGGGGGCTCCCTTTAGGGTTCCGA
TTTAGTGCTTTACGGCACCTCGACCCCAAAAAACTTGATTAGGGTGATGG
TTCACGTAGTGGGCCATCGCCCTGATAGACGGTTTTTCGCCCTTTGA
CGTTGGAGTCCACGTTCTTTAATAGTGGACTCTTGTTCCAAACTGGAACA
ACACTCAACCCTATCTCGGTCTATTCTTTTGATTTATAAGGGATTTT
GCCGATTTCGGCCTATTGGTTAAAAATGAGCTGATTTAACAAAAATTTA
ACGCGAATTAATTCTGTGGAATGTGTGTCAGTTAGGGTGTGGAAAGT
CCCCAGGCTCCCCAGCAGGCAGAAGTATGCAAAGCATGCATCTCAATTAG
TCAGCAACCAGGTGTGGAAAGTCCCCAGGCTCCCCAGCAGGCAGAAG
TATGCAAAGCATGCATCTCAATTAGTCAGCAACCATAGTCCCGCCCCTAA
CTCCGCCCATCCCGCCCCTAACTCCGCCCAGTTCCGCCCATTCTCCG
CCCCATGGCTGACTAATTTTTTTATTTATGCAGAGGCCGAGGCCGCCTC
TGCCTCTGAGCTATTCCAGAAGTAGTGAGGAGGCTTTTTGGAGGCC
TAGGCTTTTGCAAAAAGCTCCCGGGAGCTTGTATATCCATTTTCGGATCT
GATCAGCACGTGTTGACAATTAATCATCGGCATAGTATATCGGCATA
GTATAATACGACAAGGTGAGGAACTAAACCATGGCCAAGTTGACCAGTGC
CGTTCCGGTGCTCACCGCGCGCGACGTCGCCGGAGCGGTCGAGTTCT
GGACCGACCGGCTCGGGTTCTCCCGGGACTTCGTGGAGGACGACTTCGCC
GGTGTGGTCCGGGACGACGTGACCCTGTTCATCAGCGCGGTCCAGGA
CCAGGTGGTGCCGGACAACACCCTGGCCTGGGTGTGGGTGCGCGGCCTGG
ACGAGCTGTACGCCGAGTGGTCGGAGGTCGTGTCCACGAACTTCCGG
GACGCCTCCGGGCCGGCCATGACCGAGATCGGCGAGCAGCCGTGGGGCG
GGAGTTCGCCCTGCGCGACCCGGCCGGCAACTGCGTGCACTTCGTGG
CCGAGGAGCAGGACTGACACGTGCTACGAGATTTCGATTCCACCGCCGCC
TTCTATGAAAGGTTGGGCTTCGGAATCGTTTTCCGGGACGCCGGCTG
GATGATCCTCCAGCGCGGGATCTCATGCTGGAGTTCTTCGCCCACCCCA
ACTTGTTTATTGCAGCTTATAATGGTTACAAATAAAGCAATAGCATC
ACAAATTTCACAAATAAAGCATTTTTTCACTGCATTCTAGTTGTGGTTT
GTCCAAACTCATCAATGTATCTTATCATGTCTGTATACCGTCGACCT
CTAGCTAGAGCTTGGCGTAATCATGGTCATAGCTGTTTCCTGTGTGAAAT
TGTTATCCGCTCACAATTCCACACAACATACGAGCCGGAAGCATAAA
GTGTAAAGCCTGGGGTGCCTAATGAGTGAGCTAACTCACATTAATTGCGT
TGCGCTCACTGCCCGCTTTCCAGTCGGGAAACCTGTCGTGCCAGCTG
CATTAATGAATCGGCCAACGCGCGGGAGAGGCGGTTTGCGTATTGGGCG
CTCTTCCGCTTCCTCGCTCACTGACTCGCTGCGCTCGGTCGTTCGGC
TGCGGCGAGCGGTATCAGCTCACTCAAAGGCGGTAATACGGTTATCCACA
GAATCAGGGGATAACGCAGGAAAGAACATGTGAGCAAAAGGCCAGCA
AAAGGCCAGGAACCGTAAAAAGGCCGCGTTGCTGGCGTTTTTCCATAGGC
TCCGCCCCCTGACGAGCATCACAAAAATCGACGCTCAAGTCAGAGG
TGGCGAAACCCGACAGGACTATAAAGATACCAGGCGTTTCCCCCTGGAAG
CTCCCTCGTGCGCTCTCCTGTTCCGACCCTGCCGCTTACCGGATACC
TGTCCGCCTTTCTCCCTTCGGGAAGCGTGGCGCTTTCTCATAGCTCACGC
TGTAGGTATCTCAGTTCGGTGTAGGTCGTTCGCTCCAAGCTGGGCTG
TGTGCACGAACCCCCCGTTCAGCCCGACCGCTGCGCCTTATCCGGTAACT
ATCGTCTTGAGTCCAACCCGGTAAGACACGACTTATCGCCACTGGCA
GCAGCCACTGGTAACAGGATTAGCAGAGCGAGGTATGTAGGCGGTGCTAC
AGAGTTCTTGAAGTGGTGGCCTAACTACGGCTACACTAGAAGAACAG
TATTTGGTATCTGCGCTCTGCTGAAGCCAGTTACCTTCGGAAAAAGAGTT
GGTAGCTCTTGATCCGGCAAACAAACCACCGCTGGTAGCGGTGGTTT
TTTTGTTTGCAAGCAGCAGATTACGCGCAGAAAAAAAGGATCTCAAGAAG
ATCCTTTGATCTTTTCTACGGGGTCTGACGCTCAGTGGAACGAAAAC
TCACGTTAAGGGATTTTGGTCATGAGATTATCAAAAAGGATCTTCACCTA
GATCCTTTTAAATTAAAAATGAAGTTTTAAATCAATCTAAAGTATAT
ATGAGTAAACTTGGTCTGACAGTTACCAATGCTTAATCAGTGAGGCACCT
ATCTCAGCGATCTGTCTATTTCGTTCATCCATAGTTGCCTGACTCCC
CGTCGTGTAGATAACTACGATACGGGAGGGCTTACCATCTGGCCCCAGTG
CTGCAATGATACCGCGAGACCCACGCTCACCGGCTCCAGATTTATCA
GCAATAAACCAGCCAGCCGGAAGGGCCGAGCGCAGAAGTGGTCCTGCAAC
TTTATCCGCCTCCATCCAGTCTATTAATTGTTGCCGGGAAGCTAGAG
TAAGTAGTTCGCCAGTTAATAGTTTGCGCAACGTTGTTGCCATTGCTACA
GGCATCGTGGTGTCACGCTCGTCGTTTGGTATGGCTTCATTCAGCTC
CGGTTCCCAACGATCAAGGCGAGTTACATGATCCCCCATGTTGTGCAAAA
AAGCGGTTAGCTCCTTCGGTCCTCCGATCGTTGTCAGAAGTAAGTTG
GCCGCAGTGTTATCACTCATGGTTATGGCAGCACTGCATAATTCTCTTAC
TGTCATGCCATCCGTAAGATGCTTTTCTGTGACTGGTGAGTACTCAA
CCAAGTCATTCTGAGAATAGTGTATGCGGCGACCGAGTTGCTCTTGCCCG
GCGTCAATACGGGATAATACCGCGCCACATAGCAGAACTTTAAAAGT
GCTCATCATTGGAAAACGTTCTTCGGGGCGAAAACTCTCAAGGATCTTAC
CGCTGTTGAGATCCAGTTCGATGTAACCCACTCGTGCACCCAACTGA
TCTTCAGCATCTTTTACTTTCACCAGCGTTTCTGGGTCAGCAAAAACAGG
AAGGCAAAATGCCGCAAAAAAGGGAATAAGGGCGACACGGAAATGTT
GAATACTCATACTCTTCCTTTTTCAATATTATTGAAGCATTTATCAGGGT
TATTGTCTCATGAGCGGATACATATTTGAATGTATTTAGAAAAATAA
ACAAATAGGGGTTCCGCGCACATTTCCCCGAAAAGTGCCACCTGAC
```

The invention is further described by the following numbered paragraphs:

1. A polynucleotide sequence comprising one or more DNA barcodes, the or each DNA barcode comprising a target sequence designed to be recognized by a CRISPR-Cas guide and a PAM sequence of a CRISPR-Cas complex; and a sequence encoding a selection marker or reporter under the control of or operably linked to a suitable promoter.

2. The polynucleotide sequence of numbered paragraph 1, wherein two or more selection markers or reporters are under the control of or operably linked to the suitable promoter, wherein the two or more selection markers or reporters are in frame or out of frame within an open reading frame, optionally one marker is in frame and one marker is out of frame, and wherein the barcode is configured such that introducing an insertion or deletion in said barcode creates a frameshift in said open reading frame, whereby two or more selection markers or reporters are activated or inactivated, optionally one marker or reporter is activated and one marker or reporter is inactivated.

3. A polynucleotide sequence encoding a CRISPR-Cas enzyme and a selection marker or reporter.

4. The polynucleotide sequence of numbered paragraph 3, wherein the CRISPR-Cas enzyme is a Cas9 enzyme.

5. The polynucleotide sequence of numbered paragraph 3, wherein the CRISPR-Cas enzyme is a catalytically inactive CRISPR-Cas enzyme, optionally a dead or diminished nuclease activity-Cas9 enzyme.

6. The polynucleotide sequence of numbered paragraph 5 wherein the Cas9 comprises mutations at D10 and N863 in SpCas9, D10 or N580 in SaCas9 or corresponding mutations in orthologs.

7. The polynucleotide sequence of numbered paragraphs 3-6, wherein the CRISPR-Cas enzyme further comprises a functional domain.

8. A polynucleotide sequence comprising:
   guide RNA, optionally sgRNA, that recognizes the target sequence in the DNA barcode of numbered paragraph 1;
   a sequence encoding one or more adaptor proteins, each adaptor protein comprising at least one functional domain, optionally wherein the functional domain comprises a transcriptional activator; and
   a sequence encoding a selection marker or reporter.

9. A viral vector comprising the polynucleotide sequence of numbered paragraph 1 or 2.

10. A viral vector comprising the polynucleotide sequence of any of numbered paragraphs 3-7.

11. A viral vector according to any of numbered paragraphs 9 or 10, which is a retroviral vector, optionally a lentivirus, or an AAV vector.

12. A viral vector comprising the polynucleotide sequence of numbered paragraph 8.

13. The viral vector of numbered paragraph 12, which is an AAV vector.

14. A kit comprising the polynucleotide sequence according to numbered paragraph 1 or 2 and the polynucleotide sequence according to any of numbered paragraphs 3-7.

15. A kit comprising the polynucleotide sequence according to numbered paragraph 1 or 2 and the polynucleotide sequence according to numbered paragraph 8.

16. A kit comprising the polynucleotide sequence according to numbered paragraph 8 and the polynucleotide sequence according to any of numbered paragraphs 3-7.

17. A kit comprising the polynucleotide sequence according to numbered paragraph 1 or 2, the polynucleotide sequence according to numbered paragraph 8 and the polynucleotide sequence according to any of numbered paragraphs 3-7.

18. A method of sorting one or more cells or nucleic acid molecules of interest from a mixed population of cells or nucleic acid molecules, the one or more cells or nucleic acid molecules of interest comprising a DNA barcode of interest, and optionally the remaining cells or nucleic acid molecules in the population each comprising at least another DNA barcode, the cells or nucleic acid molecules comprising a CRISPR-Cas enzyme and one or more DNA barcodes, the or each DNA barcode comprising:
   a target recognisable by a CRISPR-Cas guide RNA;
   a PAM sequence for the CRISPR-Cas enzyme; and
   a selection marker or reporter under the control of (operably linked to) a suitable promoter;
the method comprising:
   a. providing the mixed population of cells or nucleic acid molecules, including the one or more cells or nucleic acid molecules of interest;
   b. providing a CRISPR-Cas guide RNA specific for the DNA barcode of interest and comprising a functional domain, optionally wherein the functional domain comprises a transcriptional activator;
   c. delivering the CRISPR-Cas guide RNA to the population of cells or nucleic acid molecules so as to form a CRISPR-Cas complex in the one or more cells of interest or with or one or more nucleic acid molecules of interest,
      the CRISPR-Cas complex comprising the CRISPR-Cas enzyme complexed with the CRISPR-Cas guide RNA and the DNA barcode of interest, thereby activating function, optionally transcription of or as to the selection marker or reporter, comprised within the DNA barcode of interest, by the functional domain optionally comprising as transcriptional activator comprised within the CRISPR-Cas guide RNA;
   and
   d. separating the cells that express said selection marker or reporter or nucleic acid molecules that include the selection marker or reporter from the remaining cells or nucleic acid molecules within the population that do not express or include said selection marker or reporter.

19. A method of sorting one or more cells or nucleic acid molecules of interest from a mixed population of cells or nucleic acid molecules, the one or more cells or nucleic acid molecules of interest comprising a DNA barcode of interest, and optionally the remaining cells or nucleic acid molecules in the population each comprising at least another DNA barcode, the cells or nucleic acid molecules comprising a CRISPR-Cas enzyme and one or more DNA barcodes, the or each DNA barcode comprising:
   a target recognizable by a CRISPR-Cas guide RNA;
   a PAM sequence for the CRISPR-Cas enzyme; and
   a selection marker or reporter under the control of (operably linked to) a suitable promoter;
the method comprising:
   a. providing the mixed population of cells or nucleic acid molecules, including the one or more cells or nucleic acid molecules of interest;
   b. providing a CRISPR-Cas guide RNA specific for the DNA barcode of interest;
   c. delivering the CRISPR-Cas guide RNA to the population of cells or nucleic acid molecules so as to form a CRISPR-Cas complex in the one or more cells of interest or with or one or more nucleic acid molecules of interest,
      the CRISPR-Cas complex comprising the CRISPR-Cas enzyme complexed with the CRISPR-Cas guide RNA and the DNA barcode of interest, wherein said CRISPR enzyme creates a targeted insertion or deletion in the barcode of interest, wherein the insertion or deletion creates a frameshift within an open reading frame of a selection marker or reporter, thereby activating or inactivating function;
   and
   d. separating the cells that express said selection marker or reporter or nucleic acid molecules that include the selection marker or reporter from the remaining cells or nucleic acid molecules within the population that do not express or include said selection marker or reporter.

20. The method of sorting cells according to numbered paragraph 18 or 19, further comprising delivering the CRISPR-Cas enzyme to the cells so as to provide the mixed population of cells, including the one or more cells of interest, with the CRISPR-Cas enzyme.

21. The method of sorting cells according to numbered paragraph 18-20, further comprising delivering the DNA barcodes, including the DNA barcode of interest, to the cells so as to provide the mixed population of cells, including the one or more cells of interest, with DNA barcodes.

22. The method of sorting cells according to any of numbered paragraphs 18-21, wherein the cells of interest comprising a phenotype of interest.

23. The method of sorting cells according numbered paragraph 22, wherein the phenotype of interest is resistance to a drug or treatment of interest.

24. The method of sorting cells according numbered paragraph 23, wherein the phenotype of interest is susceptibility to a drug or treatment of interest.

25. The method of sorting cells according to any of numbered paragraphs 18-22, wherein cells of interest, and/or the remaining cells in the population of cells, are mammalian cells.

26. The method of sorting cells according to numbered paragraph 25, wherein the cells of interest, and/or the remaining cells in the population of cells, are cancer cells.

27. The method of sorting cells according to any of numbered paragraphs 18-26, wherein the cells of interest, and/or the remaining cells in the population of cells, have been the subject of genome engineering or modification at a particular locus.

28. The method of sorting cells according to any of numbered paragraphs 18-27, wherein the cells of interest, and/or the remaining cells in the population of cells, are a heterogeneous population of cells.

29. The method of sorting cells according to any of numbered paragraphs 18-28, wherein the selection marker or reporter is a luminescent or fluorescent marker and, optionally, the cells of interest are separated by FACS.

30. The method of sorting cells according to any of numbered paragraphs 18-28, wherein the selection marker or reporter confers drug resistance to the cells of interest and, optionally, the cells of interest are separate upon provision of said drug to the mixed population of cells.

31. The method of sorting cells according to any of numbered paragraphs 18-28, wherein the selection marker or reporter is a surface protein and optionally, the cells of interest are separated by FACS, affinity capture or magnetic sorting.

32. A method of sorting one or more cells or nucleic acid molecules of interest from a mixed population of cells or nucleic acid molecules, the one or more cells or nucleic acid molecules of interest comprising a DNA barcode of interest, and optionally the remaining cells or nucleic acid molecules in the population each comprising at least another DNA barcode, the cells comprising a CRISPR-Cas enzyme comprising a functional domain optionally wherein the functional domain comprises a transcriptional activator, and one or more DNA barcodes, the or each DNA barcode comprising:
   a target recognisable by a CRISPR-Cas guide RNA;
   a PAM sequence for the CRISPR-Cas enzyme; and
   a selection marker or reporter under the control of (operably linked to) a suitable promoter;
the method comprising:
   a. providing the mixed population of cells or nucleic acid molecules, including the one or more cells or nucleic acid molecules of interest;
   b. providing a CRISPR-Cas guide RNA specific for the DNA barcode of interest;
   c. delivering the CRISPR-Cas guide RNA to the population of cells or nucleic acid molecules so as to form a CRISPR-Cas complex in the one or more cells of interest or with the one or more nucleic acid molecules of interest,
      the CRISPR-Cas complex comprising the CRISPR-Cas enzyme complexed with the CRISPR-Cas guide RNA and the DNA barcode of interest, thereby activating the functional domain as to, optionally transcription of, the selection marker or reporter, comprised within the DNA barcode of interest, by the functional domain optionally comprising a transcriptional activator comprised within the CRISPR-Cas enzyme;
   and
   d. separating the cells that express said selection marker or reporter or nucleic acid molecules that contain the selection marker or reporter from the remaining cells or nucleic acid molecules within the population that do not express or contain said selection marker or reporter.

33. A cell population from any of the methods of any one of numbered paragraphs 18-32.

34. A library of cells from any of the methods of any one of numbered paragraphs 18-32.

35. A cell or cell line of the methods of any one of numbered paragraphs 18-32, or progeny thereof.

36. The method of any one of numbered paragraphs 18-32 including testing cells that express the selection marker or reporter to confirm said cells are desired and/or testing cells that do not express the selection marker or reporter to confirm said cells are undesired.

37. The method of any of numbered paragraphs 18-21 or 36 which is non-destructive in respect of the cells of interest or the remaining cells of the mixed population.

38. A library comprising two or more of the polynucleotides according to any of numbered paragraphs 1-16 or as defined in any of numbered paragraphs 18-32.

39. An expression cassette comprising one or more of the polynucleotides according to any of numbered paragraphs 1-16 or as defined in any of numbered paragraphs 18-32.

40. A delivery cassette comprising one or more of the polynucleotides according to any of numbered paragraphs 1-19 or as defined in any of numbered paragraphs 18-32.

41. A method of sorting at least one cell of interest and/or its progeny from a mixed population of cells, the at least one cell of interest and its progeny comprising a unique DNA barcode of interest, the unique DNA barcode of interest comprising:
   a target recognizable by a CRISPR-Cas guide RNA;
   a PAM sequence for the CRISPR-Cas enzyme; and
   a selection marker or reporter operably linked to a suitable promoter;
the method comprising:
   a. providing the mixed population of cells, including the at least one cell of interest and/or its progeny;
   b. providing a CRISPR-Cas guide RNA specific for the unique DNA barcode of interest and comprising a functional domain, optionally wherein the functional domain comprises a transcriptional activator;
   c. delivering the CRISPR-Cas guide RNA to the population of cells so as to form a CRISPR-Cas complex in the at least one cell of interest, wherein the CRISPR-Cas complex comprises the CRISPR-Cas enzyme complexed
      with the CRISPR-Cas guide RNA and the unique DNA barcode of interest, thereby the functional domain activates function, optionally transcription, as to the selection marker or reporter comprised within the DNA barcode of interest; and
   d. sorting the cells that express said selection marker or reporter from the cells within the mixed population that do not express said selection marker or reporter.

42. The method of numbered paragraph 41, wherein the unique DNA barcode of interest and optionally other unique DNA barcodes of interest are introduced into a population of cells, wherein each cell in the population of cells contains a unique DNA barcode that is passed to its progeny upon propagation of the population of cells, whereby a cell of interest and/or its progeny can be isolated from a mixed population.

43. The method according to any of numbered paragraphs 32, 41 or 42, wherein the selection marker or reporter is a surface protein and optionally, the cells of interest are separated by FACS, affinity capture or magnetic sorting.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A method of recovering one or more cells of interest from a heterogeneous population of cells, wherein the heterogenous population of cells are obtained by a method comprising:
   i. delivering a plurality of reporter constructs to the heterogeneous population of cells, wherein each reporter construct comprises a unique barcode, and a selection marker or reporter under transcriptional control of a promoter, and wherein one reporter construct is integrated into the genome of each cell, whereby the reporter construct is passed to its progeny upon propagation of the population of cells;
   ii. expanding the heterogeneous population of cells for one or more generations, wherein each cell and the progeny of each cell in the heterogeneous population of cells have the same reporter construct, and
   iii. splitting the heterogeneous population of cells into two or more subpopulations;
   a. said method comprising delivering to a subpopulation of the expanded heterogeneous population of cells a CRISPR-Cas enzyme and one or more guide RNAs targeting one or more barcodes specific for one or more cells of interest, wherein said targeting activates transcription of the selection marker or reporter in the one or more cells of interest; and
   b. separating cells that express said selection marker or reporter from the remaining cells within the heterogeneous population that do not express said selection marker or reporter.

2. The method of recovering cells according to claim 1, wherein the one or more cells of interest comprises a phenotype of interest, optionally
   wherein the phenotype of interest is resistance to a drug or treatment of interest, or
   wherein the phenotype of interest is susceptibility to a drug or treatment of interest.

3. The method of recovering cells according to claim 1, wherein the one or more cells of interest, and/or the remaining cells in the population of cells, are mammalian cells, optionally,
   wherein the one or more cells of interest, and/or the remaining cells in the population of cells, are cancer cells, or
   wherein the one or more cells of interest, and/or the remaining cells in the population of cells, have been the subject of genome engineering or modification at a particular locus.

4. The method of recovering cells according to claim 1, wherein the selection marker or reporter is a luminescent or fluorescent marker, or
   wherein the selection marker or reporter confers drug resistance to the one or more cells of interest, or
   wherein the selection marker or reporter is a surface protein.

5. The method of recovering cells according to claim 1, wherein the CRISPR-Cas enzyme is Cas9.

6. The method of claim 1, comprising testing cells that express the selection marker or reporter to confirm said cells are desired and/or testing cells that do not express the selection marker or reporter to confirm said cells are undesired, and/or
   wherein the method is non-destructive in respect of the one or more cells of interest or the remaining cells of the population.

7. A method of recovering one or more cells of interest from a heterogeneous population of cells, wherein the heterogenous population of cells are obtained by a method comprising:
   i. delivering a plurality of reporter constructs to the heterogeneous population of cells,
      wherein each reporter construct comprises a unique barcode, and a selection marker or reporter under transcriptional control of a promoter, and
      wherein one reporter construct is integrated into the genome of each cell, whereby the reporter construct is passed to its progeny upon propagation of the population of cells;
   ii. expanding the heterogeneous population of cells for one or more generations, wherein each cell and the progeny of each cell in the heterogeneous population of cells have the same reporter construct, and
   iii. splitting the heterogeneous population of cells into two or more subpopulations;
   a. said method comprising delivering to a subpopulation of the expanded heterogeneous population of cells a CRISPR-Cas enzyme and one or more guide RNAs targeting one or more barcodes specific for one or more cells of interest, wherein said CRISPR-Cas enzyme creates an insertion or deletion in the barcode in the one or more cells of interest that causes a frameshift within an open reading frame of the selection marker or reporter, thereby activating or inactivating the selection marker or reporter; and
   b. separating cells that express said selection marker or reporter from the remaining cells within the heterogeneous population that do not express said selection marker or reporter.

8. The method of recovering cells according to claim 7, wherein the CRISPR-Cas enzyme is Cas9.

* * * * *

UNITED STATES PATENT AND TRADEMARK OFFICE
CERTIFICATE OF CORRECTION

| | |
|---|---|
| PATENT NO. | : 11,236,327 B2 |
| APPLICATION NO. | : 15/842315 |
| DATED | : February 1, 2022 |
| INVENTOR(S) | : Konermann et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 67 days.

Signed and Sealed this
Thirty-first Day of January, 2023

Katherine Kelly Vidal
*Director of the United States Patent and Trademark Office*